US007556949B2

(12) United States Patent
Yadav et al.

(10) Patent No.: US 7,556,949 B2

(45) Date of Patent: Jul. 7, 2009

(54) Δ17 DESATURASE AND ITS USE IN MAKING POLYUNSATURATED FATTY ACIDS

(75) Inventors: Narendra S. Yadav, Chadds Ford, PA (US); Zhixiong Xue, Chadds Ford, PA (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 36 days.

(21) Appl. No.: 11/779,915

(22) Filed: Jul. 19, 2007

(65) Prior Publication Data

US 2008/0125326 A1 May 29, 2008

Related U.S. Application Data

(60) Provisional application No. 60/855,177, filed on Oct. 30, 2006.

(51) Int. Cl.
*C12N 1/16* (2006.01)
*C12P 7/64* (2006.01)
*C12N 9/02* (2006.01)
*C07H 21/04* (2006.01)

(52) U.S. Cl. .................. 435/134; 435/254.11; 435/189; 435/254.2; 435/252.3; 435/257.2; 536/23.2

(58) Field of Classification Search ....................... None
See application file for complete search history.

(56) References Cited

U.S. PATENT DOCUMENTS

| | | | |
|---|---|---|---|
| 7,125,672 | B2 | 10/2006 | Picataggio et al. |
| 7,189,559 | B2 | 3/2007 | Damude et al. |
| 7,192,762 | B2 | 3/2007 | Macool et al. |
| 7,198,937 | B2 | 4/2007 | Xue et al. |
| 7,202,356 | B2 | 4/2007 | Pollak et al. |
| 2003/0190733 | A1 | 10/2003 | Mukerji et al. |
| 2007/0224661 | A1 | 9/2007 | Cirpus et al. |

FOREIGN PATENT DOCUMENTS

| | | | |
|---|---|---|---|
| WO | 2004101757 | A2 | 11/2004 |
| WO | 2005083093 | A2 | 9/2005 |
| WO | WO 2005/083053 | A2 | 9/2005 |
| WO | WO 2006/100241 | A2 | 9/2006 |
| WO | 2007123999 | A2 | 11/2007 |
| WO | 2008022963 | A2 | 2/2008 |

OTHER PUBLICATIONS

U.S. Appl. No. 11/787,772, filed Apr. 18, 2007, Zhixiong Xue et al.
U.S. Appl. No. 10/840,579, filed May 6, 2004, Stephen K. Picataggio et al.
U.S. Appl. No. 10/840,325, filed May 6, 2004, Narendra S. Yadav et al.
U.S. Appl. No. 10/869,630, filed Jun. 16, 2004, Stephen K. Picataggio et al.
U.S. Appl. No. 10/882,760, filed Jul. 1, 2004, Narendra S. Yadav et al.
U.S. Appl. No. 10/985,254, filed Nov. 10, 2004, Narendra S. Yadav et al.
U.S. Appl. No. 10/985,691, filed Nov. 10, 1994, Narendra S. Yadav et al.
U.S. Appl. No. 11/024,544, filed Dec. 29, 2004, Narendra S. Yadav et al.
U.S. Appl. No. 11/166,993, filed Jun. 24, 2005, Howard Glenn Damude et al.
U.S. Appl. No. 11/183,664, filed Jul. 18, 2005, Stephen K. Picataggio et al.
U.S. Appl. No. 11/185,301, filed Jul. 20, 2005, Zhixiong Xue et al.
U.S. Appl. No. 11/190,750, filed Jul. 27, 2005, Stephen K. Picataggio et al.
U.S. Appl. No. 11/198,975, filed Aug. 8, 2005, Quinn Qun Zhu et al.
U.S. Appl. No. 11/225,354, filed Sep. 13, 2005, Zhixiong Xue et al.
Dyerberg et al., Fatty Acid Composition of the Plasma Lipids in Greenland Eskimos, Amer. J. Clin. Nutr., 1975, vol. 28:958-966.
Dyerberg et al., Eicosapentaenoic Acid and Prevention of Thrombosis and Atherosclerosis?, Lancet, 1978, vol. 2:117-119.
H. Shimokawa, Benefical Effects of Eicosapentaenoic Acid on Endothelial Vasodilator Functions in Animals and Humans, World Rev. Nutr. Diet, 2001, vol. 88:100-108.
von Schacky et al., 3 Fatty Acids from Eskimos to Clinical Cardiology—What Took Us So Long?, World Rev. Nutr. Diet, 2001, vol. 88:90-99.
National Center for Biotechnology Information General Identifier No. 38426733, May 5, 2004, S.L. Pereira et al., A Novel Omega3-Fatty Acid Desaturase Involved in the Biosynthesis of Eicosapentaenoic, Accession No. AAR20444.
National Center for Biotechnology Information General Identifier No. 76059411, Jul. 13, 2006, P. Cirpus et al., Method for Producing Unsaturated Omega3 Fatty Acids in Transgenic Organisms, Accession No. CAJ30870.
Pereira et al., A Novel 3-Fatty Acid Desaturase Involved in the Biosynthesis of Eicosapentaenoic Acid, Biochem. J., 2004, vol. 378:665-671.
O'Brien et al., Production of Eicosapentaenoic Acid by the Filamentous Fungus Pythium Irregulare, Applied Microbiology & Biotechnology, 1993, vol. 40:211-214.
U.S. Appl. No. 11/253,882, filed Oct. 19, 2005, Daniel Joseph Macool et al.
U.S. Appl. No. 11/264,784, filed Nov. 1, 2005, Howard Glenn Damude et al.
U.S. Appl. No. 11/264,737, filed Nov. 1, 2005, Howard Glenn Damude et al.
U.S. Appl. No. 11/265,761, filed Nov. 2, 2005, Howard Glenn Damude et al.
U.S. Appl. No. 60/853,563, filed Oct. 23, 2006, Howard Glenn Damude et al.

(Continued)

*Primary Examiner*—Nashaat T Nashed
*Assistant Examiner*—Iqbal H Chowdhury
(74) *Attorney, Agent, or Firm*—Loretta F. Smith; S. Neil Feltham

(57) ABSTRACT

The present invention relates to Δ17 desaturases, which have the ability to convert ω-6 fatty acids into their ω-3 counterparts (i.e., conversion of arachidonic acid [20:4, ARA] to eicosapentaenoic acid [20:5, EPA]). Isolated nucleic acid fragments and recombinant constructs comprising such fragments encoding Δ17 desaturases along with a method of making long-chain polyunsaturated fatty acids (PUFAs) using these Δ17 desaturases in oleaginous yeast are disclosed.

19 Claims, 15 Drawing Sheets

OTHER PUBLICATIONS

U.S. Appl. No. 60/855,177, filed Oct. 30, 2006, Zhixiong Xue et al.

U.S. Appl. No. 11/601,563, filed Nov. 16, 2006, Howard Glenn Damude et al.

U.S. Appl. No. 11/601,564, filed Nov. 16, 2006, Howard Glenn Damude et al.

U.S. Appl. No. 11/635,258, filed Dec. 7, 2006, Howard Glenn Damude et al.

U.S. Appl. No. 11/613,420, filed Dec. 20, 2006, John E. Seip et al.

U.S. Appl. No. 60/909,790, filed Apr. 30, 2007, Howard Glenn Damude et al.

U.S. Appl. No. 60/910,831, filed Apr. 10, 2007, Howard Glenn Damude et al.

U.S. Appl. No. 60/911,925, filed Apr. 16, 2007, Howard Glenn Damude et al.

U.S. Appl. No. 60/915,733, filed May 3, 2007, Howard Glenn Damude et al.

U.S. Appl. No. 11/737,772, filed Apr. 20, 2007, Howard Glenn Damude et al.

U.S. Appl. No. 11/740,298, filed Apr. 26, 2007, Narendra S. Yadav et al.

U.S. Appl. No. 11/748,637, filed May 15, 2007, Howard Glenn Damude et al.

U.S. Appl. No. 11/748,629, filed May 15, 2007, Howard Glenn Damude et al.

Cheng, Ming H. et al., Fungal production of eicosapentaenoic and arachidonic acids from industrial waste streams and crude soybean oil, Bioresource Technology, 1999, pp. 101-110, vol. 67, No. 2, Elsevier Science Ltd.

Stredansky, M. et al., Production of polyunsaturated fatty acids by Pythium ultimum in solid-state cultivation, Enzyme and Microbial Technology, 2000, pp. 304-307, vol. 26, No. 2-4, Elsevier Science Ltd.

Vuong, H. et al., PUNA910TV Pythium ultimum ESTs Pythium ultimum DAOM BR144 cDNA clone PUNA910, mRNA sequence, EBI accession No. EL777858, Mar. 21, 2007.

Figure 2

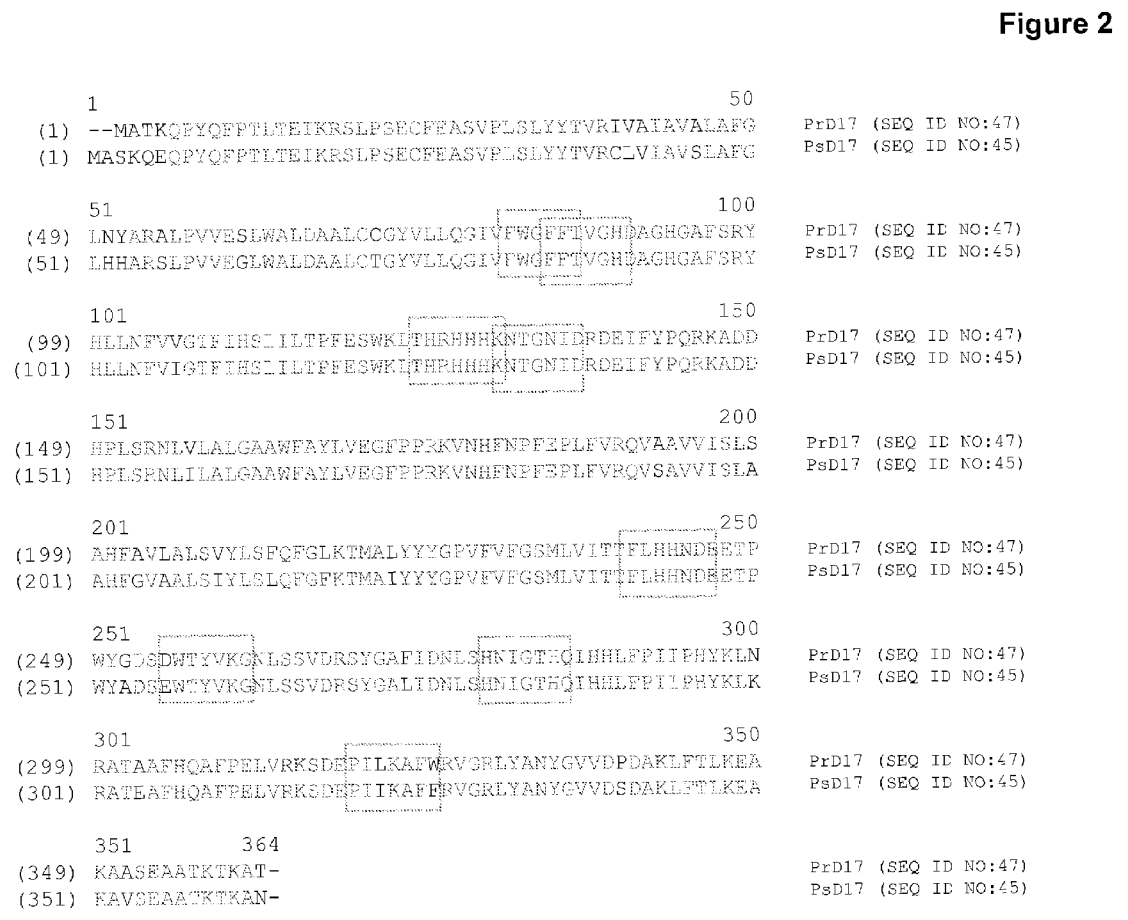

```
      1                                                50
  (1) --MATKQPYQFPTLTEIKRSLPSECFEASVPLSLYYTVRIVAIAVALAFG   PrD17 (SEQ ID NO:47)
  (1) MASKQEQPYQFPTLTEIKRSLPSECFEASVPLSLYYTVRCLVIAVSLAFG   PsD17 (SEQ ID NO:45)

      51                                              100
 (49) LNYARALPVVESLWALDAALCCGYVLLQGIVFWGFFTVGHDAGHGAFSRY   PrD17 (SEQ ID NO:47)
 (51) LHHARSLPVVEGLWALDAALCTGYVLLQGIVFWGFFTVGHDAGHGAFSRY   PsD17 (SEQ ID NO:45)

      101                                             150
 (99) HLLNFVVGTFIHSLILTPFESWKLTHRHHHKNTGNIDRDEIFYPQRKADD   PrD17 (SEQ ID NO:47)
(101) HLLNFVIGTFIHSLILTPFESWKLTHRHHHKNTGNIDRDEIFYPQRKADD   PsD17 (SEQ ID NO:45)

      151                                             200
(149) HPLSRNLVLALGAAWFAYLVEGFPPRKVNHFNPFEPLFVRQVAAVVISLS   PrD17 (SEQ ID NO:47)
(151) HPLSRNLILALGAAWFAYLVEGFPPRKVNHFNPFEPLFVRQVSAVVISLA   PsD17 (SEQ ID NO:45)

      201                                             250
(199) AHFAVLALSVYLSFQFGLKTMALYYYGPVFVFGSMLVITTFLHHNDEETP   PrD17 (SEQ ID NO:47)
(201) AHFGVAALSIYLSLQFGFKTMAIYYYGPVFVFGSMLVITTFLHHNDEETP   PsD17 (SEQ ID NO:45)

      251                                             300
(249) WYGDSDWTYVKGNLSSVDRSYGAFIDNLSHNIGTHQIHHLFPIIPHYKLN   PrD17 (SEQ ID NO:47)
(251) WYADSEWTYVKGNLSSVDRSYGALIDNLSHNIGTHQIHHLFPIIPHYKLK   PsD17 (SEQ ID NO:45)

      301                                             350
(299) RATAAFHQAFPELVRKSDEPILKAFWRVGRLYANYGVVDPDAKLFTLKEA   PrD17 (SEQ ID NO:47)
(301) RATEAFHQAFPELVRKSDEPIIKAFFRVGRLYANYGVVDSDAKLFTLKEA   PsD17 (SEQ ID NO:45)

      351          364
(349) KAASEAATKTKAT-                                       PrD17 (SEQ ID NO:47)
(351) KAVSEAATKTKAN-                                       PsD17 (SEQ ID NO:45)
```

Figure 3
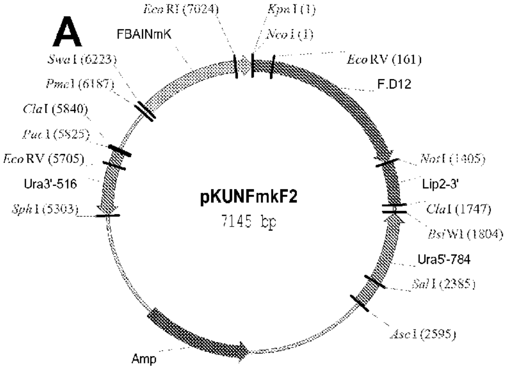
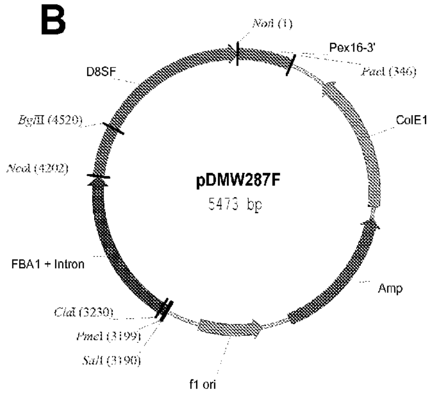
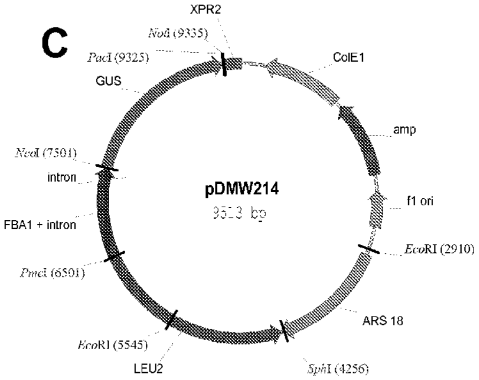
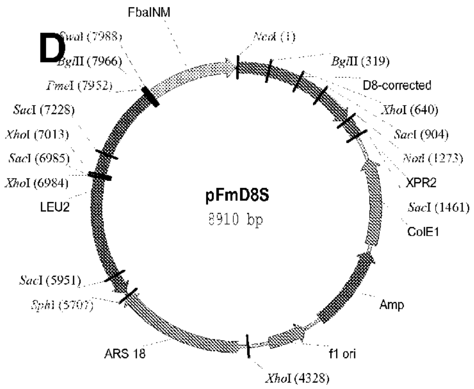

Figure 5A

```
  (1) ATGGCTTCTTCCACTGTTGCTGCGCCGTACGAGTTCCCGACGCTGACGGAGATCAAGCGCTCGCTGCCAGCGC    (SEQ ID NO:1)
  (1) ATGGCTTCCTCTACCGTTGCCGCTCCCTACGAGTTCCCTACTCTCACCGAGATCAAGCGATCCCTGCCTGCCC    (SEQ ID NO:4)

 (74) ACTGCTTTGAGGCCTCGGTCCCGTGGTCGCTCTACTACACCGTGCGCGCGCTGGGCATCGCCGGCTCGCTCGCGC (SEQ ID NO:1)
 (74) ACTGCTTCGAAGCCTCTGTTCCCTGGTCCCTCTACTATACCGTGCGAGCTCTGGGCATTGCCGGTTCCCTTGCTC (SEQ ID NO:4)

(149) TCGGCCTCTACTACGCGCGCGCGCTCGCGATCGTGCAGGAGTTTGCCCTGCTGGATGCGGTGCTCTGCACGGGGT (SEQ ID NO:1)
(149) TCGGACTGTACTATGCTCGAGCCCTTGCTATCGTGCAGGAGTTTGCACTGCTCGATGCCGTCCTTTGCACTGGCT (SEQ ID NO:4)

(224) ACATTCTGCTGCAGGGCATCGTATTCTGGGGGTTCTTCACCATCGGCCATGACTGCGGCCACGGCGCGTTCTCGC (SEQ ID NO:1)
(224) ACATTCTGCTCCAGGGTATCGTGTTCTGGGGATTCTTTACCATCGGTCACGACTGTGGACATGGTGCCTTCTCGC (SEQ ID NO:4)

(299) GTTCGCACCTGCTCAACTTCAGCGTCGGCACGCTCATTCACTCGATCATCCTCACGCCGTACGAGTCATGGAAGA (SEQ ID NO:1)
(299) GATCCCACCTGCTCAACTTCTCTGTTGGCACACTCATTCACTCCATCATTCTGACTCCCTACGAGTCGTGGAAGA (SEQ ID NO:4)

(374) TCTCGCACCGCCACCACCACAAGAACACGGGCAACATCGACAAGGACGAGATTTTCTACCCGCAGCGCGAGGCCG (SEQ ID NO:1)
(374) TCAGCCATCGACACCATCACAAGAACACCGGCAACATCGACAAGGATGAGATCTTCTACCCTCAGCGAGAAGCCG (SEQ ID NO:4)

(499) ACTCGCACCCACTGTCCCGACACATGGTGATCTCGCTCGGCTCGGCCTGGTTCGCGTACCTCGTTGCGGGCTTCC (SEQ ID NO:1)
(499) ACTCTCATCCCCTGTCCCGACACATGGTCATCTCCCTTGGTTCGGCTTGGTTTGCCTACCTCGTTGCTGGATTTC (SEQ ID NO:4)

(524) CTCCTCGCAAGGTGAACCACTTCAACCCTTGGGAACCGTTGTACCTGCGCCGCATGTCTGCCGTCATCATCTCAC (SEQ ID NO:1)
(524) CTCCCCGAAAGGTCAACCACTTCAATCCCTGGGAGCCTCTCTACCTGCGAAGAATGTCTGCCGTCATCATTTCCC (SEQ ID NO:4)
```

Figure 5B

(599) TCGGCTCGCTCGTGGCGTTCGCGGGCTTGTATGCGTATCTCACCTACGTCTATGGCCTTAAGACCATGGCGCTCT (SEQ ID NO:1)
(599) TCGGCTCTCTCGTGGCCTTTGCTGGTCTGTACGCCTACCTTACCTACGTCTACGGCCTCAAGACCATGGCTCTGT (SEQ ID NO:4)

(674) ACTACTTCGCCCCTCTCTTTGGGTTCGCCACGATGCTCGTGGTCACTACCTTTTTGCACCACAATGACGAGGAAA (SEQ ID NO:1)
(674) ATTACTTCGCACCTCTCTTTGGATTCGCCACCATGCTGGTTGTCACTACCTTCCTCCATCACAACGACGAGGAAA (SEQ ID NO:4)

(749) CGCCATGGTACGCCGACTCGGAGTGGACGTACGTCAAGGGCAACCTCTCGTCCGTGGACCGCTCGTACGGCGCGC (SEQ ID NO:1)
(749) CTCCCTGGTACGCCGATTCGGAGTGGACCTATGTCAAGGGCAACTTGTCCTCTGTGGACCGAAGCTACGGAGCCC (SEQ ID NO:4)

(824) TCATCGACAACCTGAGCCACAACATCGGCACGCACCAGATCCACCACCTGTTTCCGATCATCCCGCACTACAAGC (SEQ ID NO:1)
(824) TCATCGACAACCTGTCCCACAACATTGGTACACATCAGATCCACCATCTGTTTCCCATCATTCCTCACTACAAGC (SEQ ID NO:4)

(899) TGAACGAGGCGACGGCAGCGTTCGCGCAGGCGTTCCCGGAGCTCGTGCGCAAGAGCGCGTCGCCGATCATCCCGA (SEQ ID NO:1)
(899) TCAACGAGGCCACTGCTGCCTTCGCTCAGGCCTTTCCCGAACTGGTGCGAAAGTCGGCTTCTCCCATCATTCCCA (SEQ ID NO:4)

(974) CGTTCATCCGCATCGGGCTCATGTACGCCAAGTACGGCGTCGTGGACAAGGACGCCAAGATGTTTACGCTCAAGG (SEQ ID NO:1)
(974) CCTTCATCCGAATTGGTCTTATGTACGCCAAGTACGGCGTGGTCGACAAGGATGCCAAGATGTTTACCCTCAAGG (SEQ ID NO:4)

(1049) AGGCCAAGGCCGCCAAGACCAAGGCCAACTAG (SEQ ID NO:1)
(1049) AGGCCAAGGCTGCCAAGACCAAAGCCAACTAA (SEQ ID NO:4)

Figure 10

```
1     ATGGCGACTAAGCAGCCGTACCAGTTCCCGACCCTGACGGAGATCAAGCGGTCGCTGCCCAGCGAGTGCTTTGAGGCCTCGGTGCCGCTGTCGCTCTACT  PrD17 (SEQ ID NO:46)
1     ATGGCTACCAAGCAGCCCTACCAGTTCCCTACTCTGACCGAGATCAAGCGATCTCTTCCCTCCGAGTGCTTTGAAGCCTCGGTCCCTCTGTCCTTGTACT  PrD17S (SEQ ID NO:84)

101   ACACGGTGCGCATCGTGGCCATCGCCGTGGCGCTGGCGTTCGGCCTCAACTACGCGCGCGCGCTGCCCGTGGTCGAGAGCTTGTGGGCGCTGGACGCTGC  PrD17 (SEQ ID NO:46)
101   ACACCGTGCGAATCGTCGCTATTGCCGTTGCTCTGGCCTTCGGACTCAACTACGCTCGAGCCCTTCCCGTGGTCGAGTCTCTGTGGGCACTCGACGCTGC  PrD17S (SEQ ID NO:84)

201   GCTCTGCTGCGGTTACGTGCTGCTGCAGGGCATCGTGTTCTGGGGCTTCTTCACGGTGGGCCATGACGCCGGCCACGGCGCCTTCTCGCGTTACCACCTG  PrD17 (SEQ ID NO:46)
201   CCTTTGTTGCGGTTACGTTCTGCTCCAAGGCATTGTCTTCTGGGGATTCTTTACCGTGGGTCACGATGCTGGACATGGTGCCTTCTCTCGATACCACCTG  PrD17S (SEQ ID NO:84)

301   CTCAACTTCGTGGTGGGCACCTTCATCCACTCGCTCATCCTCACGCCCTTCGAGTCGTGGAAGCTCACGCACCGCCACCACCACAAGAACACGGGCAACA  PrD17 (SEQ ID NO:46)
301   CTCAACTTTGTCGTTGGCACCTTTATCCACTCCCTCATTCTTACTCCCTTCGAGTCGTGGAAGCTCACACATCGACACCATCACAAGAACACCGGAAACA  PrD17S (SEQ ID NO:84)

401   TTGACCGCGACGAGATCTTCTACCCGCAGCGCAAGGCCGACGACCACCCGCTGTCGCGCAACCTCGTGCTGGCGCTCGGCGCCGCGTGGTTCGCCTACCT  PrD17 (SEQ ID NO:46)
401   TCGACCGAGACGAAATCTTCTACCCTCAGCGAAAGGCCGACGATCATCCTCTGTCTCGAAACCTCGTCCTGGCTCTCGGTGCCGCTTGGTTTGCCTACCT  PrD17S (SEQ ID NO:84)

501   GGTCGAGGGCTTCCCGCCCCGCAAGGTCAACCACTTCAACCCATTCGAGCCGCTGTTTGTGCGCCAGGTGGCCGCCGTCGTCATCTCGCTCTCCGCGCAC  PrD17 (SEQ ID NO:46)
501   TGTCGAGGGCTTTCCTCCCCGAAAGGTCAACCACTTCAACCCCTTCGAACCTCTGTTTGTGCGACAGGTGGCTGCCGTTGTCATTTCCCTCTCTGCTCAC  PrD17S (SEQ ID NO:84)

601   TTCGCCGTGTTGGCGCTGTCCGTGTATCTGAGCTTCCAGTTCGGTCTCAAGACCATGGCGCTCTACTACTACGGCCCCGTCTTCGTGTTCGGCAGCATGC  PrD17 (SEQ ID NO:46)
601   TTCGCCGTCCTGGCACTGTCCGTGTATCTGAGCTTTCAGTTCGGTCTCAAGACAATGGCTCTGTACTACTATGGACCCGTCTTCGTGTTCGGCTCCATGC  PrD17S (SEQ ID NO:84)

701   TTGTGATCACCACCTTCCTGCATCACAATGACGAGGAGACCCCATGGTACGGAGACTCCGACTGGACCTACGTCAAGGGCAACCTGTCGTCCGTGGACCG  PrD17 (SEQ ID NO:46)
701   TCGTCATTACTACCTTTCTGCATCACAATGACGAGGAAACTCCTTGGTACGGAGATTCCGACTGGACCTACGTCAAGGGCAACTTGTCTTCCGTGGACCG  PrD17S (SEQ ID NO:84)

801   GTCCTACGGCGCGTTCATCGACAACCTGAGCCACAACATCGGCACGCACCAGATCCACCACCTCTTCCCCATCATCCCGCACTACAAGCTCAACCGCGCT  PrD17 (SEQ ID NO:46)
801   ATCTTACGGTGCCTTCATCGACAACCTCTCGCACAACATTGGCACACACCAGATCCACCATCTGTTTCCCATCATTCCTCACTACAAGCTCAACCGAGCC  PrD17S (SEQ ID NO:84)

901   ACGGCGGCATTCCACCAGGCCTTCCCCGAGCTCGTGCGCAAGAGCGACGAGCCGATCCTCAAGGCCTTCTGGCGCGTCGGCCGACTGTACGCCAACTACG  PrD17 (SEQ ID NO:46)
901   ACCGCTGCCTTCCACCAGGCCTTTCCCGAACTTGTCCGAAAGAGCGACGAGCCCATTCTCAAGGCTTTCTGGAGAGTTGGTCGACTTTACGCCAACTACG  PrD17S (SEQ ID NO:84)

1001  GCGTCGTGGACCCGGACGCCAAGCTCTTCACGCTCAAGGAGGCCAAGGCGGCGTCCGAGGCGGCGACCAAGACCAAGGCCACCTAA  PrD17 (SEQ ID NO:46)
1001  GAGTCGTGGATCCCGACGCAAAGCTGTTTACTCTCAAGGAGGCCAAAGCTGCCTCCGAGGCTGCCACCAAGACCAAGGCTACTTAA  PrD17S (SEQ ID NO:84)
```

Δ17 DESATURASE AND ITS USE IN MAKING POLYUNSATURATED FATTY ACIDS

This application claims the benefit of U.S. Provisional Patent Application 60/855177, filed Oct. 30, 2006.

FIELD OF THE INVENTION

This invention is in the field of biotechnology. More specifically, this invention pertains to the identification of a nucleic acid fragment encoding a Δ17 fatty acid desaturase enzyme and the use of this desaturase in making long-chain polyunsaturated fatty acids (PUFAs).

BACKGROUND OF THE INVENTION

The importance of PUFAs is undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs produces cardiovascular protective effects (Dyerberg, J. et al., *Amer. J. Clin. Nutr.,* 28:958-966 (1975); Dyerberg, J. et al., *Lancet,* 2(8081):117-119 (Jul. 15, 1978); Shimokawa, H., *World Rev. Nutr. Diet,* 88:100-108 (2001); von Schacky, C. and Dyerberg, J., *World Rev. Nutr. Diet,* 88:90-99 (2001)). Numerous other studies document wide-ranging health benefits conferred by administration of ω-3 and/or ω-6 PUFAs against a variety of symptoms and diseases (e.g., asthma, psoriasis, eczema, diabetes, cancer).

A variety of different hosts including plants, algae, fungi and yeast are being investigated as means for commercial PUFA production. Genetic engineering has demonstrated that the natural abilities of some hosts (even those natively limited to LA and ALA fatty acid production) can be substantially enhanced to produce high levels of e.g., γ-linolenic acid (GLA; 18:3 ω-6), dihomo-γ-linolenic acid (DGLA; 20:3 ω-6), arachidonic acid (ARA; 20:4 ω-6), eicosapentaenoic acid (EPA; 20:5 ω-3), docosapentaenoic acid (DPA; 22:5 ω-3) and docosahexaenoic acid (DHA; 22:6 ω-3).

Whether ω-3/ω-6 PUFA production is the result of natural abilities or recombinant technology, both strategies may require conversion of ω-6 PUFAs into their ω-3 counterparts. Specifically, a Δ15 desaturase is responsible for the conversion of LA to ALA, while a Δ17 desaturase is responsible for the conversion of ARA to EPA (although some Δ17 desaturases can also use DGLA) as a substrate to produce eicosatetraenoic acid (ETA; 20:4 ω-3)). Both of these enzymes have a role in the Δ6 desaturase/Δ6 elongase pathway (which is predominantly found in algae, mosses, fungi, nematodes and humans and which is characterized by the production of GLA and/or stearidonic acid (STA; 18:4 ω-3)) and the Δ9 elongase/Δ8 desaturase pathway (which operates in some organisms, such as euglenoid species and which is characterized by the production of eicosadienoic acid (EDA; 20:2 ω-6) and/or eicosatrienoic acid (ETrA; 20:3 ω-3)) (FIG. 1).

Because of the role Δ17 desaturase enzymes play in enabling the synthesis of ω-3 fatty acids, there has been considerable effort to identify and characterize these enzymes from various sources. However, only a few Δ17 desaturases are presently known and these have been isolated from only two different taxonomic genera. Specifically, Patent Publication No. US 2003/0190733 describes a Δ17 desaturase from *Saprolegnia diclina* (see also GenBank Accession No. AY373823). PCT Publication No. WO 2005/083053 describes a *Phytophthora infestans* "ω3 desaturase" (see also GenBank Accession No. CAJ30870), while PCT Publication No. WO 2006/100241 describes a *Phytophthora sojae* "ω3 desaturase", both of which appear to function as Δ17 desaturases. Also, commonly owned, co-pending application having U.S. patent application Ser. No. 11/787,772 (filed Apr. 18, 2007) discloses nucleic acid and amino acid sequences for Δ17 desaturases from *Phytophthora sojae* and *Phytophthora ramorum*. Thus, there is need for the identification and isolation of additional genes encoding Δ17 desaturases that will be suitable for heterologous expression in a variety of host organisms for use in the production of ω-3 fatty acids.

Applicants have solved the stated problem by isolating the gene encoding Δ17 desaturase from the oomycete, *Pythium aphanidermatum.*

SUMMARY OF THE INVENTION

The present invention relates to new genetic constructs encoding polypeptides having Δ17 desaturase activity, and their use in plants, bacteria, algae, fungi and yeast for the production of PUFAs and particularly ω-3 fatty acids.

Accordingly, the invention provides an isolated nucleic acid molecule selected from the group consisting of:

a.) an isolated nucleotide molecule encoding a Δ17 desaturase enzyme, selected from the group consisting of SEQ ID NO:2 and SEQ ID NO:3;

b.) an isolated nucleotide molecule that hybridizes with (a) under the following hybridization conditions: 0.1×SSC, 0.1% SDS, 65° C. and washed with 2×SSC, 0.1% SDS followed by 0.1×SSC, 0.1% SDS; or, an isolated nucleotide molecule that is completely complementary to (a) or (b).

In another embodiment the invention provides isolated nucleic acid molecules encoding Δ17 desaturase enzyme, selected from the group consisting of SEQ ID NO:1 and 4 or isolated nucleic acid molecules which encoding Δ17 desaturase enzyme as set forth in SEQ ID NO:2, wherein at least 175 codons are codon-optimized for expression in *Yarrowia.* Additionally the invention provides an isolated nucleic acid molecule comprising a first nucleotide sequence encoding a Δ17 desaturase enzyme of at least 359 amino acids that has at least 75.3% identity based on Clustal W algorithms when compared to a polypeptide having the sequence as set forth in SEQ ID NO:2;

or a second nucleotide sequence comprising the complement of the first nucleotide sequence.

In other embodiments the invention provides chimeric genes comprising the isolated nucleic acid molecules of the invention and transformed hosts comprising the same.

In another embodiment the invention provides a method for the production of eicosapentaenoic acid comprising:

a.) providing a host cell comprising:

(i) an isolated nucleotide molecule encoding a bifunctional Δ17/Δ15 desaturase polypeptide having at least 75.3% identity when compared to a polypeptide having the amino acid sequence as set forth in SEQ ID NO:2, based on the Clustal W method of alignment; and, (ii) a source of arachidonic acid;

b.) growing the host cell of step (a) under conditions wherein the nucleic acid molecule encoding the a bifunctional Δ17/Δ15 desaturase polypeptide is expressed and the arachidonic acid is converted to eicosapentaenoic acid; and, c.) optionally recovering the eicosapentaenoic acid of step (b).

Similarly the invention provides A method for the production of eicosatetraenoic acid comprising:

a.) providing a host cell comprising:

(i) an isolated nucleotide molecule encoding a bifunctional Δ17/Δ15 desaturase polypeptide having at least 75.3% identity when compared to a polypeptide having the amino acid sequence as set forth in SEQ ID NO:2, based on the Clustal W method of alignment; and, (ii) a source of dihomo-γ-linolenic acid;

b.) growing the host cell of step (a) under conditions wherein the nucleic acid molecule encoding the a bifunctional Δ17/Δ15 desaturase polypeptide is expressed and the dihomo-γ-linolenic acid is converted to eicosatetraenoic acid; and, c.) optionally recovering the eicosatetraenoic acid of step (c).

Alternatively the invention provides A method for the production of polyunsaturated fatty acids comprising:

a) providing a host cell comprising:

i) an isolated nucleotide molecule encoding a bifunctional Δ17/Δ15 desaturase polypeptide having at least 75.3% identity when compared to a polypeptide having the amino acid sequence as set forth in SEQ ID NO:2, based on the Clustal W method of alignment; and, ii) a source of fatty acid selected from the group consisting of: linoleic acid and eicosadienoic acid;

b) growing the host cell of step (a) under conditions wherein the nucleic acid molecule encoding the bifunctional Δ17/Δ15 desaturase polypeptide is expressed and the linoleic acid is converted to α-linolenic acid and the eicosadienoic acid is converted to eicosatrienoic acid; and, c) optionally recovering the fatty acid of step (b).

In another embodiment the invention provides an isolated nucleic acid fragment comprising a nucleic acid sequence encoding a Δ17 desaturase polypeptide comprising at least one amino acid sequence motifs selected from the group consisting of:

a) F T X G H D X G H (SEQ ID NO:96);

b) H R H HH K N T G (SEQ ID NO:97); and, c) I G T H Q X HH L F P (SEQ ID NO:98);

wherein X can be any amino acid, and wherein the Δ17 desaturase polypeptide does not have the amino acid sequence as set forth in SEQ ID NOs:43 and 95.

Alternatively the invention provides a Δ17 desaturase polypeptide comprising at least one amino acid motif selected from the group consisting of SEQ ID NO:96-98.

In other embodiments the invention provides methods for the identification and isolation of a Δ17 desaturase polypeptide comprising:

a) probing a genomic library with:

i) an isolated nucleic acid fragment encoding an amino acid sequence selected from the group consisting of SEQ ID NO:96-98; or, ii) an isolated nucleic acid fragment that is complementary to (i);

b) identifying a DNA clone that hybridizes with the nucleic acid fragment of step (a); and, c) sequencing the genomic fragment that comprises the clone identified in step (b);

wherein the sequenced genomic fragment encodes a Δ17 desaturase polypeptide, or alternatively, a) synthesizing at least one oligonucleotide primer corresponding to a portion of an isolated nucleic acid sequence encoding an amino acid motif selected from the group consisting of SEQ ID NOs 96-98; and, b) amplifying an insert present in a cloning vector using the oligonucleotide primer of step (a);

wherein the amplified insert encodes a portion of an amino acid sequence encoding a Δ17 desaturase enzyme.

Biological Deposits

The following biological material has been deposited with the American Type Culture Collection (ATCC), 10801 University Boulevard, Manassas, Va. 20110-2209, and bears the following designation, accession number and date of deposit.

| Biological Material | Accession No. | Date of Deposit |
|---|---|---|
| *Yarrowia lipolytica* Y2047 | ATCC PTA-7186 | Oct. 26, 2005 |

The biological material listed above was deposited under the terms of the Budapest Treaty on the International Recognition of the Deposit of Microorganisms for the Purposes of Patent Procedure. The listed deposit will be maintained in the indicated international depository for at least 30 years and will be made available to the public upon the grant of a patent disclosing it. The availability of a deposit does not constitute a license to practice the subject invention in derogation of patent rights granted by government action.

BRIEF DESCRIPTION OF THE DRAWINGS AND SEQUENCE LISTINGS

FIG. 2 shows a pairwise alignment of the amino acid sequences of the *Phytophthora sojae* Δ17 desaturase (SEQ ID NO:45) and the *Phytophthora ramorum* Δ17 desaturase (SEQ ID NO:47), created using default parameters of Vector NTI®'s AlignX program (Invitrogen Corporation, Carlsbad, Calif.).

FIG. 3 provides plasmid maps for the following: (A) pKUNFmkF2; (B) pDMW287F; (C) pDMW214; and, (D) pFmD8S.

Figure 4:
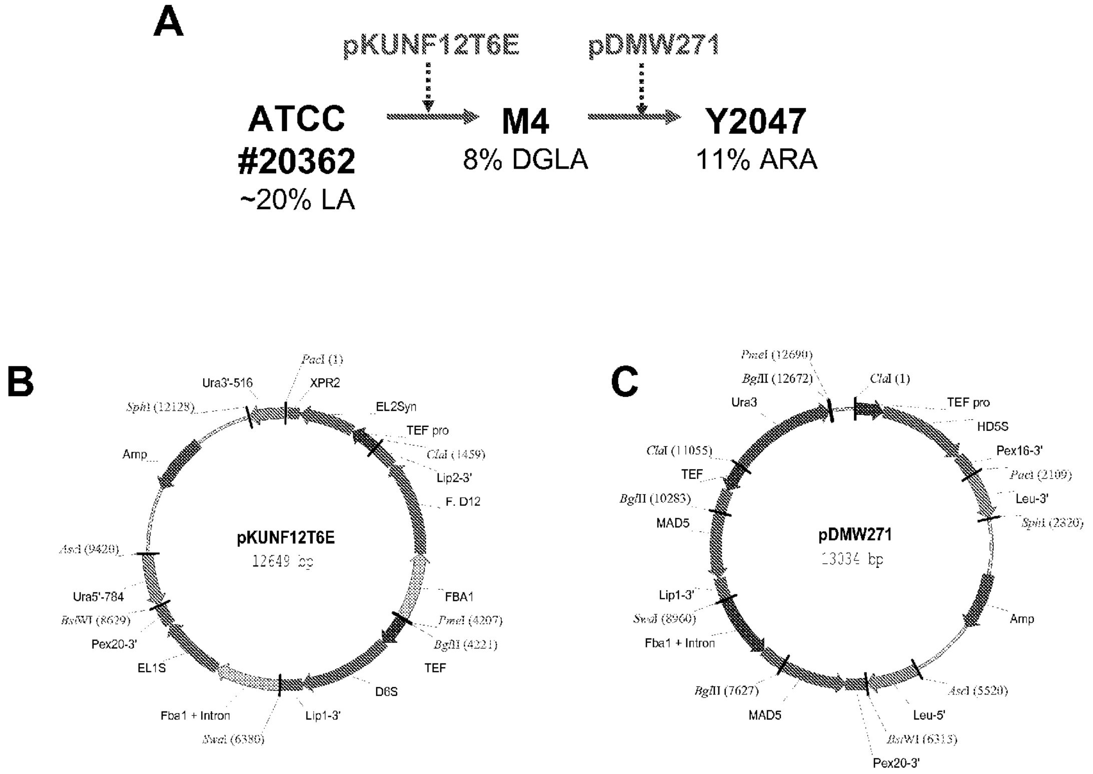

FIG. 4A diagrams the development of *Yarrowia lipolytica* strain Y2047, producing 11% ARA in the total lipid fraction. FIG. 4B provides a plasmid map for pKUNF12T6E, while FIG. 4C provides a plasmid map for pDMW271.

FIGS. 5A and 5B show a comparison of the DNA sequence of the *Phytophthora aphanidermatum* Δ17 desaturase gene (designated as "PaD 7"; SEQ ID NO:1) and the synthetic gene (designated as "PaD17S"; SEQ ID NO:4) codon-optimized for expression in *Yarrowia lipolytica.*

Figure 6:
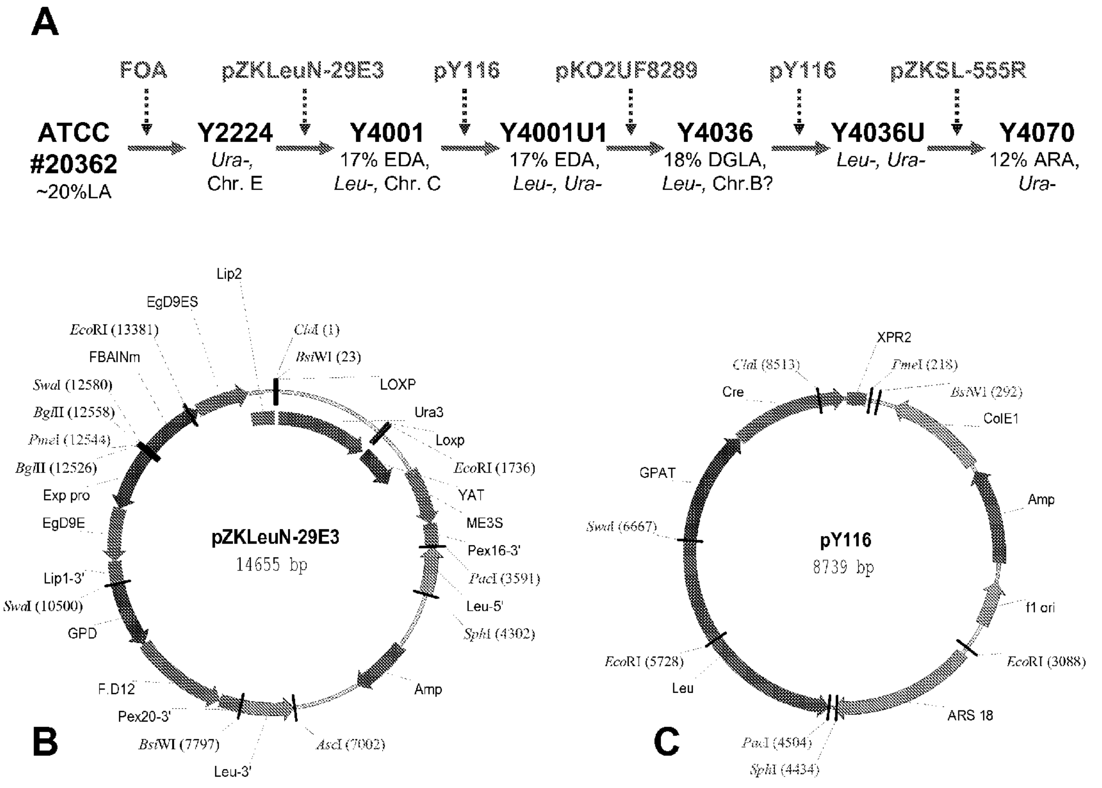

FIG. 6A diagrams the development of *Yarrowia lipolytica* strain Y4070, producing 12% ARA in the total lipid fraction. FIG. 6B provides a plasmid map for pZKLeuN-29E3, while FIG. 6C provides a plasmid map for pY116.

Figure 7:
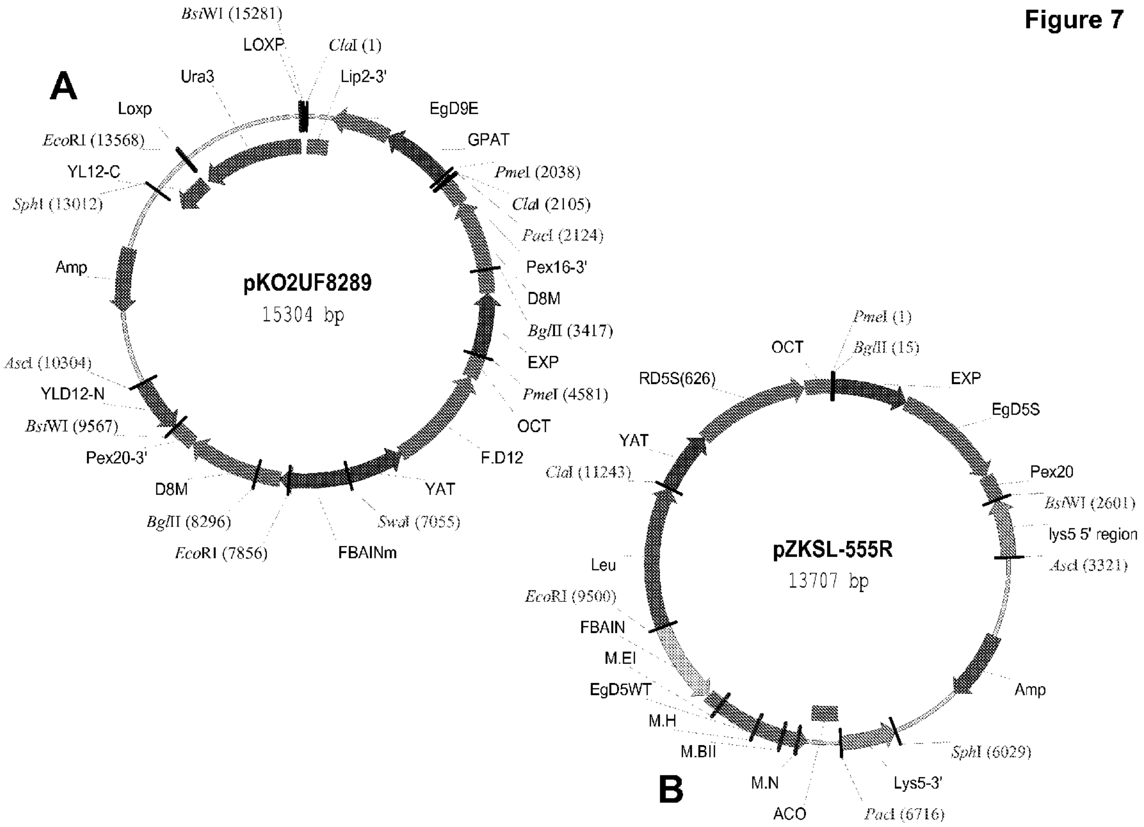

FIG. 7 provides plasmid maps for the following: (A) pKO2UF8289; and, (B) pZKSL-555R.

Figure 8:
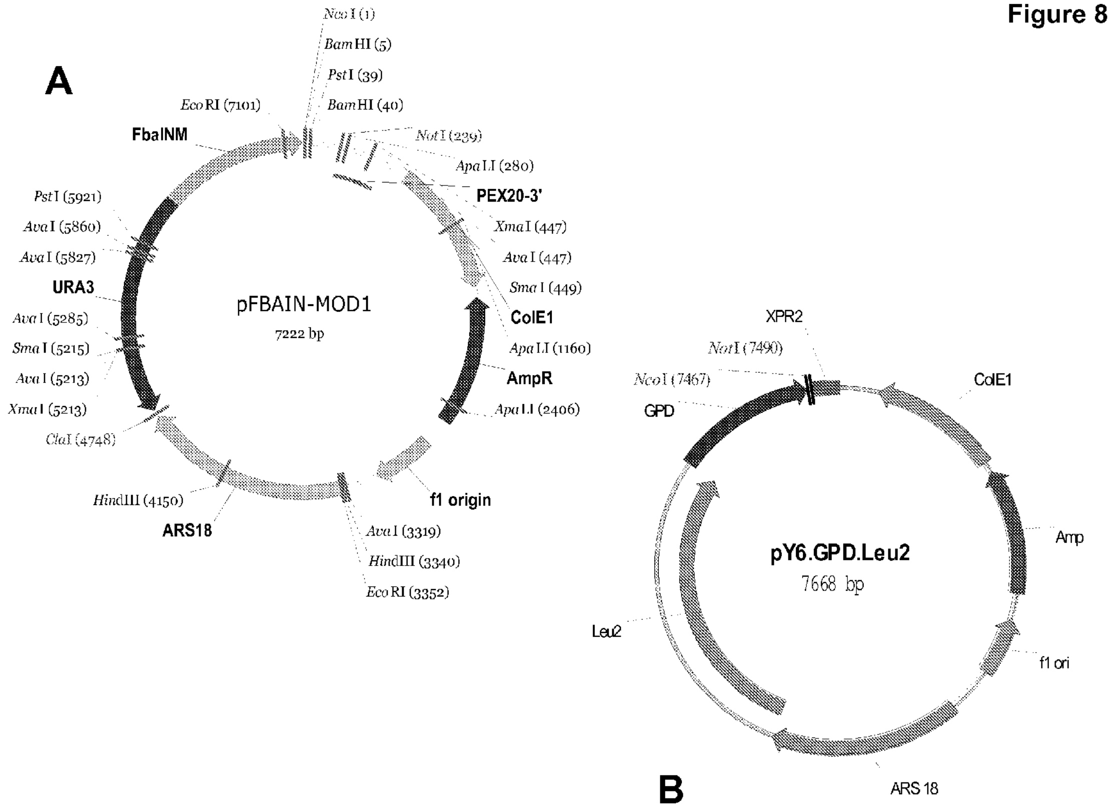

FIG. 8 provides plasmid maps for the following: (A) pFBAIN-MOD-1; and, (B) pY6.GPD.Leu2.

Figure 9:
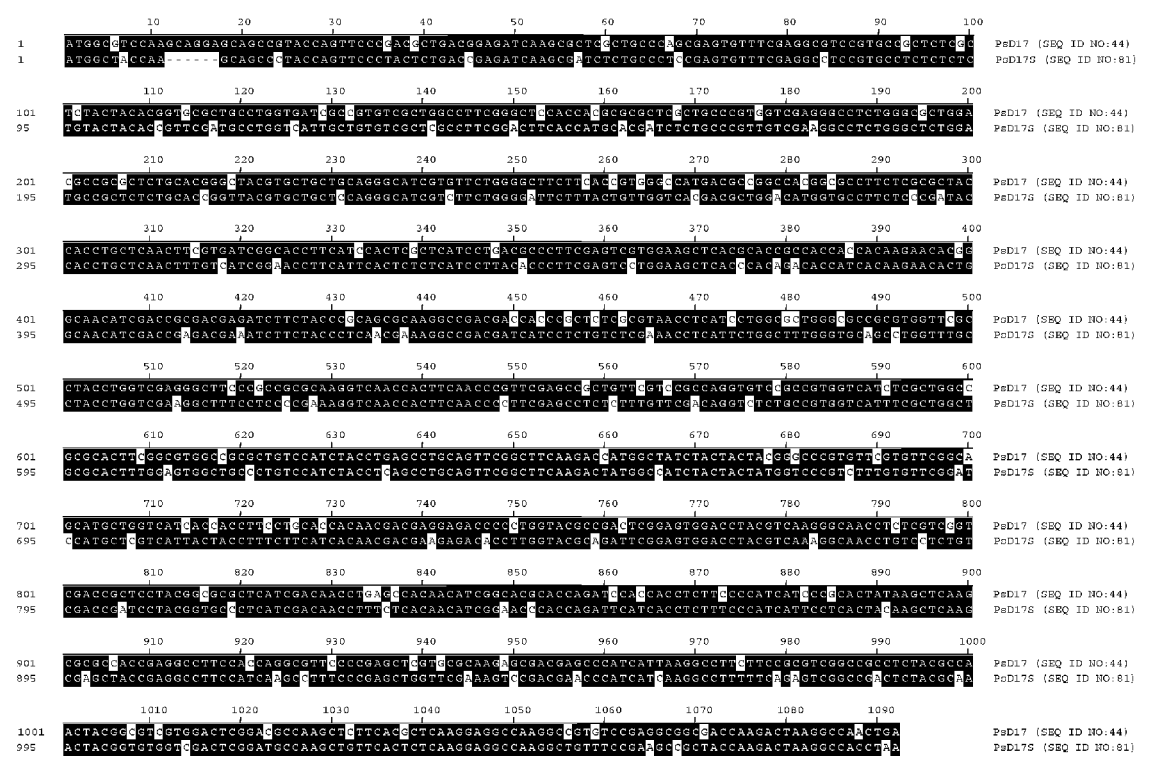

FIG. 9 shows a comparison of the DNA sequence of the *Phytophthora sojae* Δ17 desaturase gene (designated as "PsD17"; SEQ ID NO:44) and the synthetic gene (designated as "PsD17S"; SEQ ID NO:81) codon-optimized for expression in *Y. lipolytica.*

FIG. 10 shows a comparison of the DNA sequence of the *Phytophthora ramorum* Δ17 desaturase gene (designated as "PrD17"; SEQ ID NO:46) and the synthetic gene (designated as "PrD17S"; SEQ ID NO:84) codon-optimized for expression in *Y. lipolytica.*

Figure 11:
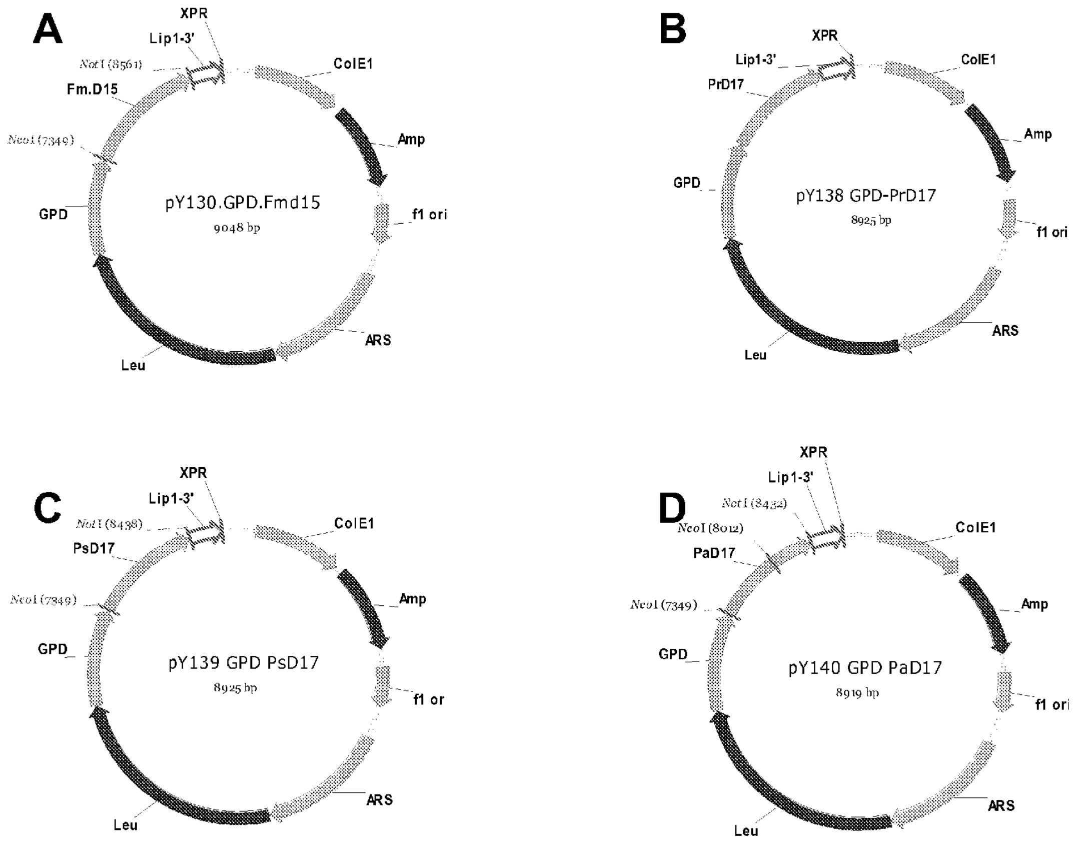

FIG. 11 provides plasmid maps for the following: (A) pY130; (B) pY138; (C) pY139; and, (D) pY140.

Figure 12:
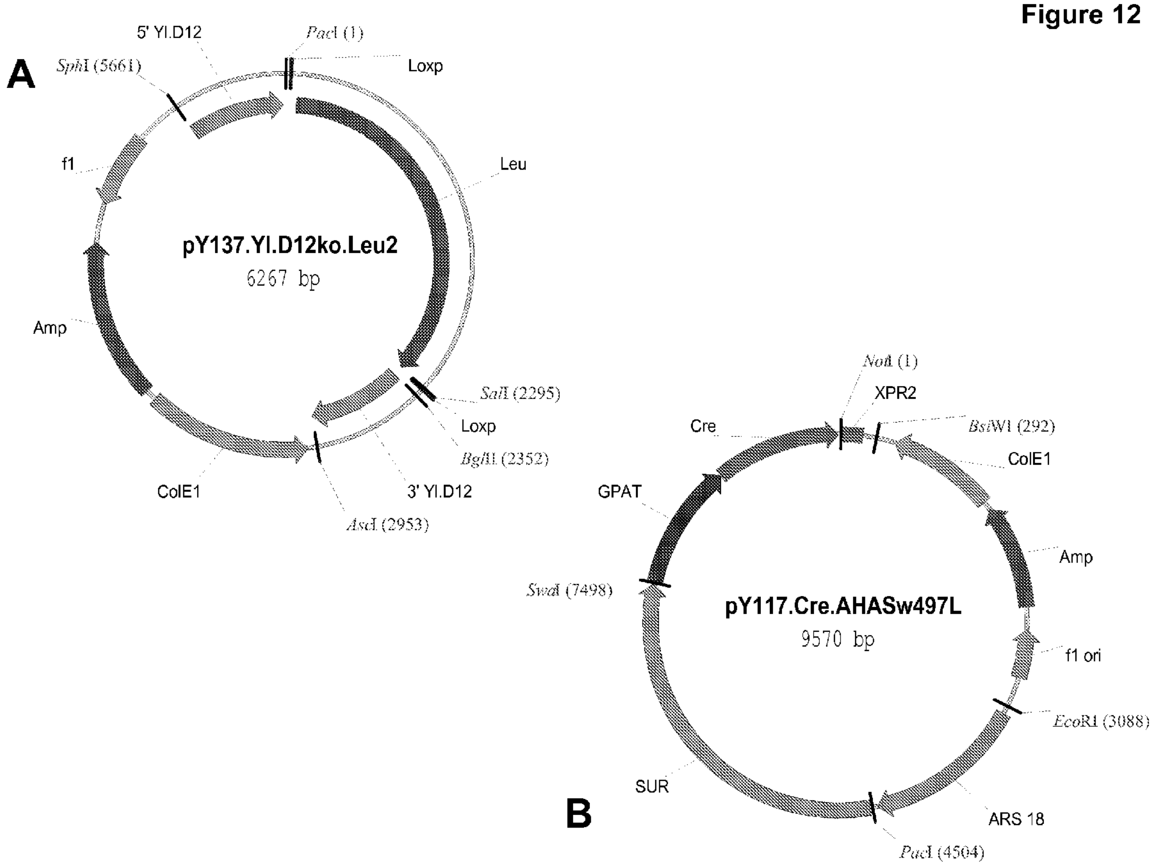

FIG. 12 provides plasmid maps for the following: (A) pY137; and, (B) pY117.

Figure 13:
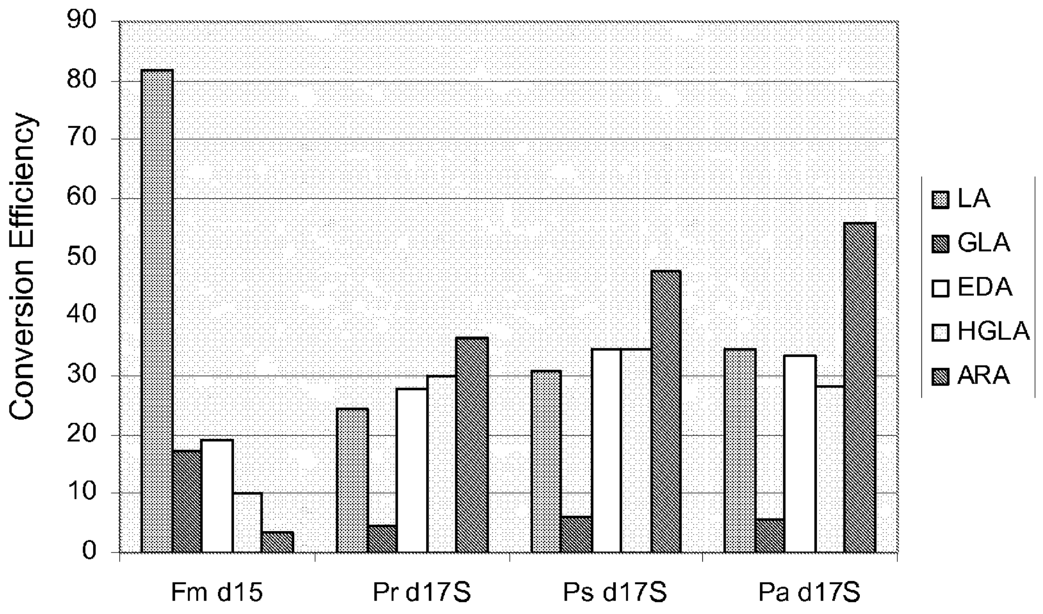

FIG. 13 is a graph showing the ω-6 fatty acid substrate specificity of the following ω-3 desaturases: *Fusarium moniliforme* Δ15 desaturase (FmD15; SEQ ID NOs:86 and 87); a synthetic Δ17 desaturase derived from *Phytopthora ramorum*, codon-optimized for expression in *Yarrowia lipolytica* (PrD17S; SEQ ID NOs:84 and 47); a synthetic Δ17 desaturase derived from *Phytopthora sojae*, codon-optimized for expression in *Yarrowia lipolytica* (PsD17S; SEQ ID NOs: 81 and 82); and the synthetic Δ17 desaturase derived from *Pythium aphanidermatum*, codon-optimized for expression in *Yarrowia lipolytica* (PaD17S; SEQ ID NOs:4 and 2).

Figure 14:
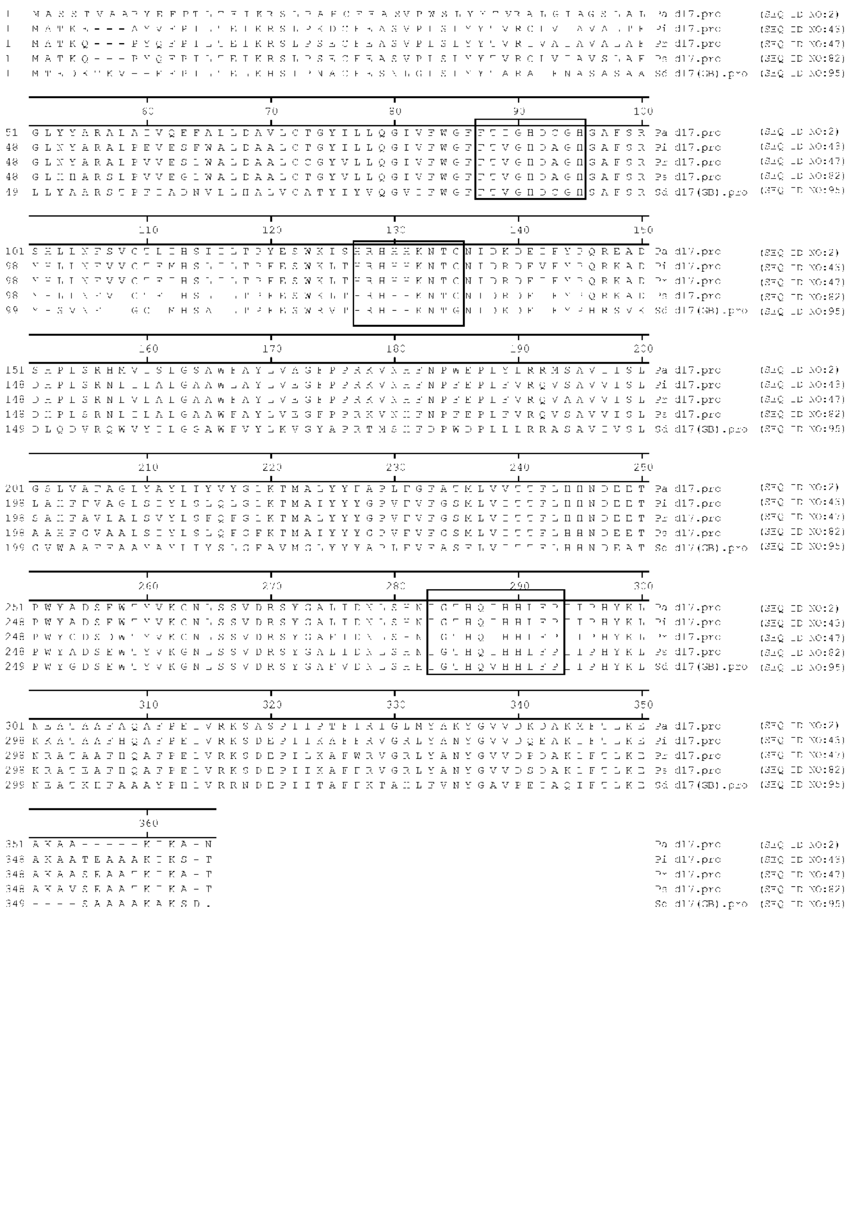

FIG. 14 shows a Clustal V alignment (with default parameters) of the of the following ω-3 desaturases: *Phytophthora infestans* Δ17 desaturase (PiD17; SEQ ID NO:43); *Phytopthora ramorum* Δ17 desaturase (PrD17; SEQ ID NO:47); synthetic Δ17 desaturase derived from *Phytopthora sojae*, codon-optimized for expression in *Yarrowia lipolytica* (PsD17S; SEQ ID NO:82); *Saprolegnia diclina* Δ17 desaturase, (SdD17; SEQ ID NO:95); and the *Pythium aphanidermatum* Δ17 desaturase of the instant invention (PaD17S; SEQ ID NO:2). Sequence regions shown in boxes correspond to delta-17 motifs #1, #2 and #3, respectively. The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37C.F.R. §1.822.

SEQ ID NOs:1-8, 42-53, 56-95 and 102 are ORFs encoding genes or proteins or plasmids, as identified in Table 1.

TABLE 1

Summary Of Gene And Protein SEQ ID Numbers

| Description and Abbreviation | Nucleic acid SEQ ID NO. | Protein SEQ ID NO. |
|---|---|---|
| *Pythium aphanidermatum* Δ17 desaturase ("PaD17") | 1 (1080 bp) | 2 (359 AA) |
| *Pythium aphanidermatum* Δ17 desaturase ("PaD17*") | — | 3 (359 AA) |
| Synthetic Δ17 desaturase derived from *Pythium aphanidermatum*, codon-optimized for expression in *Yarrowia lipolytica* ("PaD17S") | 4 (1080 bp) | 2 (359 AA) |
| *Pythium aphanidermatum* PaD17-internal cDNA fragment | 5 (614 bp) | — |
| *Pythium aphanidermatum* PaD17-5' genomic fragment | 6 (739 bp) | — |
| *Pythium aphanidermatum* PaD17-3' cDNA fragment | 7 (512 bp) | — |
| *Pythium aphanidermatum* PaD17 contig-coding sequence corresponds to nucleotides 388-1467 | 8 (1533 bp) | — |
| *Phytophthora infestans* Δ17 desaturase ("PiD17") (GenBank Accession No. CAJ30870) | 42 (1085 bp) | 43 (361 AA) |
| *Phytophthora sojae* Δ17 desaturase ("PsD17") (U.S. patent application Ser. No. 11/787,772) | 44 (1092 bp) | 45 (363 AA) |
| *Phytophthora ramorum* Δ17 desaturase ("PrD17") (U.S. patent application Ser. No. 11/787,772) | 46 (1086 bp) | 47 (361 AA) |
| Plasmid pKUNFmkF2 | 48 (7145 bp) | — |
| Plasmid pDMW287F | 49 (5473 bp) | — |
| Plasmid pDMW214 | 50 (9513 bp) | — |
| Plasmid pFmD8S | 51 (8910 bp) | — |
| Synthetic Δ8 desaturase, derived from *Euglena gracilis*, codon-optimized for expression in *Yarrowia lipolytica* ("EgD8S") (equivalent to SEQ ID NOs: 112 and 113 in PCT Publication No. WO 2006/012326) | 52 (1272 bp) | 53 (422 AA) |
| Plasmid pKUNF12T6E | 56 (12,649 bp) | — |
| Synthetic $C_{18/20}$ elongase derived from *Thraustochytrium aureum* (U.S. Pat. No. 6,677,145), codon-optimized for expression in *Yarrowia lipolytica* ("EL2S") | 57 (819 bp) | 58 (272 AA) |
| Plasmid pDMW271 | 59 (13,034 bp) | — |
| Synthetic Δ5 desaturase derived from *Homo sapiens* (GenBank Accession No. NP_037534), codon-optimized for expression in *Yarrowia lipolytica* | 60 (1335 bp) | 61 (444 AA) |
| Plasmid pPaD17S | 62 (3800 bp) | — |
| Plasmid pZKLeuN-29E3 | 63 (14,655 bp) | — |
| Synthetic Δ9 elongase derived from *Euglena gracilis* (U.S. patent applications Ser. No. 11/601,563 and Ser. No. 11/601,564), codon-optimized for expression in *Yarrowia lipolytica* ("EgD9eS") | 64 (777 bp) | 65 (258 AA) |
| *Escherichia coli* LoxP recombination site, recognized by a Cre recombinase enzyme | 66 (34 bp) | — |
| Synthetic $C_{16/18}$ elongase derived from *Mortierella alpina* ELO3 (U.S. patent application Ser. No. 11/253,882), codon-optimized for expression in *Yarrowia lipolytica* ("ME3S") | 67 (828 bp) | 68 (275 AA) |
| Plasmid pY116 | 69 (8739 bp) | — |
| Plasmid pKO2UF8289 | 70 (15,304 bp) | — |
| Synthetic mutant Δ8 desaturase ("EgD8S- | 71 | 72 |

TABLE 1-continued

Summary Of Gene And Protein SEQ ID Numbers

| Description and Abbreviation | Nucleic acid SEQ ID NO. | Protein SEQ ID NO. |
|---|---|---|
| 23"; U.S. patent application Ser. No. 11/635,258), derived from *Euglena gracilis* ("EgD8S"; PCT Publication No. WO 2006/012326) | (1272 bp) | (422 AA) |
| *Euglena gracilis* Δ9 elongase (U.S. patent applications Ser. No. 11/601563 and Ser. No. 11/601,564) ("EgD9e") | 73 (777 bp) | 65 (258 AA) |
| Plasmid pZKSL-555R | 74 (13,707 bp) | — |
| Synthetic Δ5 desaturase derived from *Euglena gracilis* (U.S. patent application Ser. No. 11/748,629), codon-optimized for expression in *Yarrowia lipolytica* ("EgD5S") | 75 (1350 bp) | 76 (449 AA) |
| Synthetic Δ5 desaturase derived from *Peridinium* sp. CCMP626 (U.S. patent application Ser. No. 11/748,637), codon-optimized for expression in *Yarrowia lipolytica* ("RD5S") | 77 (1392 bp) | 78 (463 AA) |
| *Euglena gracilis* Δ5 desaturase (U.S. patent application Ser. No. 11/748,629) ("EgD5") | 79 (1350 bp) | 76 (449 AA) |
| Plasmid pFBAIN-MOD-1 | 80 (7222 bp) | — |
| Synthetic Δ17 desaturase derived from *Phytophthora sojae*, codon-optimized for expression in *Yarrowia lipolytica* (U.S. patent application Ser. No. 11/787,772) ("PsD17S") | 81 (1086 bp) | 82 (361 AA) |
| Plasmid pPsD17S | 83 (3806 bp) | — |
| Synthetic Δ17 desaturase derived from *Phytophthora ramorum*, codon-optimized for expression in *Yarrowia lipolytica* (U.S. patent application Ser. No. 11/787,772) ("PrD17S") | 84 (1086 bp) | 47 (361 AA) |
| Plasmid pPrD17S | 85 (3806 bp) | — |
| *Fusarium moniliforme* (*Gibberella fujikuroi*) Δ15 desaturase (PCT Publication No. WO 2005/047480; GenBank Accession No. DQ272516.1) | 86 (1209 bp) | 87 (402 AA) |
| Plasmid pY6.GPD.Leu2 | 88 (7668 bp) | — |
| Plasmid pY130 | 89 (9048 bp) | — |
| Plasmid pY138 | 90 (8925 bp) | — |
| Plasmid pY139 | 91 (8925 bp) | — |
| Plasmid pY140 | 92 (8919 bp) | — |
| Plasmid pY137 | 93 (6267 bp) | — |
| Plasmid pY117 | 94 (9570 bp) | — |
| *Saprolegnia diclina* Δ17 desaturase (GenBank Accession No. AAR20444) | — | 95 (358 AA) |
| Plasmid pFBAINPaD17S | 102 (8067 bp) | — |

SEQ ID NOs:9-11 correspond to SMART™ IV oligonucleotide primer, CDSIII/3' PCR primer and 5'-PCR primer, respectively, used for *Pythium aphanidermatum* cDNA synthesis.

SEQ ID NO:12 corresponds to degenerate oligonucleotide primer PD17-F1, which encodes the peptide set forth in SEQ ID NO:13.

SEQ ID NOs:14 and 15 correspond to degenerate oligonucleotide primers PD17-F2 and PD17-F3, respectively, both of which encode the peptide set forth in SEQ ID NO:16.

SEQ ID NOs:17 and 18 correspond to degenerate oligonucleotide primers PD17-F4 and PD17-F5, respectively, both of which encode the peptide set forth in SEQ ID NO:19.

SEQ ID NOs:20 and 21 correspond to degenerate oligonucleotide primers PD17-F6 and PD17-F7, respectively, both of which encode the peptide set forth in SEQ ID NO:22.

SEQ ID NOs:23 and 24 correspond to degenerate oligonucleotide primers PD17-R1 and PD17-R2, respectively, both of which encode the peptide set forth in SEQ ID NO:25.

SEQ ID NOs:26 and 27 correspond to degenerate oligonucleotide primers PD17-R3 and PD17-R4, respectively, both of which encode the peptide set forth in SEQ ID NO:28.

SEQ ID NOs:29 and 30 correspond to degenerate oligonucleotide primers PD17-R5 and PD17-R6, respectively, both of which encode the peptide set forth in SEQ ID NO:31.

SEQ ID NO:32 corresponds to degenerate oligonucleotide primer PD17-R7, which encodes the peptide set forth in SEQ ID NO:33.

SEQ ID NOs:34 and 35 correspond to the Universal GenomeWalker™ adaptor.

SEQ ID NOs:36, 37, 38 and 39 correspond to primers PUD17-5-1, Universal GenomeWalker™ primer AP1, PUD17-5-3 and Universal GenomeWalker™ primer AP2, respectively, used for PCR amplification of the 5'-end of genomic DNA encoding the *Pythium aphanidermatum* Δ17 desaturase.

SEQ ID NOs:40 and 41 correspond to primers PUD17-3-1 and PUD17-3-2, respectively, used for PCR amplification of the 3'-end of cDNA encoding the *Pythium aphanidermatum* Δ17 desaturase.

SEQ ID NOs:54 and 55 correspond to primers PUD17-F and PUD17-R, respectively, used for amplification of the full length cDNA encoding the *Pythium aphanidermatum* Δ17 desaturase.

SEQ ID NOs:96-98 correspond to Δ17 desaturase motif #1, Δ17 desaturase motif #2 and Δ17 desaturase motif #3, respectively.

SEQ ID NOs:99-101 correspond to His-rich motifs that are featured in membrane-bound fatty acid desaturases belonging to a super-family of membrane di-iron proteins.

DETAILED DESCRIPTION OF THE INVENTION

All patents, patent applications, and publications cited herein are incorporated by reference in their entirety. This specifically includes the following Applicants' Assignee's co-pending applications: U.S. Pat. Nos. 7,125,672, 7,189,559, 7,192,762, 7,198,937, 7,202,356, U.S. patent application Ser. Nos. 10/840,579 and 10/840,325 (filed May 6, 2004), U.S. patent application Ser. No. 10/869,630 (filed Jun. 16, 2004), U.S. patent application Ser. No. 10/882,760 (filed Jul. 1, 2004), U.S. patent applications Ser. Nos. 10/985,254 and 10/985,691 (filed Nov. 10, 2004), U.S. patent application Ser. No. 11/024,544 (filed Dec. 29, 2004), U.S. patent application Ser. No. 11/166,993 (filed Jun. 24, 2005), U.S. patent application Ser. No. 11/183,664 (filed Jul. 18, 2005), U.S. patent application Ser. No. 11/185,301 (filed Jul. 20, 2005), U.S. patent application Ser. No. 11/190,750 (filed Jul. 27, 2005), U.S. patent application Ser. No. 11/198,975 (filed Aug. 8, 2005), U.S. patent application Ser. No. 11/225,354 (filed Sep. 13, 2005), U.S. patent application Ser. No. 11/253,882 (filed Oct. 19, 2005), U.S. patent applications Ser. Nos. 11/264,784 and 11/264,737 (filed Nov. 1, 2005), U.S. patent application Ser. No. 11/265,761 (filed Nov. 2, 2005), U.S. Patent Application No. 60/853,563 (filed Oct. 23, 2006), U.S. Patent Application No. 60/855,177 (filed Oct. 30, 2006), U.S. patent applications Ser. Nos. 11/601,563 and 11/601,564

(filed Nov. 16, 2006), U.S. patent application Ser. No. 11/635,258 (filed Dec. 7, 2006), U.S. patent application Ser. No. 11/613,420 (filed Dec. 20, 2006), U.S. Patent Application No. 60/909,790 (filed Apr. 3, 2007), U.S. Patent Application No. 60/910,831 (filed Apr. 10, 2007), U.S. Patent Application No. 60/911,925 (filed Apr. 16, 2007), U.S. patent application Ser. No. 11/787,772 (filed Apr. 18, 2007), U.S. patent application Ser. No. 11/737,772 (filed Apr. 20, 2007), U.S. patent application Ser. No. 11/740,298 (filed Apr. 26, 2007), U.S. Patent Application No. 60/915,733 (filed May 3, 2007) and U.S. patent application Ser. No. 11/748,629 and No. 11/748,637 (filed May 15, 2007).

The invention provides a novel Oomycota Δ17 desaturase enzyme and gene encoding the same that may be used for the manipulation of biochemical pathways for the production of healthful PUFAs.

PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary).

Supplementation of humans or animals with PUFAs produced by recombinant means can result in increased levels of the added PUFAs, as well as their metabolic progeny. For example, treatment with EPA can result not only in increased levels of EPA, but also downstream products of EPA such as eicosanoids (i.e., prostaglandins, leukotrienes, thromboxanes). Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used.

The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

As used herein the term "invention" or "present invention" is intended to refer to all aspects and embodiments of the invention as described in the claims and specification herein and should not be read so as to be limited to any particular embodiment or aspect.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in PCT Publication No. WO 2004/101757.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the specification and each compounds' chemical name.

TABLE 2

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-Linolenic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell. "Microbial oils" or "single cell oils" are those oils naturally produced by microorganisms during their lifespan.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidylethanolamine (PE) fraction and triacylglycerol (TAG or oil) fraction. However, the terms "lipid" and "oil" will be used interchangeably throughout the specification.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publication No. WO 2006/052870). Briefly, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzymes" refer to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase, a Δ9 elongase, a $C_{14/16}$ elongase, a $C_{16/18}$ elongase, a $C_{18/20}$ elongase and/or a $C_{20/22}$ elongase.

Figure 1:
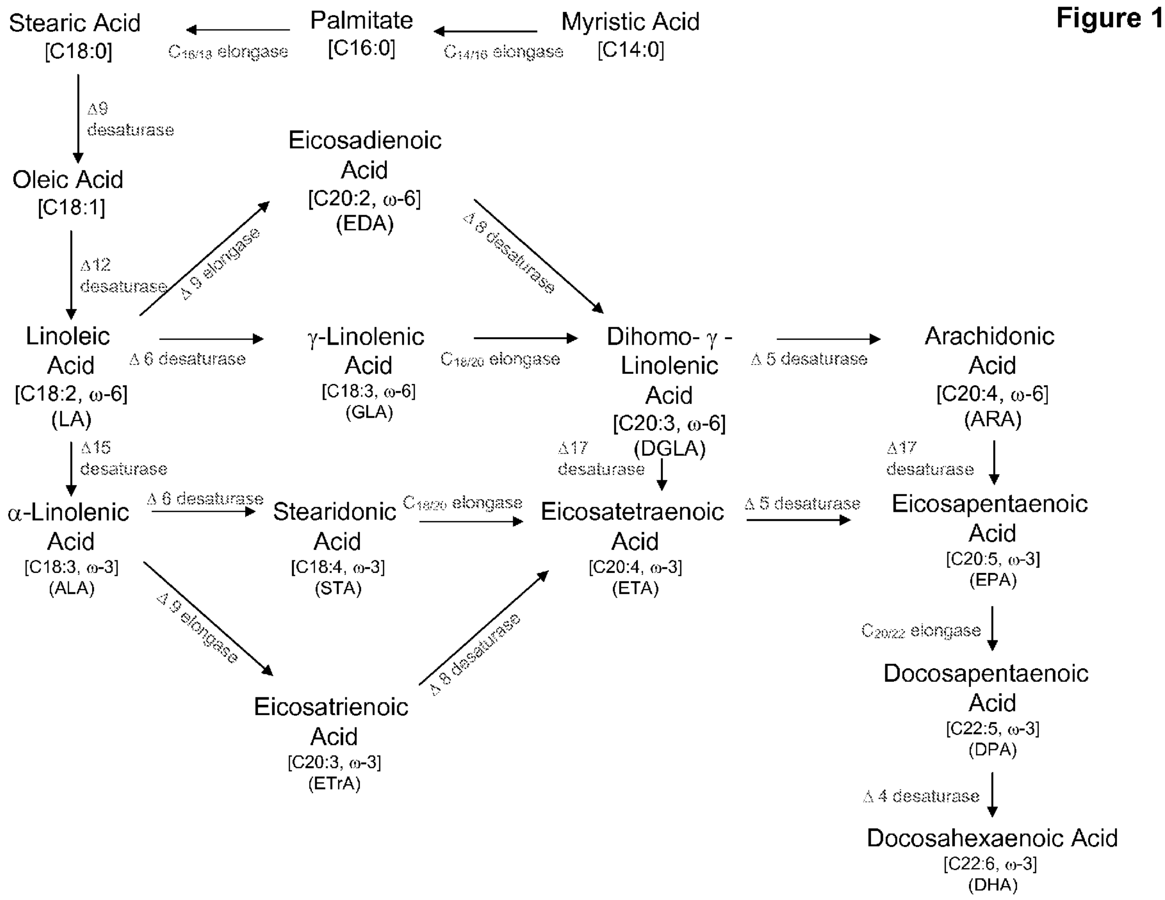
FIG. 1 illustrates the ω-3/ω-6 fatty acid biosynthetic pathway.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of myristic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the ω-3/ω-6 fatty acid biosynthetic pathway means that some (or all) of the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the genes in the above paragraph are required, as a number of fatty acid products will only require the expression of a subset of the genes of this pathway.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of interest herein are: 1.) Δ8 desaturases that will catalyze the conversion of EDA to DGLA and/or ETrA to ETA; 2.) Δ5 desaturases that catalyze the conversion of DGLA to ARA and/or ETA to EPA; 3.) Δ6 desaturases that catalyze the conversion of LA to GLA and/or ALA to STA; 4.) Δ4 desaturases that catalyze the conversion of DPA to DHA; 5.) Δ12 desaturases that catalyze the conversion of oleic acid to LA; 6.) Δ15 desaturases that catalyze the conversion of LA to ALA and/or GLA to STA; and, 7.) Δ9 desaturases that catalyze the conversion of palmitate to palmitoleic acid (16:1) and/or stearate to oleic acid (18:1).

Of particular interest herein are Δ17 desaturases that desaturate a fatty acid between the $17^{th}$ and $18^{th}$ carbon atom numbered from the carboxyl-terminal end of the molecule and which, for example, catalyze the conversion of ARA to EPA (and optionally DGLA to ETA). In the art, Δ17 desaturases (and also Δ15 desaturases) are also occasionally referred to as "omega-3 desaturases", "w-3 desaturases", and/or "(-3 desaturases", based on their ability to convert ω-6 fatty acids into their ω-3 counterparts (e.g., conversion of LA into ALA or DGLA into ETA and ARA into EPA, respectively).

Some desaturases have activity on two or more substrates. Based on this ability, these enzymes can be further classified with respect to their desaturase activities as being either "monofunctional" or "bifunctional". In some embodiments, it is most desirable to empirically determine the specificity of a fatty acid desaturase by transforming a suitable host with the gene for the fatty acid desaturase and determining its effect on the fatty acid profile of the host.

More specifically, Δ17 desaturases are defined herein as those fatty acid desaturases having monofunctional or bifunctional Δ17 desaturase activity, wherein Δ17 desaturase activity is the conversion of ARA to EPA and/or DGLA to ETA. The term "monofunctional Δ17 desaturase", "monofunctional Δ17 desaturase activity" or "exclusive Δ17 desaturase activity" refers to a Δ17 desaturase that is capable of converting ARA to EPA and/or DGLA to ETA but not LA to ALA. In contrast, "bifunctional Δ17 desaturase", "bifunctional Δ17 desaturase activity" or "primary Δ17 desaturase activity" refers to a Δ17 desaturase that preferentially converts ARA to EPA and/or DGLA to ETA but additionally has limited ability to convert LA into ALA (thus exhibiting primarily Δ17 desaturase activity and limited Δ15 desaturase activity).

It should be noted that Δ17 desaturases can have specificities other than Δ17 and Δ15 desaturation that are not relevant in this classification.

For the purposes herein, the term "PaD17" refers to a Δ17 desaturase enzyme (SEQ ID NO:2) isolated from *Pythium aphanidermatum*, encoded by SEQ ID NO:1. Similarly, the term "PaD17*" refers to a Δ17 desaturase enzyme (SEQ ID NO:3) comprising up to (and including) two conservative amino acid mutations (i.e., 155S to P and 351A to T) with respect to SEQ ID NO:2. In contrast, the term "PaD17S" refers to a synthetic Δ17 desaturase derived from *Pythium aphanidermatum* that is codon-optimized for expression in *Yarrowia lipolytica* (i.e., SEQ ID NOs:4 and 2). Based on analyses described herein, PaD17 and PaD17S are further classified as bifunctional Δ17 desaturases.

For the purposes herein, the term "PsD17" refers to a Δ17 desaturase enzyme (SEQ ID NO:45) isolated from *Phytophthora sojae*, encoded by SEQ ID NO:44. In contrast, the term "PsD17S" refers to a synthetic Δ17 desaturase derived from *Phytophthora sojae* that is codon-optimized for expression in *Yarrowia lipolytica* (i.e., SEQ ID NOs:81 and 82). Based on analyses described herein, PsD17 and PsD17S are further classified as bifunctional Δ17 desaturases.

Similarly, the term "PrD17" refers to a Δ17 desaturase enzyme (SEQ ID NO:47) isolated from *Phytophthora ramorum*, encoded by SEQ ID NO:46. In contrast, the term "PrD17S" refers to a synthetic Δ17 desaturase derived from *Phytophthora ramorum* that is codon-optimized for expression in *Yarrowia lipolytica* (i.e., SEQ ID NOs:84 and 47). Previous analyses described in U.S. patent application Ser. No. 11/787,772 classified PrD17 and PrD17S as monofunctional Δ17 desaturases; however, based on analyses described herein, PrD17 and PrD17S are now identified as bifunctional Δ17 desaturases.

Relatedly, the term "PiD17" refers to a Δ17 desaturase enzyme (SEQ ID NO:43) isolated from *Phytophthora infestans*, encoded by SEQ ID NO:42.

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, as described in PCT Publication No. WO 2004/101757. Examples of reactions catalyzed by elongase systems are the conversion of GLA to DGLA, STA to ETA and EPA to DPA. In general, the substrate selectivity of elongases is somewhat broad but segregated by both chain length and the degree and type of unsaturation. For example: a $C_{14/16}$ elongase will utilize a $C_{14}$ substrate (e.g., myristic acid); a $C_{16/18}$ elongase will utilize a $C_{16}$ substrate (e.g., palmitate); a $C_{18/20}$ elongase (also known as a Δ6 elongase as the terms can be used interchangeably) will utilize a $C_{18}$ substrate (e.g., GLA, STA); and, a $C_{20/22}$ elongase will utilize a $C_{20}$ substrate (e.g., EPA). In like manner, a Δ9 elongase is able to catalyze the conversion of LA and ALA to EDA and ETrA, respectively. It is important to note that some elongases have broad specificity and thus a single enzyme may be capable of catalyzing several elongase reactions (e.g., thereby acting as both a $C_{16/18}$ elongase and a $C_{18/20}$ elongase).

The term "oomycetes" refers to a group of heterotrophic organisms generally known as the water molds and downy mildews. They are filamentous protists that must absorb their food from the surrounding water or soil, or may invade the body of another organism to feed. As such, oomycetes play an important role in the decomposition and recycling of decaying matter. Although oomycetes have similarities to fungi through convergent evolution, they are not fungi (as previously thought); instead, the oomycetes are part of the kingdom Stramenopiles and are thereby distinct from plants, fungi and animals. Diatoms and golden-brown and brown algae (e.g., kelp) are also included within kingdom Stramenopiles.

*Pythium* is a genus of the oomycetes, comprising about eighty-five species. *Pythium* species are common pathogens causing disease in plants and fishes. The species of this genus are among the most destructive plant pathogens, inflicting serious economic losses of crops by destroying seed, storage organs, roots and other plant tissues. Members of the genus *Pythium* have been described as "aquatic fungi".

The term "oleaginous" refers to those organisms that tend to store their energy source in the form of lipid (Weete, In: Fungal Lipid Biochemistry, $2^{nd}$ Ed., Plenum, 1980). The term "oleaginous yeast" refers to those microorganisms classified as yeasts that can make oil. Generally, the cellular oil or TAG content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.,* 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces.*

The term "amino acid" will refer to the basic chemical structural unit of a protein or polypeptide. Amino acids are identified by either the one-letter code or the three-letter codes for amino acids, in conformity with the IUPAC-IYUB standards described in *Nucleic Acids Research,* 13:3021-3030 (1985) and in the *Biochemical Journal,* 219(2):345-373 (1984), which are herein incorporated by reference.

The term "conservative amino acid substitution" refers to a substitution of an amino acid residue in a given protein with another amino acid, without altering the chemical or functional nature of that protein. For example, it is well known in the art that alterations in a gene that result in the production of a chemically equivalent amino acid at a given site (but that do not affect the structural and functional properties of the encoded, folded protein) are common. For the purposes of the present invention, "conservative amino acid substitutions" are defined as exchanges within one of the following five groups:

1. Small aliphatic, nonpolar or slightly polar residues: Ala [A], Ser [S], Thr [T] (Pro [P], Gly [G]);
2. Polar, negatively charged residues and their amides: Asp [D], Asn [N], Glu [E], Gln [Q];
3. Polar, positively charged residues: H is [H], Arg [R], Lys [K];
4. Large aliphatic, nonpolar residues: Met [M], Leu [L], Ile [I], Val [V] (Cys [C]); and,
5. Large aromatic residues: Phe [F], Tyr [Y], Trp [W].

Conservative amino acid substitutions generally maintain: 1.) the structure of the polypeptide backbone in the area of the substitution; 2.) the charge or hydrophobicity of the molecule at the target site; or 3.) the bulk of the side chain. Additionally, in many cases, alterations of the N-terminal and C-terminal portions of the protein molecule would also not be expected to alter the activity of the protein.

The term "non-conservative amino acid substitution" refers to an amino acid substitution that is generally expected to produce the greatest change in protein properties. Thus, for example, a non-conservative amino acid substitution would be one whereby: 1.) a hydrophilic residue is substituted for/by a hydrophobic residue (e.g., Ser or Thr for/by Leu, Ile, Val); 2.) a Cys or Pro is substituted for/by any other residue; 3.) a residue having an electropositive side chain is substituted for/by an electronegative residue (e.g., Lys, Arg or H is for/by Asp or Glu); or, 4.) a residue having a bulky side chain is substituted for/by one not having a side chain (e.g., Phe for/by Gly). Sometimes, non-conservative amino acid substitutions between two of the five groups will not affect the activity of the encoded protein.

As used herein, an "isolated nucleic acid fragment" or "isolated nucleic acid molecule" will be used interchangeably and refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.,* 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding a particular oomycete protein. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The terms "homology" and "homologous" are used interchangeably and refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the present nucleotide sequences and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; PCT Publication No. WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragments of the invention. Expression may also refer to translation of mRNA into a polypeptide.

"Mature" protein refers to a post-translationally processed polypeptide, i.e., one from which any pre- or propeptides present in the primary translation product have been removed. "Precursor" protein refers to the primary product of translation of mRNA, i.e., with pre- and propeptides still present. Pre- and propeptides may be (but are not limited to) intracellular localization signals.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for enhanced expression of that gene in a foreign host.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and, 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS,* 5:151-153 (1989); Higgins, D. G. et al., *Comput. Appl. Biosci.,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS,* 5:151-153 (1989); Higgins, D. G. et al., *Comput. Appl. Biosci.,* 8:189-191 (1992)) and found in the MegAlign™ v 6.1 program of the LASERGENE bioinformatics computing suite (DNASTAR Inc.). Default parameters for multiple alignment correspond to GAP PENALTY=10, GAP LENGTH PENALTY=0.2, Delay Divergen Seqs (%)=30, DNA Transition Weight=0.5, Protein Weight Matrix=Gonnet Series and DNA Weight Matrix=IUB. After alignment of the sequences using the Clustal W program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Indeed, any integer amino acid identity from 70% to 100% may be useful in describing the present invention, such as 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and, 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. For the purposes herein, the following Table describes motifs of the present invention which are indicative of a protein having Δ17 desaturase activity.

TABLE 3

Summary Of Δ17 Desaturase Motifs

| Description | Sequence | Protein SEQ ID NO. |
|---|---|---|
| Δ17 Desaturase Motif #1 | F T X G H D X G H | 96 |
| Δ17 Desaturase Motif #2 | H R H H H K N T G | 97 |
| Δ17 Desaturase Motif #3 | I G T H Q X H H L F P | 98 |

The term "H is Box" refers to a histidine box having a motif selected from the group consisting of: $H(X)_3H$ (SEQ ID NO:99), $H(X)_2HH$ (SEQ ID NO:100) and $H/Q(X)_2HH$ (SEQ ID NO:101).

Standard recombinant DNA and molecular cloning techniques used herein are well known in the art and are described by Sambrook, J., Fritsch, E. F. and Maniatis, T., *Molecular*

*Cloning: A Laboratory Manual,* $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

An Overview Microbial Biosynthesis of Fatty Acids and Triacyiglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and, 4.) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to ω-3/ω-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific ω-3/ω-6 fatty acid.

Specifically, all pathways require the initial conversion of oleic acid to LA, the first of the ω-6 fatty acids, by a Δ12 desaturase. Then, using the "Δ6 desaturase/Δ6 elongase pathway", ω-6 fatty acids are formed as follows: (1) LA is converted to GLA by a Δ6 desaturase; (2) GLA is converted to DGLA by a $C_{18/20}$ elongase; and (3) DGLA is converted to ARA by a Δ5 desaturase. Alternatively, the "Δ6 desaturase/Δ6 elongase pathway" can be utilized for formation of ω-3 fatty acids as follows: (1) LA is converted to ALA, the first of the ω-3 fatty acids, by a Δ15 desaturase; (2) ALA is converted to STA by a Δ6 desaturase; (3) STA is converted to ETA by a $C_{18/20}$ elongase; (4) ETA is converted to EPA by a Δ5 desaturase; (5) EPA is converted to DPA by a $C_{20/22}$ elongase; and, (6) DPA is converted to DHA by a Δ4 desaturase. Optionally, ω-6 fatty acids may be converted to ω-3 fatty acids; for example, ETA and EPA are produced from DGLA and ARA, respectively, by Δ17 desaturase activity.

Alternate pathways for the biosynthesis of ω-3/ω-6 fatty acids utilize the Δ9 elongase/Δ8 desaturase biosynthetic pathway. More specifically, LA and ALA may be converted to EDA and ETrA, respectively, by a Δ9 elongase; then, a Δ8 desaturase converts EDA to DGLA and/or ETrA to ETA.

It is contemplated that the particular functionalities required to be expressed in a specific host organism for production of ω-3/ω-6 fatty acids will depend on the host cell (and its native PUFA profile and/or desaturase/elongase profile), the availability of substrate, and the desired end product(s). One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, oomycetes, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; 4.) co-factors required by the polypeptide; and/or, 5.) whether the polypeptide is modified after its production (e.g., by a kinase). The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of un-purified oils produced in a host cell will typically be a mixture of various PUFAs consisting of the desired ω-3/ω-6 fatty acid, as well as various upstream intermediary PUFAs. Thus, consideration of each enzyme's conversion efficiency is also a variable to consider when optimizing biosynthesis of a desired fatty acid.

With each of the considerations above in mind, candidate genes having the appropriate desaturase and elongase activities (e.g., Δ6 desaturases, $C_{18/20}$ elongases, Δ5 desaturases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Identification of a Novel Δ17 Desaturase

In the present invention, a nucleotide sequence has been isolated from *Pythium aphanidermatum* encoding a Δ17 desaturase, designated herein as "PaD17".

Comparison of the PaD17 nucleotide base and deduced amino acid sequences to public databases reveals that the most similar known sequences are about 75.3% identical to the amino acid sequence of PaD17 reported herein over a length of 359 amino acids using the Clustal W method of alignment algorithms. More preferred amino acid fragments are at least about 70%-85% identical to the sequences herein, where those sequences that are at least about 85%-90% identical are particularly suitable and those sequences that are at least about 90%-95% identical are most preferred. Similarly, preferred PaD17 encoding nucleic acid sequences corresponding to the instant Δ17 desaturase ORF are those encoding active proteins and which are at least about 70%-85% identical to the nucleic acid sequences of PaD17 reported herein, where those sequences that are at least about 85%-90% identical are particularly suitable and those sequences that are at least about 90%-95% identical are most preferred.

In alternate embodiments, the instant PaD17 sequence can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., desaturase activity can be synthesized in whole or in part using the codons preferred in the host species.

In one preferred embodiment of the invention, PaD17 was codon-optimized for expression in *Yarrowia lipolytica*. This was possible by first determining the *Y. lipolytica* codon usage profile (see PCT Publication No. WO 04/101757; U.S. Pat. No. 7,125,672) and identifying those codons that were preferred. Further optimization of gene expression in *Y. lipolytica* was achieved by determining the consensus sequence around the 'ATG' initiation codon. This optimization resulted in modification of 188 bp of the 1080 bp coding region (17.4%) and optimization of 175 codons (48.6%). None of the modifications in the codon-optimized gene ("PaD17S"; SEQ ID NO:4) changed the amino acid sequence of the encoded protein (SEQ ID NO:2). As described in Example 10, the codon-optimized gene was more efficient desaturating ARA to EPA than the wildtype gene, when expressed in *Y. lipolytica*.

One skilled in the art would be able to use the teachings herein to create various other codon-optimized Δ17 desaturase proteins suitable for optimal expression in alternate hosts (i.e., other than *Yarrowia lipolytica*), based on the wildtype PaD17 sequence (i.e., SEQ ID NO:2) or a variant thereof as set forth in SEQ ID NO:3. Accordingly, the instant invention relates to any codon-optimized Δ17 desaturase protein that is derived from either SEQ ID NO:2 or SEQ ID NO:3. This includes, but is not limited to, the nucleotide sequence set forth in SEQ ID NO:4, which encodes a synthetic Δ17 desaturase protein (i.e., PaD17S) that was codon-optimized for expression in *Yarrowia lipolytica*.

Upon identification of the Oomycete polypeptide described above, the activity of the wildtype and codon-optimized fatty acid desaturase was determined by transformation into a suitable host (i.e., *Yarrowia lipolytica*) and determination of its effect on the fatty acid profile of the host (Examples 7, 10 and 17). As expected, PaD17 and PaD17S both possessed Δ17 desaturase activity, such that the enzyme was capable of catalyzing conversion of ARA to EPA. Specifically, the ARA to EPA conversion efficiency of PaD17 ranged from 18.4-19.5%, while the ARA to EPA conversion efficiency of PaD17S ranged from 54.1-55.8% (based on determination in two different strains of *Y. lipolytica* and under different growth conditions). Conversion efficiency was measured according to the following formula: ([product]/[substrate+product])*100, where 'product' includes the immediate product and all products in the pathway derived from it.

Unexpectedly, however, PaD17S additionally possessed limited Δ15 desaturase activity (i.e., the LA to ALA conversion efficiency was 34.6%) (Example 17). Thus, the *Pythium aphanidermatum* desaturase is defined herein as a bifunctional Δ17 desaturase.

Further analysis with PaD17S revealed that the enzyme demonstrated broad catalytic promiscuity, based on greater than 25% conversion efficiency using the ω-6 fatty acid substrates EDA and DGLA (Example 17). Thus, the ω-6 fatty acid substrate specificity of PaD17S is similar to that of the synthetic Δ17 desaturase derived from *Phytopthora sojae* and codon-optimized for expression in *Yarrowia lipolytica* (i.e., PsD17S; U.S. patent application Ser. No. 11/787,772 and Example 17 herein) and the synthetic Δ17 desaturase derived from *Phytopthora ramorum* and codon-optimized for expression in *Yarrowia lipolytica* (i.e., PrD17S; U.S. patent application Ser. No. 11/787,772 and Example 17 herein). These results are in contrast to those demonstrated for the related ω-3 desaturase of *Saprolegnia diclina*, which has been reported to function exclusively on C20 ω-6 fatty acid substrates as a monofunctional Δ17 desaturase (Pereira, S. L. et. al., *Biochem. J.,* 378:665 (2004))

In another aspect this invention concerns an isolated nucleic acid fragment comprising a nucleic acid sequence encoding a Δ17 desaturase, excluding SEQ ID NO:43 (i.e., "PiD17", the ω-3 desaturase from *Phytophthora infestans* (GenBank Accession No. CAJ30870)) and SEQ ID NO:95 (i.e., "SdD17", the Δ17 desaturase from *Saprolegnia diclina* (GenBank Accession No. AAR20444)), wherein the amino acid sequence comprising said Δ17 desaturase contains at least one of the following amino acid sequence motifs selected from the group consisting of:

a) F T X G H D X G H (Δ17 Desaturase Motif #1; SEQ ID NO:96);

b) H R H HH K N T G (Δ17 Desaturase Motif #2; SEQ ID NO:97); and, c) I G T H Q X HH L F P (Δ17 Desaturase Motif #3; SEQ ID NO:98);

wherein X can be any amino acid.

The underlined amino acids represent histidine residues that are part of the desaturase H is Box motifs. The H is Box motifs are described as: $H(X)_3H$ (SEQ ID NO:99), $H(X)_2HH$ (SEQ ID NO:100) and $H/Q(X)_2HH$ (SEQ ID NO:101). FIG. 14 sets forth a comparison of the Δ17 desaturase of the present invention with other publicly disclosed Δ17 desaturases using a Clustal V alignment (with default parameters). Specifically, SEQ ID NO:2 (PaD17), SEQ ID NO:43 (PiD17), SEQ ID NO:47 (PrD17), SEQ ID NO:82 (PsD17S) and SEQ ID NO:95 (SdD17) were compared. Regions comprising the motifs of the invention (i.e., Δ17 Desaturase Motif #1, Δ17 Desaturase Motif #2 and Δ17 Desaturase Motif #3, respectively) are shown in boxes.

Identification and Isolation of Homologs

Any of the instant desaturase sequences (i.e., PaD17, PaD17*, PaD17S) or portions thereof (i.e., Δ17 Desaturase Motif #1, Δ17 Desaturase Motif #2 and/or Δ17 Desaturase Motif #3) may be used to search for Δ17 desaturase homologs in the same or other bacterial, algal, fungal, Oomycete or plant species using sequence analysis software. In general, such computer software matches similar sequences by assigning degrees of homology to various substitutions, deletions and other modifications.

Alternatively, any of the instant desaturase sequences or portions thereof may also be employed as hybridization reagents for the identification of Δ17 homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharinic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the Δ17 desaturase nucleic acid fragments described herein (or any homologs identified thereof) may be used to isolate genes encoding homologous proteins from the same or other bacterial, algal, fungal, oomycete or plant species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Natl. Acad. Sci. U.S.A.,* 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to the Δ17 desaturases described herein could be isolated directly by using all or a portion of the instant nucleic acid fragments as DNA hybridization probes to screen libraries from any desired yeast, fungus or oomycete using methodology well known to those skilled in the art (wherein those yeast or fungus producing EPA [or derivatives thereof] would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant desaturase sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *Proc. Natl. Acad. Sci. U.S.A.,* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *Proc. Natl. Acad. Sci. U.S.A.,* 86:5673 (1989); Loh et al., *Science,* 243:217 (1989)).

In other embodiments, any of the Δ17 desaturase nucleic acid fragments described herein (or any homologs identified thereof) may be used for creation of new and improved fatty acid desaturases. As is well known in the art, in vitro mutagenesis and selection, chemical mutagenesis, "gene shuffling" methods or other means can be employed to obtain mutations of naturally occurring desaturase genes. Alternatively, improved fatty acids may be synthesized by domain swapping, wherein a functional domain from any of the Δ17 desaturase nucleic acid fragments described herein are exchanged with a functional domain in an alternate desaturase gene to thereby result in a novel protein.

Methods for Production of Various ω-3 and/or ω-6 Fatty Acids

It is expected that introduction of chimeric genes encoding the Δ17 desaturases described herein (i.e., PaD17, PaD17*, PaD17S or other mutant enzymes, codon-optimized enzymes or homologs thereof), under the control of the appropriate promoters will result in increased production of EPA in the transformed host organism, respectively. As such, the present invention encompasses a method for the direct production of PUFAs comprising exposing a fatty acid substrate (i.e., ARA) to the desaturase enzymes described herein (e.g., PaD17, PaD17*, PaD17S), such that the substrate is converted to the desired fatty acid product (i.e., EPA).

More specifically, it is an object of the present invention to provide a method for the production of EPA in a host cell (e.g., oleaginous yeast), wherein the host cell comprises:

a.) an isolated nucleotide molecule encoding a Δ17 desaturase polypeptide having at least 75.3% identity when compared to a polypeptide having the amino acid sequence as set forth in SEQ ID NO:2, based on the Clustal W method of alignment; and, b) a source of ARA;

c.) growing the host cell of step (a) under conditions wherein the nucleic acid molecule encoding the Δ17 desaturase polypeptide is expressed and the ARA is converted to EPA; and, d.) optionally recovering the EPA of step (c).

The person of skill in the art will recognize that the broad substrate range of the Δ17 desaturase will allow for the use of the enzyme for the conversion of DGLA to ETA. Accordingly, the invention provides a method for the production of ETA in a host cell, wherein the host cell comprises:

a.) an isolated nucleotide molecule encoding a Δ17 desaturase polypeptide having at least 75.3% identity when compared to a polypeptide having the amino acid sequence as set forth in SEQ ID NO:2, based on the Clustal W method of alignment; and, b.) a source of DGLA;

c.) growing the host cell of step (a) under conditions wherein the nucleic acid molecule encoding the Δ17 desaturase polypeptide is expressed and the DGLA is converted to ETA; and, d.) optionally recovering the ETA of step (c).

In an alternate embodiment, based on the biofunctionality of the *Pythium aphanidermatum* Δ17 desaturases, it is an object of the present invention to provide a method for the production of polyunsaturated fatty acids in a host cell (e.g., oleaginous yeast), wherein the host cell comprises:

a.) an isolated nucleotide molecule encoding a bifunctional Δ17 desaturase polypeptide having at least 75.3% identity when compared to a polypeptide having the amino acid sequence as set forth in SEQ ID NO:2, based on the Clustal W method of alignment; and, b.) a source of fatty acid selected from the group consisting of: linoleic acid and eicosadienoic acid;

wherein the host cell is grown under conditions wherein the nucleic acid molecule encoding the bifunctional Δ17 desaturase polypeptide is expressed and the linoleic acid is converted to α-linolenic acid and the eicosadienoic acid is converted to eicosatrienoic acid; and, said fatty acid is then optionally recovered.

Substrate feeding may be required in any of the methods described above.

Alternatively, the Δ17 desaturase gene and its corresponding enzyme product described herein can be used indirectly for the production of ω-3 fatty acids (see PCT Publications No. WO 2004/101757 and No. WO 2006/052870). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the Δ17 desaturases described herein (e.g., PaD17, PaD17*, PaD17S or other mutant enzymes, codon-optimized enzymes or homologs thereof) may be expressed in conjunction with additional genes encoding enzymes of the PUFA biosynthetic pathway (e.g., Δ6 desaturases, $C_{18/20}$ elongases, Δ5 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases, $C_{20/22}$ elongases) to result in higher levels of production of longer-chain ω-3 fatty acids (e.g., EPA, DPA and DHA). The particular genes included within a particular expression cassette will depend on the host cell (and its PUFA profile and/or desaturase/elongase profile), the availability of substrate and the desired end product(s).

In alternative embodiments, it may be useful to disrupt a host organism's native Δ17 desaturase, based on the complete sequences described herein, the complement of those complete sequences, substantial portions of those sequences, codon-optimized desaturases derived therefrom and those sequences that are substantially homologous thereto. For example, the targeted disruption of the Δ17 desaturase (and optionally a Δ15 desaturase) in a host organism produces a mutant strain that has diminished ability to synthesize ω-3 fatty acids. This mutant strain could be useful for the production of "pure" ω-6 fatty acids (without co-synthesis of ω-3 fatty acids).

Expression Systems, Cassettes and Vectors

The genes and gene products of the instant sequences described herein may be expressed in heterologous host cells. Expression in recombinant hosts may be useful for the production of various PUFA pathway intermediates, or for the modulation of PUFA pathways already existing in the host for the synthesis of new products heretofore not possible using the host.

Expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate host cells via transformation to provide high-level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed host cell, although it is to be understood that such control regions need not be derived from the genes native to the specific species chosen as a production host.

Initiation control regions or promoters which are useful to drive expression of the instant Δ17 desaturase ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see PCT Publication No. WO 2006/052870 [Patent Publication US 2006-0115881-A1] for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation and correct folding of the protein in the host organism; 5.) the intrinsic stability of the mRNA and protein of the cloned gene within the host cell; and, 6.) the codon usage within the cloned gene, such that its frequency approaches the frequency of preferred codon usage of the host cell. Each of these types of modifications are encompassed in the present invention, as means to further optimize expression of the Δ17 desaturases described herein.

Transformation of Host Cells

Once the DNA encoding a polypeptide suitable for expression in an appropriate host cell has been obtained, it is placed in a plasmid vector capable of autonomous replication in the host cell, or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology,* 194:186-187 (1991)]), protoplast fusion, biolistic impact, electroporation, microinjection, or any other method that introduces the gene of interest into the host cell.

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by various selection techniques, as described in PCT Publications No. WO 2004/101757, No. WO 2005/003310 and No. WO 2006/052870.

Following transformation, substrates suitable for the instant Δ17 desaturases (and, optionally other PUFA enzymes that are co-expressed within the host cell) may be produced by the host either naturally or transgenically, or they may be provided exogenously.

Metabolic Engineering of ω-3 and/or ω-6 Fatty Acid Biosynthesis

Knowledge of the sequences of the present Δ17 desaturases will be useful for manipulating ω-3 and/or ω-6 fatty acid biosynthesis in various host cells. This may require metabolic engineering directly within the PUFA biosynthetic pathway or additional manipulation of pathways that contribute carbon to the PUFA biosynthetic pathway. Methods useful for up-regulating desirable biochemical pathways and down-regulating undesirable biochemical pathways are well known to those skilled in the art. For example, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA and zinc-finger targeting technologies).

Detailed discussion of manipulations within the PUFA biosynthetic pathway as a means to increase ARA, EPA or DHA (and associated techniques thereof) are presented in PCT Publication No. WO 2006/055322 [Patent Publication No. US 2006-0094092-A1], PCT Publication No. WO 2006/052870 [Patent Publication No. US 2006-0115881-A1] and PCT Publication No. WO 2006/052871 [Patent Publication No. US 2006-0110806-A1], respectively, as are desirable manipulations in the TAG biosynthetic pathway and the TAG degradation pathway (and associated techniques thereof).

Preferred Hosts for Recombinant Expression of Δ17 Desaturases

Host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. Based on the needs of the Applicants' Assignee, the genes described in the instant invention were initially isolated for expression in an oleaginous yeast (and in particular *Yarrowia lipolytica*); however, it is contemplated that because transcription, translation and the protein biosynthetic apparatus are highly conserved, any plant, bacteria, yeast, algae, oomycete and/or filamentous fungus will be a suitable host for expression of the present nucleic acid fragments.

Preferred hosts are oleaginous organisms, such as oleaginous yeast. These oleaginous organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #76982, ATCC #20362, ATCC #8862, ATCC #18944 and/or LGAM S(7)1 (Papanikolaou S., and Aggelis G., *Bioresour. Technol.*, 82(1):43-9 (2002)).

Specific teachings applicable for engineering EPA and DHA in *Y. lipolytica* are provided in U.S. patent application Ser. No. 11/265,761 (PCT Publication No. WO 2006/052870; Patent Publication No. US 2006-0115881-A1) and No. 11/264,737 (PCT Publication No. WO 2006/052871; Patent Publication No. US 2006-0110806-A1), respectively. Detailed means for the synthesis and transformation of expression vectors comprising Δ17 desaturases in oleaginous yeast (i.e., *Yarrowia lipolytica*) are provided in PCT Publications No. WO 2004/101757 and No. WO 2006/052870. The preferred method of expressing genes in this yeast is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene locus (GenBank Accession No. M34929), the Aco2 gene locus (Gen Bank Accession No. AJ001300), the Pox3 gene locus (Pox3: GenBank Accession No. XP_503244; or, Aco3: GenBank Accession No. AJ001301), the Δ12 desaturase gene locus (PCT Publication No. WO 2004/104167), the Lip1 gene locus (GenBank Accession No. Z50020) and/or the Lip2 gene locus (GenBank Accession No. AJ012632)].

Preferred selection methods for use in *Yarrowia lipolytica* are resistance to kanamycin, hygromycin and the amino glycoside G418, as well as ability to grow on media lacking uracil, leucine, lysine, tryptophan or histidine. In alternate embodiments, 5-fluoroorotic acid (5-fluorouracil-6-carboxylic acid monohydrate; "5-FOA") is used for selection of yeast $Ura^-$ mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of $Ura^-$ mutant yeast strains (Bartel, P. L. and Fields, S., Yeast 2-Hybrid System, Oxford University: New York, v. 7, pp 109-147, 1997).

Other preferred microbial hosts include oleaginous bacteria, algae, Oomycetes and other fungi; and, within this broad group of microbial hosts, of particular interest are microorganisms that synthesize ω-3/ω-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present Δ17 desaturase genes under the control of inducible or regulated promoters could yield a transformant organism capable of synthesizing EPA. The method of transformation of *M. alpina* is described by Mackenzie et al. (*Appl. Environ. Microbiol.*, 66:4655 (2000)). Similarly, methods for transformation of Thraustochytriales microorganisms are disclosed in U.S. Pat. No. 7,001,772.

No matter what particular host is selected for expression of the Δ17 desaturases described herein, it is preferable if multiple transformants are screened in order to obtain a strain displaying the desired expression level and pattern. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618 (1-2):133-145 (1993)), Western and/or Elisa analyses of protein expression, phenotypic analysis or GC analysis of the PUFA products.

Fermentation Processes for Omega Fatty Acid Production

The transformed host cell is grown under conditions that optimize expression of chimeric desaturase genes and produce the greatest and most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in PCT Publication No. WO 2004/101757. Although it is contemplated that the source of carbon utilized in the present invention may encompass a wide variety of carbon-containing sources, preferred carbon sources are sugars, glycerol and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in *Yarrowia lipolytica*. This approach is described in PCT Publication No. WO 2004/101757, as are various suitable fermentation process designs (i.e., batch, fed-batch and continuous) and considerations during growth.

Oils for Use in Foodstuffs, Health Food Products, Pharmaceuticals and Animal Feeds The market place currently supports a large variety of food and feed products, incorporating ω-3 and/or ω-6 fatty acids (particularly ALA, GLA, ARA, EPA, DPA and DHA). It is contemplated that the oils of the invention comprising long-chain PUFAs will function in food and feed products to impart the health benefits of current formulations. More specifically, oils of the invention containing ω-3 and/or ω-6 fatty acids will be suitable for use in a variety of food and feed products including, but not limited to: food analogs, drinks, meat products, cereal products, baked foods, snack foods and dairy products (see Patent Publication No. US 2006/0094092 for details).

Additionally the present oils may be used in formulations to impart health benefits in medical foods including medical nutritionals, dietary supplements, infant formula as well as pharmaceutical products. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and, 3.) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Comparisons of genetic sequences were accomplished using DNASTAR software (DNA Star, Inc.).

Unless otherwise specified, BLAST (Basic Local Alignment Search Tool; Altschul, S. F., et al., *J. Mol. Biol.,* 215: 403-410 (1993) and *Nucleic Acids Res.,* 25:3389-3402 (1997)) searches were conducted to identity isolated sequences having similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). Query sequences were analyzed for similarity to all publicly available DNA sequences contained in the "nr" database using the BLASTN algorithm provided by the National Center for Biotechnology Information (NCBI). Sequences were translated in all reading frames and compared for similarity to all publicly available protein sequences contained in the "nr" database, using the BLASTX algorithm (Gish, W. and States, D. J. *Nature Genetics,* 3:266-272 (1993)) provided by the NCBI. The results of BLAST comparisons summarizing the sequence to which a query sequence had the most similarity are reported according to the % identity, % similarity, and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strain ATCC #20362 was purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Y. lipolytica* was performed according to the method of Chen, D. C. et al. (*Appl. Microbiol Biotechnol.,* 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; and, 0.125 mL of 2 M DTT. Then, approximately 500 ng of linearized plasmid DNA was incubated in 100 µl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1. Supplements of leucine, lysine and/or uracil were added as appropriate to a final concentration of 0.01% (thereby producing "MMLeu", "MMLys" and "MMU" selection media, each prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Finally, High Glucose Media ("HGM") was prepared as follows, as a means to promote conditions of oleaginy: 6.3 g/L $KH_2PO_4$, 27 g/L $K_2HPO_4$ and 80 g/L glucose (pH 7.5).

The methodology used to create the strains identified herein as Y4001U1, Y4036U and L38 relied on site-specific recombinase systems. Briefly, the site-specific recombination system consists of two elements: (1) a recombination site having a characteristic DNA sequence [e.g., LoxP]; and, (2) a recombinase enzyme that binds to the DNA sequence specifically and catalyzes recombination (i.e., excision) between DNA sequences when two or more of the recombination sites are oriented in the same direction at a given interval on the same DNA molecule [e.g., Cre]. For the purposes herein, an integration construct was created comprising a target gene that was desirable to insert into the host genome (i.e., a first selection marker [i.e., Ura3 or Leu2]) that was flanked by recombination sites. Following transformation and selection of the transformants, the first selection marker was excised from the chromosome by the introduction of a replicating plasmid carrying a second selection marker (i.e., Leu2 or sulfonylurea resistance [AHAS]) and a recombinase suitable to recognize the site-specific recombination sites introduced into the genome (i.e., Cre). Upon selection of those transformants carrying the second marker, the replicating plasmid was then cured from the host in the absence of selection and excision of the first selection marker from the cured strain's host genome was confirmed by loss of Ura or Leu prototrophy. This produced a transformant that possessed neither the first nor second selection marker, and thus the cured strain was available for another round of transformation using the first selection marker. Additional details concerning site-specific recombinase based methodology for use in *Yarrowia lipolytica* is described in PCT Publication No. WO 2006/052870.

The second selection marker gene utilized in pY117 (Example 16) was a native *Yarrowia lipolytica* acetohydroxyacid synthase (AHAS or acetolactate synthase; E.C. 4.1.3.18; GenBank Accession No. XM_501277) containing a single amino acid change (W497L) that confers sulfonyl urea herbicide resistance ($SU^R$; described in PCT Publication No. WO 2006/052870). AHAS is the first common enzyme in the pathway for the biosynthesis of branched-chain amino acids and it is the target of the sulfonylurea and imidazolinone herbicides.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.,* 37:911-917 (1959)). Fatty acid methyl esters were prepared by transesterification of the lipid extract with sodium methoxide (Roughan, G., and Nishida I., *Arch Biochem Biophys.,* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

*Pythium aphanidermatum* Lipid Profile, Total RNA Isolation and Genomic DNA Isolation A *Pythium aphanidermatum* strain was obtained from Lisa Hoffman (E.I. duPont de Nemours, Inc., Wilmington, Del.).

The strain was grown on malt extract agar medium (Difco Laboratories, Detroit, Mich.) at room temperature for 3 days. Cells were scraped off the plate and resuspended in 600 µl of sodium methoxide dissolved in methanol. The sample was shaken for 20 min, and 50 µl of 1 M NaCl was added. After mixing, 600 µl of heptane was added. The sample was vortexed and centrifuged in an Eppendorf microfuge for 1 min. The upper layer was carefully separated from the lower layer and placed in a glass vial for GC analysis. The results of the analysis are shown below in Table 4. Fatty acids are identified as 16:0 (palmitate), 16:1 (palmitoleic acid), 18:0, 18:1 (oleic acid), 18:2, GLA, 20:1, 20:2, DGLA, ARA, EPA and DHA; and the composition of each is presented as a % of the total fatty acids.

TABLE 4

Lipid Profile Of *Pythium aphanidermatum* Cells

| | Fatty Acid | | | | | |
|---|---|---|---|---|---|---|
| | 16:0 | 16:1 | 18:0 | 18:1 | 18:2 | GLA |
| % of Total Fatty Acids | 15.8 | 7.1 | 0 | 30.0 | 11.2 | 0.5 |
| | **Fatty Acid** | | | | | |
| | 20:1 | 20:2 | DGLA | ARA | EPA | DHA |
| % of Total Fatty Acids | 1.3 | 0.5 | 0.7 | 7.8 | 13.4 | 0.3 |

Based on the presence of ARA and EPA, it was concluded that the *P. aphanidermatum* strain likely had both a Δ5 desaturase (capable of converting DGLA to ARA) and a Δ17 desaturase (capable of converting ARA to EPA).

Total RNA and genomic DNA were isolated from cells scraped off a malt extract agar plate using the Trizol reagent (Invitrogen, Carlsbad, Calif.). Specifically, scraped cells were resuspended in 1 mL water and centrifuged for 30 sec in an Eppendorf microfuge. The cell pellet was resuspended in 0.75 mL Trizol reagent, mixed with 0.75 mL of 0.5 mm glass beads, and homogenized in a Biospec mini beadbeater (Bartlesville, Okla.) at the highest setting for 3 min. The mixture was centrifuged in an Eppendorf centrifuge for 30 sec at 14,000 rpm to remove debris and glass beads. The supernatant was extracted with 150 µl of 24:1 chloroform:isoamyl alcohol (Invitrogen). The upper aqueous phase was used for RNA isolation and the lower organic phase for DNA isolation.

For RNA isolation, the aqueous phase was mixed with 0.375 mL of isopropyl alcohol and allowed to incubate at room temperature for 5 min. Precipitated RNA was collected by centrifugation at 8000 rpm and 4° C. for 5 min. The pellet was washed once with 0.7 mL of 80% ethanol and air-dried. Total RNA (59 µg) was obtained (i.e., 200 µl of sample at 29.5 µg/µl).

For genomic DNA isolation, the lower organic phase of the sample was mixed with 225 µl of ethanol and incubated at room temperature for 5 min. The sample was then centrifuged at 5000 rpm for 2 min in an Eppendorf centrifuge. The pellet was washed with 0.75 mL of 0.1 M sodium citrate/10% ethanol twice. Each time the sample was incubated for 15 min at room temperature in the wash solution, followed by centrifugation at 5000 rpm for 5 min at 4° C. in an Eppendorf centrifuge. The pellet was air dried and re-dissolved in 300 µl of 8 mM NaOH. The pH of the sample was adjusted to 7.5 with 1 M HEPES, and then further purified with a Qiagen PCR purification kit exactly as described in the manufacturer's protocol. A total of 7.2 µg of *P. aphanidermatum* genomic DNA was obtained.

Example 2

*Pythium aphanidermatum* cDNA Synthesis

Double-stranded cDNA was synthesized directly from the *Pythium aphanidermatum* total RNA using the BD-Clontech Creator™ Smart™ cDNA library kit (Mississauga, ON, Canada). Specifically, 3 µl of total RNA sample (0.9 µg) was mixed with 1 µl of SMART™ IV oligonucleotide (SEQ ID NO:9) and 1 µl CDSIII/3' PCR primer (SEQ ID NO:10). The mixture was heated to 75° C. for 5 min, and cooled on ice for 5 min. Two (2) µl of 5× first strand buffer, 1 µl of 20 mM DTT, 1 µl of dNTP mix (10 mM each of dATP, dCTP, dGTP and dTTP) and 1 µl of PowerScript reverse transcriptase were added to the mixture. The sample was incubated at 42° C. for 1 hr.

The resulting first strand cDNA synthesis mixture was then used as template for PCR amplification. The reaction mixture contained 2 µl of the above first strand cDNA sample, 80 µl of water, 10 µl of 10× Advantage 2 PCR buffer, 2 µl 50× dNTP mix (10 mM each of dATP, dCTP, dGTP and dTTP), 2 µl of 5' PCR primer (SEQ ID NO:11), 2 µl CDSIII/3' PCR primer (SEQ ID NO:10) and 2 µl 50× Advantage 2 polymerase mix. The thermocycler conditions were set for 95° C. for 1 min and then 20 cycles of 95° C. for 10 sec and 68° C. for 6 min.

Amplification product was purified with a Qiagen PCR purification kit following the manufacturer's protocol exactly. Purified cDNA product was eluted with 50 µl of water.

Example 3

Isolation of a Portion of the Coding Region of the *Pythium aphanidermatum* Δ17 Desaturase Gene The present Example describes the identification of a portion of the *Pythium aphanidermatum* gene encoding Δ17 desaturase (designated herein as "PaD17" (SEQ ID NOs:1 and 2)), by use of primers derived from conserved regions of other known Δ17 desaturase sequences.

The *P. aphanidermatum* cDNA sample from Example 2 was used as template for PCR using degenerated primers designed to amplify portions of the potential Δ17 desaturase gene, based on the Δ17 fatty acid desaturase sequences of *Phytophthora sojae* (SEQ ID NO:45; U.S. patent application Ser. No. 11/787,772, filed Apr. 18, 2007; see also Example 11, infra) and *Phytophthora ramorum* (SEQ ID NO:47; U.S. patent application Ser. No. 11/787,772, filed Apr. 18, 2007; see also Example 13, infra). Based on the alignment provided herein as FIG. 2, degenerate primers were designed as shown in Table 5 (location of primers with respect to SEQ ID NOs:45 and 47 are shown as dotted boxes on FIG. 2).

TABLE 5

Degenerate Oligonucleotides Used To Amplify The Δ17 Desaturase Gene From *Pythium aphanidermatum*

| Primer | Nucleotide Sequence | Amino Acid Sequence |
|---|---|---|
| PD17-F1 | TTYTGGGGNTTYTTYACNGT (SEQ ID NO: 12) | FWGFFTY (SEQ ID NO: 13) |
| PD17-F2 | TTCTTYACNGTNGGNCAYGA (SEQ ID NO: 14) | FFTVGHD (SEQ ID NO: 16) |
| PD17-F3 | TTTTTYACNGTNGGNCAYGA (SEQ ID NO: 15) | FFTVGHD (SEQ ID NO: 16) |
| PD17-F4 | ACNCAYCGNCAYCAYCAYAA (SEQ ID NO: 17) | THRHHHK (SEQ ID NO: 19) |
| PD17-F5 | ACNCAYAGRCAYCAYCAYAA (SEQ ID NO: 18) | THRHHHK (SEQ ID NO: 19) |
| PD17-F6 | AARAAYACNGGNAAYATYGA (SEQ ID NO: 20) | KNTGNID (SEQ ID NO: 22) |
| PD17-F7 | AARAAYACNGGNAAYATAGA (SEQ ID NO: 21) | KNTGNID (SEQ ID NO: 22) |
| PD17-R1 | TCRTCRTTRTGRTGNAGRAA (SEQ ID NO: 23) | FLHHNDE (SEQ ID NO: 25) |
| PD17-R2 | TCRTCRTTRTGRTGYAARAA (SEQ ID NO: 24) | FLHHNDE (SEQ ID NO: 25) |
| PD17-R3 | AARAARGCYTTDATDATNGG (SEQ ID NO: 26) | PIIKAFF (SEQ ID NO: 28) |
| PD17-R4 | AARAAYGCYTTDATDATNGG (SEQ ID NO: 27) | PIIKAFF (SEQ ID NO: 28) |
| PD17-R5 | TTRTGNGTNCCDATRTTATG (SEQ ID NO: 29) | HNIGTHQ (SEQ ID NO: 31) |
| PD17-R6 | TTRTGNGTNCCDATRTTGTG (SEQ ID NO: 30) | HNIGTHQ (SEQ ID NO: 31) |

TABLE 5-continued

| Degenerate Oligonucleotides Used To Amplify The Δ17 Desaturase Gene From *Pythium aphanidermatum* | | |
|---|---|---|
| Primer | Nucleotide Sequence | Amino Acid Sequence |
| PD17-R7 | CCYTTNACRTANGTCCAYTC (SEQ ID NO: 32) | EWTYVKG (SEQ ID NO: 33) |

[Note:
The nucleic acid degeneracy code used for SEQ ID NOs: 12, 14, 15, 17, 18, 20, 21, 23, 24, 26, 27, 29, 30 and 32 was as follows: R = A/G; Y = C/T; D = A/G/T; and N = A/C/T/G.]

A total of 49 different PCR amplification reactions were performed, using all possible combinations of the 7 forward and 7 reverse primers. Each reaction mixture contained 1 μl of 1:10 diluted *P. aphanidermatum* cDNA, 5 μl each of the forward and reverse primers (20 μM), 14 μl water and 25 μl of TaKaRa ExTaq 2× premix (TaKaRa Bio, Mountain View, Calif.). The thermocycler conditions were set for 94° C. for 1 min, then 30 cycles of 94° C. for 20 sec, 55° C. for 20 sec and 72° C. for 1 min, followed by a final extension at 72° C. for 7 min. PCR products were analyzed by electrophoresis on standard agarose gels, and putative Δ17 desaturase fragments were detected as shown below in Table 6.

TABLE 6

| Detected Putative Δ17 Desaturase Fragments | | |
|---|---|---|
| Product | Forward Primer | Reverse Primer |
| ~460 bp fragment | PD17-F1 | PD17-R5 |
| ~400 bp fragment | PD17-F4 | PD17-R2 |
| ~350 bp fragment | PD17-F6 | PD17-R2 |

Each of the fragments described above in Table 6 were purified with a Qiagen PCR purification kit (Valencia, Calif.), cloned into pCR2,1-TOPO (Invitrogen) and sequenced.

BLAST sequence analysis showed that each of the fragments were from a single gene that showed extensive homology to the known Δ17 desaturases from other organisms. The sequences were assembled into a 614 bp contig (SEQ ID NO:5), which was assumed to encode a putative Δ17 desaturase from *P. aphanidermatum.*

Example 4

Isolation of the Full-Length Δ17 Desaturase from *Pythium aphanidermatum*

Primers were designed to isolate the 5' and 3' ends of the putative Δ17 desaturase gene from cDNA and genomic DNA samples of *P. aphanidermatum*, based on the partial sequence set forth in SEQ ID NO:5 and described in Example 3.

The 5' region of the putative Δ17 desaturase from *P. aphanidermatum* was isolated by genome walking using the Universal GenomeWalker™ kit (BD Biosciences Clonetech, Palo Alto, Calif.), according to the manufacturer's protocol. First, genomic DNA from *P. aphanidermatum* (1 μg per digestion) was digested with DraI, EcoRV, PvuII and StuI separately. Digested DNA samples were purified with Qiagen enzyme reaction clean-up kits according to the manufacturer's protocol and each sample was eluted with 20 μl of water.

The digested genomic DNA samples were ligated with Universal GenomeWalker™ adaptor (SEQ ID NOs:34 [top strand] and 35 [bottom strand]), as shown below:

```
5'-
GTAATACGACTCACTATAGGGCACGCGTGGTCGACGGCCCGGGCTGGT-3'

                                    3'-H2N-CCCGACCA-5'
```

Specifically, 4 μl each of the digested DNA was mixed with 1.9 μl of 25 μM GenomeWalker™ adaptor, 1.6 μl of 10× ligation buffer and 0.5 μl of T4 DNA ligase. The reaction was carried out overnight at 16° C. After heating at 70° C. for 5 min, 72 μl of 10 mM Tris, 1 mM EDTA, pH 7.4 buffer was added to each reaction mixture. These reaction mixtures were then used as template for PCR amplification.

For the first round of PCR, primers PUD17-5-1 (SEQ ID NO:36) and Universal GenomeWalker™ primer AP1 (SEQ ID NO:37) from the kit were used. The reaction mixture contained 1 μl of each primer at 10 μM, 2 μl of the purified ligation products as template, 21 μl water and 25 μl of TaKaRa ExTaq 2× premix. The thermocycler conditions were set for 94° C. for 90 sec, then 30 cycles at 94° C. for 20 sec, 55° C. for 20 sec and 72° C. for 2 min, followed by a final extension at 72° C. for 5 min.

PCR products were diluted 1:20, and 1 μl of diluted PCR product was used as template for a second round of PCR using primers PUD17-5-3 (SEQ ID NO:38) and Universal GenomeWalker™ primer AP2 (SEQ ID NO:39). PCR components and amplification conditions were as described above.

A ~750 bp DNA fragment was generated from the second-round of PCR. This fragment was purified with a Qiagen PCR purification kit, cloned into pCR2.1-TOPO (Invitrogen) and sequenced. Subsequent sequence analysis showed that this fragment contained the 5' end of the putative Δ17 desaturase gene, including the translation initiation codon and 387 bp of additional untranslated 5' sequence. The 5' fragment (SEQ ID NO:6) shared significant homology to the *Saprolegnia diclina* Δ17 desaturase (GenBank Accession No. AAR20444; SEQ ID NO:95).

The 3' region of the putative Δ17 desaturase was isolated by PCR amplification using *P. aphanidermatum* cDNA as template. Primers PUD17-3-1 (SEQ ID NO:40) and CDSIII/3' PCR primer (SEQ ID NO:10; from BD-Clontech Creator™ Smart™ cDNA library construction kit, see Example 1) were used for the first round of amplification. The reaction mixture contained 1 μl of each primer (10 μM), 1 μl of *P. aphanidermatum* cDNA, 22 μl water and 25 μl TaKaRa ExTaq 2× premix. The thermocycler conditions were set for 94° C. for 90 sec, then 30 cycles at 94° C. for 30 sec, 55° C. for 30 sec and 72° C. for 30 sec, followed by a final extension at 72° C. for 5 min.

PCR product was diluted 1:20, and 1 μl of the diluted product was used as template for a second round of PCR using PUD17-3-2 (SEQ ID NO:41) and CDSIII/3' PCR primer (SEQ ID NO:10), using components and amplification conditions as described above. The second round PCR generated a ~550 bp DNA fragment. This was purified with a Qiagen PCR purification kit, cloned into pCR2.1-TOPO and sequenced. Sequence analysis showed that this fragment contained the 3'-region of the putative Δ17 desaturase cDNA, including the polyA tail. The 3' fragment (SEQ ID NO:7) shared significant homology to the *Saprolegnia diclina* Δ17 desaturase (GenBank Accession No. AAR20444; SEQ ID NO:95).

Assembly of the 5' genomic region (SEQ ID NO:6), the original partial cDNA sequence (SEQ ID NO:5) and the 3' cDNA sequence (SEQ ID NO:7) resulted in a 1533 bp contig (SEQ ID NO:8), comprising the complete sequence of the putative Δ17 desaturase from *P. aphanidermatum* and additional untranslated 5' and 3' ends. The coding region of SEQ ID NO:8, which is set forth as SEQ ID NO:1, is 1080 bp long (corresponding to bases 388-1467 of SEQ ID NO:8) and encodes a peptide of 359 amino acids (SEQ ID NO:2). The coding sequence of *Pythium aphanidermatum* was designated herein as "PaD17".

The results of BLAST searches using the full length PaD17 gene (i.e., SEQ ID NO:1) as the query sequence showed that it shared 58% identity and 71% similarity with the amino acid sequence of the Δ17 desaturase of *Saprolegnia diclina* (GenBank Accession No. AAR20444), with an Expectation value of e-121; additionally, it shared identity and similarity with other omega-3 desaturases.

Similarly, pairwise comparison between and among Δ17 desaturase proteins from *Phytophthora infestans* ("PiD17"; SEQ ID NO:43), *Phytophthora sojae* ("PsD17"; SEQ ID NO:45), *Phytophthora ramorum* ("PrD17"; SEQ ID NO:47) and *Pythium aphanidermatum* ("PaD17"; SEQ ID NO:2) using a Clustal W analysis (MegAlign™ program of DNASTAR software) resulted in the following percent similarities: 74.5% between PiD17 and PaD17; 75.0% between PrD17 and PaD17; and 75.3% between PsD17 and PaD17.

Example 5

Generation of *Yarrowia lipolytica* Expression Vectors Comprising the *Pythium aphanidermatum* Δ17 Desaturase ("PaD17")

The present Example describes the construction of plasmids pFmD17-1, pFmD17-2, pFmD17-3 and pFmD17-4, each comprising a chimeric FBAINm::PaD17*::XPR gene, wherein PaD17*(SEQ ID NO:3) comprises up to (and including) 2 amino acid mutations with respect to SEQ ID NO:2. Plasmids pFmD17-1, pFmD17-2, pFmD17-3 and pFmD17-4 were utilized to test functional expression of PaD17*, as described in Example 7, infra.

Plasmids pFmD17-1, pFmD17-2, pFmD17-3 and pFmD17-4 were constructed by three-way ligation using fragments from plasmid pFmD8S, a 5' portion of PaD17 and a 3' portion of PaD17. Plasmid pFmD8S (SEQ ID NO:51; FIG. 3D) was constructed by three-way ligation using fragments from plasmids pKUNFmkF2, pDMW287F and pDMW214.

Plasmid pKUNFmkF2 pKUNFmkF2 (SEQ ID NO:48; FIG. 3A; PCT Publication No. WO 2006/012326) is a construct comprising a chimeric FBAINm::F.D12::Lip2 gene (wherein "FBAINmK" is the *Yarrowia lipolytica* FBAINm promoter [PCT Publication No. WO 2005/049805; U.S. Pat. No. 7,202,356], "F.D12" is the *Fusarium moniliforme* Δ12 desaturase [PCT Publication No. WO 2005/047485], and "Lip2" is the *Yarrowia lipolytica* Lip2 terminator sequence (GenBank Accession No. AJ012632)).

Plasmid pDMW287F pDMW287F (SEQ ID NO:49; FIG. 3B; PCT Publication No. WO 2006/012326) is a construct comprising a synthetic Δ8 desaturase ("EgD8S"; SEQ ID NO:52 herein), derived from wildtype *Euglena gracilis*, and codon-optimized for expression in *Yarrowia lipolytica* (wherein EgD8S is identified as "D8SF" in the Figure). The desaturase gene is flanked by a *Yarrowia lipolytica* FBAIN promoter (PCT Publication No. WO 2005/049805; U.S. Pat. No. 7,202,356; identified as "FBA1+intron" in the Figure) and a Pex16 terminator sequence of the *Yarrowia* Pex16 gene (GenBank Accession No. U75433).

Plasmid pDMW214 pDMW214 (SEQ ID NO:50; FIG. 3C; PCT Publication No. WO 2005/049805; U.S. Pat. No. 7,202,356) is a shuttle plasmid that replicates both in *E. coli* and *Yarrowia lipolytica*. It contained the following components:

TABLE 7

Description Of Plasmid pDMW214 (SEQ ID NO: 50)

| RE Sites And Nucleotides Within SEQ ID NO: 50 | Description Of Fragment And Chimeric Gene Components |
|---|---|
| 1150-270 | ColE1 plasmid origin of replication |
| 2080-1220 | Ampicillin-resistance gene ($Amp^R$) for selection in *E. coli* |
| 2979-4256 | *Yarrowia* autonomous replication sequence (ARS18; GenBank Accession No. A17608) |
| PmeI/SphI 6501-4256 | *Yarrowia* Leu2 gene (GenBank Accession No. AF260230) |
| 6501-1 | FBA1 + intron::GUS::XPR, comprising:<br>FBA1 + intron: *Yarrowia lipolytica* FBAIN promoter (PCT Publication No. WO 2005/049805; U.S. Pat. No. 7,202,356);<br>GUS: *E. coli* gene encoding β-glucuronidase (Jefferson, R. A., Nature, 342: 837-838 (1989));<br>XPR: ~100 bp of the 3' region of the *Yarrowia* Xpr gene (GenBank Accession No. M17741) |

Plasmid pFmD8S

The PmeI/NcoI fragment of plasmid pKUNFmkF2 (FIG. 3A; comprising the FBAINm promoter) and the NcoI/NotI fragment of plasmid pDMW287F (FIG. 3B; comprising the synthetic Δ8 desaturase gene "EgD8S") were used directionally to replace the PmeI/Not I fragment of pDMW214 (FIG. 3C). This resulted in generation of pFmD8S (SEQ ID NO:51; FIG. 3D), comprising a chimeric FBAINm::EgD8S::XPR gene. Thus, the components of pFmD8S are as described in Table 8 below.

TABLE 8

Components Of Plasmid pFmD8S (SEQ ID NO: 51)

| RE Sites And Nucleotides Within SEQ ID NO: 51 | Description Of Fragment And Chimeric Gene Components |
|---|---|
| Swa I/Sac II (7988-1461) | FBAINm::EgD8S::XPR, comprising:<br>FBAINm: *Yarrowia lipolytica* FBAINm promoter (PCT Publication No. WO 2005/049805; U.S. Pat. No. 7,202,356);<br>EgD8S: codon-optimized Δ8 desaturase gene (SEQ ID NO: 52, identified as "D8-corrected" in FIG. 3D), derived from *E. gracilis* (PCT Publication No. WO 2006/012326);<br>XPR: ~100 bp of the 3' region of the *Yarrowia* Xpr gene (GenBank Accession No. M17741) |
| 2601-1721 | ColE1 plasmid origin of replication |
| 3531-2671 | Ampicillin-resistance gene ($Amp^R$) for selection in *E. coli* |
| 4430-5734 | *Yarrowia* autonomous replication sequence (ARS18; GenBank Accession No. A17608) |
| 7942-5741 | *Yarrowia* Leu2 gene (GenBank Accession No. AF260230) |

Generation of Plasmids pFmD17-1, pFmD17-2, pFmD17-3 and pFmD17-4

The *P. aphanidermatum* Δ17 desaturase was amplified from cDNA via a reaction mixture that contained: 1 μl of 20 μM forward primer PUD17-F (SEQ ID NO:54), 1 μl of 20 μM reverse primer PUD17-R (SEQ ID NO:55), 1 µl *P. aphanidermatum* cDNA, 10 µl 5×PCR buffer, 1 µl dNTP mix (10 µM each), 35 µl water and 1 µl Phusion polymerase (New England Biolabs). The thermocycler conditions were set for 98° C. for 1 min, then 30 cycles at 98° C. for 10 sec, 55° C. for 10 sec and 72° C. for 30 sec, followed by a final extension at 72° C. for 5 min.

The PCR product was cloned into pCR2.1-TOPO (Invitrogen) and 8 individual clones were sequenced. Based on the sequence results, 2 clones (i.e., clone 2 and clone 4) were used to construct the final expression plasmid. Clone 2 contained a 351A to T mutation with respect to SEQ ID NO:2, while clone 4 contained a 155S to P mutation with respect to SEQ ID NO:2; thus, they differed from one another by two conservative amino acid substitutions and they each differed from the wildtype cDNA PaD17 sequence set forth in SEQ ID NO:2 by one conservative amino acid substitution.

Each clone was digested with NcoI and BglII to generate a ~370 bp fragment that contained the 5' region of the Δ17 desaturase cDNA; and, each clone was also digested with BglII and NotI to generate a 710 bp fragment that contained the 3' region of the cDNA. The ~370 bp fragment comprising the 5' region of the Δ17 desaturase and the 710 bp fragment comprising the 3' region of the Δ17 desaturase were ligated into pFmD8S predigested with NcoI and NotI (such that the codon-optimized Δ8 desaturase gene ["EgD8S"] was excised from the plasmid) in a three-way ligation reaction. The reaction mixture contained 10 µl 2× ligation buffer and 1 µl T4 DNA ligase (Promega), 4 µl each of the 5' and the 3' Δ17 desaturase fragments (~300 ng each) and 1 µl pFmD8S (~150 ng).

Using the above methodology, the components of the newly created expression plasmids pFmD17-1, pFmD17-2, pFmD17-3 and pFmD17-4 are identical to those described in Table 8 for pFmD8S (SEQ ID NO:51), with the exception that the pFmD17 vectors possessed chimeric FBAINm::PaD17*::XPR genes instead of the chimeric FBAINm::EgD8S::XPR gene within pFmD8S. The notation of "PaD17*" corresponds to the below mutations with respect to SEQ ID NO:2 (i.e., the amino acid of PaD17 as described in Example 4). The null mutation, 155S to P mutation, 351A to T mutation, and 155S to P and 351A to T mutations are each encompassed in SEQ ID NO:3, hereinafter referred to as PaD17*. Based on the combination of the two clones, the four variant expression plasmids contained the following mutations, as shown below in Table 9.

TABLE 9

Variant pFmD17 *Yarrowia lipolytica* Expression Vectors Comprising Chimeric FBAINm::PaD17*::XPR Genes

| Plasmid | 5' Fragment | 3' Fragment | Mutation With Respect To SEQ ID NO: 2 |
|---|---|---|---|
| pFmD17-1 | clone 2 | clone 2 | 351A to T |
| pFmD17-2 | clone 4 | clone 4 | 155S to P |
| pFmD17-3 | clone 2 | clone 4 | None |
| pFmD17-4 | clone 4 | clone 2 | 155S to P, 351A to T |

Each reaction mixture was incubated at room temperature for 2 hrs and used to transform *E. coli* Top10 competent cells. Plasmid DNA from transformants was recovered with Qiagen Miniprep kits.

Example 6

Generation of *Yarrowia lipolytica* Strain Y2047 to Produce about 11% ARA of Total Lipids Via the Δ6 Desaturase/Δ6 Elongase Pathway The present Example describes the construction of strain Y2047, derived from *Yarrowia lipolytica* ATCC #20362, capable of producing 11% ARA relative to the total lipids via expression of a Δ6 desaturase/Δ6 elongase pathway (FIG. 4A). This strain was utilized to test the functional expression of PaD17* in Example 7, infra.

*Yarrowia lipolytica* strain Y2047 has been deposited under the terms of the Budapest Treaty and bears the ATCC number PTA-7186. Additionally, construction of Y2047 has been described in co-pending U.S. patent application Ser. No. 11/265,761 (Patent Publication No. US 2006-0115881 A1 and PCT Publication No. WO 2006/052870), herein incorporated by reference.

The development of strain Y2047 first required the construction of strain M4 (producing 8% DGLA).

Generation of M4 Strain to Produce about 8% DGLA of Total Lipids

Construct pKUNF12T6E (FIG. 4B; SEQ ID NO:56) was generated to integrate four chimeric genes (comprising a Δ12 desaturase, a Δ6 desaturase and two $C_{18/20}$ elongases) into the Ura3 loci of wild type *Yarrowia* strain ATCC #20362, to thereby enable production of DGLA. The pKUNF12T6E plasmid contained the following components:

TABLE 10

| Description Of Plasmid pKUNF12T6E (SEQ ID NO: 56) | |
|---|---|
| RE Sites And Nucleotides Within SEQ ID NO: 56 | Description Of Fragment And Chimeric Gene Components |
| AscI/BsiWI (9420-8629) | 784 bp 5' portion of *Yarrowia* Ura3 gene (GenBank Accession No. AJ306421) |
| SphI/PacI (12128-1) | 516 bp 3' portion of *Yarrowia* Ura3 gene (GenBank Accession No. AJ306421) |
| SwaI/BsiWI (6380-8629) | FBAIN::EL1S::Pex20, comprising: FBAIN: *Yarrowia lipolytica* FBAIN promoter (PCT Publication No. WO 2005/049805; U.S. Pat. No. 7,202,356); EL1S: codon-optimized elongase 1 gene (PCT Publication No. WO 2004/101753), derived from *Mortierella alpina* (GenBank Accession No. AX464731); Pex20: Pex20 terminator sequence from *Yarrowia* Pex20 gene (GenBank Accession No. AF054613) |
| BglII/SwaI (4221-6380) | TEF::Δ6S::Lip1, comprising: TEF: *Yarrowia lipolytica* TEF promoter (GenBank Accession No. AF054508); Δ6S: codon-optimized Δ6 desaturase gene (PCT Publication No. WO 2004/101753; U.S. Pat. No. 7,125,672), derived from *Mortierella alpina* (GenBank Accession No. AF465281); Lip1: Lip1 terminator sequence from *Yarrowia* Lip1 gene (GenBank Accession No. Z50020) |
| PmeI/ClaI (4207-1459) | FBA::F.Δ12::Lip2, comprising: FBA: *Yarrowia lipolytica* FBA promoter (PCT Publication No. WO 2005/049805; U.S. Pat. No. 7,202,356); F.Δ12: *Fusarium moniliforme* Δ12 desaturase gene (PCT Publication No. WO 2005/047485); |

TABLE 10-continued

| Description Of Plasmid pKUNF12T6E (SEQ ID NO: 56) | |
|---|---|
| RE Sites And Nucleotides Within SEQ ID NO: 56 | Description Of Fragment And Chimeric Gene Components |
| | Lip2: Lip2 terminator sequence from *Yarrowia* Lip2 gene (GenBank Accession No. AJ012632) |
| ClaI/PacI (1459-1) | TEF::EL2S::XPR, comprising:<br>TEF: TEF promoter (GenBank Accession No. AF054508);<br>EL2S: codon-optimized elongase gene (SEQ ID NO: 57), derived from *Thraustochytrium aureum* (U.S. Pat. No. 6,677,145);<br>XPR: ~100 bp of the 3' region of the *Yarrowia* Xpr gene (GenBank Accession No. M17741) |

The pKUNF12T6E plasmid was digested with AscI/SphI, and then used for transformation of wild type *Y. lipolytica* ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura− strains. Single colonies of Ura− strains were then inoculated into liquid MMU at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKUNF12T6E, but not in the wild type *Yarrowia* control strain. Most of the selected 32 $Ura^-$ strains produced about 6% DGLA of total lipids. There were 2 strains (i.e., strains M4 and 13-8) that produced about 8% DGLA of total lipids.

Generation of Y2047 Strain to Produce about 11% ARA of Total Lipids

Construct pDMW271 (FIG. 4C; SEQ ID NO:59) was generated to integrate three Δ5 chimeric genes into the Leu2 gene of *Yarrowia* strain M4. Plasmid pDMW271 contained the following components, as described in Table 11:

TABLE 11

| Description Of Plasmid pDMW271 (SEQ ID NO: 59) | |
|---|---|
| RE Sites And Nucleotides Within SEQ ID NO: 59 | Description Of Fragment And Chimeric Gene Components |
| AscI/BsiWI (5520-6315) | 788 bp 5' portion of *Yarrowia* Leu2 gene (GenBank Accession No. AF260230) |
| SphI/PacI (2820-2109) | 703 bp 3' portion of *Yarrowia* Leu2 gene (GenBank Accession No. AF260230) |
| SwaI/BsiWI (8960-6315) | FBAIN::MAΔ5::Pex20, comprising:<br>FBAIN: *Yarrowia lipolytica* FBAIN promoter (PCT Publication No. WO 2005/049805; U.S. Pat. No. 7,202,356);<br>MAΔ5: *Mortierella alpina* Δ5 desaturase gene (GenBank Accession No. AF067654);<br>Pex20: Pex20 terminator sequence of *Yarrowia* Pex20 gene (GenBank Accession No. AF054613) |
| SwaI/ClaI (8960-11055) | TEF::MAΔ5::Lip1, comprising:<br>TEF: TEF promoter (GenBank Accession No. AF054508);<br>MAΔ5: *Mortierella alpina* Δ5 desaturase gene (GenBank Accession No. AF067654); |

TABLE 11-continued

| Description Of Plasmid pDMW271 (SEQ ID NO: 59) | |
|---|---|
| RE Sites And Nucleotides Within SEQ ID NO: 59 | Description Of Fragment And Chimeric Gene Components |
| | Lip1: Lip1 terminator sequence of *Yarrowia* Lip1 gene (GenBank Accession No. Z50020) |
| PmeI/ClaI (12690-11055) | Yarrowia Ura3 gene (GenBank Accession No. AJ306421) |
| ClaI/PacI (1-2109) | TEF::HΔ5S::Pex16, comprising:<br>TEF: TEF promoter (GenBank Accession No. AF054508);<br>HΔ5S: codon-optimized Δ5 desaturase gene (SEQ ID NO: 60), derived from *Homo sapiens* (GenBank Accession No. NP_037534);<br>Pex16: Pex16 terminator sequence of *Yarrowia* Pex16 gene (GenBank Accession No. U75433) |

Plasmid pDMW271 was digested with AscI/SphI, and then used to transform strain M4 according to the General Methods. Following transformation, the cells were plated onto MMLeu plates and maintained at 30° C. for 2 to 3 days. The individual colonies grown on MMLeu plates were picked and streaked onto MM and MMLeu plates. Those colonies that could grow on MMLeu plates but not on MM plates were selected as $Leu2^-$ strains. Single colonies of $Leu2^-$ strains were then inoculated into liquid MMLeu media at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of ARA in pDMW271 transformants, but not in the parental M4 strain. Specifically, among the 48 selected $Leu2^-$ transformants with pDMW271, there were 35 strains that produced less than 5% ARA of total lipids, 12 strains that produced 6-8% ARA, and 1 strain that produced about 11% ARA of total lipids in the engineered *Yarrowia*. The strain that produced 11% ARA was named "Y2047".

Example 7

Functional Analysis of the *Pythium aphanidermatum* Δ17 Desaturase ("PaD17*") in *Yarrowia lipolytica* Strain Y2047

The present Example describes functional analysis of PaD17* in *Yarrowia lipolytica* strain Y2047 (Example 6). Thus, following transformation of the variant pFmD17 plasmids comprising PaD17*(from Example 5), lipid profiles within the transformant organisms were compared.

Transformation of *Yarrowia lipolytica*

Plasmids pFmD17-1, pFmD17-2, pFm17-3 and pFmD17-4 (comprising the chimeric FBAINm::PaD17*::XPR genes) were transformed into *Yarrowia lipolytica* strain Y2047 as described in the General Methods. The transformant cells were plated onto MM plates lacking uracil and maintained at 30° C. for 2 to 3 days. Then, single colonies of transformant *Yarrowia lipolytica* were patched onto fresh MM plates lacking uracil and allowed to grow at 30° C. for 1 day. The patches were then used to inoculate 3 mL MM liquid medium. Cells were grown for 2 days in MM medium and then 4 days in HGM medium. The cells were collected by centrifugation, lipids were extracted, and fatty acid methyl esters were prepared by trans-esterification, and subsequently analyzed with a Hewlett-Packard 6890 GC, as described in the General Methods.

As shown in Table 12, GC analyses demonstrated conversion of ARA to EPA in each of the clones comprising pFmD17-1, pFmD17-2, pFmD17-3 and pFmD17-4, respectively. Composition of ARA and EPA are presented as a % of the total fatty acids. The conversion efficiency ("Conv. Effic.") was measured according to the following formula: ([product]/[substrate+product])*100, where 'product' includes the immediate product and all products in the pathway derived from it.

TABLE 12

Comparison Of Fatty Acid Composition In *Yarrowia* Strain Y2047 Transformed With pFmD17-1, pFmD17-2, pFmD17-3 and pFmD17-4

| Clone | Plasmid | Mutation With Respect To SEQ ID NO: 2 | % ARA | % EPA | Conv. Effic |
|---|---|---|---|---|---|
| 1 | pFmD17-1 | 351A to T | 3.99 | 1.09 | 21.46 |
| 2 | pFmD17-1 | 351A to T | 3.98 | 1.2 | 23.17 |
| 3 | pFmD17-2 | 155S to P | 4.22 | 1.06 | 20.08 |
| 4 | pFmD17-2 | 155S to P | 4.22 | 1.07 | 20.23 |
| 5 | pFmD17-2 | 155S to P | 4.22 | 1.07 | 20.23 |
| 6 | pFmD17-3 | None | 4.17 | 0.94 | 18.40 |
| 7 | pFmD17-3 | None | 4.04 | 0.98 | 19.52 |
| 8 | pFmD17-3 | None | 4.04 | 0.92 | 18.55 |
| 9 | pFmD17-4 | 155S to P, 351A to T | 4.01 | 1.22 | 23.33 |
| 10 | pFmD17-4 | 155S to P, 351A to T | 4.01 | 1.31 | 24.62 |
| 11 | pFmD17-4 | 155S to P, 351A to T | 3.99 | 1.09 | 21.46 |

The conversion efficiency whereby PaD17* converted ARA to EPA ranged from 18.4 to 24.6%. More specifically, the experimental data demonstrated that the cloned cDNA from *P. aphanidermatum* (SEQ ID NO:2; PaD17) that was present in vector pFmD17-3 functioned as a Δ17 desaturase, efficiently desaturating ARA to EPA (conversion efficiency ranged from 18.4% to 19.52%); however, neither the Ser at amino acid position 155 of SEQ ID NO:2 nor the Ala at amino acid position 351 of SEQ ID NO:2 were required for enzyme activity. The PaD17* variants encoded by SEQ ID NO:3 comprising the 155S to P mutation, the 351A to T mutation, or both mutations (expressed in pFmD17-2, pFmD17-1 and pFmD17-4, respectively) all had greater conversion efficiency than that of PaD17 (SEQ ID NO:2) in pFmD17-3. Transformant cells demonstrating the highest Δ17 desaturase conversion efficiency were those expressing vector pFmD17-4, comprising the PaD17* variant with the S155 to P and A351 to T mutations (SEQ ID NO:3).

Example 8

Synthesis of a Codon-Optimized Δ17 Desaturase Gene of *Pythium aphanidermatum* ("PaD17S") for *Yarrowia lipolytica*

The codon usage of the Δ17 desaturase gene of *Pythium aphanidermatum* (SEQ ID NOs:1 and 2) was optimized for expression in *Yarrowia lipolytica*, in a manner similar to that described in PCT Publication No. WO 2004/101753 and U.S. Pat. No. 7,125,672. Specifically, a codon-optimized Δ17 desaturase gene of *Pythium aphanidermatum* (designated "PaD17S", SEQ ID NO:4) was designed based on the coding sequence of PaD17, according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene,* 265(1-2):11-23 (2001)). In addition to modification of the translation initiation site, 188 bp of the 1080 bp coding region (including the stop codon) were modified (17.4%; FIGS. 5A and 5B) and 175 codons were optimized (48.6%). The GC content was reduced from 61.8% within the wild type gene (i.e., PaD17) to 54.5% within the synthetic gene (i.e., PaD17S). A NcoI site and a NotI site were incorporated around the translation initiation codon and after the stop codon of PaD17S, respectively. None of the modifications in the codon-optimized gene changed the amino acid sequence of the encoded protein (SEQ ID NO:2). The designed PaD17S gene (SEQ ID NO:4) was synthesized by GenScript Corporation (Piscataway, N.J.) and cloned into pUC57 (GenBank Accession No. Y14837) to generate pPaD17S (SEQ ID NO:62).

Example 9

Generation of *Yarrowia lipolytica* Strain Y4070 to Produce about 12% ARA of Total Lipids Via the Δ9 Elongase/Δ8 Desaturase Pathway The present Example describes *Yarrowia lipolytica* strain Y4070, derived from *Yarrowia lipolytica* ATCC #20362, capable of producing about 12% ARA relative to the total lipids via expression of a Δ9 elongase/Δ8 desaturase pathway (FIG. 6A). Strain Y4070 was utilized to test the functional expression of PaD17S in Example 10, infra.

The development of strain Y4070 required the construction of strain Y2224 (a FOA resistant mutant from an autonomous mutation of the Ura3 gene of wildtype *Yarrowia* strain ATCC #20362), strain Y4001 (producing 17% EDA with a Leu− phenotype), strain Y4001U (producing 17% EDA with a Leu− and Ura− phenotype), strain Y4036 (producing 18% DGLA with a Leu− phenotype) and strain Y4036U (producing 18% DGLA with a Leu− and Ura− phenotype).

Generation of Strain Y2224

Strain Y2224 was isolated in the following manner: *Yarrowia lipolytica* ATCC #20362 cells from a YPD agar plate (1% yeast extract, 2% bactopeptone, 2% glucose, 2% agar) were streaked onto a MM plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Generation of Strain Y4001 to Produce about 17% EDA of Total Lipids

Strain Y4001 was created via integration of construct pZKLeuN-29E3 (FIG. 6B). This construct, comprising four chimeric genes (i.e., a Δ12 desaturase, a $C_{16/18}$ elongase and two Δ9 elongases), was integrated into the Leu2 loci of strain Y2224 to thereby enable production of EDA.

Construct pZKLeuN-29E3 contained the components shown in Table 13.

TABLE 13

Description of Plasmid pZKLeuN-29E3 (SEQ ID NO: 63)

| RE Sites And Nucleotides Within SEQ ID NO: 63 | Description Of Fragment And Chimeric Gene Components |
|---|---|
| BsiWI/AscI (7797-7002) | 788 bp 3' portion of *Yarrowia* Leu2 gene (GenBank Accession No. AF260230) |
| SphI/PacI (4302-3591) | 703 bp 5' portion of *Yarrowia* Leu2 gene (GenBank Accession No. AF260230) |
| SwaI/BsiWI (10500-7797) | GPD::F.D12::Pex20, comprising:<br>GPD: *Yarrowia lipolytica* GPD promoter (PCT Publication No. WO 2005/003310);<br>F.D12: *Fusarium moniliforme* Δ12 desaturase gene (PCT Publication No. WO 2005/047485);<br>Pex20: Pex20 terminator sequence from *Yarrowia* Pex20 gene (GenBank Accession No. AF054613) |
| BglII/SwaI (12526-10500) | Exp pro::EgD9E::Lip1, comprising:<br>Exp pro: *Yarrowia lipolytica* export protein (EXP1) promoter (PCT Publication No. WO 2006/052870 and U.S. patent application Ser. No. 11/265,761);<br>EgD9E: codon-optimized Δ9 elongase (SEQ ID NO: 64), derived from *Euglena gracilis* ("EgD9eS"; U.S. patent applications Ser. No. 11/601,563 and Ser. No. 11/601,564);<br>Lip1: Lip1 terminator sequence from *Yarrowia* Lip1 gene (GenBank Accession No. Z50020) |
| PmeI/ClaI (12544-1) | FBAINm::EgD9S::Lip2, comprising:<br>FBAINm: *Yarrowia lipolytica* FBAINm promoter (PCT Publication No. WO 2005/049805);<br>EgD9S: codon-optimized Δ9 elongase gene (SEQ ID NO: 64), derived from *Euglena gracilis* ("EgD9eS"; U.S. patent applications Ser. No. 11/601,563 and Ser. No. 11/601,564);<br>Lip2: Lip2 terminator sequence from *Yarrowia* Lip2 gene (GenBank Accession No. AJ012632) |
| ClaI/EcoRI (1-1736) | LoxP::Ura3::LoxP, comprising:<br>LoxP sequence (SEQ ID NO: 66);<br>*Yarrowia* Ura3 gene (GenBank Accession No. AJ306421);<br>LoxP sequence (SEQ ID NO: 66) |
| EcoRI/PacI (1736-3591) | YAT::ME3S::Pex16, comprising:<br>NT: *Yarrowia lipolytica* YAT1 promoter (Patent Publication No. US 2006/0094102-A1);<br>ME3S: codon-optimized $C_{16/18}$ elongase gene (SEQ ID NO: 67), derived from *M. alpina* (U.S. patent application Ser. No. 11/253,882 and also PCT Publication No. WO 2006/052870);<br>Pex16: Pex16 terminator sequence of *Yarrowia* Pex 16 gene (GenBank Accession No. U75433) |

Plasmid pZKLeuN-29E3 was digested with Asc I/Sph I, and then used for transformation of *Y. lipolytica* strain Y2224 (i.e., ATCC #20362 Ura3−) according to the General Methods. The transformant cells were plated onto MMLeu media plates and maintained at 30° C. for 2 to 3 days. The colonies were picked and streaked onto MM and MMLeu selection plates. The colonies that could grow on MMLeu plates but not on MM plates were selected as Leu− strains. Single colonies of Leu− strains were then inoculated into liquid MMLeu at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EDA in the transformants containing the 4 chimeric genes of pZKLeuN-29E3, but not in the *Yarrowia* Y2224 control strain. Most of the selected 36 Leu− strains produced about 12 to 16.9% EDA of total lipids. There were 3 strains (i.e., strains #11, #30 and

#34) that produced about 17.4%, 17% and 17.5% EDA of total lipids; they were designated as strains Y4001, Y4002 and Y4003, respectively.

Generation of Strain Y4001U (Leu− Ura−) to Produce about 17% EDA of Total Lipids Strain Y4001U was created via temporary expression of the Cre recombinase enzyme in plasmid pY116 (FIG. 6C) within strain Y4001 to produce a Leu− and Ura− phenotype. Construct pY116 contained the following components:

TABLE 14

Description of Plasmid pY116 (SEQ ID NO: 69)

| RE Sites And Nucleotides Within SEQ ID NO: 69 | Description Of Fragment And Chimeric Gene Components |
|---|---|
| 1328-448 | ColE1 plasmid origin of replication |
| 2258-1398 | Ampicillin-resistance gene ($Amp^R$) for selection in *E. coli* |
| 3157-4461 | *Yarrowia autonomous* replication sequence (ARS18; GenBank Accession No. A17608) |
| PacI/SawI 6667-4504 | *Yarrowia* Leu2 gene (GenBank Accession No. AF260230) |
| SwaI/PmeI (6667-218 | GPAT::Cre::XPR2, comprising:<br>GPAT: *Yarrowia lipolytica* GPAT promoter (PCT Publication No. WO 2006/031937);<br>Cre: Enterobacteria phage P1 Cre gene for recombinase protein (GenBank Accession No. X03453);<br>XPR2: ~100 bp of the 3' region of the *Yarrowia* Xpr gene (GenBank Accession No. M17741) |

Plasmid pY116 was used for transformation of freshly grown Y4001 cells according to the General Methods. The transformants were plated onto MMLeu+Ura plates (MMU plus Leucine) containing 280 μg/mL sulfonylurea and maintained at 30° C. for 3 to 4 days. Four colonies were picked, inoculated into 3 mL liquid YPD media at 30° C. and shaken at 250 rpm/min for 1 day. The cultures were diluted to 1:50,000 with liquid MMLeu+Ura media, and 100 μL was plated onto new YPD plates and maintained at 30° C. for 2 days. Colonies were picked and streaked onto MMLeu and MMLeu+Ura selection plates. The colonies that could grow on MMLeu+Ura plates but not on MMLeu plates were selected and analyzed by GC to confirm the presence of C20:2 (EDA). One strain, having a Leu− and Ura− phenotype, produced about 17% EDA of total lipids and was designated as Y4001U.

Generation of Y4036 Strain to Produce about 18% DGLA of Total Lipids

Construct pKO2UF8289 (FIG. 7A; SEQ ID NO:70) was generated to integrate four chimeric genes (comprising a Δ12 desaturase, one Δ9 elongase and two mutant Δ8 desaturases) into the Δ12 loci of strain Y4001U1, to thereby enable production of DGLA. Construct pKO2UF8289 contained the following components:

TABLE 15

Description of Plasmid pKO2UF8289 (SEQ ID NO: 70)

| RE Sites And Nucleotides Within SEQ ID NO: 70 | Description Of Fragment And Chimeric Gene Components |
|---|---|
| AscI/BsiWI (10304-9567) | 5' portion of *Yarrowia* Δ12 desaturase gene (PCT Publication No. WO 2004/104167) |
| EcoRI/SphI (13568-13012) | 3' portion of *Yarrowia* Δ12 desaturase gene (PCT Publication No. WO 2004/104167) |
| SwaI/BsiWI (7055-9567) | FBAINm::EgD8M::Pex20, comprising: FBAINm: *Yarrowia lipolytica* FBAINm promoter (PCT Publication No. WO 2005/049805; U.S. Pat. No. 7,202,356); EgD8M: Synthetic mutant Δ8 desaturase ("EgD8S-23"; SEQ ID NO: 71; U.S. patent application Ser. No. 11/635,258), derived from *Euglena gracilis* ("EgD8S"; PCT Publication No. WO 2006/012326); Pex20: Pex20 terminator sequence from *Yarrowia* Pex20 gene (GenBank Accession No. AF054613) |
| SwaI/PmeI (7055-4581) | YAT::F.D12::OCT, comprising: YAT: *Yarrowia lipolytica* YAT1 promoter (Patent Publication No. US 2006/0094102-A1); F.D12: *Fusarium moniliforme* Δ12 desaturase gene (PCT Publication No. WO 2005/047485); OCT terminator sequence of Yarrowia OCT gene (GenBank Accession No. X69988) |
| PmeI/PacI (4581-2124) | EXP::EgD8M::Pex16, comprising: EXP: *Yarrowia lipolytica* export protein (EXP1) promoter (PCT Publication No. WO 2006/052870 and U.S. patent application Ser. No. 11/265,761); EgD8M: Synthetic mutant Δ8 desaturase ("EgD8S-23"; SEQ ID NO: 71; U.S. patent application Ser. No. 11/635,258), derived from *Euglena gracilis* ("EgD8S"; PCT Publication No. WO 2006/012326); Pex16: Pex16 terminator of *Yarrowia* Pex16 gene (GenBank Accession No. U75433) |
| PmeI/ClaI (2038-1) | GPAT::EgD9e::Lip2, comprising: GPAT: *Yarrowia lipolytica* GPAT promoter (PCT Publication No. WO 2006/031937); EgD9e: *Euglena gracilis* Δ9 elongase gene (SEQ ID NO: 73) (U.S. patent applications Ser. No. 11/601,563 and Ser. No. 11/601,564); Lip2: Lip2 terminator sequence from *Yarrowia* Lip2 gene (GenBank Accession No. AJ012632) |
| ClaI/EcoRI (13568-1) | LoxP::Ura3::LoxP, comprising: LoxP sequence (SEQ ID NO: 66); *Yarrowia* Ura3 gene (GenBank Accession No. AJ306421); LoxP sequence (SEQ ID NO: 66) |

The pKO2UF8289 plasmid was digested with AscI/SphI, and then used for transformation of strain Y4001U1 according to the General Methods. The transformants were plated onto MMLeu plates and maintained at 30° C. for 2 to 3 days. The colonies were picked and streaked onto MMLeu selection plates at 30° C. for 2 days. These cells were then inoculated into liquid MMLeu at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKO2UF8289, but not in the parent Y4001U1 strain. Most of the selected 96 strains produced between 7 and 13% DGLA of total lipids. There were 6 strains (i.e., #32, #42, #60, #68, #72 and #94) that produced about 15%, 13.8%, 18.2%, 13.1%, 15.6% and 13.9% DGLA of total lipids. These six strains were designated as Y4034, Y4035, Y4036, Y4037, Y4038 and Y4039, respectively.

Generation of Strain Y4036U (Leu−, Ura3−) to Produce about 18% DGLA of Total Lipids Construct pY116 (FIG. 6C; SEQ ID NO:69) was utilized to temporarily express a Cre recombinase enzyme in strain Y4036. This released the LoxP sandwiched Ura3 gene from the genome.

Plasmid pY116 was used to transform strain Y4036 according to the General Methods. Following transformation, the cells were plated onto MMLeu+Ura plates (MMU plus Leucine) and maintained at 30° C. for 2 to 3 days. The individual colonies grown on MMLeu+Ura plates were picked, and streaked into YPD liquid media at 30° C. and shaken at 250 rpm/min for 1 day to cure the pY116 plasmid. The grown cultures were streaked on MMLeu+Ura u plates. After two days at 30° C., the individual colonies were re-streaked on MMLeu+Ura, MMU and MMLeu plates. Those colonies that could grow on MMLeu+Ura, but not on MMU or MMLeu plates were selected. One of these strains with Leu− and Ura− phenotypes was designated as Y4036U (Ura−, Leu−).

Generation of Y4070 Strain to Produce about 12% ARA of Total Lipids

Construct pZKSL-555R (FIG. 7B; SEQ ID NO:74) was generated to integrate three Δ5 desaturase genes into the Lys loci of strain Y4036U, to thereby enable production of ARA. The pZKSL-555R plasmid contained the following components:

TABLE 16

Description of Plasmid pZKSL-555R (SEQ ID NO: 74)

| RE Sites And Nucleotides Within SEQ ID NO: 74 | Description Of Fragment And Chimeric Gene Components |
|---|---|
| AscI/BsiWI (3321-2601) | 720 bp 5' portion of *Yarrowia* Lys5 gene (GenBank Accession No. M34929) |
| PacI/SphI (6716-6029) | 687 bp 3' portion of *Yarrowia* Lys5 gene (GenBank Accession No. M34929) |
| BglII/BsiWI (15-2601) | EXP::EgD5S::Pex20, comprising: EXP: *Yarrowia lipolytica* export protein (EXP1) promoter (PCT Publication No. WO 2006/052870 and U.S. patent application Ser. No. 11/265,761); EgD5S: codon-optimized Δ5 desaturase (SEQ ID NO: 75), derived from *Euglena gracilis* (U.S. patent application Ser. No. 11/748,629); Pex20: Pex20 terminator sequence from *Yarrowia* Pex20 gene (Gen Bank Accession No. AF054613) |
| ClaI/PmeI (11243-1) | YAT::RD5S::OCT, comprising: YAT: *Yarrowia lipolytica* YAT1 promoter (Patent Publication No. US 2006/0094102-A1); RD5S: codon-optimized Δ5 desaturase (SEQ ID NO: 77), derived from *Peridinium* sp. CCMP626 (U.S. patent application Ser. No. 11/748,637); OCT: OCT terminator sequence of *Yarrowia* OCT gene (GenBank Accession No. X69988) |
| EcoRI/PacI (9500-6716) | FBAIN::EgD5WT::Aco, comprising: FBAIN: *Yarrowia lipolytica* FBAIN promoter (PCT Publication No. WO 2005/049805); EgD5WT: *Euglena gracilis* Δ5 desaturase (SEQ ID NO: 79; U.S. patent application Ser. No. 11/748,629) with elimination of internal BglII, HindIII and NcoI restriction enzyme sites; Aco: Aco terminator of *Yarrowia* Aco gene (GenBank Accession No. AJ001300) |
| EcoRI/ClaI (9500-11243) | *Yarrowia* Leu2 gene (GenBank Accession No. M37309) |

The pZKSL-555R plasmid was digested with AscI/SphI, and then used for transformation of strain Y4036U according to the General Methods. The transformant cells were plated onto MMLeuLys plates (MMLeu plus Lysine) and maintained at 30° C. for 2 to 3 days. Single colonies were then re-streaked onto MMLeuLys plates, and then inoculated into liquid MMLeuLys at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of ARA in the transformants containing the 3 chimeric genes of pZKSL-555R, but not in the parent Y4036U strain. Most of the selected 96 strains produced ~10% ARA of total lipids. There were 4 strains (i.e., #57, #58, #69 and #75) that produced about 11.7%, 11.8%, 11.9% and 11.7% ARA of total lipids. These four strains were designated as Y4068, Y4069, Y4070 and Y4071, respectively. Further analyses showed that the three chimeric genes of pZKSL-555R were not integrated into the Lys5 site in the Y4068, Y4069, Y4070 and Y4071 strains. All strains possessed a Lys+ phenotype.

The final genotype of strain Y4070 with respect to wildtype *Yarrowia lipolytica* ATCC #20362 was Ura3−, Leu+, Lys+, GPD::F.D12::Pex20, YAT::F.D12::OCT, YAT::ME3S::Pex16, GPAT::EgD9e::Lip2, Exp::EgD9eS::Lip1, FBAINm::EgD9eS::Lip2, FBAINm::EgD8M::Pex20, EXP::EgD8M::Pex16, FBAIN::EgD5WT::Aco, EXP::EgD5S::Pex20, YAT::RD5S::OCT.

Example 10

Generation of Construct pFBAINPaD17S (Comprising the Codon-Optimized Δ17 Desaturase Gene "PaD17S") and Expression in *Yarrowia lipolytica*

The present Example describes functional analysis of PaD17S in *Yarrowia lipolytica* strain Y4070 (Example 9). Thus, following construction of plasmid pFBAINPaD17S (SEQ ID NO:102) comprising a chimeric FBAINm::PaD17S::Pex20 gene and transformation, lipid profiles within the transformant organisms were compared.

Specifically, plasmid pFBAINPaD17S was constructed by three-way ligation using 5' PaD17S and 3' PaD17S fragments from plasmid pPaD17S (Example 8; wherein the 5' PaD17S fragment was generated by NcoI and BglII digestion and wherein the 3' PaD17S fragment was generated by BglII and NotI digestion, as described in Example 5) and plasmid pFBAIN-MOD-1 (SEQ ID NO:80; FIG. 8A) predigested with NcoI and NotI. Thus, PaD17S was operably linked with the *Yarrowia lipolytica* FBAINm promoter (PCT Publication No. WO 2005/049805; U.S. Pat. No. 7,202,356) and the PEX20-3' terminator region of the *Yarrowia* Pex20 gene (GenBank Accession No. AF054613).

Plasmid pFBAINPaD17S (SEQ ID NO:102) was transformed into *Yarrowia lipolytica* strain Y4070 and transformants were selected on SD-Ura plates (comprising: 20 g/L agar; 6.7 g/L YNB without amino acids but with ammonium sulfate; 20 g/L glucose; 20 mg/L each of adenine sulfate, L-tryptophan, L-histidine-HCl, L-arginine-HCl, L-methionine; 30 mg/L each of L-tyrosine, L-leucine, L-isoleucine, L-lysine-HCl; 50 mg/L L-phenylalanine; 100 mg/mL each of L-glutamic acid, L-aspartic acid; 150 mg/L L-valine; 200 mg/L L-threonine; and 400 mg/L L-serine).

The fatty acid profile and conversion efficiency of four transformants were determined as described in Example 7. The results of GC analysis are shown in Table 17; composition of ARA and EPA are presented as a % of the total fatty acids.

TABLE 17

Comparison Of Fatty Acid Composition In *Yarrowia* Strain Y4070 Transformed With pFBAINPaD17S, Comprising PaD17S

| Clone | Plasmid | % ARA | % EPA | Conver. Effic. (%) |
|---|---|---|---|---|
| 1 | pFBAIN-MOD-1 | 13.23 | 0 | 0 |
| 2 | pFBAIN-MOD-1 | 13.20 | 0 | 0 |
| 3 | pFBAINPaD17S | 6.22 | 7.34 | 54.1 |
| 4 | pFBAINPaD17S | 6.15 | 7.73 | 54.7 |
| 5 | pFBAINPaD17S | 6.04 | 7.34 | 54.9 |
| 6 | pFBAINPaD17S | 6.02 | 7.53 | 55.6 |

The GC results demonstrated production of ARA and EPA in the transformants carrying pFBAINPaD17S, but only production of ARA in transformants carrying the control plasmid pFBAIN-MOD-1 (FIG. 8A, vector only). The conversion efficiency of the codon-optimized *P. aphanidermatum* Δ17 desaturase (PaD17S; SEQ ID NO:4) ranged between 54.1% to 55.6%, compared with 18.4 to 19.5% conversion efficiency for the wild-type PaD17 (SEQ ID NO:2).

Example 11

Identification of a *Phytophthora sojae* Gene Encoding Δ17 Desaturase

The present Example, disclosed in U.S. patent application Ser. No. 11/787,772, describes the identification of a Δ17 desaturase from *Phytophthora sojae* (SEQ ID NOs:44 and 45).

The U.S. Department of Energy's Joint Genome Institute ("JGI"; Walnut Creek, Calif.) created version 1.0 of the *Phytophthora sojae* genome (estimated genome size is 95 Mbp). This genomic sequence was generated using a whole genome shotgun strategy and comprises a total of 19,276 gene models.

Using the amino acid sequence of the Δ17 desaturase of *Phytophthora infestans* (GenBank Accession No. CAJ30870; designated as "PiD17" herein and corresponding to SEQ ID NO:43) as a query sequence, a TBLASTN (BLAST protein versus translated nucleotide) search was conducted against JGI's *Phytophthora sojae* database (using the default parameters available from JGI). One *P. sojae* ORF located on scaffold 17:338148-339167 was found to share extensive homology with PiD17 (i.e., 91.8% identity and 95.6% similarity, with an Expectation value of 0). Based on this homology, the *P. sojae* ORF was tentatively identified as a Δ17 desaturase and was designated as "PsD17". When the 1092 bp DNA sequence of PsD17 (SEQ ID NO:44) was retrieved from the database, it was found to encode a polypeptide of 363 amino acids in length (SEQ ID NO:45). Amino acid sequence alignment using a Clustal W analysis (MegAlign™ program of DNASTAR software) showed that there was 90.9% identity between PiD17 and PsD17; in contrast, the nucleotide sequences shared only 86.6% identity.

The sequence homology of PsD17 to all publicly available protein sequences contained in the "nr" database (see General Methods) was also determined by conducting protein-protein BLAST searches using PsD17 (SEQ ID NO:45) as the query sequence. Based on this analysis, PsD17 was found to share the most homology with the omega-3 fatty acid desaturase of *Saprolegnia diclina* (GenBank Accession No. AAR20444); specifically, PsD17 had 60% identity and 74% similarity with the amino acid sequence of GenBank Accession No. AAR20444 with an Expectation value of 7E-117. Additionally, PsD17 had 39% identity and 57% similarity with the amino acid sequence of the fatty acid desaturase of *Anabaena variabilis* ATCC #29413 (GenBank Accession No. ABA23809), with an Expectation value of 4E-57.

Example 12

Synthesis of a Codon-Optimized Δ17 Desaturase Gene ("PsD17S") for *Yarrowia lipolytica*

The present Example, disclosed in U.S. patent application Ser. No. 11/787,772, describes the creation of a synthetic Δ17 desaturase, derived from *Phytophthora sojae* (SEQ ID NOs: 44 and 45) and codon-optimized for expression in *Yarrowia lipolytica* (SEQ ID NOs:81 and 82).

The codon usage of the Δ17 desaturase gene of *Phytophthora* sojae was optimized for expression in *Yarrowia lipolytica*, in a manner similar to that described in U.S. Pat. No. 7,125,672. Specifically, a codon-optimized Δ17 desaturase gene (designated "PsD17S", SEQ ID NOs:81 and 82) was designed based on the coding sequence of PsD17 (SEQ ID NOs:44 and 45), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, Gene, 265(1-2):11-23 (2001)). In addition to modification of the translation initiation site, 175 bp of the 1092 bp coding region were modified (16.0%) and 168 codons were optimized (46.2%). The GC content was reduced from 65.1% within the wild type gene (i.e., PsD17) to 54.5% within the synthetic gene (i.e., PsD17S). A NcoI site and NotI sites were incorporated around the translation initiation codon and after the stop codon of PsD17S (SEQ ID NO:81), respectively. FIG. 9 shows a comparison of the nucleotide sequences of PsD17 and PsD17S. At the amino acid level, PsD17S lacked the third and forth amino acid, as compared with the wild type PsD17; thus, the total length of PsD17S is 361 amino acids (SEQ ID NO:82). The designed PsD17S gene was synthesized by GenScript Corporation (Piscataway, N.J.) and cloned into pUC57 (GenBank Accession No. Y14837) to generate pPsD17S (SEQ ID NO:83).

Example 13

Identification of a *Phytophthora ramorum* Gene Encoding Δ17 Desaturase

The present Example, disclosed in U.S. patent application Ser. No. 11/787,772, describes the identification of a Δ17 desaturase from *Phytophthora ramorum* (SEQ ID NOs:46 and 47).

The U.S. Department of Energy's Joint Genome Institute ("JGI"; Walnut Creek, Calif.) created version 1.0 of the *Phytophthora ramorum* genome (estimated genome size is 65 Mbp). This genomic sequence was generated using a whole genome shotgun strategy and comprises a total of 16,066 gene models.

In a manner similar to that described in Example 11, the amino acid sequence of PiD17 (SEQ ID NO:43) was used as a query sequence to perform a TBLASTN search against JGI's *Phytophthora ramorum* database (using the default parameters available from JGI).

Two ORFs were found to share extensive homology with PiD17 in the genome sequence of *Phytophthora ramorum*. Specifically, ORF 80222 shared 89% identity and 94% similarity with SEQ ID NO:43, with an Expectation value of 0, Similarly, ORF48790 shared up to 40% identity and 61% similarity with SEQ ID NO:43, with an Expectation value of 6E-44. Based on these results, ORF 80222 was tentatively identified as a Δ17 desaturase and was designated as "PrD17".

When the 1086 bp DNA sequence of PrD17 (SEQ ID NO:46) was retrieved from the database, it was found to encode a polypeptide of 361 amino acids in length (SEQ ID NO:47). Amino acid sequence alignment using a Clustal W analysis (MegAlign™ program of DNASTAR software) showed that there was 89.5% identity between PiD17 and PrD17; in contrast, the nucleotide sequences shared only 85.7% identity.

The sequence homology of PrD17 was in turn compared with all publicly available protein sequences contained in the "nr" database (see General Methods) by conducting protein-protein BLAST searches using PrD17 (SEQ ID NO:47) as the query sequence. The sequence that showed the highest degree of similarity was that of the omega-3 fatty acid desaturase of *Saprolegnia diclina* (GenBank Accession No. AAR20444), sharing 59% identity and 74% similarity, with an Expectation value of E-124. Additionally, PrD17 had 38% identity and 57% similarity with the amino acid sequence of the fatty acid desaturase of *Anabaena variabilis* ATCC #29413 (GenBank Accession No. ABA23809), with an Expectation value of 6E-61.

Example 14

Synthesis of a Codon-Optimized Δ17 Desaturase Gene ("PrD17S") for *Yarrowia lipolytica*

The present Example, disclosed in U.S. patent application Ser. No. 11/787,772, describes the creation of a synthetic Δ17 desaturase, derived from *Phytophthora ramorum* (SEQ ID NOs:46 and 47) and codon-optimized for expression in *Yarrowia lipolytica* (SEQ ID NOs:84 and 47).

The codon usage of the Δ17 desaturase gene of *Phytophthora* ramorum was optimized for expression in *Yarrowia lipolytica*, in a manner similar to that described in U.S. Pat. No. 7,125,672. Specifically, a codon-optimized Δ17 desaturase gene (designated "PrD17S", SEQ ID NO:84) was designed based on the coding sequence of PrD17 (SEQ ID NOs:46 and 47), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, Gene, 265(1-2):11-23 (2001)). In addition to modification of the translation initiation site, 168 bp of the 1086 bp coding region were modified (15.5%) and 160 codons were optimized (44.2%). The GC content was reduced from 64.4% within the wild type gene (i.e., PrD17) to 54.5% within the synthetic gene (i.e., PrD17S). A NcoI site and NotI sites were incorporated around the translation initiation codon and after the stop codon of PrD17S (SEQ ID NO:84), respectively. FIG. 10 shows a comparison of the nucleotide sequences of PrD17 and PrD17S, None of the modifications in the codon-optimized gene changed the amino acid sequence of the encoded protein (SEQ ID NO:47). The designed PrD17S gene was synthesized by GenScript Corporation (Piscataway, N.J.) and cloned into pUC57 (GenBank Accession No. Y14837) to generate pPrD17S (SEQ ID NO:85).

Example 15

Generation of Constructs pY130, pY138, pY139 and pY140 (Comprising A *Fusarium moniliforme* Δ15 Desaturase. PrD17S, PsD17S And PaD17S) for Comparison of Omega-6 Fatty Acid Substrate Specificity The present Example, and related Examples 16 and 17 (infra) describe comparison of the substrate specificity of a *Fusarium moniliforme* Δ15 desaturase (FmD15; SEQ ID NOs:86 and 87) to that of PaD17S (SEQ ID NOs:4 and 2), PrD17S (SEQ ID NOs:84 and 47) and PsD17S (SEQ ID NOs:81 and 82) in *Yarrowia lipolytica.*

This work included the following steps: (1) construction of *Yarrowia* expression vectors pY130 (comprising FmD15), pY138 (comprising PrD17S), pY139 (comprising PsD17S) and pY140 (comprising PaD17S), as described in Example 15 herein; (2) construction of a Δ12 desaturase-disrupted strain of *Yarrowia lipolytica* ATCC #76982, identified as strain L38, as described in Example 16; 3.) transformation of pY130, pY138, pY139 and pY140 into wildtype *Yarrowia* and *Yarrowia* strain L38, as described in Example 17; and, 4.) comparison of lipid profiles within transformant organisms comprising of pY130, pY138, pY139 or pY140 after feeding fatty acid substrates, as described in Example 17.

Experimental Basis

Omega-3 desaturases, which include both Δ15 desaturases that act on C18 fatty acids substrates and Δ17 desaturases that act on C20 fatty acids substrates, play an important role in the biosynthesis of long chain PUFAs by converting ω-6 fatty acids into their ω-3 counterparts (FIG. 1). It is well known that some fungal ω-3 desaturases show broad catalytic promiscuity. For example, the Δ15 desaturases of *Fusarium moniliforme* (GenBank Accession No. DQ272516.1) and *Magnaporthe grisea* (GenBank Accession No. XP_362963) both additionally have limited Δ17 desaturase activity (PCT Publications No. WO 2005/047485 and No. WO 2005/047480; U.S. patent application Ser. No. 11/740,298).

Similarly, the synthetic Δ17 desaturase derived from *Phytopthora sojae* and codon-optimized for expression in *Yarrowia lipolytica* (i.e., PsD17S) was previously demonstrated in U.S. patent application Ser. No. 11/787,772 to have both Δ17 and Δ15 desaturase activities. More specifically, PsD17S displayed "bifunctional Δ17 desaturase activity" or "primary Δ17 desaturase activity", wherein the desaturase preferentially converts ARA to EPA and/or DGLA to ETA but additionally has limited ability to convert LA into ALA (thus exhibiting primarily Δ17 desaturase activity and limited Δ15 desaturase activity).

Despite the broad catalytic promiscuity described above, not all ω-3 desaturases possess bifunctional activity. For example, the *Saprolegnia diclina* Δ17 desaturase functions exclusively on C20 ω6 fatty acid substrates (Pereira, S. L. et. al., *Biochem. J.,* 378:665 (2004)).

The purpose of the following Examples was to compare the relative ω-6 fatty acid substrate specificities of Δ17 desaturases from *Phytopthora sojae* (PsD17S; SEQ ID NOs:81 and 82), *Phytopthora ramorum* (PrD17S; SEQ ID NOs:84 and 47) and *Pythium aphanidermatum* (PaD17S; SEQ ID NOs:4 and 2) with that of the previously characterized *Fusarium moniliforme* Δ15 desaturase (FmD15; SEQ ID NOs:86 and 87). In contrast to previous work performed with PsD17S and PrD17S in U.S. patent application Ser. No. 11/787,772, the ω-3 desaturases were expressed herein in *Yarrowia lipolytica* strains lacking desaturases and elongases involved in converting LA to EPA, since their presence allows alternative routes for long-chain PUFA biosynthesis (FIG. 1). As a result, interpretation concerning ω-6 substrate specificity in PrD17S, PsD17S and PaD17S is much clearer than in previous work.

Construction of *Yarrowia* Expression Vector pY130, Comprising FmD15 Plasmid pY6.GPD.Leu2 (SEQ ID NO:88) is a shuttle plasmid that can replicate both in *E. coli* and *Yarrowia lipolytica*, containing the following: a *Yarrowia* autonomous replication sequence (ARS18; GenBank Accession No. M91600); a ColE1 plasmid origin of replication; an *E. coli* f1 origin of replication; an ampicillin-resistance gene (AmpR) for selection in *E. coli*; a *Yarrowia* Leu2 gene (GenBank Accession No. AF260230) for selection in *Yarrowia*; and, a chimeric GPD::NcoI/NotI::XPR cassette. The *Yarrowia* "GPD promoter" refers to the 5' upstream untranslated region in front of the 'ATG' translation initiation codon of a protein encoded by the *Yarrowia lipolytica* glyceraldehyde-3-phosphate dehydrogenase (GPD) gene and that is necessary for expression (PCT Publication No. WO 2005/003310). "XPR" refers to ~100 bp of the 3' region of the *Yarrowia* Xpr gene (GenBank Accession No. M117741). Although the construction of plasmid pY6.GPD.Leu2 is not described herein in detail, it was derived from pY28 GPD.YID12d (previously described in U.S. patent application Ser. No. 11/740,298, filed Apr. 26, 2007, and comprising a chimeric GPD::*Yarrowia lipolytica* Δ12 desaturase (Yld12d)::Lip1 gene cassette).

The *Fusarium moniliforme* Δ15 desaturase was derived from plasmid pY34 which was previously described in PCT Publication No. WO 2005/047485 (the contents of which are hereby incorporated by reference), first by a single bp substitution at position 180 of the FmD15 desaturase ORF. This C180T "silent" mutation resulted in the loss of the NcoI site in the ORF for cloning convenience. Then, the modified sequence was used to PCR the ORF using 5' and 3' PCR primers with NcoI and NotI restriction sites, and the resultant NcoI-NotI fragment containing the FmD15 desaturase ORF (SEQ ID NO:86) was used to replace the Yld12d ORF in plasmid pY28 described supra using NcoI and Not I sites to produce pY130 (SEQ ID NO:89; FIG. 11A [labeled as "pY130.GPD.Fmd15" therein]).

The 9048 bp sequence of expression vector pY130 containing the chimeric GPD::FmD15::Lip1 gene is disclosed in SEQ ID NO:89 and described in the table below.

TABLE 18

Description of Plasmid pY130 (SEQ ID NO: 89)

| RE Sites And Nucleotides Within SEQ ID NO: 89 | Description Of Fragment And Chimeric Gene Components |
|---|---|
| BsiWI-SphI | Contains:<br>ColE1 plasmid origin of replication (157-1037 bp);<br>ampicillin resistance gene ($Amp^R$) for selection in *E. coli* (1107-1967 bp);<br>*E. coli* f1 origin of replication (2147-2537 bp);<br>*Yarrowia* autonomous replication sequence (ARS18; GenBank Accession No. A17608) (2866-4143 bp) |
| SphI-NcoI | Contains:<br>*Yarrowia* LEU2 gene (GenBank Accession No. AF260230) (4152-6379 bp);<br>*Yarrowia* GPD promoter (corresponding to 825835-826763 bp in GenBank Accession No. CR382129, except for a single bp change (C826238T) made to destroy the NcoI for cloning convenience and two unexpected changes: a single A insertion at position 826161 and a 37 bp direct repeat of nucleotides 825884-825922) (6382-7346 bp) |

TABLE 18-continued

| Description of Plasmid pY130 (SEQ ID NO: 89) | |
|---|---|
| RE Sites And Nucleotides Within SEQ ID NO: 89 | Description Of Fragment And Chimeric Gene Components |
| NcoI-NotI | Contains *Fusarium moniliforme* (*Gibberella fujikuroi*) Δ15 desaturase ORF (SEQ ID NO: 86) (GenBank Accession No. DQ272516.1; PCT Publication No. WO 2005/047480; except for a single silent bp change (C180A) to destroy the NcoI site for cloning convenience) (7350-8558 bp) |
| NotI-BsiWI | Contains Lip1: Lip1 terminator sequence from *Yarrowia* Lip1 gene (GenBank Accession No. Z50020) (8567-8888 bp) |

Construction of *Yarrowia* Expression Vectors pY138 (Comprising PrD17S). pY139 (Comprising PsD17S) and pY140 (Comprising PaD17S)

The NcoI-NotI fragment comprising FmD15 in pY130 was replaced by similarly digested fragments comprising the synthetic Δ17 desaturase ORFs of *Phytopthora ramorum* and *Phytopthora sojae* that had been codon-optimized for expression in *Yarrowia* (i.e., PrD17S and PsD17S, respectively) from the source plasmids pPrD17S (SEQ ID NO:85; Example 14, supra) and pPsD17S (SEQ ID NO:83; Example 12, supra). This produced plasmids pY138 (SEQ ID NO:90; FIG. 11B [labeled as "pY138 GPD-PrD17" therein]) and pY139 (SEQ ID NO:91; FIG. 11C [labeled as "pY139 GPD PsD17" therein]), respectively.

A similar strategy was used to substitute the FmD15 ORF in pY130 with the synthetic Δ17 desaturase ORF of *Pythium aphanidermatum* from the source plasmid pPaD17S (SEQ ID NO:62; Example 8, supra); however, since PaD17S contained an internal NcoI site, this was achieved by a three-way ligation of the NcoI-BglII and BglII-NotI fragments of PaD17S into the pY130 vector backbone. This resulted in formation of plasmid pY140 (SEQ ID NO:92), as shown in FIG. 11D (labeled as "pY140 GPD-PaD17" therein).

Example 16

Generation of *Yarrowia lipolytica* Δ12 Knockout Strain L38

The present Example, disclosed in U.S. patent application Ser. No. 11/740,298, describes the creation of a Δ12 desaturase-disrupted [Δ12 knockout (KO)] strain of *Yarrowia lipolytica* ATCC #76982, identified as strain L38 and referred to generically as a "d12KO" strain. The only native Δ12 desaturase gene of this strain was disrupted by replacement with a disrupted version via homologous recombination.

The methodology used to create the d12KO strain identified herein as L38 relied on site-specific recombinase systems, as described in the General Methods.

Experimental Methodology

*Yarrowia lipolytica* ATCC #76982 was transformed with SphI and AscI linearized plasmid pY137. The sequence of plasmid pY137 (labeled as pY137.YlD12ko.Leu2 in FIG. 12A) is disclosed as SEQ ID NO:93 and pY137 Is described in the table below.

TABLE 19

| Description of pY137 (SEQ ID NO: 93) | |
|---|---|
| RE Sites And Nucleotides Within SEQ ID NO: 93 | Description Of Fragment And Chimeric Gene Components |
| PacI-BglII [digestion with PacI-Sa/I releases LoxP::Leu2] | Contains LoxP::Leu2::LoxP, comprising: LoxP sequence (SEQ ID NO: 66) (28-61 bp); *Yarrowia* LEU2 gene (GenBank Accession No. AF260230) (68-2228 bp); LoxP sequence (SEQ ID NO: 66) (2308-2341) |
| BglII-AscI | Contains 3' portion of *Yarrowia lipolytica* Δ12 desaturase gene (2357-2950 bp) that corresponds to 661-1254 bp of GenBank Accession No. XM_500707 |
| AscI-SphI | Contains: ColE1 plasmid origin of replication (3003-3883); ampicillin resistance gene ($Amp^R$) for selection in *E. coli* (3941-4801); *E. coli* f1 origin of replication (5009-5409) |
| SphI-PacI | Contains 5' portion of *Yarrowia lipolytica* Δ12 desaturase gene (5662-6262 bp) that corresponds to 1-601 bp of GenBank Accession No. XM_500707 |

Eleven LEU prototrophic pY137 transformants were analyzed by GC and four were identified as Δ12 knockout (d12KO) strains by the absence of detectable 18:2 (LA) upon GC analysis. One of these was designated strain L37.

The LEU2 gene in d12KO strain L37 was excised by transient expression of Cre recombinase under the control of the *Yarrowia* glycerol-3-phosphate acyltransferase (GPAT) promoter. Specifically, strain L37 was transformed with plasmid pY117. The mutated *Yarrowia* AHAS enzyme in plasmid pY117 conferred $SU^R$, which was used as a positive screening marker.

Plasmid pY117 was derived from plasmid pY116 (described in Table 14 herein and in U.S. patent application Ser. No. 11/635,258) by inserting the mutant AHAS gene flanked by PacI-SwaI sites into PacI-SwaI digested pY116 thereby replacing the LEU selectable marker with the sulfonylurea marker. Plasmid pY117 (SEQ ID NO:94) is represented in FIG. 12B (labeled therein as pY117.Cre.AHASw497L) and is described in Table 20 below.

TABLE 20

| Description of pY117 (SEQ ID NO: 94) | |
|---|---|
| RE Sites And Nucleotides Within SEQ ID NO: 94 | Description Of Fragment And Chimeric Gene Components |
| BsiWI-Eco RI | Contains: ColE1 plasmid origin of replication (448-1328); ampicillin resistance gene ($Amp^R$) for selection in *E. coli* (1328-2258, complementary); *E. coli* f1 origin of replication (2438-2838) |
| Eco RI-PacI | *Yarrowia* autonomous replication sequence (ARS18; GenBank Accession No. A17608) (3157-4461 bp) |
| PacI-SwaI | *Yarrowia lipolytica* AHAS gene (corresponding to 27040-30026 bp [complementary] in Genbank Accession No. CR382129) comprising a W497L mutation (3157-4461 bp) |
| SwaI/BsiWI [digestion with SwaI-NotI | Contains GPAT::Cre::XPR2 comprising: GPAT: *Yarrowia lipolytica* GPAT promoter (PCT Publication No. WO 2006/031937) (7498-8535 bp); |

TABLE 20-continued

| Description of pY117 (SEQ ID NO: 94) | |
|---|---|
| RE Sites And Nucleotides Within SEQ ID NO: 94 | Description Of Fragment And Chimeric Gene Components |
| releases GPAT::Cre] | Cre: Enterobacteria phage P1 Cre gene for recombinase protein (GenBank Accession No. X03453) (8537-9570 bp) except for single base change (T4G) resulting in a single amino acid change (S2A) to create a NcoI site for cloning convenience;<br>XPR2: ~170 bp of the 3' region of the *Yarrowia* Xpr gene (GenBank Accession No. M17741) |

L37 transformed by pY117 were plated on minimal plates containing Leu and 280 μg/mL sulfonylurea (chlorimuron ethyl, E.I. duPont de Nemours & Co., Inc., Wilmington, Del.). To cure the strains of pY117, two $SU^R$ colonies were used to inoculate 3 mL YPD. After overnight growth at 30° C., 100 μl of 1:250,000 diluted cultures were plated on YPD plates. After overnight growth at 30° C., 6 single colonies were streaked on both YPD and MM plates. All grew on YPD but not on MM plates, confirming their Leu auxotrophy. One of these was designated as strain L38.

Example 17

Expression of Constructs pY130, pY138, pY139 and pY140 (Comprising FmD15. PrD17S, PsD17S And PaD17S) in *Yarrowia lipolytica* Strains for Comparison of Omega-6 Fatty Acid Substrate Specificity The present Example describes transformation of expression plasmids pY130, pY138, pY139 and pY140 into *Yarrowia lipolytica* ATCC #76982, followed by comparison of lipid profiles within transformant organisms.

Transformation

The following expression plasmids were transformed into wild type (WT) *Yarrowia lipolytica* ATCC #76982 and its Δ12 desaturase-disrupted derivative (Δ12 KO) strain L38 (Example 16), as described in the General Methods: 1.) plasmid pY130 (comprising FmD15); 2.) plasmid pY138 (comprising PrD17S); 3.) plasmid pY139 (comprising PsD17S); 4.) plasmid pY140 (comprising PaD17S); and, 5.) plasmid pY6.GPD.Leu2 (empty vector control lacking any desaturase ORF; also referred to as plasmid "pY6").

Comparison of Lipid Profiles without Substrate Feeding

Three independent transformants from each transformation were streaked on MM plates. Fresh cultures were used to separately inoculate 3 mL MM in triplicate. After growth in a shaker at 30° C. for 2 days, cells from 2 mL aliquots of each were collected by centrifugation, lipids were extracted, and fatty acid methyl esters were prepared by trans-esterification, and subsequently analyzed with a Hewlett-Packard 6890 GC.

The fatty acid profiles for *Yarrowia lipolytica* expressing pY6 (SEQ ID NO:88), pY130 (SEQ ID NO:89), pY138 (SEQ ID NO:90), pY139 (SEQ ID NO:91) and pY140 (SEQ ID NO:92) are shown below in Table 21. In Table 21, fatty acids are identified as 16:0 (palmitate), 16:1, 18:0 (stearic acid), 18:1 (oleic acid), 18:2 (LA) and ALA. Fatty acid compositions were expressed as the weight percent (wt. %) of total fatty acids. The conversion efficiency ("CE") was measured according to the following formula: ([product]/[substrate+product])*100, where 'product' includes the immediate product and all products in the pathway derived from it. Thus, Δ12 activity (i.e., "d12d CE") was calculated according to the following formula: ([LA]/[oleic acid+LA])*100 and represents percent substrate conversion to LA. "Δ15 Activity" (i.e., "d15d CE") was calculated according to the following formula: ([ALA]/[LA+ALA])*100 and represents percent substrate conversion to ALA. Standard deviation is abbreviated "SD", while "nd" is not detected.

TABLE 21

Comparison Of Fatty Acid Composition In Wild Type and Δ12 Knockout *Yarrowia* Transformed With pY130, pY138, pY139 And pY140 (Comprising FmD15, PrD17S, PsD17S And PaD17S)

| Strain | Plasmid | 16:0 | 16:1 | 18:0 | 18:1 | 18:2 | ALA | d12d CE | d15d CE |
|---|---|---|---|---|---|---|---|---|---|
| WT | pY6 (vector ctrl) | 9.2 | 12.2 | 1.5 | 28.9 | 39.6 | nd | 57.8 | nd |
| | SD | 0.3 | 0.2 | 0.1 | 0.3 | 0.6 | 0.0 | 0.6 | nd |
| WT | pY130 (FmD15) | 8.5 | 12.3 | 2.1 | 33.7 | 6.5 | 29.1 | 51.4 | 81.7 |
| | SD | 0.3 | 0.3 | 0.3 | 1.1 | 0.2 | 0.8 | 1.5 | 0.1 |
| WT | pY138 (PrD17S) | 9.2 | 13.8 | 1.6 | 30.4 | 29.1 | 9.5 | 56.0 | 24.6 |
| | SD | 0.3 | 0.3 | 0.2 | 0.7 | 0.4 | 0.2 | 0.9 | 0.2 |
| WT | pY139 (PsD17S) | 9.2 | 14.1 | 1.5 | 30.8 | 26.5 | 11.8 | 55.4 | 30.8 |
| | SD | 0.2 | 0.3 | 0.1 | 0.1 | 0.5 | 0.0 | 0.3 | 0.5 |
| WT | pY140 (PaD17S) | 9.0 | 13.3 | 1.7 | 33.6 | 23.1 | 12.2 | 51.2 | 34.6 |
| | SD | 0.2 | 0.3 | 0.2 | 0.3 | 0.3 | 0.3 | 0.5 | 0.7 |
| d12 KO | pY6 (vector ctrl) | 6.7 | 10.8 | 2.1 | 71.4 | nd | nd | nd | nd |
| | SD | 0.3 | 0.3 | 0.3 | 1.2 | 0.0 | 0.0 | nd | nd |
| d12 KO | pY130 (FmD15) | 7.1 | 10.6 | 2.5 | 55.0 | 0.6 | 15.7 | 22.8 | 96.6 |
| | SD | 0.1 | 0.1 | 0.2 | 0.2 | 0.0 | 0.3 | 0.4 | 0.0 |

TABLE 21-continued

Comparison Of Fatty Acid Composition In Wild Type and Δ12 Knockout *Yarrowia* Transformed With pY130, pY138, pY139 And pY140 (Comprising FmD15, PrD17S, PsD17S And PaD17S)

| Strain | Plasmid | 16:0 | 16:1 | 18:0 | 18:1 | 18:2 | ALA | d12d CE | d15d CE |
|---|---|---|---|---|---|---|---|---|---|
| d12 KO | pY138 (PrD17S) | 6.8 | 11.7 | 2.2 | 69.5 | nd | nd | nd | nd |
| | SD | 0.0 | 0.1 | 0.0 | 0.2 | 0.0 | 0.0 | nd | nd |
| d12 KO | pY139 (PsD17S) | 7.0 | 11.9 | 2.1 | 70.2 | nd | nd | nd | nd |
| | SD | 0.3 | 0.1 | 0.2 | 0.1 | 0.0 | 0.0 | nd | nd |
| d12 KO | pY140 (PaD17S) | 7.7 | 11.4 | 2.6 | 69.5 | nd | nd | nd | nd |
| | SD | 0.1 | 0.1 | 0.0 | 0.3 | 0.0 | 0.0 | nd | nd |

Comparison of Lipid Profiles with Substrate Feeding

To study the relative substrate specificities of the different ω-3 desaturases on ω6 substrates other than LA, d12 KO strains transformed with the different plasmids (i.e., pY6, pY130, pY138, pY139 and pY140) were fed a mixture of different FAs, For this, the strains were streaked onto MM plates and fresh cultures were used to inoculate 3 mL MM. After overnight growth at 30° C., all cultures were diluted to an $OD_{600}$ of 0.5 before aliquoting them into three 3-mL cultures. After growth for another 6 hrs, the cultures were harvested and resuspended in 3 mL MM containing 1% Tergitol and 0.5 mM each of GLA, EDA and ARA and allowed to grow for 24 hr at which time they were harvested, washed once with 12 mL 0.5% Triton X-100, and once with 12 mL distilled water. The pellets were analyzed for fatty acid composition, as described above.

The fatty acid profiles for d12 KO *Yarrowia lipolytica* expressing pY6 (SEQ ID NO:88), pY130 (SEQ ID NO:89), pY138 (SEQ ID NO:90), pY139 (SEQ ID NO:91) and pY140 (SEQ ID NO:92) are shown below in Table 22. In the Table, fatty acids are identified as GLA (ω-6), EDA (ω-6), DGLA (ω-6), ARA (ω-6), ALA (ω-3), STA (ω-3), ETrA (ω-3), ETA (ω-3) and EPA (ω-3). Fatty acid compositions were expressed as the weight percent (wt. %) of total fatty acids. The ω-3 desaturase conversion efficiency ("Conv. Effic.") of the ω-6 substrates GLA, EDA, DGLA, and ARA to their ω-3 products, STA, ETrA, ETA, and EPA, respectively, was calculated according to the following formula: [product/(substrate+product)]*100. Standard deviation is abbreviated "SD", while "nd" is not detected.

Results concerning ω-6 fatty acid substrate specificity of FmD15, PsD17S, PrD17S and PaD17S are visually summarized in FIG. 13. Specifically, data relating to LA is from wild type *Y. lipolytica* transformants, as shown in Table 21; all other data are from Δ12-desaturase disrupted (d12KO) *Yarrowia lipolytica* strains fed different ω-6 fatty acid substrates, as shown in Table 22. The fatty acid DGLA is abbreviated as "HGLA" in the Figure.

Based on the data presented herein, FmD15 had the highest Δ15 desaturase activity as compared to PsD17S, PrD17S and PaD17S (Table 21, FIG. 13). Unlike FmD15 (which has bifunctional Δ12/Δ15 desaturase activity), however, none of the tested three Δ17 desaturases possessed any detectable Δ12 desaturase activity on oleate (Table 21). Growth in the presence of ω-6 fatty acid substrates showed that all Δ17 desaturases had the strongest preference for ARA, relatively lower activities on EDA and DGLA, and least activity on GLA. PaD17S had the strongest activity on ARA. The Δ17 desaturase had significant Δ15 desaturase activity on the C18 substrate LA, wherein the activity was comparable to the Δ17 desaturase activity on the C20 substrates EDA and DGLA (PsD17S and PrD17S also displayed significant Δ15 desaturase activity on LA, although activity was slightly diminished with respect to the Δ17 desaturase activity on C20 substrates). The broad catalytic promiscuity of the three Δ17 desaturases distinguishes them from the *Saprolegnia diclina* Δ17 desaturase that works exclusively on C20 ω-6 fatty acid substrates.

TABLE 22

Comparison Of Fatty Acid Composition In Δ12 Knockout *Yarrowia* Transformed With pY130, pY138, pY139 And pY140 (Comprising FmD15, PrD17S, PsD17S And PaD17S)

| | | Fatty acid composition (% total fatty acid) | | | | | | | | | ω3 desaturase Conv. Effic. on | | | |
|---|---|---|---|---|---|---|---|---|---|---|---|---|---|---|
| Host | Plasmid | GLA | EDA | DGLA | ARA | ALA | STA | ETrA | ETA | EPA | GLA | EDA | DGLA | ARA |
| d12 KO | pY6 (control) | 9.0 | 3.5 | 6.9 | 2.3 | nd | nd | nd | nd | nd | nd | nd | nd | nd |
| | SD | 0.3 | 0.1 | 0.3 | 0.1 | 0.0 | 0.0 | 0.0 | 0.0 | 0.0 | 0.0 | 0.0 | 0.0 | 0.0 |
| d12 KO | pY130 (FmD15) | 13.1 | 4.9 | 9.6 | 4.6 | 8.2 | 2.7 | 1.2 | 1.1 | 0.2 | 17.3 | 19.3 | 10.1 | 3.3 |
| | SD | 0.1 | 0.1 | 0.1 | 0.1 | 0.0 | 0.0 | 0.0 | 0.0 | 0.0 | 0.2 | 0.1 | 0.2 | 0.3 |
| d12 KO | pY138 (PrD17S) | 12.5 | 3.3 | 6.2 | 2.2 | 1.0 | 0.6 | 1.3 | 2.7 | 1.3 | 4.5 | 27.7 | 30.1 | 36.5 |
| | SD | 0.3 | 0.2 | 0.2 | 0.3 | 0.0 | 0.0 | 0.0 | 0.0 | 0.1 | 0.1 | 1.0 | 0.9 | 1.2 |
| d12 KO | pY139 (PsD17S) | 11.8 | 3.0 | 5.9 | 1.6 | 1.2 | 0.8 | 1.6 | 3.1 | 1.5 | 6.0 | 34.6 | 34.3 | 47.5 |
| | SD | 0.3 | 0.0 | 0.1 | 0.1 | 0.0 | 0.0 | 0.0 | 0.0 | 0.0 | 0.2 | 0.2 | 0.2 | 0.3 |
| d12 KO | pY140 (PaD17S) | 9.8 | 2.5 | 5.3 | 1.2 | 1.1 | 0.6 | 1.2 | 2.1 | 1.5 | 5.5 | 33.2 | 28.3 | 55.8 |
| | SD | 0.4 | 0.1 | 0.2 | 0.1 | 0.0 | 0.0 | 0.0 | 0.0 | 0.1 | 0.3 | 1.1 | 0.8 | 1.7 |

What is claimed is:

1. An isolated nucleic acid molecule selected from the group consisting of:

a) an isolated nucleotide molecule encoding a Δ17 desaturase enzyme, selected from the group consisting of SEQ ID NO:2 and SEQ ID NO:3;

b) an isolated nucleotide molecule encoding Δ17 desaturase enzyme that hybridizes with (a) under the following hybridization conditions: 0.1X SSC, 0.1% SDS, 65° C. and washed with 2X SSC, 0.1% SDS followed by 0.1X SSC, 0.1% SDS; or c) an isolated nucleotide molecule that is completely complementary to (a) or (b).

2. The isolated nucleic acid molecule which encodes a Δ17 desaturase enzyme selected from the group consisting of SEQ ID NO: 1 and SEQ ID NO: 4.

3. The isolated nucleic acid molecule which encodes a Δ17 desaturase enzyme as set forth in SEQ ID NO: 2, wherein at least 175 codons are codon-optimized for expression in *Yarrowia.*

4. An isolated nucleic acid molecule comprising a first nucleotide sequence encoding a Δ17 desaturase enzyme of at least 359 amino acids that has at least 95% identity based on Clustal W algorithms when compared to a polypeptide having the sequence as set forth in SEQ ID NO: 2; or a second nucleotide sequence comprising the full-complement of the first nucleotide sequence.

5. A chimeric gene comprising the isolated nucleic acid molecule of claim 1 operably linked to suitable regulatory sequences.

6. An isolated transformed host cell comprising the isolated nucleic acid molecule of claim 1.

7. The transformed host cell of claim 6 selected from the group consisting of algae, bacteria, yeast, oomycetes and fungi.

8. The transformed host cell of claim 7 wherein the yeast is an oleaginous yeast.

9. The transformed host cell of claim 8 wherein the oleaginous yeast is selected from the group consisting of: *Yarrowia, Candida, Rhodotorula, Rhodosporidium, Cryptococcus, Trichosporon* and *Lipomyces.*

10. A method for the production of eicosapentaenoic acid comprising:

a) providing a host cell comprising:

(i) an isolated nucleotide molecule encoding a bifunctional Δ17/ Δ15 desaturase polypeptide having at least 95% identity when compared to a polypeptide having the amino acid sequence as set forth in SEQ ID NO: 2, based on the Clustal W method of alignment; and (ii) a source of arachidonic acid;

b) growing the host cell of step (a) under conditions wherein the nucleic acid molecule encoding the bifunctional Δ17/ Δ15 desaturase polypeptide is expressed and the arachidonic acid is converted to eicosapentaenoic acid; and c) optionally recovering the eicosapentaenoic acid of step (b).

11. A method for the production of eicosatetraenoic acid comprising:

a) providing a host cell comprising:

(i) an isolated nucleotide molecule encoding a bifunctional Δ17/ Δ15 desaturase polypeptide having at least 95% identity when compared to a polypeptide having the amino acid sequence as set forth in SEQ ID NO: 2, based on the Clustal W method of alignment; and (ii) a source of dihomo-γ-linolenic acid;

b) growing the host cell of step (a) under conditions wherein the nucleic acid molecule encoding the bifunctional Δ17/ Δ15 desaturase polypeptide is expressed and the dihomo-γ-linolenic acid is converted to eicosatetraenoic acid; and c) optionally recovering the eicosapentaenoic acid of step (b).

12. A method for the production of polyunsaturated fatty acids comprising:

a) providing a host cell comprising:

i) an isolated nucleotide molecule encoding a bifunctional Δ17/ Δ15 desaturase polypeptide having at least 95% identity when compared to a polypeptide having the amino acid sequence as set forth in SEQ ID NO: 2, based on the Clustal W method of alignment; and ii) a source of fatty acid selected from the group consisting of: linoleic acid and eicosadienoic acid;

b) growing the host cell of step (a) under conditions wherein the nucleic acid molecule encoding the bifunctional Δ17/ Δ15 desaturase polypeptide is expressed and the linoleic acid is converted to α-linolenic acid and the eicosadienoic acid is converted to eicosatrienoic acid; and c) optionally recovering the fatty acid of step (b).

13. A method according to any of claims 10, 11 or 12 wherein the isolated nucleic acid molecule encodes a bifunctional Δ17/ Δ15 desaturase polypeptide having the amino acid sequence as set forth in SEQ ID NO:2, wherein at least 175 codons are codon-optimized for expression in *Yarrowia*.

14. A method according to any of claims 10, 11 or 12 wherein the isolated nucleic acid molecule encodes a bifunctional Δ17/ Δ15 desaturase polypeptide having the amino acid sequence selected from the group consisting of SEQ ID NO:2 and SEQ ID NO: 3.

15. A method according to any of claims 10, 11 or 12 wherein:

a.) the isolated nucleic acid molecule has a nucleic acid sequence selected from the group consisting of SEQ ID NO: 1 and SEQ ID NO: 4; and, b.) the host cell is *Yarrowia lipolytica*.

16. A method according to any of claims 10, 11 or 12, wherein the host cell is selected from the group consisting of: algae, bacteria, yeast, oomycetes and fungi.

17. A method according to claim 16 wherein the host cell is a fungus selected from the group consisting of: *Thraustochytrium* sp., *Schizochytrium* sp. and *Mortierella* sp.

18. A method according to claim 16 wherein the yeast is an oleaginous yeast.

19. A method according to claim 18 wherein the oleaginous yeast is selected from the group consisting of: *Yarrowia, Candida, Rhodotorula, Rhodosporidium, Cryptococcus, Trichosporon* and *Lipomyces*.

* * * * *

SEQUENCE LISTING

<160> NUMBER OF SEQ ID NOS: 102

<210> SEQ ID NO 1
<211> LENGTH: 1080
<212> TYPE: DNA
<213> ORGANISM: Pythium aphanidermatum

<400> SEQUENCE: 1
atggcttctt ccactgttgc tgcgccgtac gagttcccga cgctgacgga gatcaagcgc 60
tcgctgccag cgcactgctt tgaggcctcg gtcccgtggt cgctctacta caccgtgcgc 120
gcgctgggca tcgccggctc gctcgcgctc ggcctctact acgcgcgcgc gctcgcgatc 180
gtgcaggagt ttgccctgct ggatgcggtg ctctgcacgg ggtacattct gctgcagggc 240
atcgtattct gggggttctt caccatcggc catgactgcg gccacggcgc gttctcgcgt 300
tcgcacctgc tcaacttcag cgtcggcacg ctcattcact cgatcatcct cacgccgtac 360
gagtcatgga agatctcgca ccgccaccac cacaagaaca cgggcaacat cgacaaggac 420
gagattttct acccgcagcg cgaggccgac tcgcacccac tgtcccgaca catggtgatc 480
tcgctcggct cggcctggtt cgcgtacctc gttgcgggct tccctcctcg caaggtgaac 540
cacttcaacc cttgggaacc gttgtacctg cgccgcatgt ctgccgtcat catctcactc 600
ggctcgctcg tggcgttcgc gggcttgtat gcgtatctca cctacgtcta tggccttaag 660
accatggcgc tgtactactt cgcccctctc tttgggttcg ccacgatgct cgtggtcact 720
acctttttgc accacaatga cgaggaaacg ccatggtacg ccgactcgga gtggacgtac 780
gtcaagggca acctctcgtc cgtggaccgc tcgtacggcg cgctcatcga caacctgagc 840
cacaacatcg gcacgcacca gatccaccac ctgtttccga tcatcccgca ctacaagctg 900
aacgaggcga cggcagcgtt cgcgcaggcg ttcccggagc tcgtgcgcaa gagcgcgtcg 960
ccgatcatcc cgacgttcat ccgcatcggg ctcatgtacg ccaagtacgg cgtcgtggac 1020
aaggacgcca agatgtttac gctcaaggag gccaaggccg ccaagaccaa ggccaactag 1080

<210> SEQ ID NO 2
<211> LENGTH: 359
<212> TYPE: PRT
<213> ORGANISM: Pythium aphanidermatum
<220> FEATURE:
<221> NAME/KEY: MISC_FEATURE
<223> OTHER INFORMATION: delta-17 desaturase

<400> SEQUENCE: 2

Met Ala Ser Ser Thr Val Ala Ala Pro Tyr Glu Phe Pro Thr Leu Thr
1 5 10 15

Glu Ile Lys Arg Ser Leu Pro Ala His Cys Phe Glu Ala Ser Val Pro
20 25 30

Trp Ser Leu Tyr Tyr Thr Val Arg Ala Leu Gly Ile Ala Gly Ser Leu
35 40 45

Ala Leu Gly Leu Tyr Tyr Ala Arg Ala Leu Ala Ile Val Gln Glu Phe
50 55 60

Ala Leu Leu Asp Ala Val Leu Cys Thr Gly Tyr Ile Leu Leu Gln Gly
65 70 75 80

Ile Val Phe Trp Gly Phe Phe Thr Ile Gly His Asp Cys Gly His Gly
85 90 95

Ala Phe Ser Arg Ser His Leu Leu Asn Phe Ser Val Gly Thr Leu Ile
100 105 110

-continued

His Ser Ile Ile Leu Thr Pro Tyr Glu Ser Trp Lys Ile Ser His Arg
115 120 125

His His His Lys Asn Thr Gly Asn Ile Asp Lys Asp Glu Ile Phe Tyr
130 135 140

Pro Gln Arg Glu Ala Asp Ser His Pro Leu Ser Arg His Met Val Ile
145 150 155 160

Ser Leu Gly Ser Ala Trp Phe Ala Tyr Leu Val Ala Gly Phe Pro Pro
165 170 175

Arg Lys Val Asn His Phe Asn Pro Trp Glu Pro Leu Tyr Leu Arg Arg
180 185 190

Met Ser Ala Val Ile Ile Ser Leu Gly Ser Leu Val Ala Phe Ala Gly
195 200 205

Leu Tyr Ala Tyr Leu Thr Tyr Val Tyr Gly Leu Lys Thr Met Ala Leu
210 215 220

Tyr Tyr Phe Ala Pro Leu Phe Gly Phe Ala Thr Met Leu Val Val Thr
225 230 235 240

Thr Phe Leu His His Asn Asp Glu Glu Thr Pro Trp Tyr Ala Asp Ser
245 250 255

Glu Trp Thr Tyr Val Lys Gly Asn Leu Ser Ser Val Asp Arg Ser Tyr
260 265 270

Gly Ala Leu Ile Asp Asn Leu Ser His Asn Ile Gly Thr His Gln Ile
275 280 285

His His Leu Phe Pro Ile Ile Pro His Tyr Lys Leu Asn Glu Ala Thr
290 295 300

Ala Ala Phe Ala Gln Ala Phe Pro Glu Leu Val Arg Lys Ser Ala Ser
305 310 315 320

Pro Ile Ile Pro Thr Phe Ile Arg Ile Gly Leu Met Tyr Ala Lys Tyr
325 330 335

Gly Val Val Asp Lys Asp Ala Lys Met Phe Thr Leu Lys Glu Ala Lys
340 345 350

Ala Ala Lys Thr Lys Ala Asn
355

<210> SEQ ID NO 3
<211> LENGTH: 359
<212> TYPE: PRT
<213> ORGANISM: Pythium aphanidermatum
<220> FEATURE:
<221> NAME/KEY: MISC_FEATURE
<223> OTHER INFORMATION: delta-17 desaturase
<220> FEATURE:
<221> NAME/KEY: MISC_FEATURE
<222> LOCATION: (155)..(155)
<223> OTHER INFORMATION: Xaa = Ser or Pro
<220> FEATURE:
<221> NAME/KEY: MISC_FEATURE
<222> LOCATION: (351)..(351)
<223> OTHER INFORMATION: Xaa = Ala or Thr

<400> SEQUENCE: 3

Met Ala Ser Ser Thr Val Ala Ala Pro Tyr Glu Phe Pro Thr Leu Thr
1 5 10 15

Glu Ile Lys Arg Ser Leu Pro Ala His Cys Phe Glu Ala Ser Val Pro
20 25 30

Trp Ser Leu Tyr Tyr Thr Val Arg Ala Leu Gly Ile Ala Gly Ser Leu
35 40 45

Ala Leu Gly Leu Tyr Tyr Ala Arg Ala Leu Ala Ile Val Gln Glu Phe
50 55 60

-continued

```
Ala Leu Leu Asp Ala Val Leu Cys Thr Gly Tyr Ile Leu Leu Gln Gly
65                  70                  75                  80

Ile Val Phe Trp Gly Phe Phe Thr Ile Gly His Asp Cys Gly His Gly
                85                  90                  95

Ala Phe Ser Arg Ser His Leu Leu Asn Phe Ser Val Gly Thr Leu Ile
            100                 105                 110

His Ser Ile Ile Leu Thr Pro Tyr Glu Ser Trp Lys Ile Ser His Arg
        115                 120                 125

His His His Lys Asn Thr Gly Asn Ile Asp Lys Asp Glu Ile Phe Tyr
    130                 135                 140

Pro Gln Arg Glu Ala Asp Ser His Pro Leu Xaa Arg His Met Val Ile
145                 150                 155                 160

Ser Leu Gly Ser Ala Trp Phe Ala Tyr Leu Val Ala Gly Phe Pro Pro
                165                 170                 175

Arg Lys Val Asn His Phe Asn Pro Trp Glu Pro Leu Tyr Leu Arg Arg
            180                 185                 190

Met Ser Ala Val Ile Ile Ser Leu Gly Ser Leu Val Ala Phe Ala Gly
        195                 200                 205

Leu Tyr Ala Tyr Leu Thr Tyr Val Tyr Gly Leu Lys Thr Met Ala Leu
    210                 215                 220

Tyr Tyr Phe Ala Pro Leu Phe Gly Phe Ala Thr Met Leu Val Val Thr
225                 230                 235                 240

Thr Phe Leu His His Asn Asp Glu Glu Thr Pro Trp Tyr Ala Asp Ser
                245                 250                 255

Glu Trp Thr Tyr Val Lys Gly Asn Leu Ser Ser Val Asp Arg Ser Tyr
            260                 265                 270

Gly Ala Leu Ile Asp Asn Leu Ser His Asn Ile Gly Thr His Gln Ile
        275                 280                 285

His His Leu Phe Pro Ile Ile Pro His Tyr Lys Leu Asn Glu Ala Thr
    290                 295                 300

Ala Ala Phe Ala Gln Ala Phe Pro Glu Leu Val Arg Lys Ser Ala Ser
305                 310                 315                 320

Pro Ile Ile Pro Thr Phe Ile Arg Ile Gly Leu Met Tyr Ala Lys Tyr
                325                 330                 335

Gly Val Val Asp Lys Asp Ala Lys Met Phe Thr Leu Lys Glu Xaa Lys
            340                 345                 350

Ala Ala Lys Thr Lys Ala Asn
        355
```

<210> SEQ ID NO 4
<211> LENGTH: 1080
<212> TYPE: DNA
<213> ORGANISM: Pythium aphanidermatum
<220> FEATURE:
<221> NAME/KEY: misc_feature
<223> OTHER INFORMATION: syntthetic delta-17 desaturase, codon-optimized
for Yarrowia lipolytica

<400> SEQUENCE: 4

```
atggcttcct ctaccgttgc cgctccctac gagttcccta ctctcaccga gatcaagcga      60

tccctgcctg cccactgctt cgaagcctct gttccctggt ccctctacta taccgtgcga     120

gctctgggca ttgccggttc ccttgctctc ggactgtact atgctcgagc ccttgctatc     180

gtgcaggagt ttgcactgct cgatgccgtc ctttgcactg gctacattct gctccagggt     240

atcgtgttct ggggattctt taccatcggt cacgactgtg gacatggtgc cttctcgcga     300
```

-continued

```
tcccacctgc tcaacttctc tgttggcaca ctcattcact ccatcattct gactccctac    360

gagtcgtgga agatcagcca tcgacaccat cacaagaaca ccggcaacat cgacaaggat    420

gagatcttct accctcagcg agaagccgac tctcatcccc tgtcccgaca catggtcatc    480

tcccttggtt cggcttggtt tgcctacctc gttgctggat ttcctccccg aaaggtcaac    540

cacttcaatc cctgggagcc tctctacctg cgaagaatgt ctgccgtcat catttccctc    600

ggctctctcg tggcctttgc tggtctgtac gcctacctta cctacgtcta cggcctcaag    660

accatggctc tgtattactt cgcacctctc tttggattcg ccaccatgct ggttgtcact    720

accttcctcc atcacaacga cgaggaaact ccctggtacg ccgattcgga gtggacctat    780

gtcaagggca acttgtcctc tgtggaccga agctacggag ccctcatcga caacctgtcc    840

cacaacattg gtacacatca gatccaccat ctgtttccca tcattcctca ctacaagctc    900

aacgaggcca ctgctgcctt cgctcaggcc tttcccgaac tggtgcgaaa gtcggcttct    960

cccatcattc ccaccttcat ccgaattggt cttatgtacg ccaagtacgg cgtggtcgac   1020

aaggatgcca agatgtttac cctcaaggag gccaaggctg ccaagaccaa agccaactaa   1080
```

<210> SEQ ID NO 5
<211> LENGTH: 614
<212> TYPE: DNA
<213> ORGANISM: Pythium aphanidermatum

<400> SEQUENCE: 5

```
ttttgggggt tcttcaccgt cggccatgac tgcggccacg gcgcgttctc gcgttcgcac     60

ctgctcaact tcagcgtcgg cacgctcatt cactcgatca tcctcacgcc gtacgagtca    120

tggaagatct cgcaccgcca ccaccacaag aacacgggca acatcgacaa ggacgagatt    180

ttctacccgc agcgcgaggc cgactcgcac ccactgtccc gacacatggt gatctcgctc    240

ggctcggcct ggttcgcgta cctcgttgcg ggcttccctc ctcgcatggt gaaccacttc    300

aacccttggg aaccgttgta cctgcgccgc atgtctgccg tcatcatctc actcggctcg    360

ctcgtggcgt tcgcgggctt gtatgcgtat ctcacctacg tctatggcct taagaccatg    420

gcgctgtact acttcgcccc tctctttggg ttcgccacga tgctcgtggt cactaccttt    480

ttgcaccaca atggcgagga aacgccatgg tacgccgact cggagtggac gtacgtcaag    540

ggcaacctct cgtccgtgga ccgctcgtac ggcgcgctca tcgacaacct gagccacaac    600

atcggcacgc acaa                                                      614
```

<210> SEQ ID NO 6
<211> LENGTH: 739
<212> TYPE: DNA
<213> ORGANISM: Pythium aphanidermatum
<220> FEATURE:
<221> NAME/KEY: misc_feature
<222> LOCATION: (132)..(132)
<223> OTHER INFORMATION: n is a, c, g, or t

<400> SEQUENCE: 6

```
actatagggc acgcgtggtc gacggcccgg gctggtatca aatacttttt ctaatttaat     60

atctacgaaa cgtttttttg ctatgattgg cacctattca atgctcatga atctgatgat    120

agtatttgca tnacttcatc ctctcttcca ttttatgctg actcaaacct ctttcgcgct    180

cggtttcaaa gggttacact actcgtgcgt ggtaccgagt gtaaccagca gcaaaaccgc    240

tccatacaac cgccaagtgt gaatgagggg cagacactgc gcgtgatctt gttctatgcg    300
```

-continued

```
cagccagcca gtggaggtct ctcccgggcg tggacctcac ttcagcttga gccgcggacc    360

gcgcagacca cccgacccgc acccgccatg gcttcttcca ctgttgctgc gccgtacgag    420

ttcccgacgc tgacggagat caagcgctcg ctgccagcgc actgctttga ggcctcggtc    480

ccgtggtcgc tctactacac cgtgcgcgcg ctgggcatcg ccggctcgct cgcgctcggc    540

ctctactacg cgcgcgcgct cgcgatcgtg caggagtttg ccctgctgga tgcggtgctc    600

tgcacggggt acattctgct gcagggcatc gtattctggg ggttcttcac catcggccat    660

gactgcggcc acggcgcgtt ctcgcgttcg cacctgctca acttcagcgt cggcacgctc    720

attcactcga tcatcctca                                                 739


<210> SEQ ID NO 7
<211> LENGTH: 512
<212> TYPE: DNA
<213> ORGANISM: Pythium aphanidermatum

<400> SEQUENCE: 7

ctgtactact tcgcccctct ctttgggttc gccacgatgc tcgtggtcac taccttttttg     60

caccacaatg acgaggaaac gccatggtac gccgactcgg agtggacgta cgtcaagggc    120

aacctctcgt ccgtggaccg ctcgtacggc gcgctcattg acaacctgag ccacaacatc    180

ggcacgcacc agatccacca cctgtttccg atcatcccgc actacaagct gaacgaggcg    240

acggcagcgt tcgcgcaggc gttcccggag ctcgtgcgca agagcgcgtc gccgatcatc    300

ccgacgttca tccgcatcgg gctcatgtac gccaagtacg gcgtcgtgga caaggacgcc    360

aagatgttta cgctcaagga ggccaaggcc gccaagacca aggccaacta ggcagaggca    420

aacaaggaag agaagttgtg tataggctcg taatgaacat gcgggttttt tgtttttwww    480

aaaaaaaaaa aaaaaaaaaa aaaaaaaaaa aa                                  512


<210> SEQ ID NO 8
<211> LENGTH: 1533
<212> TYPE: DNA
<213> ORGANISM: Pythium aphanidermatum
<220> FEATURE:
<221> NAME/KEY: misc_feature
<223> OTHER INFORMATION: delta-17 desaturase contig (CDS corresponds to
      nucleotides 388-1467)
<220> FEATURE:
<221> NAME/KEY: misc_feature
<222> LOCATION: (132)..(132)
<223> OTHER INFORMATION: n is a, c, g, or t

<400> SEQUENCE: 8

actatagggc acgcgtggtc gacggcccgg gctggtatca aatacttttt ctaatttaat     60

atctacgaaa cgttttttttg ctatgattgg cacctattca atgctcatga atctgatgat    120

agtatttgca tnacttcatc ctctcttcca ttttatgctg actcaaacct ctttcgcgct    180

cggtttcaaa gggttacact actcgtgcgt ggtaccgagt gtaaccagca gcaaaaccgc    240

tccatacaac cgccaagtgt gaatgagggg cagacactgc gcgtgatctt gttctatgcg    300

cagccagcca gtggaggtct ctcccgggcg tggacctcac ttcagcttga gccgcggacc    360

gcgcagacca cccgacccgc acccgccatg gcttcttcca ctgttgctgc gccgtacgag    420

ttcccgacgc tgacggagat caagcgctcg ctgccagcgc actgctttga ggcctcggtc    480

ccgtggtcgc tctactacac cgtgcgcgcg ctgggcatcg ccggctcgct cgcgctcggc    540

ctctactacg cgcgcgcgct cgcgatcgtg caggagtttg ccctgctgga tgcggtgctc    600

tgcacggggt acattctgct gcagggcatc gtattctggg ggttcttcac catcggccat    660
```

-continued gactgcggcc acggcgcgtt ctcgcgttcg cacctgctca acttcagcgt cggcacgctc 720
attcactcga tcatcctcac gccgtacgag tcatggaaga tctcgcaccg ccaccaccac 780
aagaacacgg gcaacatcga caaggacgag attttctacc cgcagcgcga ggccgactcg 840
cacccactgt cccgacacat ggtgatctcg ctcggctcgg cctggttcgc gtacctcgtt 900
gcgggcttcc ctcctcgcat ggtgaaccac ttcaaccctt gggaaccgtt gtacctgcgc 960
cgcatgtctg ccgtcatcat ctcactcggc tcgctcgtgg cgttcgcggg cttgtatgcg 1020
tatctcacct acgtctatgg ccttaagacc atggcgctgt actacttcgc ccctctcttt 1080
gggttcgcca cgatgctcgt ggtcactacc tttttgcacc acaatgrcga ggaaacgcca 1140
tggtacgccg actcggagtg gacgtacgtc aagggcaacc tctcgtccgt ggaccgctcg 1200
tacggcgcgc tcattgacaa cctgagccac aacatcggca cgcaccagat ccaccacctg 1260
tttccgatca tcccgcacta caagctgaac gaggcgacgg cagcgttcgc gcaggcgttc 1320
ccggagctcg tgcgcaagag cgcgtcgccg atcatcccga cgttcatccg catcgggctc 1380
atgtacgcca agtacggcgt cgtggacaag gacgccaaga tgtttacgct caaggaggcc 1440
aaggccgcca agaccaaggc caactaggca gaggcaaaca aggaagagaa gttgtgtata 1500
ggctcgtaat gaacatgcgg gttttttgtt ttt 1533

<210> SEQ ID NO 9
<211> LENGTH: 39
<212> TYPE: DNA
<213> ORGANISM: Artificial Sequence
<220> FEATURE:
<223> OTHER INFORMATION: SMART IV oligonucleotide

<400> SEQUENCE: 9
aagcagtggt atcaacgcag agtggccatt acggccggg 39

<210> SEQ ID NO 10
<211> LENGTH: 59
<212> TYPE: DNA
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's
SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 10
attctagagg ccgaggcggc cgacatgttt tttttttttt tttttttttt ttttttttvn 59

<210> SEQ ID NO 11
<211> LENGTH: 23
<212> TYPE: DNA
<213> ORGANISM: Artificial Sequence
<220> FEATURE:
<223> OTHER INFORMATION: 5'-PCR primer

<400> SEQUENCE: 11
aagcagtggt atcaacgcag agt 23

<210> SEQ ID NO 12
<211> LENGTH: 20

-continued

<212> TYPE: DNA
<213> ORGANISM: Artificial Sequence
<220> FEATURE:
<223> OTHER INFORMATION: Primer PD17-F1
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 12
ttytggggnt tyttyacngt 20

<210> SEQ ID NO 13
<211> LENGTH: 7
<212> TYPE: PRT
<213> ORGANISM: Artificial Sequence
<220> FEATURE:
<223> OTHER INFORMATION: Translation of primer PD17-F1

<400> SEQUENCE: 13

Phe Trp Gly Phe Phe Thr Tyr
1 5

<210> SEQ ID NO 14
<211> LENGTH: 20
<212> TYPE: DNA
<213> ORGANISM: Artificial Sequence
<220> FEATURE:
<223> OTHER INFORMATION: Primer PD17-F2
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 14
ttcttyacng tnggncayga 20

<210> SEQ ID NO 15
<211> LENGTH: 20
<212> TYPE: DNA
<213> ORGANISM: Artificial Sequence
<220> FEATURE:
<223> OTHER INFORMATION: Primer PD17-F3
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 15
tttttyacng tnggncayga 20

-continued

<210> SEQ ID NO 16
<211> LENGTH: 7
<212> TYPE: PRT
<213> ORGANISM: Artificial Sequence
<220> FEATURE:
<223> OTHER INFORMATION: Translation of primers PD17-F2 and PD17-F3

<400> SEQUENCE: 16

Phe Phe Thr Val Gly His Asp
1 5

<210> SEQ ID NO 17
<211> LENGTH: 20
<212> TYPE: DNA
<213> ORGANISM: Artificial Sequence
<220> FEATURE:
<223> OTHER INFORMATION: Primer PD17-F4
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 17
acncaycgnc aycaycayaa 20

<210> SEQ ID NO 18
<211> LENGTH: 20
<212> TYPE: DNA
<213> ORGANISM: Artificial Sequence
<220> FEATURE:
<223> OTHER INFORMATION: Primer PD17-F5
<220> FEATURE:
<221> NAME/KEY: misc_feature
<222> LOCATION: (3)..(3)
<223> OTHER INFORMATION: n is a, c, g, or t

<400> SEQUENCE: 18
acncayagrc aycaycayaa 20

<210> SEQ ID NO 19
<211> LENGTH: 7
<212> TYPE: PRT
<213> ORGANISM: Artificial Sequence
<220> FEATURE:
<223> OTHER INFORMATION: Translation of primers PD17-F4 and PD17-F5

<400> SEQUENCE: 19

Thr His Arg His His His Lys
1 5

<210> SEQ ID NO 20
<211> LENGTH: 20
<212> TYPE: DNA
<213> ORGANISM: Artificial Sequence
<220> FEATURE:
<223> OTHER INFORMATION: Primer PD17-F6
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 20

-continued

```
aaraayacng gnaayatyga                                              20


<210> SEQ ID NO 21
<211> LENGTH: 20
<212> TYPE: DNA
<213> ORGANISM: Artificial Sequence
<220> FEATURE:
<223> OTHER INFORMATION: Primer PD17-F7
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 21

aaraayacng gnaayataga                                              20


<210> SEQ ID NO 22
<211> LENGTH: 7
<212> TYPE: PRT
<213> ORGANISM: Artificial Sequence
<220> FEATURE:
<223> OTHER INFORMATION: Translation of primers PD17-F6 and PD17-F7

<400> SEQUENCE: 22

Lys Asn Thr Gly Asn Ile Asp
1               5


<210> SEQ ID NO 23
<211> LENGTH: 20
<212> TYPE: DNA
<213> ORGANISM: Artificial Sequence
<220> FEATURE:
<223> OTHER INFORMATION: Primer PD17-R1
<220> FEATURE:
<221> NAME/KEY: misc_feature
<222> LOCATION: (15)..(15)
<223> OTHER INFORMATION: n is a, c, g, or t

<400> SEQUENCE: 23

tcrtcrttrt grtgnagraa                                              20


<210> SEQ ID NO 24
<211> LENGTH: 20
<212> TYPE: DNA
<213> ORGANISM: Artificial Sequence
<220> FEATURE:
<223> OTHER INFORMATION: Primer PD17-R2

<400> SEQUENCE: 24

tcrtcrttrt grtgyaaraa                                              20


<210> SEQ ID NO 25
<211> LENGTH: 7
<212> TYPE: PRT
<213> ORGANISM: Artificial Sequence
<220> FEATURE:
<223> OTHER INFORMATION: Translation of primers PD17-R1 and PD17-R2

<400> SEQUENCE: 25

Phe Leu His His Asn Asp Glu
1               5


<210> SEQ ID NO 26
<211> LENGTH: 20
```

-continued

<212> TYPE: DNA
<213> ORGANISM: Artificial Sequence
<220> FEATURE:
<223> OTHER INFORMATION: Primer PD17-R3
<220> FEATURE:
<221> NAME/KEY: misc_feature
<222> LOCATION: (18)..(18)
<223> OTHER INFORMATION: n is a, c, g, or t

<400> SEQUENCE: 26
aaraargcyt tdatdatngg 20

<210> SEQ ID NO 27
<211> LENGTH: 20
<212> TYPE: DNA
<213> ORGANISM: Artificial Sequence
<220> FEATURE:
<223> OTHER INFORMATION: Primer PD17-R4
<220> FEATURE:
<221> NAME/KEY: misc_feature
<222> LOCATION: (18)..(18)
<223> OTHER INFORMATION: n is a, c, g, or t

<400> SEQUENCE: 27
aaraaygcyt tdatdatngg 20

<210> SEQ ID NO 28
<211> LENGTH: 7
<212> TYPE: PRT
<213> ORGANISM: Artificial Sequence
<220> FEATURE:
<223> OTHER INFORMATION: Translation of primers PD17-R3 and PD17-R4

<400> SEQUENCE: 28

Pro Ile Ile Lys Ala Phe Phe
1 5

<210> SEQ ID NO 29
<211> LENGTH: 20
<212> TYPE: DNA
<213> ORGANISM: Artificial Sequence
<220> FEATURE:
<223> OTHER INFORMATION: Primer PD17-R5
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 29
ttrtgngtnc cdatrttatg 20

<210> SEQ ID NO 30
<211> LENGTH: 20
<212> TYPE: DNA
<213> ORGANISM: Artificial Sequence
<220> FEATURE:
<223> OTHER INFORMATION: Primer PD17-R6
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 30
ttrtgngtnc cdatrttgtg 20

<210> SEQ ID NO 31
<211> LENGTH: 7
<212> TYPE: PRT
<213> ORGANISM: Artificial Sequence
<220> FEATURE:
<223> OTHER INFORMATION: Translation of primers PD17-R5 and PD17-R6

<400> SEQUENCE: 31

His Asn Ile Gly Thr His Gln
1 5

<210> SEQ ID NO 32
<211> LENGTH: 20
<212> TYPE: DNA
<213> ORGANISM: Artificial Sequence
<220> FEATURE:
<223> OTHER INFORMATION: Primer PD17-R7
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 32
ccyttnacrt angtccaytc 20

<210> SEQ ID NO 33
<211> LENGTH: 7
<212> TYPE: PRT
<213> ORGANISM: Artificial Sequence
<220> FEATURE:
<223> OTHER INFORMATION: Translation of primer PD17-R7

<400> SEQUENCE: 33

Glu Trp Thr Tyr Val Lys Gly
1 5

<210> SEQ ID NO 34
<211> LENGTH: 44
<212> TYPE: DNA
<213> ORGANISM: Artificial Sequence
<220> FEATURE:
<223> OTHER INFORMATION: Genome Walker adaptor-1

<400> SEQUENCE: 34
gtaatacgac tatagggcac gcgtggtcga cggcccgggc tggt 44

<210> SEQ ID NO 35
<211> LENGTH: 8
<212> TYPE: DNA
<213> ORGANISM: Artificial Sequence
<220> FEATURE:
<223> OTHER INFORMATION: Genome Walker adaptor-2
<220> FEATURE:
<221> NAME/KEY: misc_feature
<222> LOCATION: (1)..(1)
<223> OTHER INFORMATION: 5' end is associated with a -PO4 group
<220> FEATURE:
<221> NAME/KEY: misc_feature
<222> LOCATION: (8)..(8)
<223> OTHER INFORMATION: 3' end is associated with a -H2N group

<400> SEQUENCE: 35

-continued

```
accagccc                                                                 8


<210> SEQ ID NO 36
<211> LENGTH: 22
<212> TYPE: DNA
<213> ORGANISM: Artificial Sequence
<220> FEATURE:
<223> OTHER INFORMATION: Primer PUD17-5-1

<400> SEQUENCE: 36

aatctcgtcc ttgtcgatgt tg                                                22


<210> SEQ ID NO 37
<211> LENGTH: 22
<212> TYPE: DNA
<213> ORGANISM: Artificial Sequence
<220> FEATURE:
<223> OTHER INFORMATION: Primer AP1

<400> SEQUENCE: 37

gtaatacgac tcactatagg gc                                                22


<210> SEQ ID NO 38
<211> LENGTH: 22
<212> TYPE: DNA
<213> ORGANISM: Artificial Sequence
<220> FEATURE:
<223> OTHER INFORMATION: Primer PUD17-5-3

<400> SEQUENCE: 38

tgaggatgat cgagtgaatg ag                                                22


<210> SEQ ID NO 39
<211> LENGTH: 19
<212> TYPE: DNA
<213> ORGANISM: Artificial Sequence
<220> FEATURE:
<223> OTHER INFORMATION: Primer AP2

<400> SEQUENCE: 39

actatagggc acgcgtggt                                                    19


<210> SEQ ID NO 40
<211> LENGTH: 22
<212> TYPE: DNA
<213> ORGANISM: Artificial Sequence
<220> FEATURE:
<223> OTHER INFORMATION: Primer PUD17-3-1

<400> SEQUENCE: 40

cacctacgtc tatggcctta ag                                                22


<210> SEQ ID NO 41
<211> LENGTH: 22
<212> TYPE: DNA
<213> ORGANISM: Artificial Sequence
<220> FEATURE:
<223> OTHER INFORMATION: Primer PUD17-3-2

<400> SEQUENCE: 41

ctgtactact tcgcccctct ct                                                22


<210> SEQ ID NO 42
<211> LENGTH: 1085
<212> TYPE: DNA
<213> ORGANISM: Phytophthora infestans (GenBank Accession No. CAJ30870)
```

-continued

<400> SEQUENCE: 42

```
atggcgacga aggaggcgta tgtgttcccc actctgacgg agatcaagcg gtcgctacct      60
aagactgttt cgaggcttcg gtgcctctgt cgctctacta caccgtgcgt tgtctggtga     120
tcgcggtggc tctaaccttc ggtctcaact acgctcgcgc tctgcccgag gtcgagagct     180
tctgggctct ggacgccgca ctctgcacgg gctacatctt gctgcagggc atcgtgttct     240
ggggcttctt cacggtgggc cacgatgccg gccacggcgc cttctcgcgc taccacctgc     300
ttaacttcgt ggtgggcact ttcatgcact cgctcatcct cacgcccttc gagtcgtgga     360
agctcacgca ccgtcaccac cacaagaaca cgggcaacat tgaccgtgac gaggtcttct     420
acccgcaacg caaggccgac gaccacccgc tgtctcgcaa cctgattctg gcgctcgggg     480
cagcgtggct cgcctatttg gtcgagggct tccctcctcg taaggtcaac cacttcaacc     540
cgttcgagcc tctgttcgtg cgtcaggtgt cagctgtggt aatctctctt ctcgcccact     600
tcttcgtggc cggactctcc atctatctga gcctccagct gggccttaag acgatggcaa     660
tctactacta tggacctgtt tttgtgttcg gcagcatgct ggtcattacc accttcctac     720
accacaatga tgaggagacc ccatggtacg ccgactcgga gtggacgtac gtcaagggca     780
acctctcgtc cgtggaccga tcgtacggcg cgctcattga caacctgagc cacaacatcg     840
gcacgcacca gatccaccac cttttcccta tcattccgca ctacaaactc aagaaagcca     900
ctgcggcctt ccaccaggct ttccctgagc tcgtgcgcaa gagcgacgag ccaattatca     960
aggctttctt ccgggttgga cgtctctacg caaactacgg cgttgtggac caggaggcga    1020
agctcttcac gctaaaggaa gccaaggcgg cgaccgaggc ggcggccaag accaagtcca    1080
cgtaa                                                                1085
```

<210> SEQ ID NO 43
<211> LENGTH: 361
<212> TYPE: PRT
<213> ORGANISM: Phytophthora infestans
<300> PUBLICATION INFORMATION:
<302> TITLE: METHOD FOR PRODUCING UNSATURATED Omega3 FATTY ACIDS IN
      TRANSGENIC ORGANISMS
<308> DATABASE ACCESSION NUMBER: CAJ30870
<309> DATABASE ENTRY DATE: 2005-09-21
<310> PATENT DOCUMENT NUMBER: WO 2005083053
<311> PATENT FILING DATE: 2005-02-23
<312> PUBLICATION DATE: 2005-09-09
<313> RELEVANT RESIDUES: (1)..(361)

<400> SEQUENCE: 43

```
Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Met His Ser Leu
            100                 105                 110
```

-continued

```
Ile Leu Thr Pro Phe Glu Ser Trp Lys Leu Thr His Arg His His His
        115                 120                 125

Lys Asn Thr Gly Asn Ile Asp Arg Asp Glu Val Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
        355                 360
```

<210> SEQ ID NO 44
<211> LENGTH: 1092
<212> TYPE: DNA
<213> ORGANISM: Phytophthora sojae (US Patent Application No. 11/787772;
      filed 4/18/2007)

<400> SEQUENCE: 44

```
atggcgtcca agcaggagca gccgtaccag ttcccgacgc tgacggagat caagcgctcg     60

ctgcccagcg agtgtttcga ggcgtccgtg ccgctctcgc tctactacac ggtgcgctgc    120

ctggtgatcg ccgtgtcgct ggccttcggg ctccaccacg cgcgctcgct gcccgtggtc    180

gagggcctct gggcgctgga cgccgcgctc tgcacgggct acgtgctgct gcagggcatc    240

gtgttctggg gcttcttcac cgtgggccat gacgccggcc acggcgcctt ctcgcgctac    300

cacctgctca acttcgtgat cggcaccttc atccactcgc tcatcctgac gcccttcgag    360

tcgtggaagc tcacgcaccg ccaccaccac aagaacacgg gcaacatcga ccgcgacgag    420

atcttctacc cgcagcgcaa ggccgacgac cacccgctct cgcgtaacct catcctggcg    480

ctgggcgccg cgtggttcgc ctacctggtc gagggcttcc cgccgcgcaa ggtcaaccac    540

ttcaacccgt tcgagccgct gttcgtccgc caggtgtccg ccgtggtcat ctcgctggcc    600

gcgcacttcg gcgtggccgc gctgtccatc tacctgagcc tgcagttcgg cttcaagacc    660
```

-continued

```
atggctatct actactacgg gcccgtgttc gtgttcggca gcatgctggt catcaccacc    720

ttcctgcacc acaacgacga ggagaccccc tggtacgccg actcggagtg gacctacgtc    780

aagggcaacc tctcgtcggt cgaccgctcc tacggcgcgc tcatcgacaa cctgagccac    840

aacatcggca cgcaccagat ccaccacctc ttccccatca tcccgcacta taagctcaag    900

cgcgccaccg aggccttcca ccaggcgttc cccgagctcg tgcgcaagag cgacgagccc    960

atcattaagg ccttcttccg cgtcggccgc ctctacgcca actacggcgt cgtggactcg   1020

gacgccaagc tcttcacgct caaggaggcc aaggccgtgt ccgaggcggc gaccaagact   1080

aaggccaact ga                                                       1092


<210> SEQ ID NO 45
<211> LENGTH: 363
<212> TYPE: PRT
<213> ORGANISM: Phytophthora sojae (US Patent Application No. 11/787772;
      filed 4/18/2007)

<400> SEQUENCE: 45

Met Ala Ser Lys Gln Glu Gln Pro Tyr Gln Phe Pro Thr Leu Thr Glu
1               5                   10                  15

Ile Lys Arg Ser Leu Pro Ser Glu Cys Phe Glu Ala Ser Val Pro Leu
            20                  25                  30

Ser Leu Tyr Tyr Thr Val Arg Cys Leu Val Ile Ala Val Ser Leu Ala
        35                  40                  45

Phe Gly Leu His His Ala Arg Ser Leu Pro Val Val Glu Gly Leu Trp
    50                  55                  60

Ala Leu Asp Ala Ala Leu Cys Thr Gly Tyr Val Leu Leu Gln Gly Ile
65                  70                  75                  80

Val Phe Trp Gly Phe Phe Thr Val Gly His Asp Ala Gly His Gly Ala
                85                  90                  95

Phe Ser Arg Tyr His Leu Leu Asn Phe Val Ile Gly Thr Phe Ile His
            100                 105                 110

Ser Leu Ile Leu Thr Pro Phe Glu Ser Trp Lys Leu Thr His Arg His
        115                 120                 125

His His Lys Asn Thr Gly Asn Ile Asp Arg Asp Glu Ile Phe Tyr Pro
    130                 135                 140

Gln Arg Lys Ala Asp Asp His Pro Leu Ser Arg Asn Leu Ile Leu Ala
145                 150                 155                 160

Leu Gly Ala Ala Trp Phe Ala Tyr Leu Val Glu Gly Phe Pro Pro Arg
                165                 170                 175

Lys Val Asn His Phe Asn Pro Phe Glu Pro Leu Phe Val Arg Gln Val
            180                 185                 190

Ser Ala Val Val Ile Ser Leu Ala Ala His Phe Gly Val Ala Ala Leu
        195                 200                 205

Ser Ile Tyr Leu Ser Leu Gln Phe Gly Phe Lys Thr Met Ala Ile Tyr
    210                 215                 220

Tyr Tyr Gly Pro Val Phe Val Phe Gly Ser Met Leu Val Ile Thr Thr
225                 230                 235                 240

Phe Leu His His Asn Asp Glu Glu Thr Pro Trp Tyr Ala Asp Ser Glu
                245                 250                 255

Trp Thr Tyr Val Lys Gly Asn Leu Ser Ser Val Asp Arg Ser Tyr Gly
            260                 265                 270

Ala Leu Ile Asp Asn Leu Ser His Asn Ile Gly Thr His Gln Ile His
        275                 280                 285
```

-continued

```
His Leu Phe Pro Ile Ile Pro His Tyr Lys Leu Lys Arg Ala Thr Glu
    290                 295                 300

Ala Phe His Gln Ala Phe Pro Glu Leu Val Arg Lys Ser Asp Glu Pro
305                 310                 315                 320

Ile Ile Lys Ala Phe Phe Arg Val Gly Arg Leu Tyr Ala Asn Tyr Gly
                325                 330                 335

Val Val Asp Ser Asp Ala Lys Leu Phe Thr Leu Lys Glu Ala Lys Ala
            340                 345                 350

Val Ser Glu Ala Ala Thr Lys Thr Lys Ala Asn
        355                 360


<210> SEQ ID NO 46
<211> LENGTH: 1086
<212> TYPE: DNA
<213> ORGANISM: Phytophthora ramorum (US Patent Application No.
      11/787772; filed 4/18/2007)

<400> SEQUENCE: 46

atggcgacta agcagccgta ccagttcccg accctgacgg agatcaagcg gtcgctgccc      60

agcgagtgct ttgaggcctc ggtgccgctg tcgctctact acacggtgcg catcgtggcc     120

atcgccgtgg cgctggcgtt cggcctcaac tacgcgcgcg cgctgcccgt ggtcgagagc     180

ttgtgggcgc tggacgctgc gctctgctgc ggttacgtgc tgctgcaggg catcgtgttc     240

tggggcttct tcacggtggg ccatgacgcc ggccacggcg ccttctcgcg ttaccacctg     300

ctcaacttcg tggtgggcac cttcatccac tcgctcatcc tcacgccctt cgagtcgtgg     360

aagctcacgc accgccacca ccacaagaac acgggcaaca ttgaccgcga cgagatcttc     420

tacccgcagc gcaaggccga cgaccacccg ctgtcgcgca acctcgtgct ggcgctcggc     480

gccgcgtggt tcgcctacct ggtcgagggc ttcccgcccc gcaaggtcaa ccacttcaac     540

ccattcgagc cgctgtttgt gcgccaggtg gccgccgtcg tcatctcgct ctccgcgcac     600

ttcgccgtgt tggcgctgtc cgtgtatctg agcttccagt tcggtctcaa gaccatggcg     660

ctctactact acggccccgt cttcgtgttc ggcagcatgc ttgtgatcac caccttcctg     720

catcacaatg acgaggagac cccatggtac ggagactccg actggaccta cgtcaagggc     780

aacctgtcgt ccgtggaccg gtcctacggc gcgttcatcg acaacctgag ccacaacatc     840

ggcacgcacc agatccacca cctcttcccc atcatcccgc actacaagct caaccgcgct     900

acggcggcat tccaccaggc cttccccgag ctcgtgcgca agagcgacga gccgatcctc     960

aaggccttct ggcgcgtcgg ccgactgtac gccaactacg gcgtcgtgga cccggacgcc    1020

aagctcttca cgctcaagga ggccaaggcg gcgtccgagg cggcgaccaa gaccaaggcc    1080

acctaa                                                               1086


<210> SEQ ID NO 47
<211> LENGTH: 361
<212> TYPE: PRT
<213> ORGANISM: Phytophthora ramorum (US Patent Application No.
      11/787772; filed 4/18/2007)

<400> SEQUENCE: 47

Met Ala Thr Lys Gln Pro Tyr Gln Phe Pro Thr Leu Thr Glu Ile Lys
1               5                   10                  15

Arg Ser Leu Pro Ser Glu Cys Phe Glu Ala Ser Val Pro Leu Ser Leu
            20                  25                  30

Tyr Tyr Thr Val Arg Ile Val Ala Ile Ala Val Ala Leu Ala Phe Gly
        35                  40                  45
```

-continued

```
Leu Asn Tyr Ala Arg Ala Leu Pro Val Val Glu Ser Leu Trp Ala Leu
    50                  55                  60

Asp Ala Ala Leu Cys Cys Gly Tyr Val Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Ile His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Ile Phe Tyr Pro Gln Arg
    130                 135                 140

Lys Ala Asp Asp His Pro Leu Ser Arg Asn Leu Val Leu Ala Leu Gly
145                 150                 155                 160

Ala Ala Trp Phe Ala Tyr Leu Val Glu Gly Phe Pro Pro Arg Lys Val
                165                 170                 175

Asn His Phe Asn Pro Phe Glu Pro Leu Phe Val Arg Gln Val Ala Ala
            180                 185                 190

Val Val Ile Ser Leu Ser Ala His Phe Ala Val Leu Ala Leu Ser Val
        195                 200                 205

Tyr Leu Ser Phe Gln Phe Gly Leu Lys Thr Met Ala Leu Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Gly Asp Ser Asp Trp Thr
                245                 250                 255

Tyr Val Lys Gly Asn Leu Ser Ser Val Asp Arg Ser Tyr Gly Ala Phe
            260                 265                 270

Ile Asp Asn Leu Ser His Asn Ile Gly Thr His Gln Ile His His Leu
        275                 280                 285

Phe Pro Ile Ile Pro His Tyr Lys Leu Asn Arg Ala Thr Ala Ala Phe
    290                 295                 300

His Gln Ala Phe Pro Glu Leu Val Arg Lys Ser Asp Glu Pro Ile Leu
305                 310                 315                 320

Lys Ala Phe Trp Arg Val Gly Arg Leu Tyr Ala Asn Tyr Gly Val Val
                325                 330                 335

Asp Pro Asp Ala Lys Leu Phe Thr Leu Lys Glu Ala Lys Ala Ala Ser
            340                 345                 350

Glu Ala Ala Thr Lys Thr Lys Ala Thr
        355                 360
```

<210> SEQ ID NO 48
<211> LENGTH: 7145
<212> TYPE: DNA
<213> ORGANISM: Artificial Sequence
<220> FEATURE:
<223> OTHER INFORMATION: Plasmid pKUNFmkF2
<220> FEATURE:
<221> NAME/KEY: misc_feature
<222> LOCATION: (692)..(695)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t

<400> SEQUENCE: 48

-continued

```
catggcgtcc acttcggctc tgcccaagca gaaccctgcg cttagacgca ccgtcacctc      60
aactactgtg acggattctg agtctgccgc cgtctctcct tcagactctc cccgccactc     120
ggcctcttcc acatcgctct cgtccatgtc cgaggttgat atcgccaagc ccaagtccga     180
gtatggtgtc atgctcgaca cctacggcaa ccagttcgag gttcccgact ttaccatcaa     240
ggacatctac aatgccatcc ctaagcactg cttcaagcgc tccgctctca agggatacgg     300
ttatatcctc cgcgacattg tcctcctgac taccactttc agcatctggt acaactttgt     360
gacccccgaa tatatcccct ccacccccgc ccgcgctggt ctgtgggccg tgtacaccgt     420
tcttcagggt cttttcggta ctggtctctg ggttattgcc catgagtgcg gtcacggtgc     480
tttctccgat tctcgcatca tcaacgacat tactggctgg gttcttcact cttccctcct     540
tgtcccctac ttcagctggc aaatctccca ccgaaagcac cacaaggcca ctggcaacat     600
ggagcgtgac atggtcttcg ttccccgaac ccgcgagcag caggctactc gtctcggaaa     660
gatgacccac gagctcgctc atcttactga gnnnntcgtn ggctggccca actacctcat     720
caccaatgtt accggccaca actaccacga gcgccagcgt gagggtcgcg gcaagggcaa     780
gcataacggc ctcggcggtg gtgttaacca cttcgatccc cgcagccctc tgtacgagaa     840
cagtgacgct aagctcatcg tcctcagcga tattggtatc ggtctgatgg ccactgctct     900
gtacttcctc gttcagaagt tcggtttcta caacatggcc atctggtact ttgttcccta     960
cctctgggtt aaccactggc tcgttgccat caccttcctc cagcacaccg accctacct     1020
tccccactac accaacgacg agtggaactt cgtccgtggt gccgctgcta ccattgaccg    1080
tgagatgggc ttcatcggcc gccaccttct ccacggcatc atcgagactc atgtcctcca    1140
ccactacgtc agcagcatcc ccttctacaa cgcggacgag gccaccgagg ccattaagcc    1200
catcatgggc aagcactacc gggctgatgt ccaggatggt cctcgtggct tcatccgcgc    1260
catgtaccgc agtgcgcgta tgtgccagtg ggttgagccc agcgctggtg ccgagggtgc    1320
tggtaagggt gttctgttct tccgcaaccg caacaacgtg ggcacccccc ccgctgttat    1380
caagcccgtt gcttaagtag gcgcggccgc tatttatcac tctttacaac ttctacctca    1440
actatctact ttaataaatg aatatcgttt attctctatg attactgtat atgcgttcct    1500
ctaagacaaa tcgaaaccag catgtgatcg aatggcatac aaaagtttct tccgaagttg    1560
atcaatgtcc tgatagtcag gcagcttgag aagattgaca caggtggagg ccgtagggaa    1620
ccgatcaacc tgtctaccag cgttacgaat ggcaaatgac gggttcaaag ccttgaatcc    1680
ttgcaatggt gccttggata ctgatgtcac aaacttaaga agcagccgct tgtcctcttc    1740
ctcgatcgat ggtcatagct gtttcctgtg tgaaattgtt atccgctcac aattccacac    1800
aacgtacgaa gtcgtcaatg atgtcgatat gggttttgat catgcacaca taaggtccga    1860
ccttatcggc aagctcaatg agctccttgg tggtggtaac atccagagaa gcacacaggt    1920
tggttttctt ggctgccacg agcttgagca ctcgagcggc aaaggcggac ttgtggacgt    1980
tagctcgagc ttcgtaggag ggcattttgg tggtgaagag gagactgaaa taaatttagt    2040
ctgcagaact ttttatcgga accttatctg ggcagtgaa gtatatgtta tggtaatagt     2100
tacgagttag ttgaacttat agatagactg gactatacgg ctatcggtcc aaattagaaa    2160
gaacgtcaat ggctctctgg gcgtcgcctt tgccgacaaa aatgtgatca tgatgaaagc    2220
cagcaatgac gttgcagctg atattgttgt cggccaaccg cgccgaaaac gcagctgtca    2280
gacccacagc ctccaacgaa gaatgtatcg tcaaagtgat ccaagcacac tcatagttgg    2340
agtcgtactc caaaggcggc aatgacgagt cagacagata ctcgtcgacc ttttccttgg    2400
```

-continued

```
gaaccaccac cgtcagccct tctgactcac gtattgtagc caccgacaca ggcaacagtc   2460
cgtggatagc agaatatgtc ttgtcggtcc atttctcacc aactttaggc gtcaagtgaa   2520
tgttgcagaa gaagtatgtg ccttcattga gaatcggtgt tgctgatttc aataaagtct   2580
tgagatcagt ttggcgcgcc agctgcatta atgaatcggc caacgcgcgg ggagaggcgg   2640
tttgcgtatt gggcgctctt ccgcttcctc gctcactgac tcgctgcgct cggtcgttcg   2700
gctgcggcga gcggtatcag ctcactcaaa ggcggtaata cggttatcca cagaatcagg   2760
ggataacgca ggaaagaaca tgtgagcaaa aggccagcaa aaggccagga accgtaaaaa   2820
ggccgcgttg ctggcgtttt tccataggct ccgcccccct gacgagcatc acaaaaatcg   2880
acgctcaagt cagaggtggc gaaacccgac aggactataa agataccagg cgtttccccc   2940
tggaagctcc ctcgtgcgct ctcctgttcc gaccctgccg cttaccggat acctgtccgc   3000
ctttctccct tcgggaagcg tggcgctttc tcatagctca cgctgtaggt atctcagttc   3060
ggtgtaggtc gttcgctcca agctgggctg tgtgcacgaa ccccccgttc agcccgaccg   3120
ctgcgcctta tccggtaact atcgtcttga gtccaacccg gtaagacacg acttatcgcc   3180
actggcagca gccactggta acaggattag cagagcgagg tatgtaggcg gtgctacaga   3240
gttcttgaag tggtggccta actacggcta cactagaaga acagtatttg gtatctgcgc   3300
tctgctgaag ccagttacct tcggaaaaag agttggtagc tcttgatccg gcaaacaaac   3360
caccgctggt agcggtggtt tttttgtttg caagcagcag attacgcgca gaaaaaaagg   3420
atctcaagaa gatcctttga tcttttctac ggggtctgac gctcagtgga acgaaaactc   3480
acgttaaggg attttggtca tgagattatc aaaaaggatc ttcacctaga tccttttaaa   3540
ttaaaaatga agttttaaat caatctaaag tatatatgag taaacttggt ctgacagtta   3600
ccaatgctta atcagtgagg cacctatctc agcgatctgt ctatttcgtt catccatagt   3660
tgcctgactc cccgtcgtgt agataactac gatacgggag ggcttaccat ctggccccag   3720
tgctgcaatg ataccgcgag acccacgctc accggctcca gatttatcag caataaacca   3780
gccagccgga agggccgagc gcagaagtgg tcctgcaact ttatccgcct ccatccagtc   3840
tattaattgt tgccgggaag ctagagtaag tagttcgcca gttaatagtt tgcgcaacgt   3900
tgttgccatt gctacaggca tcgtggtgtc acgctcgtcg tttggtatgg cttcattcag   3960
ctccggttcc caacgatcaa ggcgagttac atgatccccc atgttgtgca aaaaagcggt   4020
tagctccttc ggtcctccga tcgttgtcag aagtaagttg gccgcagtgt tatcactcat   4080
ggttatggca gcactgcata attctcttac tgtcatgcca tccgtaagat gcttttctgt   4140
gactggtgag tactcaacca agtcattctg agaatagtgt atgcggcgac cgagttgctc   4200
ttgcccggcg tcaatacggg ataataccgc gccacatagc agaactttaa aagtgctcat   4260
cattggaaaa cgttcttcgg ggcgaaaact ctcaaggatc ttaccgctgt tgagatccag   4320
ttcgatgtaa cccactcgtg cacccaactg atcttcagca tcttttactt tcaccagcgt   4380
ttctgggtga gcaaaaacag gaaggcaaaa tgccgcaaaa aagggaataa gggcgacacg   4440
gaaatgttga atactcatac tcttcctttt tcaatattat tgaagcattt atcagggtta   4500
ttgtctcatg agcggataca tatttgaatg tatttagaaa aataaacaaa taggggttcc   4560
gcgcacattt ccccgaaaag tgccacctga tgcggtgtga aataccgcac agatgcgtaa   4620
ggagaaaata ccgcatcagg aaattgtaag cgttaatatt ttgttaaaat tcgcgttaaa   4680
tttttgttaa atcagctcat tttttaacca ataggccgaa atcggcaaaa tcccttataa   4740
```

-continued

```
atcaaaagaa tagaccgaga tagggttgag tgttgttcca gtttggaaca agagtccact   4800
attaaagaac gtggactcca acgtcaaagg gcgaaaaacc gtctatcagg gcgatggccc   4860
actacgtgaa ccatcaccct aatcaagttt tttggggtcg aggtgccgta aagcactaaa   4920
tcggaaccct aaagggagcc cccgatttag agcttgacgg ggaaagccgg cgaacgtggc   4980
gagaaaggaa gggaagaaag cgaaaggagc gggcgctagg gcgctggcaa gtgtagcggt   5040
cacgctgcgc gtaaccacca cacccgccgc gcttaatgcg ccgctacagg gcgcgtccat   5100
tcgccattca ggctgcgcaa ctgttgggaa gggcgatcgg tgcgggcctc ttcgctatta   5160
cgccagctgg cgaaaggggg atgtgctgca aggcgattaa gttgggtaac gccagggttt   5220
tcccagtcac gacgttgtaa aacgacggcc agtgaattgt aatacgactc actatagggc   5280
gaattgggcc cgacgtcgca tgcagtggtg gtattgtgac tggggatgta gttgagaata   5340
agtcatacac aagtcagctt tcttcgagcc tcatataagt ataagtagtt caacgtatta   5400
gcactgtacc cagcatctcc gtatcgagaa acacaacaac atgccccatt ggacagatca   5460
tgcggataca caggttgtgc agtatcatac atactcgatc agacaggtcg tctgaccatc   5520
atacaagctg aacaagcgct ccatacttgc acgctctcta tatacacagt taaattacat   5580
atccatagtc taacctctaa cagttaatct tctggtaagc ctcccagcca gccttctggt   5640
atcgcttggc ctcctcaata ggatctcggt tctggccgta cagacctcgg ccgacaatta   5700
tgatatccgt tccggtagac atgacatcct caacagttcg gtactgctgt ccgagagcgt   5760
ctcccttgtc gtcaagaccc accccggggg tcagaataag ccagtcctca gagtcgccct   5820
taattaattt gaatcgaatc gatgagccta aaatgaaccc gagtatatct cataaaattc   5880
tcggtgagag gtctgtgact gtcagtacaa ggtgccttca ttatgccctc aaccttacca   5940
tacctcactg aatgtagtgt acctctaaaa atgaaataca gtgccaaaag ccaaggcact   6000
gagctcgtct aacggacttg atatacaacc aattaaaaca aatgaaaaga aatacagttc   6060
tttgtatcat ttgtaacaat taccctgtac aaactaaggt attgaaatcc cacaatattc   6120
ccaaagtcca cccctttcca aattgtcatg cctacaactc atataccaag cactaaccta   6180
ccgtttaaac agtgtacgca gatctactat agaggaacat ttaaattgcc ccggagaaga   6240
cggccaggcc gcctagatga caaattcaac aactcacagc tgactttctg ccattgccac   6300
taggggggggg cctttttata tggccaagcc aagctctcca cgtcggttgg gctgcaccca   6360
acaataaatg ggtagggttg caccaacaaa gggatgggat ggggggtaga agatacgagg   6420
ataacggggc tcaatggcac aaataagaac gaatactgcc attaagactc gtgatccagc   6480
gactgacacc attgcatcat ctaagggcct caaaactacc tcggaactgc tgcgctgatc   6540
tggacaccac agaggttccg agcactttag gttgcaccaa atgtcccacc aggtgcaggc   6600
agaaaacgct ggaacagcgt gtacagtttg tcttaacaaa aagtgagggc gctgaggtcg   6660
agcagggtgg tgtgacttgt tatagccttt agagctgcga aagcgcgtat ggatttggct   6720
catcaggcca gattgagggt ctgtggacac atgtcatgtt agtgtacttc aatcgccccc   6780
tggatatagc cccgacaata ggccgtggcc tcattttttt gccttccgca catttccatt   6840
gctcgatacc cacaccttgc ttctcctgca cttgccaacc ttaatactgg tttacattga   6900
ccaacatctt acaagcgggg ggcttgtcta gggtatatat aaacagtggc tctcccaatc   6960
ggttgccagt ctcttttttc ctttctttcc ccacagattc gaaatctaaa ctacacatca   7020
cagaattccg agccgtgagt atccacgaca agatcagtgt cgagacgacg cgttttgtgt   7080
aatgacacaa tccgaaagtc gctagcaaca cacactctct acacaaacta acccagctct   7140
```

-continued

```
ggtac                                                              7145

<210> SEQ ID NO 49
<211> LENGTH: 5473
<212> TYPE: DNA
<213> ORGANISM: Artificial Sequence
<220> FEATURE:
<223> OTHER INFORMATION: Plasmid pDMW287F

<400> SEQUENCE: 49

ggccgcattg atgattggaa acacacacat gggttatatc taggtgagag ttagttggac     60

agttatatat taaatcagct atgccaacgg taacttcatt catgtcaacg aggaaccagt    120

gactgcaagt aatatagaat ttgaccacct tgccattctc ttgcactcct ttactatatc    180

tcatttattt cttatataca aatcacttct tcttcccagc atcgagctcg gaaacctcat    240

gagcaataac atcgtggatc tcgtcaatag agggcttttt ggactccttg ctgttggcca    300

ccttgtcctt gctgtctggc tcattctgtt tcaacgcctt ttaattaatc gagcttggcg    360

taatcatggt catagctgtt tcctgtgtga aattgttatc cgctcacaat tccacacaac    420

atacgagccg gaagcataaa gtgtaaagcc tggggtgcct aatgagtgag ctaactcaca    480

ttaattgcgt tgcgctcact gcccgctttc cagtcgggaa acctgtcgtg ccagctgcat    540

taatgaatcg gccaacgcgc ggggagaggc ggtttgcgta ttgggcgctc ttccgcttcc    600

tcgctcactg actcgctgcg ctcggtcgtt cggctgcggc gagcggtatc agctcactca    660

aaggcggtaa tacggttatc cacagaatca ggggataacg caggaaagaa catgtgagca    720

aaaggccagc aaaaggccag gaaccgtaaa aaggccgcgt tgctggcgtt tttccatagg    780

ctccgccccc ctgacgagca tcacaaaaat cgacgctcaa gtcagaggtg gcgaaacccg    840

acaggactat aaagatacca ggcgtttccc cctggaagct ccctcgtgcg ctctcctgtt    900

ccgaccctgc cgcttaccgg atacctgtcc gcctttctcc cttcgggaag cgtggcgctt    960

tctcatagct cacgctgtag gtatctcagt tcggtgtagg tcgttcgctc caagctgggc   1020

tgtgtgcacg aaccccccgt tcagcccgac cgctgcgcct tatccggtaa ctatcgtctt   1080

gagtccaacc cggtaagaca cgacttatcg ccactggcag cagccactgg taacaggatt   1140

agcagagcga ggtatgtagg cggtgctaca gagttcttga agtggtggcc taactacggc   1200

tacactagaa ggacagtatt tggtatctgc gctctgctga agccagttac cttcggaaaa   1260

agagttggta gctcttgatc cggcaaacaa accaccgctg gtagcggtgg tttttttgtt   1320

tgcaagcagc agattacgcg cagaaaaaaa ggatctcaag aagatccttt gatcttttct   1380

acggggtctg acgctcagtg gaacgaaaac tcacgttaag ggattttggt catgagatta   1440

tcaaaaagga tcttcaccta gatcctttta aattaaaaat gaagttttaa atcaatctaa   1500

agtatatatg agtaaacttg gtctgacagt taccaatgct taatcagtga ggcacctatc   1560

tcagcgatct gtctatttcg ttcatccata gttgcctgac tccccgtcgt gtagataact   1620

acgatacggg agggcttacc atctggcccc agtgctgcaa tgataccgcg agacccacgc   1680

tcaccggctc cagatttatc agcaataaac cagccagccg gaagggccga gcgcagaagt   1740

ggtcctgcaa ctttatccgc ctccatccag tctattaatt gttgccggga agctagagta   1800

agtagttcgc cagttaatag tttgcgcaac gttgttgcca ttgctacagg catcgtggtg   1860

tcacgctcgt cgtttggtat ggcttcattc agctccggtt cccaacgatc aaggcgagtt   1920

acatgatccc ccatgttgtg caaaaaagcg gttagctcct tcggtcctcc gatcgttgtc   1980
```

-continued agaagtaagt tggccgcagt gttatcactc atggttatgg cagcactgca taattctctt 2040
actgtcatgc catccgtaag atgcttttct gtgactggtg agtactcaac caagtcattc 2100
tgagaatagt gtatgcggcg accgagttgc tcttgcccgg cgtcaatacg ggataatacc 2160
gcgccacata gcagaacttt aaaagtgctc atcattggaa aacgttcttc ggggcgaaaa 2220
ctctcaagga tcttaccgct gttgagatcc agttcgatgt aacccactcg tgcacccaac 2280
tgatcttcag catcttttac tttcaccagc gtttctgggt gagcaaaaac aggaaggcaa 2340
aatgccgcaa aaaagggaat aagggcgaca cggaaatgtt gaatactcat actcttcctt 2400
tttcaatatt attgaagcat ttatcagggt tattgtctca tgagcggata catatttgaa 2460
tgtatttaga aaaataaaca aataggggtt ccgcgcacat ttccccgaaa agtgccacct 2520
gacgcgccct gtagcggcgc attaagcgcg gcgggtgtgg tggttacgcg cagcgtgacc 2580
gctacacttg ccagcgccct agcgcccgct cctttcgctt tcttcccttc ctttctcgcc 2640
acgttcgccg gctttccccg tcaagctcta aatcgggggc tccctttagg gttccgattt 2700
agtgctttac ggcacctcga ccccaaaaaa cttgattagg gtgatggttc acgtagtggg 2760
ccatcgccct gatagacggt ttttcgccct ttgacgttgg agtccacgtt ctttaatagt 2820
ggactcttgt tccaaactgg aacaacactc aaccctatct cggtctattc ttttgattta 2880
taagggattt tgccgatttc ggcctattgg ttaaaaaatg agctgattta acaaaaattt 2940
aacgcgaatt ttaacaaaat attaacgctt acaatttcca ttcgccattc aggctgcgca 3000
actgttggga agggcgatcg gtgcgggcct cttcgctatt acgccagctg gcgaaagggg 3060
gatgtgctgc aaggcgatta agttgggtaa cgccagggtt ttcccagtca cgacgttgta 3120
aaacgacggc cagtgaattg taatacgact cactataggg cgaattgggt accgggcccc 3180
ccctcgaggt cgacgtttaa acagtgtacg cagtactata gaggaacatc gattgccccg 3240
gagaagacgg ccaggccgcc tagatgacaa attcaacaac tcacagctga ctttctgcca 3300
ttgccactag gggggggcct ttttatatgg ccaagccaag ctctccacgt cggttgggct 3360
gcacccaaca ataaatgggt agggttgcac caacaaaggg atgggatggg gggtagaaga 3420
tacgaggata acggggctca atggcacaaa taagaacgaa tactgccatt aagactcgtg 3480
atccagcgac tgacaccatt gcatcatcta agggcctcaa aactacctcg gaactgctgc 3540
gctgatctgg acaccacaga ggttccgagc actttaggtt gcaccaaatg tcccaccagg 3600
tgcaggcaga aaacgctgga acagcgtgta cagtttgtct taacaaaaag tgagggcgct 3660
gaggtcgagc agggtggtgt gacttgttat agcctttaga gctgcgaaag cgcgtatgga 3720
tttggctcat caggccagat tgagggtctg tggacacatg tcatgttagt gtacttcaat 3780
cgccccctgg atatagcccc gacaataggc cgtggcctca tttttttgcc ttccgcacat 3840
ttccattgct cggtacccac accttgcttc tcctgcactt gccaacctta atactggttt 3900
acattgacca acatcttaca agcggggggc ttgtctaggg tatatataaa cagtggctct 3960
cccaatcggt tgccagtctc ttttttcctt tctttcccca cagattcgaa atctaaacta 4020
cacatcacac aatgcctgtt actgacgtcc ttaagcgaaa gtccggtgtc atcgtcggcg 4080
acgatgtccg agccgtgagt atccacgaca agatcagtgt cgagacgacg cgttttgtgt 4140
aatgacacaa tccgaaagtc gctagcaaca cacactctct acacaaacta acccagctct 4200
ccatggtgaa gtccaagcga caggctctgc ccctcaccat cgacggaact acctacgacg 4260
tctccgcttg ggtgaacttc caccctggtg gagctgaaat cattgagaac taccagggac 4320
gagatgctac tgacgccttc atggttatgc actctcagga agccttcgac aagctcaagc 4380

-continued

```
gaatgcccaa gatcaacccc tcctccgagc tgcctcccca ggctgccgtc aacgaagctc   4440

aggaggattt ccgaaagctc cgagaagagc tgatcgccac tggcatgttt gacgcctctc   4500

ccctctggta ctcgtacaag atctccacca ccctgggtct tggcgtgctt ggatacttcc   4560

tgatggtcca gtaccagatg tacttcattg gtgctgtgct gctcggtatg cactaccagc   4620

aaatgggatg gctgtctcat gacatctgcc accaccagac cttcaagaac cgaaactgga   4680

ataacctcgt gggtctggtc tttggcaacg gactccaggg cttctccgtg acctggtgga   4740

aggacagaca caacgcccat cattctgcta ccaacgttca gggtcacgat cccgacattg   4800

ataacctgcc tctgctcgcc tggtccgagg acgatgtcac tcgagcttct cccatctccc   4860

gaaagctcat tcagttccaa cagtactatt tcctggtcat ctgtattctc ctgcgattca   4920

tctggtgttt ccagtctgtg ctgaccgttc gatccctcaa ggaccgagac aaccagttct   4980

accgatctca gtacaagaaa gaggccattg gactcgctct gcactggact ctcaagaccc   5040

tgttccacct cttctttatg ccctccatcc tgacctcgct cctggtgttc tttgtttccg   5100

agctcgtcgg tggcttcgga attgccatcg tggtcttcat gaaccactac cctctggaga   5160

agatcggtga ttccgtctgg gacggacatg gcttctctgt gggtcagatc catgagacca   5220

tgaacattcg acgaggcatc attactgact ggttctttgg aggcctgaac taccagatcg   5280

agcaccatct ctggcccacc ctgcctcgac acaacctcac tgccgtttcc taccaggtgg   5340

aacagctgtg ccagaagcac aacctcccct accgaaaccc tctgccccat gaaggtctcg   5400

tcatcctgct ccgatacctg gccgtgttcg ctcgaatggc cgagaagcag cccgctggca   5460

aggctctcta agc                                                      5473
```

<210> SEQ ID NO 50
<211> LENGTH: 9513
<212> TYPE: DNA
<213> ORGANISM: Artificial Sequence
<220> FEATURE:
<223> OTHER INFORMATION: Plasmid pDMW214

<400> SEQUENCE: 50

```
ggtggagctc cagcttttgt tccctttagt gagggttaat ttcgagcttg gcgtaatcat     60

ggtcatagct gtttcctgtg tgaaattgtt atccgctcac aattccacac aacatacgag    120

ccggaagcat aaagtgtaaa gcctggggtg cctaatgagt gagctaactc acattaattg    180

cgttgcgctc actgcccgct ttccagtcgg gaaacctgtc gtgccagctg cattaatgaa    240

tcggccaacg cgcggggaga ggcggtttgc gtattgggcg ctcttccgct tcctcgctca    300

ctgactcgct gcgctcggtc gttcggctgc ggcgagcggt atcagctcac tcaaaggcgg    360

taatacggtt atccacagaa tcaggggata acgcaggaaa gaacatgtga gcaaaaggcc    420

agcaaaaggc caggaaccgt aaaaaggccg cgttgctggc gtttttccat aggctccgcc    480

cccctgacga gcatcacaaa aatcgacgct caagtcagag gtggcgaaac ccgacaggac    540

tataaagata ccaggcgttt ccccctggaa gctccctcgt gcgctctcct gttccgaccc    600

tgccgcttac cggatacctg tccgcctttc tcccttcggg aagcgtggcg ctttctcata    660

gctcacgctg taggtatctc agttcggtgt aggtcgttcg ctccaagctg ggctgtgtgc    720

acgaaccccc cgttcagccc gaccgctgcg ccttatccgg taactatcgt cttgagtcca    780

acccggtaag acacgactta tcgccactgg cagcagccac tggtaacagg attagcagag    840

cgaggtatgt aggcggtgct acagagttct tgaagtggtg gcctaactac ggctacacta    900
```

-continued

```
gaaggacagt atttggtatc tgcgctctgc tgaagccagt taccttcgga aaaagagttg    960
gtagctcttg atccggcaaa caaaccaccg ctggtagcgg tggttttttt gtttgcaagc   1020
agcagattac gcgcagaaaa aaaggatctc aagaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt taaatcaatc taaagtatat   1200
atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggtttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa aatattaacg cttacaattt ccattcgcca ttcaggctgc gcaactgttg   2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg ggtaccgggc ccccccctcga   2880
ggtcgatggt gtcgataagc ttgatatcga attcatgtca cacaaaccga tcttcgcctc   2940
aaggaaacct aattctacat ccgagagact gccgagatcc agtctacact gattaatttt   3000
cgggccaata atttaaaaaa atcgtgttat ataatattat atgtattata tatatacatc   3060
atgatgatac tgacagtcat gtcccattgc taaatagaca gactccatct gccgcctcca   3120
actgatgttc tcaatattta aggggtcatc tcgcattgtt taataataaa cagactccat   3180
ctaccgcctc caaatgatgt tctcaaaata tattgtatga acttattttt attacttagt   3240
attattagac aacttacttg ctttatgaaa aacacttcct atttaggaaa caatttataa   3300
```

-continued

```
tggcagttcg ttcatttaac aatttatgta gaataaatgt tataaatgcg tatgggaaat   3360
cttaaatatg gatagcataa atgatatctg cattgcctaa ttcgaaatca acagcaacga   3420
aaaaaatccc ttgtacaaca taaatagtca tcgagaaata tcaactatca aagaacagct   3480
attcacacgt tactattgag attattattg gacgagaatc acacactcaa ctgtctttct   3540
ctcttctaga aatacaggta caagtatgta ctattctcat tgttcatact tctagtcatt   3600
tcatcccaca tattccttgg atttctctcc aatgaatgac attctatctt gcaaattcaa   3660
caattataat aagatatacc aaagtagcgg tatagtggca atcaaaaagc ttctctggtg   3720
tgcttctcgt atttattttt attctaatga tccattaaag gtatatattt atttcttgtt   3780
atataatcct tttgtttatt acatgggctg gatacataaa ggtattttga tttaattttt   3840
tgcttaaatt caatcccccc tcgttcagtg tcaactgtaa tggtaggaaa ttaccatact   3900
tttgaagaag caaaaaaaat gaaagaaaaa aaaaatcgta tttccaggtt agacgttccg   3960
cagaatctag aatgcggtat gcggtacatt gttcttcgaa cgtaaaagtt gcgctccctg   4020
agatattgta catttttgct tttacaagta caagtacatc gtacaactat gtactactgt   4080
tgatgcatcc acaacagttt gttttgtttt tttttgtttt tttttttct aatgattcat   4140
taccgctatg tatacctact tgtacttgta gtaagccggg ttattggcgt tcaattaatc   4200
atagacttat gaatctgcac ggtgtgcgct gcgagttact tttagcttat gcatgctact   4260
tgggtgtaat attgggatct gttcggaaat caacggatgc tcaaccgatt tcgacagtaa   4320
taatttgaat cgaatcggag cctaaaatga acccgagtat atctcataaa attctcggtg   4380
agaggtctgt gactgtcagt acaaggtgcc ttcattatgc cctcaacctt accatacctc   4440
actgaatgta gtgtacctct aaaaatgaaa tacagtgcca aaagccaagg cactgagctc   4500
gtctaacgga cttgatatac aaccaattaa aacaaatgaa aagaaataca gttctttgta   4560
tcatttgtaa caattaccct gtacaaacta aggtattgaa atcccacaat attcccaaag   4620
tccacccctt tccaaattgt catgcctaca actcatatac caagcactaa cctaccaaac   4680
accactaaaa ccccacaaaa tatatcttac cgaatataca gtaacaagct accaccacac   4740
tcgttgggtg cagtcgccag cttaaagata tctatccaca tcagccacaa ctcccttcct   4800
ttaataaacc gactacaccc ttggctattg aggttatgag tgaatatact gtagacaaga   4860
cactttcaag aagactgttt ccaaaacgta ccactgtcct ccactacaaa cacacccaat   4920
ctgcttcttc tagtcaaggt tgctacaccg gtaaattata aatcatcatt tcattagcag   4980
ggcagggccc tttttataga gtcttataca ctagcggacc ctgccggtag accaacccgc   5040
aggcgcgtca gtttgctcct tccatcaatg cgtcgtagaa acgacttact ccttcttgag   5100
cagctccttg accttgttgg caacaagtct ccgacctcgg aggtggagga agagcctccg   5160
atatcggcgg tagtgatacc agcctcgacg gactccttga cggcagcctc aacagcgtca   5220
ccggcgggct tcatgttaag agagaacttg agcatcatgg cggcagacag aatggtggca   5280
atggggttga ccttctgctt gccgagatcg ggggcagatc cgtgacaggg ctcgtacaga   5340
ccgaacgcct cgttggtgtc gggcagagaa gccagagagg cggagggcag cagacccaga   5400
gaaccgggga tgacggaggc ctcgtcggag atgatatcgc caaacatgtt ggtggtgatg   5460
atgataccat tcatcttgga gggctgcttg atgaggatca tggcggccga gtcgatcagc   5520
tggtggttga gctcgagctg ggggaattcg tccttgagga ctcgagtgac agtctttcgc   5580
caaagtcgag aggaggccag cacgttggcc ttgtcaagag accacacggg aagagggggg   5640
```

-continued

```
ttgtgctgaa gggccaggaa ggcggccatt cgggcaattc gctcaacctc aggaacggag   5700

taggtctcgg tgtcggaagc gacgccagat ccgtcatcct cctttcgctc tccaaagtag   5760

atacctccga cgagctctcg gacaatgatg aagtcggtgc cctcaacgtt tcggatgggg   5820

gagagatcgg cgagcttggg cgacagcagc tggcagggtc gcaggttggc gtacaggttc   5880

aggtcctttc gcagcttgag gagaccctgc tcgggtcgca cgtcggttcg tccgtcggga   5940

gtggtccata cggtgttggc agcgcctccg acagcaccga gcataataga gtcagccttt   6000

cggcagatgt cgagagtagc gtcggtgatg ggctcgccct ccttctcaat ggcagctcct   6060

ccaatgagtc ggtcctcaaa cacaaactcg gtgccggagg cctcagcaac agacttgagc   6120

accttgacgg cctcggcaat cacctcgggg ccacagaagt cgccgccgag aagaacaatc   6180

ttcttggagt cagtcttggt cttcttagtt tcgggttcca ttgtggatgt gtgtggttgt   6240

atgtgtgatg tggtgtgtgg agtgaaaatc tgtggctggc aaacgctctt gtatatatac   6300

gcacttttgc ccgtgctatg tggaagacta aacctccgaa gattgtgact caggtagtgc   6360

ggtatcggct agggacccaa accttgtcga tgccgatagc gctatcgaac gtaccccagc   6420

cggccgggag tatgtcggag gggacatacg agatcgtcaa gggtttgtgg ccaactggta   6480

aataaatgat gtcgacgttt aaacagtgta cgcagtacta tagaggaaca attgccccgg   6540

agaagacggc caggccgcct agatgacaaa ttcaacaact cacagctgac tttctgccat   6600

tgccactagg ggggggcctt tttatatggc caagccaagc tctccacgtc ggttgggctg   6660

cacccaacaa taaatgggta gggttgcacc aacaaaggga tgggatgggg ggtagaagat   6720

acgaggataa cggggctcaa tggcacaaat aagaacgaat actgccatta agactcgtga   6780

tccagcgact gacaccattg catcatctaa gggcctcaaa actacctcgg aactgctgcg   6840

ctgatctgga caccacagag gttccgagca ctttaggttg caccaaatgt cccaccaggt   6900

gcaggcagaa aacgctggaa cagcgtgtac agtttgtctt aacaaaaagt gagggcgctg   6960

aggtcgagca gggtggtgtg acttgttata gcctttagag ctgcgaaagc gcgtatggat   7020

ttggctcatc aggccagatt gagggtctgt ggacacatgt catgttagtg tacttcaatc   7080

gccccctgga tatagccccg acaataggcc gtggcctcat ttttttgcct tccgcacatt   7140

tccattgctc ggtacccaca ccttgcttct cctgcacttg ccaaccttaa tactggttta   7200

cattgaccaa catcttacaa gcggggggct tgtctagggt atatataaac agtggctctc   7260

ccaatcggtt gccagtctct tttttccttt ctttccccac agattcgaaa tctaaactac   7320

acatcacaca atgcctgtta ctgacgtcct taagcgaaag tccggtgtca tcgtcggcga   7380

cgatgtccga gccgtgagta tccacgacaa gatcagtgtc gagacgacgc gttttgtgta   7440

atgacacaat ccgaaagtcg ctagcaacac acactctcta cacaaactaa cccagctctc   7500

catggcatgg atggtacgtc ctgtagaaac cccaacccgt gaaatcaaaa aactcgacgg   7560

cctgtgggca ttcagtctgg atcgcgaaaa ctgtggaatt gatcagcgtt ggtgggaaag   7620

cgcgttacaa gaaagccggg caattgctgt gccaggcagt tttaacgatc agttcgccga   7680

tgcagatatt cgtaattatg cgggcaacgt ctggtatcag cgcgaagtct ttataccgaa   7740

aggttgggca ggccagcgta tcgtgctgcg tttcgatgcg gtcactcatt acggcaaagt   7800

gtgggtcaat aatcaggaag tgatggagca tcagggcggc tatacgccat ttgaagccga   7860

tgtcacgccg tatgttattg ccgggaaaag tgtacgtatc accgtttgtg tgaacaacga   7920

actgaactgg cagactatcc cgccgggaat ggtgattacc gacgaaaacg gcaagaaaaa   7980

gcagtcttac ttccatgatt tctttaacta tgccgggatc catcgcagcg taatgctcta   8040
```

-continued

```
caccacgccg aacacctggg tggacgatat caccgtggtg acgcatgtcg cgcaagactg   8100
taaccacgcg tctgttgact ggcaggtggt ggccaatggt gatgtcagcg ttgaactgcg   8160
tgatgcggat caacaggtgg ttgcaactgg acaaggcact agcgggactt tgcaagtggt   8220
gaatccgcac ctctggcaac cgggtgaagg ttatctctat gaactgtgcg tcacagccaa   8280
aagccagaca gagtgtgata tctacccgct tcgcgtcggc atccggtcag tggcagtgaa   8340
gggcgaacag ttcctgatta accacaaacc gttctacttt actggctttg gtcgtcatga   8400
agatgcggac ttacgtggca aaggattcga taacgtgctg atggtgcacg accacgcatt   8460
aatggactgg attggggcca actcctaccg tacctcgcat tacccttacg ctgaagagat   8520
gctcgactgg gcagatgaac atggcatcgt ggtgattgat gaaactgctg ctgtcggctt   8580
taacctctct ttaggcattg gtttcgaagc gggcaacaag ccgaaagaac tgtacagcga   8640
agaggcagtc aacggggaaa ctcagcaagc gcacttacag gcgattaaag agctgatagc   8700
gcgtgacaaa aaccacccaa gcgtggtgat gtggagtatt gccaacgaac cggatacccg   8760
tccgcaagtg cacgggaata tttcgccact ggcggaagca acgcgtaaac tcgacccgac   8820
gcgtccgatc acctgcgtca atgtaatgtt ctgcgacgct cacaccgata ccatcagcga   8880
tctctttgat gtgctgtgcc tgaaccgtta ttacggatgg tatgtccaaa gcggcgattt   8940
ggaaacggca gagaaggtac tggaaaaaga acttctggcc tggcaggaga aactgcatca   9000
gccgattatc atcaccgaat acggcgtgga tacgttagcc gggctgcact caatgtacac   9060
cgacatgtgg agtgaagagt atcagtgtgc atggctggat atgtatcacc gcgtctttga   9120
tcgcgtcagc gccgtcgtcg gtgaacaggt atggaatttc gccgattttg cgacctcgca   9180
aggcatattg cgcgttggcg gtaacaagaa agggatcttc actcgcgacc gcaaaccgaa   9240
gtcggcggct tttctgctgc aaaaacgctg gactggcatg aacttcggtg aaaaaccgca   9300
gcagggaggc aaacaatgat taattaacta gagcggccgc caccgcggcc cgagattccg   9360
gcctcttcgg ccgccaagcg acccgggtgg acgtctagag gtacctagca attaacagat   9420
agtttgccgg tgataattct cttaacctcc cacactcctt tgacataacg atttatgtaa   9480
cgaaactgaa atttgaccag atattgtgtc cgc                                 9513
```

<210> SEQ ID NO 51
<211> LENGTH: 8910
<212> TYPE: DNA
<213> ORGANISM: Artificial Sequence
<220> FEATURE:
<223> OTHER INFORMATION: Plasmid pFmD8S

<400> SEQUENCE: 51

```
catggtgaag tccaagcgac aggctctgcc cctcaccatc gacggaacta cctacgacgt     60
ctccgcttgg gtgaacttcc accctggtgg agctgaaatc attgagaact accagggacg    120
agatgctact gacgccttca tggttatgca ctctcaggaa gccttcgaca agctcaagcg    180
aatgcccaag atcaacccct cctccgagct gcctccccag gctgccgtca acgaagctca    240
ggaggatttc cgaaagctcc gagaagagct gatcgccact ggcatgtttg acgcctctcc    300
cctctggtac tcgtacaaga tctccaccac cctgggtctt ggcgtgcttg gatacttcct    360
gatggtccag taccagatgt acttcattgg tgctgtgctg ctcggtatgc actaccagca    420
aatgggatgg ctgtctcatg acatctgcca ccaccagacc ttcaagaacc gaaactggaa    480
taacctcgtg ggtctggtct ttggcaacgg actccagggc ttctccgtga cctggtggaa    540
```

-continued

```
ggacagacac aacgcccatc attctgctac caacgttcag ggtcacgatc ccgacattga    600
taacctgcct ctgctcgcct ggtccgagga cgatgtcact cgagcttctc ccatctcccg    660
aaagctcatt cagttccaac agtactattt cctggtcatc tgtattctcc tgcgattcat    720
ctggtgtttc cagtctgtgc tgaccgttcg atccctcaag gaccgagaca accagttcta    780
ccgatctcag tacaagaaag aggccattgg actcgctctg cactggactc tcaagaccct    840
gttccacctc ttctttatgc cctccatcct gacctcgctc ctggtgttct ttgtttccga    900
gctcgtcggt ggcttcggaa ttgccatcgt ggtcttcatg aaccactacc ctctggagaa    960
gatcggtgat tccgtctggg acggacatgg cttctctgtg ggtcagatcc atgagaccat   1020
gaacattcga cgaggcatca ttactgactg gttctttgga ggcctgaact accagatcga   1080
gcaccatctc tggcccaccc tgcctcgaca caacctcact gccgtttcct accaggtgga   1140
acagctgtgc cagaagcaca acctccccta ccgaaaccct ctgccccatg aaggtctcgt   1200
catcctgctc cgatacctgg ccgtgttcgc tcgaatggcc gagaagcagc ccgctggcaa   1260
ggctctctaa gcggccgcca ccgcggcccg agattccggc ctcttcggcc gccaagcgac   1320
ccgggtggac gtctagaggt acctagcaat taacagatag tttgccggtg ataattctct   1380
taacctccca cactcctttg acataacgat ttatgtaacg aaactgaaat ttgaccagat   1440
attgtgtccg cggtggagct ccagcttttg ttccctttag tgagggttaa tttcgagctt   1500
ggcgtaatca tggtcatagc tgtttcctgt gtgaaattgt tatccgctca caattccaca   1560
caacatacga gccggaagca taaagtgtaa agcctggggt gcctaatgag tgagctaact   1620
cacattaatt gcgttgcgct cactgcccgc tttccagtcg ggaaacctgt cgtgccagct   1680
gcattaatga atcggccaac gcgcggggag aggcggtttg cgtattgggc gctcttccgc   1740
ttcctcgctc actgactcgc tgcgctcggt cgttcggctg cggcgagcgg tatcagctca   1800
ctcaaaggcg gtaatacggt tatccacaga atcaggggat aacgcaggaa agaacatgtg   1860
agcaaaaggc cagcaaaagg ccaggaaccg taaaaaggcc gcgttgctgg cgtttttcca   1920
taggctccgc ccccctgacg agcatcacaa aaatcgacgc tcaagtcaga ggtggcgaaa   1980
cccgacagga ctataaagat accaggcgtt tccccctgga agctccctcg tgcgctctcc   2040
tgttccgacc ctgccgctta ccggatacct gtccgccttt ctcccttcgg gaagcgtggc   2100
gctttctcat agctcacgct gtaggtatct cagttcggtg taggtcgttc gctccaagct   2160
gggctgtgtg cacgaacccc ccgttcagcc cgaccgctgc gccttatccg gtaactatcg   2220
tcttgagtcc aacccggtaa gacacgactt atcgccactg gcagcagcca ctggtaacag   2280
gattagcaga gcgaggtatg taggcggtgc tacagagttc ttgaagtggt ggcctaacta   2340
cggctacact agaaggacag tatttggtat ctgcgctctg ctgaagccag ttaccttcgg   2400
aaaaagagtt ggtagctctt gatccggcaa acaaaccacc gctggtagcg gtggtttttt   2460
tgtttgcaag cagcagatta cgcgcagaaa aaaaggatct caagaagatc ctttgatctt   2520
ttctacgggg tctgacgctc agtggaacga aaactcacgt taagggattt tggtcatgag   2580
attatcaaaa aggatcttca cctagatcct tttaaattaa aaatgaagtt ttaaatcaat   2640
ctaaagtata tatgagtaaa cttggtctga cagttaccaa tgcttaatca gtgaggcacc   2700
tatctcagcg atctgtctat ttcgttcatc catagttgcc tgactccccg tcgtgtagat   2760
aactacgata cgggagggct taccatctgg ccccagtgct gcaatgatac cgcgagaccc   2820
acgctcaccg gctccagatt tatcagcaat aaaccagcca gccggaaggg ccgagcgcag   2880
aagtggtcct gcaactttat ccgcctccat ccagtctatt aattgttgcc gggaagctag   2940
```

-continued

```
agtaagtagt tcgccagtta atagtttgcg caacgttgtt gccattgcta caggcatcgt   3000
ggtgtcacgc tcgtcgtttg gtatggcttc attcagctcc ggttcccaac gatcaaggcg   3060
agttacatga tcccccatgt tgtgcaaaaa agcggttagc tccttcggtc ctccgatcgt   3120
tgtcagaagt aagttggccg cagtgttatc actcatggtt atggcagcac tgcataattc   3180
tcttactgtc atgccatccg taagatgctt ttctgtgact ggtgagtact caaccaagtc   3240
attctgagaa tagtgtatgc ggcgaccgag ttgctcttgc ccggcgtcaa tacgggataa   3300
taccgcgcca catagcagaa ctttaaaagt gctcatcatt ggaaaacgtt cttcggggcg   3360
aaaactctca aggatcttac cgctgttgag atccagttcg atgtaaccca ctcgtgcacc   3420
caactgatct tcagcatctt ttactttcac cagcgtttct gggtgagcaa aaacaggaag   3480
gcaaaatgcc gcaaaaaagg gaataagggc gacacggaaa tgttgaatac tcatactctt   3540
cctttttcaa tattattgaa gcatttatca gggttattgt ctcatgagcg gatacatatt   3600
tgaatgtatt tagaaaaata aacaaatagg ggttccgcgc acatttcccc gaaaagtgcc   3660
acctgacgcg ccctgtagcg gcgcattaag cgcggcgggt gtggtggtta cgcgcagcgt   3720
gaccgctaca cttgccagcg ccctagcgcc cgctcctttc gctttcttcc cttcctttct   3780
cgccacgttc gccggctttc cccgtcaagc tctaaatcgg gggctccctt tagggttccg   3840
atttagtgct ttacggcacc tcgaccccaa aaaacttgat tagggtgatg gttcacgtag   3900
tgggccatcg ccctgataga cggtttttcg ccctttgacg ttggagtcca cgttctttaa   3960
tagtggactc ttgttccaaa ctggaacaac actcaaccct atctcggtct attcttttga   4020
tttataaggg attttgccga tttcggccta ttggttaaaa aatgagctga tttaacaaaa   4080
atttaacgcg aattttaaca aaatattaac gcttacaatt tccattcgcc attcaggctg   4140
cgcaactgtt gggaagggcg atcggtgcgg gcctcttcgc tattacgcca gctggcgaaa   4200
gggggatgtg ctgcaaggcg attaagttgg gtaacgccag ggttttccca gtcacgacgt   4260
tgtaaaacga cggccagtga attgtaatac gactcactat agggcgaatt gggtaccggg   4320
ccccccctcg aggtcgatgg tgtcgataag cttgatatcg aattcatgtc acacaaaccg   4380
atcttcgcct caaggaaacc taattctaca tccgagagac tgccgagatc cagtctacac   4440
tgattaattt tcgggccaat aatttaaaaa aatcgtgtta tataatatta tatgtattat   4500
atatatacat catgatgata ctgacagtca tgtcccattg ctaaatagac agactccatc   4560
tgccgcctcc aactgatgtt ctcaatattt aaggggtcat ctcgcattgt ttaataataa   4620
acagactcca tctaccgcct ccaaatgatg ttctcaaaat atattgtatg aacttatttt   4680
tattacttag tattattaga caacttactt gctttatgaa aaacacttcc tatttaggaa   4740
acaatttata atggcagttc gttcatttaa caatttatgt agaataaatg ttataaatgc   4800
gtatgggaaa tcttaaatat ggatagcata aatgatatct gcattgccta attcgaaatc   4860
aacagcaacg aaaaaaatcc cttgtacaac ataaatagtc atcgagaaat atcaactatc   4920
aaagaacagc tattcacacg ttactattga gattattatt ggacgagaat cacacactca   4980
actgtctttc tctcttctag aaatacaggt acaagtatgt actattctca ttgttcatac   5040
ttctagtcat ttcatcccac atattccttg gatttctctc caatgaatga cattctatct   5100
tgcaaattca acaattataa taagatatac caaagtagcg gtatagtggc aatcaaaaag   5160
cttctctggt gtgcttctcg tatttatttt tattctaatg atccattaaa ggtatatatt   5220
tatttcttgt tatataatcc ttttgtttat tacatgggct ggatacataa aggtattttg   5280
```

-continued

```
atttaatttt ttgcttaaat tcaatccccc ctcgttcagt gtcaactgta atggtaggaa   5340
attaccatac ttttgaagaa gcaaaaaaaa tgaaagaaaa aaaaaatcgt atttccaggt   5400
tagacgttcc gcagaatcta gaatgcggta tgcggtacat tgttcttcga acgtaaaagt   5460
tgcgctccct gagatattgt acatttttgc ttttacaagt acaagtacat cgtacaacta   5520
tgtactactg ttgatgcatc cacaacagtt tgttttgttt tttttgttt tttttttttc    5580
taatgattca ttaccgctat gtatacctac ttgtacttgt agtaagccgg gttattggcg   5640
ttcaattaat catagactta tgaatctgca cggtgtgcgc tgcgagttac ttttagctta   5700
tgcatgctac ttgggtgtaa tattgggatc tgttcggaaa tcaacggatg ctcaaccgat   5760
ttcgacagta ataatttgaa tcgaatcgga gcctaaaatg aacccgagta tatctcataa   5820
aattctcggt gagaggtctg tgactgtcag tacaaggtgc cttcattatg ccctcaacct   5880
taccatacct cactgaatgt agtgtacctc taaaaatgaa atacagtgcc aaaagccaag   5940
gcactgagct cgtctaacgg acttgatata caaccaatta aaacaaatga aaagaaatac   6000
agttctttgt atcatttgta acaattaccc tgtacaaact aaggtattga aatcccacaa   6060
tattcccaaa gtccacccct ttccaaattg tcatgcctac aactcatata ccaagcacta   6120
acctaccaaa caccactaaa accccacaaa atatatctta ccgaatatac agtaacaagc   6180
taccaccaca ctcgttgggt gcagtcgcca gcttaaagat atctatccac atcagccaca   6240
actcccttcc tttaataaac cgactacacc cttggctatt gaggttatga gtgaatatac   6300
tgtagacaag acactttcaa gaagactgtt tccaaaacgt accactgtcc tccactacaa   6360
acacacccaa tctgcttctt ctagtcaagg ttgctacacc ggtaaattat aaatcatcat   6420
ttcattagca gggcagggcc ctttttatag agtcttatac actagcggac cctgccggta   6480
gaccaacccg caggcgcgtc agtttgctcc ttccatcaat gcgtcgtaga aacgacttac   6540
tccttcttga gcagctcctt gaccttgttg gcaacaagtc tccgacctcg gaggtggagg   6600
aagagcctcc gatatcggcg gtagtgatac cagcctcgac ggactccttg acggcagcct   6660
caacagcgtc accggcgggc ttcatgttaa gagagaactt gagcatcatg gcggcagaca   6720
gaatggtggc aatggggttg accttctgct tgccgagatc gggggcagat ccgtgacagg   6780
gctcgtacag accgaacgcc tcgttggtgt cgggcagaga agccagagag gcggagggca   6840
gcagacccag agaaccgggg atgacggagg cctcgtcgga gatgatatcg ccaaacatgt   6900
tggtggtgat gatgatacca ttcatcttgg agggctgctt gatgaggatc atggcggccg   6960
agtcgatcag ctggtggttg agctcgagct gggggaattc gtccttgagg actcgagtga   7020
cagtctttcg ccaaagtcga gaggaggcca gcacgttggc cttgtcaaga gaccacacgg   7080
gaagaggggg gttgtgctga agggccagga aggcggccat tcgggcaatt cgctcaacct   7140
caggaacgga gtaggtctcg gtgtcggaag cgacgccaga tccgtcatcc tcctttcgct   7200
ctccaaagta gatacctccg acgagctctc ggacaatgat gaagtcggtg ccctcaacgt   7260
ttcggatggg ggagagatcg gcgagcttgg gcgacagcag ctggcagggt cgcaggttgg   7320
cgtacaggtt caggtccttt cgcagcttga ggagaccctg ctcgggtcgc acgtcggttc   7380
gtccgtcggg agtggtccat acggtgttgg cagcgcctcc gacagcaccg agcataatag   7440
agtcagcctt tcggcagatg tcgagagtag cgtcggtgat gggctcgccc tccttctcaa   7500
tggcagctcc tccaatgagt cggtcctcaa acacaaactc ggtgccggag gcctcagcaa   7560
cagacttgag caccttgacg gcctcggcaa tcacctcggg gccacagaag tcgccgccga   7620
gaagaacaat cttcttggag tcagtcttgg tcttcttagt ttcgggttcc attgtggatg   7680
```

-continued

```
tgtgtggttg tatgtgtgat gtggtgtgtg gagtgaaaat ctgtggctgg caaacgctct   7740

tgtatatata cgcacttttg cccgtgctat gtggaagact aaacctccga agattgtgac   7800

tcaggtagtg cggtatcggc tagggaccca aaccttgtcg atgccgatag cgctatcgaa   7860

cgtaccccag ccggccggga gtatgtcgga ggggacatac gagatcgtca agggtttgtg   7920

gccaactggt aaataaatga tgtcgacgtt taaacagtgt acgcagatct actatagagg   7980

aacatttaaa ttgccccgga gaagacggcc aggccgccta gatgacaaat tcaacaactc   8040

acagctgact ttctgccatt gccactaggg gggggccttt ttatatggcc aagccaagct   8100

ctccacgtcg gttgggctgc acccaacaat aaatgggtag ggttgcacca acaaagggat   8160

gggatggggg gtagaagata cgaggataac ggggctcaat ggcacaaata agaacgaata   8220

ctgccattaa gactcgtgat ccagcgactg acaccattgc atcatctaag ggcctcaaaa   8280

ctacctcgga actgctgcgc tgatctggac accacagagg ttccgagcac tttaggttgc   8340

accaaatgtc ccaccaggtg caggcagaaa acgctggaac agcgtgtaca gtttgtctta   8400

acaaaaagtg agggcgctga ggtcgagcag ggtggtgtga cttgttatag cctttagagc   8460

tgcgaaagcg cgtatggatt tggctcatca ggccagattg agggtctgtg gacacatgtc   8520

atgttagtgt acttcaatcg ccccctggat atagccccga caataggccg tggcctcatt   8580

tttttgcctt ccgcacattt ccattgctcg gtacccacac cttgcttctc ctgcacttgc   8640

caaccttaat actggtttac attgaccaac atcttacaag cggggggctt gtctagggta   8700

tatataaaca gtggctctcc caatcggttg ccagtctctt ttttcctttc tttccccaca   8760

gattcgaaat ctaaactaca catcacagaa ttccgagccg tgagtatcca cgacaagatc   8820

agtgtcgaga cgacgcgttt tgtgtaatga cacaatccga aagtcgctag caacacacac   8880

tctctacaca aactaaccca gctctggtac                                    8910


<210> SEQ ID NO 52
<211> LENGTH: 1272
<212> TYPE: DNA
<213> ORGANISM: Euglena gracilis
<220> FEATURE:
<221> NAME/KEY: misc_feature
<222> LOCATION: (2)..(1270)
<223> OTHER INFORMATION: synthetic delta-8 desaturase CDS, codon-
      optimized for Yarrowia lipolytica ("D8SF" or "EgD8S")
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES: (1)..(1272)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: US-2005-0287652-A1
<311> PATENT FILING DATE: 2005-06-24
<312> PUBLICATION DATE: 2005-12-29
<313> RELEVANT RESIDUES: (1)..(1272)

<400> SEQUENCE: 52

catggtgaag tccaagcgac aggctctgcc cctcaccatc gacggaacta cctacgacgt     60

ctccgcttgg gtgaacttcc accctggtgg agctgaaatc attgagaact accagggacg    120

agatgctact gacgccttca tggttatgca ctctcaggaa gccttcgaca agctcaagcg    180

aatgcccaag atcaacccct cctccgagct gcctccccag gctgccgtca acgaagctca    240

ggaggatttc cgaaagctcc gagaagagct gatcgccact ggcatgtttg acgcctctcc    300
```

-continued

```
cctctggtac tcgtacaaga tctccaccac cctgggtctt ggcgtgcttg gatacttcct    360

gatggtccag taccagatgt acttcattgg tgctgtgctg ctcggtatgc actaccagca    420

aatgggatgg ctgtctcatg acatctgcca ccaccagacc ttcaagaacc gaaactggaa    480

taacctcgtg ggtctggtct ttggcaacgg actccagggc ttctccgtga cctggtggaa    540

ggacagacac aacgcccatc attctgctac caacgttcag ggtcacgatc ccgacattga    600

taacctgcct ctgctcgcct ggtccgagga cgatgtcact cgagcttctc ccatctcccg    660

aaagctcatt cagttccaac agtactattt cctggtcatc tgtattctcc tgcgattcat    720

ctggtgtttc cagtctgtgc tgaccgttcg atccctcaag gaccgagaca accagttcta    780

ccgatctcag tacaagaaag aggccattgg actcgctctg cactggactc tcaagaccct    840

gttccacctc ttctttatgc cctccatcct gacctcgctc ctggtgttct ttgtttccga    900

gctcgtcggt ggcttcggaa ttgccatcgt ggtcttcatg aaccactacc ctctggagaa    960

gatcggtgat tccgtctggg acggacatgg cttctctgtg ggtcagatcc atgagaccat   1020

gaacattcga cgaggcatca ttactgactg gttctttgga ggcctgaact accagatcga   1080

gcaccatctc tggcccaccc tgcctcgaca caacctcact gccgtttcct accaggtgga   1140

acagctgtgc cagaagcaca acctccccta ccgaaaccct ctgccccatg aaggtctcgt   1200

catcctgctc cgatacctgg ccgtgttcgc tcgaatggcc gagaagcagc ccgctggcaa   1260

ggctctctaa gc                                                       1272
```

```
<210> SEQ ID NO 53
<211> LENGTH: 422
<212> TYPE: PRT
<213> ORGANISM: Euglena gracilis
<220> FEATURE:
<221> NAME/KEY: MISC_FEATURE
<223> OTHER INFORMATION: synthetic delta-8 desaturase codon-optimized
      for Yarrowia lipolytica ("D8SF" or "EgD8S")
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES: (1)..(422)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: US-2005-0287652-A1
<311> PATENT FILING DATE: 2005-06-24
<312> PUBLICATION DATE: 2005-12-29
<313> RELEVANT RESIDUES: (1)..(422)

<400> SEQUENCE: 53

Met Val Lys Ser Lys Arg Gln Ala Leu Pro Leu Thr Ile Asp Gly Thr
1               5                   10                  15

Thr Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Pro Ser Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95
```

-continued

```
Asp Ala Ser Pro Leu Trp Tyr Ser Tyr Lys Ile Ser Thr Thr Leu Gly
            100                 105                 110

Leu Gly Val Leu Gly Tyr Phe Leu Met Val Gln Tyr Gln Met Tyr Phe
        115                 120                 125

Ile Gly Ala Val Leu Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Leu Val Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Leu Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ala Val Phe Ala Arg Met Ala Glu Lys Gln
                405                 410                 415

Pro Ala Gly Lys Ala Leu
            420
```

<210> SEQ ID NO 54
<211> LENGTH: 27
<212> TYPE: DNA
<213> ORGANISM: Artificial Sequence
<220> FEATURE:
<223> OTHER INFORMATION: Primer PUD17-F

<400> SEQUENCE: 54
aagatcccat ggcttcttcc actgttg 27

<210> SEQ ID NO 55
<211> LENGTH: 33
<212> TYPE: DNA

-continued

<213> ORGANISM: Artificial Sequence
<220> FEATURE:
<223> OTHER INFORMATION: Primer PUD17-R

<400> SEQUENCE: 55
atcatcgcgg ccgcctagtt ggccttggtc ttg 33

<210> SEQ ID NO 56
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 56
taaccctcac taaagggaac aaaagctgga gctccaccgc ggacacaata tctggtcaaa 60
tttcagtttc gttacataaa tcgttatgtc aaaggagtgt gggaggttaa gagaattatc 120
accggcaaac tatctgttaa ttgctaggta cctctagacg tccacccggg tcgcttggcg 180
gccgaagagg ccggaatctc gggccgcggt ggcggccgct tagttggtct tggacttctt 240
gggcttcttc aggtaggact ggacaaagaa gttgccgaac agagcgagca gggtgatcat 300
gtacacgccg agcagctgga ccagagcctg agggtagtcg caggggaaga ggtagtcgta 360
cagggactgc accagcatag ccatgaactg ggtcatctgc agagtggtga tgtagggctt 420
gatgggcttg acgaagccga agccctgaga ggaaaagaag tagtaggcgt acatgacggt 480
gtggacgaag gagttgagga tgacggagaa gtaggcgtcg ccaccaggag cgtacttggc 540
aatagcccac cagatggcga agatggtggc atggtggtac acgtgcagga aggagacctg 600
gttgaacttc ttgcacagga tcatgatagc ggtgtccagg aactcgtagg ccttggagac 660
gtagaacacg tagacgattc gggacatgcc ctgagcgtgg gactcgttgc ccttctccat 720
gtcgttgccg aagaccttgt agccacccag gatagcctgt cggatggtct cgacgcacat 780
gtagagggac agtccgaaga ggaacaggtt gtggagcagc ttgatggtct tcagctcgaa 840
gggcttctcc atctgcttca tgatgggaat gccgaagagc agcatggcca tgtagccgac 900
ctcgaaggcg agcatggtgg agacgtccat catgggcaga ccgtcggtca gagcgtaggg 960
cttagctccg tccatccact ggtcgacacc ggtctcgact cgtccgacca cgtcgtccca 1020
gacagaggag ttggccatgg tgaatgattc ttatactcag aaggaaatgc ttaacgattt 1080
cgggtgtgag ttgacaagga gagagagaaa agaagaggaa aggtaattcg gggacggtgg 1140
tcttttatac ccttggctaa agtcccaacc acaaagcaaa aaaattttca gtagtctatt 1200
ttgcgtccgg catgggttac ccggatggcc agacaaagaa actagtacaa agtctgaaca 1260
agcgtagatt ccagactgca gtaccctacg cccttaacgg caagtgtggg aaccggggga 1320
ggtttgatat gtggggtgaa gggggctctc gccggggttg ggcccgctac tgggtcaatt 1380
tggggtcaat tggggcaatt ggggctgttt tttgggacac aaatacgccg ccaacccggt 1440
ctctcctgaa ttctgcatcg atcgaggaag aggacaagcg gctgcttctt aagtttgtga 1500
catcagtatc caaggcacca ttgcaaggat tcaaggcttt gaacccgtca tttgccattc 1560
gtaacgctgg tagacaggtt gatcggttcc ctacggcctc cacctgtgtc aatcttctca 1620

-continued

```
agctgcctga ctatcaggac attgatcaac ttcggaagaa acttttgtat gccattcgat   1680
cacatgctgg tttcgatttg tcttagagga acgcatatac agtaatcata gagaataaac   1740
gatattcatt tattaaagta gatagttgag gtagaagttg taaagagtga taaatagcgg   1800
ccgcgcctac ttaagcaacg ggcttgataa cagcgggggg ggtgcccacg ttgttgcggt   1860
tgcggaagaa cagaacaccc ttaccagcac cctcggcacc agcgctgggc tcaacccact   1920
ggcacatacg cgcactgcgg tacatggcgc ggatgaagcc acgaggacca tcctggacat   1980
cagcccggta gtgcttgccc atgatgggct taatggcctc ggtggcctcg tccgcgttgt   2040
agaaggggat gctgctgacg tagtggtgga ggacatgagt ctcgatgatg ccgtggagaa   2100
ggtggcggcc gatgaagccc atctcacggt caatggtagc agcggcacca cggacgaagt   2160
tccactcgtc gttggtgtag tggggaaggg tagggtcggt gtgctggagg aaggtgatgg   2220
caacgagcca gtggttaacc cagaggtagg gaacaaagta ccagatggcc atgttgtaga   2280
aaccgaactt ctgaacgagg aagtacagag cagtggccat cagaccgata ccaatatcgc   2340
tgaggacgat gagcttagcg tcactgttct cgtacagagg gctgcgggga tcgaagtggt   2400
taacaccacc gccgaggccg ttatgcttgc ccttgccgcg accctcacgc tggcgctcgt   2460
ggtagttgtg gccggtaaca ttggtgatga ggtagttggg ccagccnacg annnnctcag   2520
taagatgagc gagctcgtgg gtcatctttc cgagacgagt agcctgctgc tcgcgggttc   2580
ggggaacgaa gaccatgtca cgctccatgt tgccagtggc cttgtggtgc tttcggtggg   2640
agatttgcca gctgaagtag gggacaagga gggaagagtg aagaacccag ccagtaatgt   2700
cgttgatgat gcgagaatcg gagaaagcac cgtgaccgca ctcatgggca ataacccaga   2760
gaccagtacc gaaaagaccc tgaagaacgg tgtacacggc ccacagacca gcgcgggcgg   2820
gggtggaggg gatatattcg ggggtcacaa agttgtacca gatgctgaaa gtggtagtca   2880
ggaggacaat gtcgcggagg atataaccgt atcccttgag agcggagcgc ttgaagcagt   2940
gcttagggat ggcattgtag atgtccttga tggtaaagtc gggaacctcg aactggttgc   3000
cgtaggtgtc gagcatgaca ccatactcgg acttgggctt ggcgatatca acctcggaca   3060
tggacgagag cgatgtggaa gaggccgagt ggcggggaga gtctgaagga gagacggcgg   3120
cagactcaga atccgtcaca gtagttgagg tgacggtgcg tctaagcgca gggttctgct   3180
tgggcagagc cgaagtggac gccatggaga gctgggttag tttgtgtaga gagtgtgtgt   3240
tgctagcgac tttcggattg tgtcattaca caaaacgcgt cgtctcgaca ctgatcttgt   3300
cgtggatact cacggctcgg acatcgtcgc cgacgatgac accggacttt cgcttaagga   3360
cgtcagtaac aggcattgtg tgatgtgtag tttagatttc gaatctgtgg ggaaagaaag   3420
gaaaaaagag actggcaacc gattgggaga gccactgttt atatataccc tagacaagcc   3480
ccccgcttgt aagatgttgg tcaatgtaaa ccagtattaa ggttggcaag tgcaggagaa   3540
gcaaggtgtg ggtaccgagc aatggaaatg tgcggaaggc aaaaaaatga ggccacggcc   3600
tattgtcggg gctatatcca gggggcgatt gaagtacact aacatgacat gtgtccacag   3660
accctcaatc tggcctgatg agccaaatcc atacgcgctt tcgcagctct aaaggctata   3720
acaagtcaca ccaccctgct cgacctcagc gccctcactt tttgttaaga caaactgtac   3780
acgctgttcc agcgttttct gcctgcacct ggtgggacat ttggtgcaac ctaaagtgct   3840
cggaacctct gtggtgtcca gatcagcgca gcagttccga ggtagttttg aggcccttag   3900
atgatgcaat ggtgtcagtc gctggatcac gagtcttaat ggcagtattc gttcttattt   3960
```

-continued

```
gtgccattga gccccgttat cctcgtatct tctacccccc atcccatccc tttgttggtg   4020
caaccctacc catttattgt tgggtgcagc ccaaccgacg tggagagctt ggcttggcca   4080
tataaaaagg cccccccccta gtggcaatgg cagaaagtca gctgtgagtt gttgaatttg  4140
tcatctaggc ggcctggccg tcttctccgg ggcaattgtt cctctatagt actgcgtaca   4200
ctgtttaaac agtgtacgca gatctgcgac gacggaattc ctgcagccca tctgcagaat   4260
tcaggagaga ccgggttggc ggcgtatttg tgtcccaaaa aacagcccca attgccccaa   4320
ttgaccccaa attgacccag tagcgggccc aaccccggcg agagcccccct tcaccccaca  4380
tatcaaacct cccccggttc ccacacttgc cgttaagggc gtagggtact gcagtctgga   4440
atctacgctt gttcagactt tgtactagtt tctttgtctg gccatccggg taacccatgc   4500
cggacgcaaa atagactact gaaaattttt ttgctttgtg gttgggactt tagccaaggg   4560
tataaaagac caccgtcccc gaattacctt tcctcttctt ttctctctct ccttgtcaac   4620
tcacacccga aatcgttaag catttccttc tgagtataag aatcattcac catggctgcc   4680
gctccctctg tgcgaacctt tacccgagcc gaggttctga acgctgaggc tctgaacgag   4740
ggcaagaagg acgctgaggc tcccttcctg atgatcatcg acaacaaggt gtacgacgtc   4800
cgagagttcg tccctgacca tcctggaggc tccgtgattc tcacccacgt tggcaaggac   4860
ggcaccgacg tctttgacac ctttcatccc gaggctgctt gggagactct cgccaacttc   4920
tacgttggag acattgacga gtccgaccga gacatcaaga acgatgactt tgccgctgag   4980
gtccgaaagc tgcgaaccct gttccagtct ctcggctact acgactcctc taaggcctac   5040
tacgccttca aggtctcctt caacctctgc atctggggac tgtccaccgt cattgtggcc   5100
aagtggggtc agacctccac cctcgccaac gtgctctctg ctgccctgct cggcctgttc   5160
tggcagcagt gcggatggct ggctcacgac tttctgcacc accaggtctt ccaggaccga   5220
ttctggggtg atctcttcgg agccttcctg ggaggtgtct gccagggctt ctcctcttcc   5280
tggtggaagg acaagcacaa cactcaccat gccgctccca acgtgcatgg cgaggatcct   5340
gacattgaca cccaccctct cctgacctgg tccgagcacg ctctggagat gttctccgac   5400
gtccccgatg aggagctgac ccgaatgtgg tctcgattca tggtcctgaa ccagacctgg   5460
ttctacttcc ccattctctc cttcgctcga ctgtcttggt gcctccagtc cattctcttt   5520
gtgctgccca acggtcaggc tcacaagccc tccggagctc gagtgcccat ctccctggtc   5580
gagcagctgt ccctcgccat gcactggacc tggtacctcg ctaccatgtt cctgttcatc   5640
aaggatcctg tcaacatgct cgtgtacttc ctggtgtctc aggctgtgtg cggaaacctg   5700
ctcgccatcg tgttctccct caaccacaac ggtatgcctg tgatctccaa ggaggaggct   5760
gtcgacatgg atttctttac caagcagatc atcactggtc gagatgtcca tcctggactg   5820
ttcgccaact ggttcaccgg tggcctgaac taccagatcg agcatcacct gttcccttcc   5880
atgcctcgac acaacttctc caagatccag cctgccgtcg agaccctgtg caagaagtac   5940
aacgtccgat accacaccac tggtatgatc gagggaactg ccgaggtctt ctcccgactg   6000
aacgaggtct ccaaggccac ctccaagatg ggcaaggctc agtaagcggc cgcatgagaa   6060
gataaatata taaatacatt gagatattaa atgcgctaga ttagagagcc tcatactgct   6120
cggagagaag ccaagacgag tactcaaagg ggattacacc atccatatcc acagacacaa   6180
gctggggaaa ggttctatat acactttccg gaataccgta gtttccgatg ttatcaatgg   6240
gggcagccag gatttcaggc acttcggtgt ctcggggtga aatggcgttc ttggcctcca   6300
tcaagtcgta ccatgtcttc atttgcctgt caaagtaaaa cagaagcaga tgaagaatga   6360
```

-continued

```
actttgaagtg aaggaattta aattgccccg gagaagacgg ccaggccgcc tagatgacaa   6420
attcaacaac tcacagctga ctttctgcca ttgccactag ggggggcct ttttatatgg   6480
ccaagccaag ctctccacgt cggttgggct gcacccaaca ataaatgggt agggttgcac   6540
caacaaaggg atgggatggg gggtagaaga tacgaggata acggggctca atggcacaaa   6600
taagaacgaa tactgccatt aagactcgtg atccagcgac tgacaccatt gcatcatcta   6660
agggcctcaa aactacctcg gaactgctgc gctgatctgg acaccacaga ggttccgagc   6720
actttaggtt gcaccaaatg tcccaccagg tgcaggcaga aaacgctgga acagcgtgta   6780
cagtttgtct taacaaaaag tgagggcgct gaggtcgagc agggtggtgt gacttgttat   6840
agcctttaga gctgcgaaag cgcgtatgga tttggctcat caggccagat tgagggtctg   6900
tggacacatg tcatgttagt gtacttcaat cgccccctgg atatagcccc gacaataggc   6960
cgtggcctca ttttttgcc ttccgcacat ttccattgct cggtacccac accttgcttc   7020
tcctgcactt gccaacctta atactggttt acattgacca acatcttaca agcggggggc   7080
ttgtctaggg tatatataaa cagtggctct cccaatcggt tgccagtctc tttttccctt   7140
tctttcccca cagattcgaa atctaaacta cacatcacac aatgcctgtt actgacgtcc   7200
ttaagcgaaa gtccggtgtc atcgtcggcg acgatgtccg agccgtgagt atccacgaca   7260
agatcagtgt cgagacgacg cgttttgtgt aatgacacaa tccgaaagtc gctagcaaca   7320
cacactctct acacaaacta acccagctct ccatggagtc cattgctccc ttcctgccct   7380
ccaagatgcc tcaggacctg ttcatggacc tcgccagcgc tatcggtgtc cgagctgctc   7440
cctacgtcga tcccctggag gctgccctgg ttgcccaggc cgagaagtac attcccacca   7500
ttgtccatca cactcgaggc ttcctggttg ccgtggagtc tcccctggct cgagagctgc   7560
ctctgatgaa ccccttccac gtgctcctga tcgtgctcgc ctacctggtc accgtgtttg   7620
tgggtatgca gatcatgaag aactttgaac gattcgaggt caagaccttc tccctcctgc   7680
acaacttctg tctggtctcc atctccgcct acatgtgcgg tggcatcctg tacgaggctt   7740
atcaggccaa ctatggactg tttgagaacg ctgccgatca caccttcaag ggtctcccta   7800
tggctaagat gatctggctc ttctacttct ccaagatcat ggagtttgtc gacaccatga   7860
tcatggtcct caagaagaac aaccgacaga tttcctttct gcacgtgtac caccactctt   7920
ccatcttcac catctggtgg ctggtcacct tcgttgctcc caacggtgaa gcctacttct   7980
ctgctgccct gaactccttc atccacgtca tcatgtacgg ctactacttt ctgtctgccc   8040
tgggcttcaa gcaggtgtcg ttcatcaagt tctacatcac tcgatcccag atgacccagt   8100
tctgcatgat gtctgtccag tcttcctggg acatgtacgc catgaaggtc cttggccgac   8160
ctggataccc cttcttcatc accgctctgc tctggttcta catgtggacc atgctcggtc   8220
tcttctacaa cttttaccga aagaacgcca agctcgccaa gcaggccaag gctgacgctg   8280
ccaaggagaa ggccagaaag ctccagtaag cggccgcaag tgtggatggg gaagtgagtg   8340
cccggttctg tgtgcacaat tggcaatcca agatggatgg attcaacaca gggatatagc   8400
gagctacgtg gtggtgcgag gatatagcaa cggatattta tgtttgacac ttgagaatgt   8460
acgatacaag cactgtccaa gtacaatact aaacatactg tacatactca tactcgtacc   8520
cgggcaacgg tttcacttga gtgcagtggc tagtgctctt actcgtacag tgtgcaatac   8580
tgcgtatcat agtctttgat gtatatcgta ttcattcatg ttagttgcgt acgaagtcgt   8640
caatgatgtc gatatgggtt ttgatcatgc acacataagg tccgacctta tcggcaagct   8700
```

-continued

```
caatgagctc cttggtggtg gtaacatcca gagaagcaca caggttggtt ttcttggctg   8760

ccacgagctt gagcactcga gcggcaaagg cggacttgtg gacgttagct cgagcttcgt   8820

aggagggcat tttggtggtg aagaggagac tgaaataaat ttagtctgca gaacttttta   8880

tcggaacctt atctggggca gtgaagtata tgttatggta atagttacga gttagttgaa   8940

cttatagata gactggacta tacggctatc ggtccaaatt agaaagaacg tcaatggctc   9000

tctgggcgtc gcctttgccg acaaaaatgt gatcatgatg aaagccagca atgacgttgc   9060

agctgatatt gttgtcggcc aaccgcgccg aaaacgcagc tgtcagaccc acagcctcca   9120

acgaagaatg tatcgtcaaa gtgatccaag cacactcata gttggagtcg tactccaaag   9180

gcggcaatga cgagtcagac agatactcgt cgaccttttc cttgggaacc accaccgtca   9240

gcccttctga ctcacgtatt gtagccaccg acacaggcaa cagtccgtgg atagcagaat   9300

atgtcttgtc ggtccatttc tcaccaactt taggcgtcaa gtgaatgttg cagaagaagt   9360

atgtgccttc attgagaatc ggtgttgctg atttcaataa agtcttgaga tcagtttggc   9420

gcgccagctg cattaatgaa tcggccaacg cgcggggaga ggcggtttgc gtattgggcg   9480

ctcttccgct tcctcgctca ctgactcgct gcgctcggtc gttcggctgc ggcgagcggt   9540

atcagctcac tcaaaggcgg taatacggtt atccacagaa tcaggggata acgcaggaaa   9600

gaacatgtga gcaaaaggcc agcaaaaggc caggaaccgt aaaaaggccg cgttgctggc   9660

gtttttccat aggctccgcc cccctgacga gcatcacaaa aatcgacgct caagtcagag   9720

gtggcgaaac ccgacaggac tataaagata ccaggcgttt ccccctggaa gctccctcgt   9780

gcgctctcct gttccgaccc tgccgcttac cggatacctg tccgcctttc tcccttcggg   9840

aagcgtggcg ctttctcata gctcacgctg taggtatctc agttcggtgt aggtcgttcg   9900

ctccaagctg ggctgtgtgc acgaaccccc cgttcagccc gaccgctgcg ccttatccgg   9960

taactatcgt cttgagtcca acccggtaag acacgactta tcgccactgg cagcagccac  10020

tggtaacagg attagcagag cgaggtatgt aggcggtgct acagagttct tgaagtggtg  10080

gcctaactac ggctacacta gaagaacagt atttggtatc tgcgctctgc tgaagccagt  10140

taccttcgga aaaagagttg gtagctcttg atccggcaaa caaaccaccg ctggtagcgg  10200

tggttttttt gtttgcaagc agcagattac gcgcagaaaa aaaggatctc aagaagatcc  10260

tttgatcttt tctacggggt ctgacgctca gtggaacgaa aactcacgtt aagggatttt  10320

ggtcatgaga ttatcaaaaa ggatcttcac ctagatcctt ttaaattaaa aatgaagttt  10380

taaatcaatc taaagtatat atgagtaaac ttggtctgac agttaccaat gcttaatcag  10440

tgaggcacct atctcagcga tctgtctatt tcgttcatcc atagttgcct gactccccgt  10500

cgtgtagata actacgatac gggagggctt accatctggc cccagtgctg caatgatacc  10560

gcgagaccca cgctcaccgg ctccagattt atcagcaata aaccagccag ccggaagggc  10620

cgagcgcaga agtggtcctg caactttatc cgcctccatc cagtctatta attgttgccg  10680

ggaagctaga gtaagtagtt cgccagttaa tagtttgcgc aacgttgttg ccattgctac  10740

aggcatcgtg gtgtcacgct cgtcgtttgg tatggcttca ttcagctccg gttcccaacg  10800

atcaaggcga gttacatgat cccccatgtt gtgcaaaaaa gcggttagct ccttcggtcc  10860

tccgatcgtt gtcagaagta agttggccgc agtgttatca ctcatggtta tggcagcact  10920

gcataattct cttactgtca tgccatccgt aagatgcttt tctgtgactg gtgagtactc  10980

aaccaagtca ttctgagaat agtgtatgcg gcgaccgagt tgctcttgcc cggcgtcaat  11040

acgggataat accgcgccac atagcagaac tttaaaagtg ctcatcattg gaaaacgttc  11100
```

-continued ttcggggcga aaactctcaa ggatcttacc gctgttgaga tccagttcga tgtaacccac 11160
tcgtgcaccc aactgatctt cagcatcttt tactttcacc agcgtttctg ggtgagcaaa 11220
aacaggaagg caaaatgccg caaaaaaggg aataagggcg acacggaaat gttgaatact 11280
catactcttc ctttttcaat attattgaag catttatcag ggttattgtc tcatgagcgg 11340
atacatattt gaatgtattt agaaaaataa acaaataggg gttccgcgca catttccccg 11400
aaaagtgcca cctgatgcgg tgtgaaatac cgcacagatg cgtaaggaga aaataccgca 11460
tcaggaaatt gtaagcgtta atattttgtt aaaattcgcg ttaaattttt gttaaatcag 11520
ctcatttttt aaccaatagg ccgaaatcgg caaaatccct tataaatcaa aagaatagac 11580
cgagataggg ttgagtgttg ttccagtttg gaacaagagt ccactattaa agaacgtgga 11640
ctccaacgtc aaagggcgaa aaaccgtcta tcagggcgat ggcccactac gtgaaccatc 11700
accctaatca agttttttgg ggtcgaggtg ccgtaaagca ctaaatcgga accctaaagg 11760
gagcccccga tttagagctt gacggggaaa gccggcgaac gtggcgagaa aggaagggaa 11820
gaaagcgaaa ggagcgggcg ctagggcgct ggcaagtgta gcggtcacgc tgcgcgtaac 11880
caccacaccc gccgcgctta atgcgccgct acagggcgcg tccattcgcc attcaggctg 11940
cgcaactgtt gggaagggcg atcggtgcgg gcctcttcgc tattacgcca gctggcgaaa 12000
gggggatgtg ctgcaaggcg attaagttgg gtaacgccag ggttttccca gtcacgacgt 12060
tgtaaaacga cggccagtga attgtaatac gactcactat agggcgaatt gggcccgacg 12120
tcgcatgcag tggtggtatt gtgactgggg atgtagttga gaataagtca tacacaagtc 12180
agctttcttc gagcctcata taagtataag tagttcaacg tattagcact gtacccagca 12240
tctccgtatc gagaaacaca acaacatgcc ccattggaca gatcatgcgg atacacaggt 12300
tgtgcagtat catacatact cgatcagaca ggtcgtctga ccatcataca agctgaacaa 12360
gcgctccata cttgcacgct ctctatatac acagttaaat tacatatcca tagtctaacc 12420
tctaacagtt aatcttctgg taagcctccc agccagcctt ctggtatcgc ttggcctcct 12480
caataggatc tcggttctgg ccgtacagac ctcggccgac aattatgata tccgttccgg 12540
tagacatgac atcctcaaca gttcggtact gctgtccgag agcgtctccc ttgtcgtcaa 12600
gacccacccc gggggtcaga ataagccagt cctcagagtc gcccttaat 12649

<210> SEQ ID NO 57
<211> LENGTH: 819
<212> TYPE: DNA
<213> ORGANISM: Thraustochytrium aureum
<220> FEATURE:
<221> NAME/KEY: misc_feature
<223> OTHER INFORMATION: synthetic elongase (codon-optimized)

<400> SEQUENCE: 57
atggccaact cctctgtctg ggacgacgtg gtcggacgag tcgagaccgg tgtcgaccag 60
tggatggacg gagctaagcc ctacgctctg accgacggtc tgcccatgat ggacgtctcc 120
accatgctcg ccttcgaggt cggctacatg gccatgctgc tcttcggcat tcccatcatg 180
aagcagatgg agaagccctt cgagctgaag accatcaagc tgctccacaa cctgttcctc 240
ttcggactgt ccctctacat gtgcgtcgag accatccgac aggctatcct gggtggctac 300
aaggtcttcg gcaacgacat ggagaagggc aacgagtccc acgctcaggg catgtcccga 360
atcgtctacg tgttctacgt ctccaaggcc tacgagttcc tggacaccgc tatcatgatc 420
ctgtgcaaga agttcaacca ggtctccttc ctgcacgtgt accaccatgc caccatcttc 480

-continued gccatctggt gggctattgc caagtacgct cctggtggcg acgcctactt ctccgtcatc 540
ctcaactcct tcgtccacac cgtcatgtac gcctactact tcttttcctc tcagggcttc 600
ggcttcgtca agcccatcaa gccctacatc accactctgc agatgaccca gttcatggct 660
atgctggtgc agtccctgta cgactacctc ttcccctgcg actaccctca ggctctggtc 720
cagctgctcg gcgtgtacat gatcaccctg ctcgctctgt tcggcaactt ctttgtccag 780
tcctacctga agaagcccaa gaagtccaag accaactaa 819

<210> SEQ ID NO 58
<211> LENGTH: 272
<212> TYPE: PRT
<213> ORGANISM: Thraustochytrium aureum

<400> SEQUENCE: 58

Met Ala Asn Ser Ser Val Trp Asp Asp Val Val Gly Arg Val Glu Thr
1 5 10 15

Gly Val Asp Gln Trp Met Asp Gly Ala Lys Pro Tyr Ala Leu Thr Asp
20 25 30

Gly Leu Pro Met Met Asp Val Ser Thr Met Leu Ala Phe Glu Val Gly
35 40 45

Tyr Met Ala Met Leu Leu Phe Gly Ile Pro Ile Met Lys Gln Met Glu
50 55 60

Lys Pro Phe Glu Leu Lys Thr Ile Lys Leu Leu His Asn Leu Phe Leu
65 70 75 80

Phe Gly Leu Ser Leu Tyr Met Cys Val Glu Thr Ile Arg Gln Ala Ile
85 90 95

Leu Gly Gly Tyr Lys Val Phe Gly Asn Asp Met Glu Lys Gly Asn Glu
100 105 110

Ser His Ala Gln Gly Met Ser Arg Ile Val Tyr Val Phe Tyr Val Ser
115 120 125

Lys Ala Tyr Glu Phe Leu Asp Thr Ala Ile Met Ile Leu Cys Lys Lys
130 135 140

Phe Asn Gln Val Ser Phe Leu His Val Tyr His His Ala Thr Ile Phe
145 150 155 160

Ala Ile Trp Trp Ala Ile Ala Lys Tyr Ala Pro Gly Gly Asp Ala Tyr
165 170 175

Phe Ser Val Ile Leu Asn Ser Phe Val His Thr Val Met Tyr Ala Tyr
180 185 190

Tyr Phe Phe Ser Ser Gln Gly Phe Gly Phe Val Lys Pro Ile Lys Pro
195 200 205

Tyr Ile Thr Thr Leu Gln Met Thr Gln Phe Met Ala Met Leu Val Gln
210 215 220

Ser Leu Tyr Asp Tyr Leu Phe Pro Cys Asp Tyr Pro Gln Ala Leu Val
225 230 235 240

Gln Leu Leu Gly Val Tyr Met Ile Thr Leu Leu Ala Leu Phe Gly Asn
245 250 255

Phe Phe Val Gln Ser Tyr Leu Lys Lys Pro Lys Lys Ser Lys Thr Asn
260 265 270

<210> SEQ ID NO 59
<211> LENGTH: 13034
<212> TYPE: DNA
<213> ORGANISM: Artificial Sequence
<220> FEATURE:
<223> OTHER INFORMATION: Plasmid pDMW271

-continued

<400> SEQUENCE: 59

```
cgatgcagaa ttcaggagag accgggttgg cggcgtattt gtgtcccaaa aaacagcccc     60
aattgcccca attgacccca aattgaccca gtagcgggcc caaccccggc gagagccccc    120
ttcaccccac atatcaaacc tcccccggtt cccacacttg ccgttaaggg cgtagggtac    180
tgcagtctgg aatctacgct tgttcagact ttgtactagt ttctttgtct ggccatccgg    240
gtaacccatg ccggacgcaa aatagactac tgaaaatttt tttgctttgt ggttgggact    300
ttagccaagg gtataaaaga ccaccgtccc cgaattacct ttcctcttct tttctctctc    360
tccttgtcaa ctcacacccg aaatcgttaa gcatttcctt ctgagtataa gaatcattca    420
ccatggatgg ctcccgaccc tgtcgctgcc gagaccgctg cccagggtcc cactccccga    480
tacttcacct gggacgaggt cgcccagcga tccggttgcg aggaacgatg gctggtcatc    540
gaccgaaagg tgtacaacat ctctgagttc acccgacgac atcccggtgg ctcccgagtg    600
atctcgcact acgctggaca ggacgccact gacccettcg ttgcctttca cattaacaag    660
ggcctggtta agaagtacat gaactccctg ctcattggag agctgtctcc cgaacagcct    720
tcgtttgagc ctaccaagaa caaggagctg accgacgagt ttcgagagct ccgagccacc    780
gttgagcgaa tgggactgat gaaggccaac catgtcttct ttctgctcta cctgctccac    840
attcttctcc ttgacggagc tgcctggctt accctgtggg tcttcggcac ttcctttctg    900
ccctttcttc tctgcgccgt cctgctctct gccgtgcagg ctcaggctgg ttggcttcag    960
catgactttg gtcacctttc cgtgttctct acctccaagt ggaaccacct gctccatcac   1020
ttcgtgatcg gccacctcaa gggtgctcct gcctcgtggt ggaaccacat gcatttccag   1080
caccatgcca agcccaactg ttttcgaaag gatcccgaca tcaacatgca cccettcttt   1140
ttcgctcttg gcaagatcct gtccgtcgag ctcggaaagc agaagaagaa gtacatgccc   1200
tacaaccacc agcacaagta cttcttcctg attggacctc ccgctctcct gcctctttac   1260
tttcagtggt acatctttta ctttgttatt cagcgaaaga agtgggttga tcttgcctgg   1320
atgatcacct tctacgtccg attcttcctg acctacgtcc ctctccttgg actgaaggcc   1380
tttctcggtc tgttctttat cgtccgattc ctggagtcca actggttcgt gtgggtgacc   1440
cagatgaacc acattcccat gcacattgac catgatcgaa acatggactg ggtgtcgact   1500
cagctgcagg ccacctgcaa cgttcacaag tctgctttca acgactggtt ttccggtcac   1560
ctcaactttc agattgagca ccatctgttt cccaccatgc ctcgacacaa ctaccacaag   1620
gttgctcccc tggtccagtc gctctgtgcc aagcatggca tcgagtacca gtccaagccc   1680
ctgctctctg ccttcgctga catcattcac tcgctgaagg aatctggcca gctctggctc   1740
gatgcctacc tgcaccagta agcggccgca ttgatgattg gaaacacaca catgggttat   1800
atctaggtga gagttagttg gacagttata tattaaatca gctatgccaa cggtaacttc   1860
attcatgtca acgaggaacc agtgactgca agtaatatag aatttgacca ccttgccatt   1920
ctcttgcact cctttactat atctcattta tttcttatat acaaatcact tcttcttccc   1980
agcatcgagc tcggaaacct catgagcaat aacatcgtgg atctcgtcaa tagagggctt   2040
tttggactcc ttgctgttgg ccaccttgtc cttgctgtct ggctcattct gtttcaacgc   2100
cttttaatta acggagtagg tctcggtgtc ggaagcgacg ccagatccgt catcctcctt   2160
tcgctctcca aagtagatac ctccgacgag ctctcggaca atgatgaagt cggtgccctc   2220
aacgtttcgg atgggggaga gatcggcgag cttgggcgac agcagctggc agggtcgcag   2280
```

-continued

```
gttggcgtac aggttcaggt cctttcgcag cttgaggaga ccctgctcgg gtcgcacgtc   2340
ggttcgtccg tcgggagtgg tccatacggt gttggcagcg cctccgacag caccgagcat   2400
aatagagtca gcctttcggc agatgtcgag agtagcgtcg gtgatgggct cgccctcctt   2460
ctcaatggca gctcctccaa tgagtcggtc ctcaaacaca aactcggtgc cggaggcctc   2520
agcaacagac ttgagcacct tgacggcctc ggcaatcacc tcggggccac agaagtcgcc   2580
gccgagaaga acaatcttct tggagtcagt cttggtcttc ttagtttcgg gttccattgt   2640
ggatgtgtgt ggttgtatgt gtgatgtggt gtgtggagtg aaaatctgtg gctggcaaac   2700
gctcttgtat atatacgcac ttttgcccgt gctatgtgga agactaaacc tccgaagatt   2760
gtgactcagg tagtgcggta tcggctaggg acccaaacct tgtcgatgcc gatagcatgc   2820
gacgtcgggc ccaattcgcc ctatagtgag tcgtattaca attcactggc cgtcgtttta   2880
caacgtcgtg actgggaaaa ccctggcgtt acccaactta atcgccttgc agcacatccc   2940
cctttcgcca gctggcgtaa tagcgaagag gcccgcaccg atcgcccttc ccaacagttg   3000
cgcagcctga atggcgaatg gacgcgccct gtagcggcgc attaagcgcg gcgggtgtgg   3060
tggttacgcg cagcgtgacc gctacacttg ccagcgccct agcgcccgct cctttcgctt   3120
tcttcccttc ctttctcgcc acgttcgccg gctttccccg tcaagctcta aatcgggggc   3180
tccctttagg gttccgattt agtgctttac ggcacctcga ccccaaaaaa cttgattagg   3240
gtgatggttc acgtagtggg ccatcgccct gatagacggt ttttcgccct ttgacgttgg   3300
agtccacgtt ctttaatagt ggactcttgt tccaaactgg aacaacactc aaccctatct   3360
cggtctattc ttttgattta taagggattt tgccgatttc ggcctattgg ttaaaaaatg   3420
agctgattta acaaaaattt aacgcgaatt ttaacaaaat attaacgctt acaatttcct   3480
gatgcggtat tttctcctta cgcatctgtg cggtatttca caccgcatca ggtggcactt   3540
ttcggggaaa tgtgcgcgga acccctattt gtttattttt ctaaatacat tcaaatatgt   3600
atccgctcat gagacaataa ccctgataaa tgcttcaata atattgaaaa aggaagagta   3660
tgagtattca acatttccgt gtcgccctta ttcccttttt tgcggcattt tgccttcctg   3720
tttttgctca cccagaaacg ctggtgaaag taaaagatgc tgaagatcag ttgggtgcac   3780
gagtgggtta catcgaactg gatctcaaca gcggtaagat ccttgagagt tttcgccccg   3840
aagaacgttt tccaatgatg agcactttta aagttctgct atgtggcgcg gtattatccc   3900
gtattgacgc cgggcaagag caactcggtc gccgcataca ctattctcag aatgacttgg   3960
ttgagtactc accagtcaca gaaaagcatc ttacggatgg catgacagta agagaattat   4020
gcagtgctgc cataaccatg agtgataaca ctgcggccaa cttacttctg acaacgatcg   4080
gaggaccgaa ggagctaacc gcttttttgc acaacatggg ggatcatgta actcgccttg   4140
atcgttggga accggagctg aatgaagcca taccaaacga cgagcgtgac accacgatgc   4200
ctgtagcaat ggcaacaacg ttgcgcaaac tattaactgg cgaactactt actctagctt   4260
cccggcaaca attaatagac tggatggagg cggataaagt tgcaggacca cttctgcgct   4320
cggcccttcc ggctggctgg tttattgctg ataaatctgg agccggtgag cgtgggtctc   4380
gcggtatcat tgcagcactg gggccagatg gtaagccctc ccgtatcgta gttatctaca   4440
cgacggggag tcaggcaact atggatgaac gaaatagaca gatcgctgag ataggtgcct   4500
cactgattaa gcattggtaa ctgtcagacc aagtttactc atatatactt tagattgatt   4560
taaaacttca tttttaattt aaaaggatct aggtgaagat cctttttgat aatctcatga   4620
ccaaaatccc ttaacgtgag ttttcgttcc actgagcgtc agaccccgta gaaaagatca   4680
```

-continued

```
aaggatcttc ttgagatcct ttttttctgc gcgtaatctg ctgcttgcaa acaaaaaaac   4740
caccgctacc agcggtggtt tgtttgccgg atcaagagct accaactctt tttccgaagg   4800
taactggctt cagcagagcg cagataccaa atactgttct tctagtgtag ccgtagttag   4860
gccaccactt caagaactct gtagcaccgc ctacatacct cgctctgcta atcctgttac   4920
cagtggctgc tgccagtggc gataagtcgt gtcttaccgg gttggactca agacgatagt   4980
taccggataa ggcgcagcgg tcgggctgaa cggggggttc gtgcacacag cccagcttgg   5040
agcgaacgac ctacaccgaa ctgagatacc tacagcgtga gctatgagaa agcgccacgc   5100
ttcccgaagg gagaaaggcg gacaggtatc cggtaagcgg cagggtcgga acaggagagc   5160
gcacgaggga gcttccaggg ggaaacgcct ggtatcttta tagtcctgtc gggtttcgcc   5220
acctctgact tgagcgtcga tttttgtgat gctcgtcagg ggggcggagc ctatggaaaa   5280
acgccagcaa cgcggccttt ttacggttcc tggccttttg ctggcctttt gctcacatgt   5340
tctttcctgc gttatcccct gattctgtgg ataaccgtat taccgccttt gagtgagctg   5400
ataccgctcg ccgcagccga acgaccgagc gcagcgagtc agtgagcgag gaagcggaag   5460
agcgcccaat acgcaaaccg cctctccccg cgcgttggcc gattcattaa tgcagctggc   5520
gcgcccactg agctcgtcta acggacttga tatacaacca attaaaacaa atgaaaagaa   5580
atacagttct ttgtatcatt tgtaacaatt accctgtaca aactaaggta ttgaaatccc   5640
acaatattcc caaagtccac ccctttccaa attgtcatgc ctacaactca tataccaagc   5700
actaacctac caaacaccac taaaacccca caaaatatat cttaccgaat atacagtaac   5760
aagctaccac cacactcgtt gggtgcagtc gccagcttaa agatatctat ccacatcagc   5820
cacaactccc ttcctttaat aaaccgacta cacccttggc tattgaggtt atgagtgaat   5880
atactgtaga caagacactt tcaagaagac tgtttccaaa acgtaccact gtcctccact   5940
acaaacacac ccaatctgct tcttctagtc aaggttgcta caccggtaaa ttataaatca   6000
tcatttcatt agcagggcag ggcccttttt atagagtctt atacactagc ggaccctgcc   6060
ggtagaccaa cccgcaggcg cgtcagtttg ctccttccat caatgcgtcg tagaaacgac   6120
ttactccttc ttgagcagct ccttgacctt gttggcaaca agtctccgac ctcggaggtg   6180
gaggaagagc ctccgatatc ggcggtagtg ataccagcct cgacggactc cttgacggca   6240
gcctcaacag cgtcaccggc gggcttcatg ttaagagaga acttgagcat catggcggca   6300
gacagaatgg tggcgtacgc aactaacatg aatgaatacg atatacatca aagactatga   6360
tacgcagtat tgcacactgt acgagtaaga gcactagcca ctgcactcaa gtgaaaccgt   6420
tgcccgggta cgagtatgag tatgtacagt atgtttagta ttgtacttgg acagtgcttg   6480
tatcgtacat tctcaagtgt caaacataaa tatccgttgc tatatcctcg caccaccacg   6540
tagctcgcta tatccctgtg ttgaatccat ccatcttgga ttgccaattg tgcacacaga   6600
accgggcact cacttcccca tccacacttg cggccgctta gctgcctact cttccttggg   6660
acggagtcca agaacacgca agtgctccaa atgtgaagca aatgcttgcc aaaacgtatc   6720
cttgacaagg tatggaacct tgtactcgct gcaggtgttc ttgatgatgg ccagaatatc   6780
gggataatgg tgctgcgaca cgttggggaa cagatggtgc acagcctggt agttcaagct   6840
gccagtgatg ctggtccaga ggtgcgaatc gtgtgcgtaa tcctgcgtag tctcgacctg   6900
catagctgcc cagtcctttt ggatgatccc gttctcgtca ggcaacggcc actgaacttc   6960
ctcaacaacg tggttcgcct ggaaggtcag cgccagccag taagacgaca ccatgtccgc   7020
```

-continued

```
gaccgtgaac aagagcagca ccttgcccag gggcagatac tgcaggggaa caatcaggcg   7080
ataccagaca aagaaagcct tgccgcccca gaacatcaca gtgtgccatg tcgagatggg   7140
attgacacga atagcgtcat tggtcttgac aaagtacaaa atgttgatgt cctgaatgcg   7200
caccttgaac gccagcagtc cgtacaggaa aggaacaaac atgtgctggt tgatgtggtt   7260
gacaaaccac ttttggttgg gcttgatacg acgaacatcg ggctcagacg tcgacacgtc   7320
gggatctgct ccagcaatgt tggtgtaggg gtgatggccg agcatatgtt ggtacatcca   7380
caccaggtac gatgctccgt tgaaaaagtc gtgcgtggct cccagaatct tccagacagt   7440
ggggttgtgg gtcactgaaa agtgagacgc atcatgaaga gggttgagtc cgacttgtgc   7500
gcacgcaaat cccatgatga ttgcaaacac cacctgaagc catgtgcgtt cgacaacgaa   7560
aggcacaaag agctgcgcgt agtaggaagc gatcaaggat ccaaagataa gagcgtatcg   7620
tccccagatc tctggtctat tcttgggatc aatgttccga tccgtaaagt agccctcgac   7680
tctcgtcttg atggttttgt ggaacaccgt tggctccggg aagatgggca gctcattcga   7740
gaccagtgta ccgacatagt acttcttcat aatggcatct gcagccccaa acgcgtgata   7800
catctcaaag accggagtaa catctcggcc agctccgagc aggagagtgt ccactccacc   7860
aggatggcgg ctcaagaact ttgtgacatc gtacaccctg ccgcggatgg ccaagagtag   7920
gtcgtccttg gtgttatggg ccgccagctc ttcccaggtg aaggtttttc cttggtccgt   7980
tcccatggag agctgggtta gtttgtgtag agagtgtgtg ttgctagcga ctttcggatt   8040
gtgtcattac acaaaacgcg tcgtctcgac actgatcttg tcgtggatac tcacggctcg   8100
gacatcgtcg ccgacgatga caccggactt tcgcttaagg acgtcagtaa caggcattgt   8160
gtgatgtgta gtttagattt cgaatctgtg gggaaagaaa ggaaaaaaga gactggcaac   8220
cgattgggag agccactgtt tatatatacc ctagacaagc cccccgcttg taagatgttg   8280
gtcaatgtaa accagtatta aggttggcaa gtgcaggaga agcaaggtgt gggtaccgag   8340
caatggaaat gtgcggaagg caaaaaaatg aggccacggc ctattgtcgg ggctatatcc   8400
agggggcgat tgaagtacac taacatgaca tgtgtccaca gaccctcaat ctggcctgat   8460
gagccaaatc catacgcgct ttcgcagctc taaaggctat aacaagtcac accaccctgc   8520
tcgacctcag cgccctcact ttttgttaag acaaactgta cacgctgttc cagcgttttc   8580
tgcctgcacc tggtgggaca tttggtgcaa cctaaagtgc tcggaacctc tgtggtgtcc   8640
agatcagcgc agcagttccg aggtagtttt gaggccctta gatgatgcaa tggtgtcagt   8700
cgctggatca cgagtcttaa tggcagtatt cgttcttatt tgtgccattg agccccgtta   8760
tcctcgtatc ttctaccccc catcccatcc ctttgttggt gcaaccctac ccatttattg   8820
ttgggtgcag cccaaccgac gtggagagct tggcttggcc atataaaaag gccccccccct   8880
agtggcaatg gcagaaagtc agctgtgagt tgttgaattt gtcatctagg cggcctggcc   8940
gtcttctccg gggcaattta aattccttca cttcaagttc attcttcatc tgcttctgtt   9000
ttactttgac aggcaaatga agacatggta cgacttgatg gaggccaaga acgccatttc   9060
accccgagac accgaagtgc ctgaaatcct ggctgccccc attgataaca tcggaaacta   9120
cggtattccg gaaagtgtat atagaacctt tccccagctt gtgtctgtgg atatggatgg   9180
tgtaatcccc tttgagtact cgtcttggct tctctccgag cagtatgagg ctctctaatc   9240
tagcgcattt aatatctcaa tgtatttata tatttatctt ctcatgcggc cgcttagctg   9300
cctactcttc cttgggacgg agtccaagaa cacgcaagtg ctccaaatgt gaagcaaatg   9360
cttgccaaaa cgtatccttg acaaggtatg gaaccttgta ctcgctgcag gtgttcttga   9420
```

-continued

```
tgatggccag aatatcggga taatggtgct gcgacacgtt ggggaacaga tggtgcacag   9480
cctggtagtt caagctgcca gtgatgctgg tccagaggtg cgaatcgtgt gcgtaatcct   9540
gcgtagtctc gacctgcata gctgcccagt ccttttggat gatcccgttc tcgtcaggca   9600
acggccactg aacttcctca acaacgtggt tcgcctggaa ggtcagcgcc agccagtaag   9660
acgacaccat gtccgcgacc gtgaacaaga gcagcacctt gcccaggggc agatactgca   9720
ggggaacaat caggcgatac cagacaaaga aagccttgcc gccccagaac atcacagtgt   9780
gccatgtcga gatgggattg acacgaatag cgtcattggt cttgacaaag tacaaaatgt   9840
tgatgtcctg aatgcgcacc ttgaacgcca gcagtccgta caggaaagga acaaacatgt   9900
gctggttgat gtggttgaca aaccactttt ggttgggctt gatacgacga acatcgggct   9960
cagacgtcga cacgtcggga tctgctccag caatgttggt gtaggggtga tggccgagca  10020
tatgttggta catccacacc aggtacgatg ctccgttgaa aaagtcgtgc gtggctccca  10080
gaatcttcca gacagtgggg ttgtgggtca ctgaaaagtg agacgcatca tgaagagggt  10140
tgagtccgac ttgtgcgcac gcaaatccca tgatgattgc aaacaccacc tgaagccatg  10200
tgcgttcgac aacgaaaggc acaaagagct gcgcgtagta ggaagcgatc aaggatccaa  10260
agataagagc gtatcgtccc cagatctctg gtctattctt gggatcaatg ttccgatccg  10320
taaagtagcc ctcgactctc gtcttgatgg ttttgtggaa caccgttggc tccgggaaga  10380
tgggcagctc attcgagacc agtgtaccga catagtactt cttcataatg gcatctgcag  10440
ccccaaacgc gtgatacatc tcaaagaccg gagtaacatc tcggccagct ccgagcagga  10500
gagtgtccac tccaccagga tggcggctca agaactttgt gacatcgtac accctgccgc  10560
ggatggccaa gagtaggtcg tccttggtgt tatgggccgc cagctcttcc caggtgaagg  10620
tttttccttg gtccgttccc atggtgaatg attcttatac tcagaaggaa atgcttaacg  10680
atttcgggtg tgagttgaca aggagagaga gaaaagaaga ggaaaggtaa ttcggggacg  10740
gtggtctttt atacccttgg ctaaagtccc aaccacaaag caaaaaaatt ttcagtagtc  10800
tattttgcgt ccggcatggg ttacccggat ggccagacaa agaaactagt acaaagtctg  10860
aacaagcgta gattccagac tgcagtaccc tacgccctta acggcaagtg tgggaaccgg  10920
gggaggtttg atatgtgggg tgaagggggc tctcgccggg gttgggcccg ctactgggtc  10980
aatttggggt caattggggc aattggggct gttttttggg acacaaatac gccgccaacc  11040
cggtctctcc tgatcgatgg gctgcaggaa ttctacaata cgtgagtcag aagggctgac  11100
ggtggtggtt cccaaggaaa aggtcgacga gtatctgtct gactcgtcat tgccgccttt  11160
ggagtacgac tccaactatg agtgtgcttg gatcactttg acgatacatt cttcgttgga  11220
ggctgtgggt ctgacagctg cgttttcggc gcggttggcc gacaacaata tcagctgcaa  11280
cgtcattgct ggctttcatc atgatcacat ttttgtcggc aaaggcgacg cccagagagc  11340
cattgacgtt ctttctaatt tggaccgata gccgtatagt ccagtctatc tataagttca  11400
actaactcgt aactattacc ataacatata cttcactgcc ccagataagg ttccgataaa  11460
aagttctgca gactaaattt atttcagtct cctcttcacc accaaaatgc cctcctacga  11520
agctcgagct aacgtccaca agtccgcctt tgccgctcga gtgctcaagc tcgtggcagc  11580
caagaaaacc aacctgtgtg cttctctgga tgttaccacc accaaggagc tcattgagct  11640
tgccgataag gtcggacctt atgtgtgcat gatcaaaacc catatcgaca tcattgacga  11700
cttcacctac gccggcactg tgctccccct caaggaactt gctcttaagc acggtttctt  11760
```

-continued

```
cctgttcgag gacagaaagt tcgcagatat tggcaacact gtcaagcacc agtaccggtg  11820

tcaccgaatc gccgagtggt ccgatatcac caacgcccac ggtgtacccg gaaccggaat  11880

cattgctggc ctgcgagctg gtgccgagga aactgtctct gaacagaaga aggaggacgt  11940

ctctgactac gagaactccc agtacaagga gttcctagtc ccctctccca acgagaagct  12000

ggccagaggt ctgctcatgc tggccgagct gtcttgcaag ggctctctgg ccactggcga  12060

gtactccaag cagaccattg agcttgcccg atccgacccc gagtttgtgg ttggcttcat  12120

tgcccagaac cgacctaagg gcgactctga ggactggctt attctgaccc ccggggtggg  12180

tcttgacgac aagggagacg ctctcggaca gcagtaccga actgttgagg atgtcatgtc  12240

taccggaacg gatatcataa ttgtcggccg aggtctgtac ggccagaacc gagatcctat  12300

tgaggaggcc aagcgatacc agaaggctgg ctgggaggct taccagaaga ttaactgtta  12360

gaggttagac tatggatatg taatttaact gtgtatatag agagcgtgca agtatggagc  12420

gcttgttcag cttgtatgat ggtcagacga cctgtctgat cgagtatgta tgatactgca  12480

caacctgtgt atccgcatga tctgtccaat ggggcatgtt gttgtgtttc tcgatacgga  12540

gatgctgggt acagtgctaa tacgttgaac tacttatact tatatgaggc tcgaagaaag  12600

ctgacttgtg tatgacttat tctcaactac atccccagtc acaataccac cactgcacta  12660

ccactacacc agatctgcgt acactgttta aacggtaggt tagtgcttgg tatatgagtt  12720

gtaggcatga caatttggaa aggggtggac tttgggaata ttgtgggatt tcaatacctt  12780

agtttgtaca gggtaattgt tacaaatgat acaaagaact gtatttcttt tcatttgttt  12840

taattggttg tatatcaagt ccgttagacg agctcagtgc cttggctttt ggcactgtat  12900

ttcattttta gaggtacact acattcagtg aggtatggta aggttgaggg cataatgaag  12960

gcaccttgta ctgacagtca cagacctctc accgagaatt ttatgagata tactcgggtt  13020

cattttaggc tcat                                                    13034
```

<210> SEQ ID NO 60
<211> LENGTH: 1335
<212> TYPE: DNA
<213> ORGANISM: Homo sapiens
<220> FEATURE:
<221> NAME/KEY: misc_feature
<223> OTHER INFORMATION: synthetic delta-5 desaturase (codon-optimized)

<400> SEQUENCE: 60

```
atggctcccg accctgtcgc tgccgagacc gctgcccagg gtcccactcc ccgatacttc     60

acctgggacg aggtcgccca gcgatccggt tgcgaggaac gatggctggt catcgaccga    120

aaggtgtaca acatctctga gttcacccga cgacatcccg gtggctcccg agtgatctcg    180

cactacgctg gacaggacgc cactgacccc ttcgttgcct ttcacattaa caagggcctg    240

gttaagaagt acatgaactc cctgctcatt ggagagctgt ctcccgaaca gccttcgttt    300

gagcctacca agaacaagga gctgaccgac gagtttcgag agctccgagc caccgttgag    360

cgaatgggac tgatgaaggc caaccatgtc ttctttctgc tctacctgct ccacattctt    420

ctccttgacg gagctgcctg gcttaccctg tgggtcttcg gcacttcctt tctgcccttt    480

cttctctgcg ccgtcctgct ctctgccgtg caggctcagg ctggttggct tcagcatgac    540

tttggtcacc tttccgtgtt ctctacctcc aagtggaacc acctgctcca tcacttcgtg    600

atcggccacc tcaagggtgc tcctgcctcg tggtggaacc acatgcattt ccagcaccat    660

gccaagccca actgttttcg aaaggatccc gacatcaaca tgcacccctt ctttttcgct    720
```

-continued

```
cttggcaaga tcctgtccgt cgagctcgga aagcagaaga agaagtacat gccctacaac    780

caccagcaca agtacttctt cctgattgga cctcccgctc tcctgcctct ttactttcag    840

tggtacatct tttactttgt tattcagcga aagaagtggg ttgatcttgc ctggatgatc    900

accttctacg tccgattctt cctgacctac gtccctctcc ttggactgaa ggcctttctc    960

ggtctgttct ttatcgtccg attcctggag tccaactggt tcgtgtgggt gacccagatg   1020

aaccacattc ccatgcacat tgaccatgat cgaaacatgg actgggtgtc gactcagctg   1080

caggccacct gcaacgttca caagtctgct ttcaacgact ggttttccgg tcacctcaac   1140

tttcagattg agcaccatct gtttcccacc atgcctcgac acaactacca caaggttgct   1200

cccctggtcc agtcgctctg tgccaagcat ggcatcgagt accagtccaa gcccctgctc   1260

tctgccttcg ctgacatcat tcactcgctg aaggaatctg gccagctctg gctcgatgcc   1320

tacctgcacc agtaa                                                    1335


<210> SEQ ID NO 61
<211> LENGTH: 444
<212> TYPE: PRT
<213> ORGANISM: Homo sapiens

<400> SEQUENCE: 61

Met Ala Pro Asp Pro Val Ala Ala Glu Thr Ala Ala Gln Gly Pro Thr
1               5                   10                  15

Pro Arg Tyr Phe Thr Trp Asp Glu Val Ala Gln Arg Ser Gly Cys Glu
            20                  25                  30

Glu Arg Trp Leu Val Ile Asp Arg Lys Val Tyr Asn Ile Ser Glu Phe
        35                  40                  45

Thr Arg Arg His Pro Gly Gly Ser Arg Val Ile Ser His Tyr Ala Gly
    50                  55                  60

Gln Asp Ala Thr Asp Pro Phe Val Ala Phe His Ile Asn Lys Gly Leu
65                  70                  75                  80

Val Lys Lys Tyr Met Asn Ser Leu Leu Ile Gly Glu Leu Ser Pro Glu
                85                  90                  95

Gln Pro Ser Phe Glu Pro Thr Lys Asn Lys Glu Leu Thr Asp Glu Phe
            100                 105                 110

Arg Glu Leu Arg Ala Thr Val Glu Arg Met Gly Leu Met Lys Ala Asn
        115                 120                 125

His Val Phe Phe Leu Leu Tyr Leu Leu His Ile Leu Leu Leu Asp Gly
    130                 135                 140

Ala Ala Trp Leu Thr Leu Trp Val Phe Gly Thr Ser Phe Leu Pro Phe
145                 150                 155                 160

Leu Leu Cys Ala Val Leu Leu Ser Ala Val Gln Ala Gln Ala Gly Trp
                165                 170                 175

Leu Gln His Asp Phe Gly His Leu Ser Val Phe Ser Thr Ser Lys Trp
            180                 185                 190

Asn His Leu Leu His His Phe Val Ile Gly His Leu Lys Gly Ala Pro
        195                 200                 205

Ala Ser Trp Trp Asn His Met His Phe Gln His His Ala Lys Pro Asn
    210                 215                 220

Cys Phe Arg Lys Asp Pro Asp Ile Asn Met His Pro Phe Phe Phe Ala
225                 230                 235                 240

Leu Gly Lys Ile Leu Ser Val Glu Leu Gly Lys Gln Lys Lys Lys Tyr
                245                 250                 255

Met Pro Tyr Asn His Gln His Lys Tyr Phe Phe Leu Ile Gly Pro Pro
```

-continued

```
            260                 265                 270

Ala Leu Leu Pro Leu Tyr Phe Gln Trp Tyr Ile Phe Tyr Phe Val Ile
        275                 280                 285

Gln Arg Lys Lys Trp Val Asp Leu Ala Trp Met Ile Thr Phe Tyr Val
    290                 295                 300

Arg Phe Phe Leu Thr Tyr Val Pro Leu Leu Gly Leu Lys Ala Phe Leu
305                 310                 315                 320

Gly Leu Phe Phe Ile Val Arg Phe Leu Glu Ser Asn Trp Phe Val Trp
                325                 330                 335

Val Thr Gln Met Asn His Ile Pro Met His Ile Asp His Asp Arg Asn
            340                 345                 350

Met Asp Trp Val Ser Thr Gln Leu Gln Ala Thr Cys Asn Val His Lys
        355                 360                 365

Ser Ala Phe Asn Asp Trp Phe Ser Gly His Leu Asn Phe Gln Ile Glu
    370                 375                 380

His His Leu Phe Pro Thr Met Pro Arg His Asn Tyr His Lys Val Ala
385                 390                 395                 400

Pro Leu Val Gln Ser Leu Cys Ala Lys His Gly Ile Glu Tyr Gln Ser
                405                 410                 415

Lys Pro Leu Leu Ser Ala Phe Ala Asp Ile Ile His Ser Leu Lys Glu
            420                 425                 430

Ser Gly Gln Leu Trp Leu Asp Ala Tyr Leu His Gln
        435                 440
```

<210> SEQ ID NO 62
<211> LENGTH: 3800
<212> TYPE: DNA
<213> ORGANISM: Artificial Sequence
<220> FEATURE:
<223> OTHER INFORMATION: Plasmid pPaD17S

<400> SEQUENCE: 62

```
ggccgcatcg gatcccgggc ccgtcgactg cagaggcctg catgcaagct tggcgtaatc      60

atggtcatag ctgtttcctg tgtgaaattg ttatccgctc acaattccac acaacatacg     120

agccggaagc ataaagtgta aagcctgggg tgcctaatga gtgagctaac tcacattaat     180

tgcgttgcgc tcactgcccg ctttccagtc gggaaacctg tcgtgccagc tgcattaatg     240

aatcggccaa cgcgcgggga gaggcggttt gcgtattggg cgctcttccg cttcctcgct     300

cactgactcg ctgcgctcgg tcgttcggct gcggcgagcg gtatcagctc actcaaaggc     360

ggtaatacgg ttatccacag aatcagggga taacgcagga aagaacatgt gagcaaaagg     420

ccagcaaaag gccaggaacc gtaaaaaggc cgcgttgctg gcgtttttcc ataggctccg     480

cccccctgac gagcatcaca aaaatcgacg ctcaagtcag aggtggcgaa acccgacagg     540

actataaaga taccaggcgt ttccccctgg aagctccctc gtgcgctctc ctgttccgac     600

cctgccgctt accggatacc tgtccgcctt tctcccttcg ggaagcgtgg cgctttctca     660

tagctcacgc tgtaggtatc tcagttcggt gtaggtcgtt cgctccaagc tgggctgtgt     720

gcacgaaccc cccgttcagc ccgaccgctg cgccttatcc ggtaactatc gtcttgagtc     780

caacccggta agacacgact tatcgccact ggcagcagcc actggtaaca ggattagcag     840

agcgaggtat gtaggcggtg ctacagagtt cttgaagtgg tggcctaact acggctacac     900

tagaagaaca gtatttggta tctgcgctct gctgaagcca gttaccttcg gaaaaagagt     960

tggtagctct tgatccggca aacaaaccac cgctggtagc ggtggttttt ttgtttgcaa    1020
```

-continued

```
gcagcagatt acgcgcagaa aaaaaggatc tcaagaagat cctttgatct tttctacggg   1080
gtctgacgct cagtggaacg aaaactcacg ttaagggatt ttggtcatga gattatcaaa   1140
aaggatcttc acctagatcc ttttaaatta aaaatgaagt tttaaatcaa tctaaagtat   1200
atatgagtaa acttggtctg acagttacca atgcttaatc agtgaggcac ctatctcagc   1260
gatctgtcta tttcgttcat ccatagttgc ctgactcccc gtcgtgtaga taactacgat   1320
acgggagggc ttaccatctg gccccagtgc tgcaatgata ccgcgagacc cacgctcacc   1380
ggctccagat ttatcagcaa taaaccagcc agccggaagg gccgagcgca gaagtggtcc   1440
tgcaacttta tccgcctcca tccagtctat taattgttgc cgggaagcta gagtaagtag   1500
ttcgccagtt aatagtttgc gcaacgttgt tgccattgct acaggcatcg tggtgtcacg   1560
ctcgtcgttt ggtatggctt cattcagctc cggttcccaa cgatcaaggc gagttacatg   1620
atcccccatg ttgtgcaaaa aagcggttag ctccttcggt cctccgatcg ttgtcagaag   1680
taagttggcc gcagtgttat cactcatggt tatggcagca ctgcataatt ctcttactgt   1740
catgccatcc gtaagatgct tttctgtgac tggtgagtac tcaaccaagt cattctgaga   1800
atagtgtatg cggcgaccga gttgctcttg cccggcgtca atacgggata ataccgcgcc   1860
acatagcaga actttaaaag tgctcatcat tggaaaacgt tcttcggggc gaaaactctc   1920
aaggatctta ccgctgttga gatccagttc gatgtaaccc actcgtgcac ccaactgatc   1980
ttcagcatct tttactttca ccagcgtttc tgggtgagca aaaacaggaa ggcaaaatgc   2040
cgcaaaaaag ggaataaggg cgacacggaa atgttgaata ctcatactct tcctttttca   2100
atattattga agcatttatc agggttattg tctcatgagc ggatacatat ttgaatgtat   2160
ttagaaaaat aaacaaatag gggttccgcg cacatttccc cgaaaagtgc cacctgacgt   2220
ctaagaaacc attattatca tgacattaac ctataaaaat aggcgtatca cgaggccctt   2280
tcgtctcgcg cgtttcggtg atgacggtga aaacctctga cacatgcagc tcccggagac   2340
ggtcacagct tgtctgtaag cggatgccgg gagcagacaa gcccgtcagg gcgcgtcagc   2400
gggtgttggc gggtgtcggg gctggcttaa ctatgcggca tcagagcaga ttgtactgag   2460
agtgcaccat atgcggtgtg aaataccgca cagatgcgta aggagaaaat accgcatcag   2520
gcgccattcg ccattcaggc tgcgcaactg ttgggaaggg cgatcggtgc gggcctcttc   2580
gctattacgc cagctggcga aagggggatg tgctgcaagg cgattaagtt gggtaacgcc   2640
agggttttcc cagtcacgac gttgtaaaac gacggccagt gaattcgagc tcggtacctc   2700
gcgaatgcat ctagatccat ggcttcctct accgttgccg ctccctacga gttccctact   2760
ctcaccgaga tcaagcgatc cctgcctgcc cactgcttcg aagcctctgt tccctggtcc   2820
ctctactata ccgtgcgagc tctgggcatt gccggttccc ttgctctcgg actgtactat   2880
gctcgagccc ttgctatcgt gcaggagttt gcactgctcg atgccgtcct ttgcactggc   2940
tacattctgc tccagggtat cgtgttctgg ggattcttta ccatcggtca cgactgtgga   3000
catggtgcct tctcgcgatc ccacctgctc aacttctctg ttggcacact cattcactcc   3060
atcattctga ctccctacga gtcgtggaag atcagccatc gacaccatca caagaacacc   3120
ggcaacatcg acaaggatga gatcttctac cctcagcgag aagccgactc tcatcccctg   3180
tcccgacaca tggtcatctc ccttggttcg gcttggtttg cctacctcgt tgctggattt   3240
cctccccgaa aggtcaacca cttcaatccc tgggagcctc tctacctgcg aagaatgtct   3300
gccgtcatca tttccctcgg ctctctcgtg gcctttgctg gtctgtacgc ctaccttacc   3360
tacgtctacg gcctcaagac catggctctg tattacttcg cacctctctt tggattcgcc   3420
```

-continued

```
accatgctgg ttgtcactac cttcctccat cacaacgacg aggaaactcc ctggtacgcc   3480

gattcggagt ggacctatgt caagggcaac ttgtcctctg tggaccgaag ctacggagcc   3540

ctcatcgaca acctgtccca caacattggt acacatcaga tccaccatct gtttcccatc   3600

attcctcact acaagctcaa cgaggccact gctgccttcg ctcaggcctt tcccgaactg   3660

gtgcgaaagt cggcttctcc catcattccc accttcatcc gaattggtct tatgtacgcc   3720

aagtacggcg tggtcgacaa ggatgccaag atgtttaccc tcaaggaggc caaggctgcc   3780

aagaccaaag ccaactaagc                                               3800
```

<210> SEQ ID NO 63
<211> LENGTH: 14655
<212> TYPE: DNA
<213> ORGANISM: Artificial Sequence
<220> FEATURE:
<223> OTHER INFORMATION: Plasmid pZKLeuN-29E3
<220> FEATURE:
<221> NAME/KEY: misc_feature
<222> LOCATION: (8822)..(8822)
<223> OTHER INFORMATION: n is a, c, g, or t
<220> FEATURE:
<221> NAME/KEY: misc_feature
<222> LOCATION: (8827)..(8830)
<223> OTHER INFORMATION: n is a, c, g, or t

<400> SEQUENCE: 63

```
cgattgttgt ctactaacta tcgtacgata acttcgtata gcatacatta tacgaagtta     60

tcgcgtcgac gagtatctgt ctgactcgtc attgccgcct ttggagtacg actccaacta    120

tgagtgtgct tggatcactt tgacgataca ttcttcgttg gaggctgtgg gtctgacagc    180

tgcgttttcg gcgcggttgg ccgacaacaa tatcagctgc aacgtcattg ctggctttca    240

tcatgatcac atttttgtcg gcaaaggcga cgcccagaga gccattgacg ttctttctaa    300

tttggaccga tagccgtata gtccagtcta tctataagtt caactaactc gtaactatta    360

ccataacata tacttcactg ccccagataa ggttccgata aaaagttctg cagactaaat    420

ttatttcagt ctcctcttca ccaccaaaat gccctcctac gaagctcgag ctaacgtcca    480

caagtccgcc tttgccgctc gagtgctcaa gctcgtggca gccaagaaaa ccaacctgtg    540

tgcttctctg gatgttacca ccaccaagga gctcattgag cttgccgata aggtcggacc    600

ttatgtgtgc atgatcaaaa cccatatcga catcattgac gacttcacct acgccggcac    660

tgtgctcccc ctcaaggaac ttgctcttaa gcacggtttc ttcctgttcg aggacagaaa    720

gttcgcagat attggcaaca ctgtcaagca ccagtaccgg tgtcaccgaa tcgccgagtg    780

gtccgatatc accaacgccc acggtgtacc cggaaccgga atcattgctg gcctgcgagc    840

tggtgccgag gaaactgtct ctgaacagaa gaaggaggac gtctctgact acgagaactc    900

ccagtacaag gagttcctag tcccctctcc caacgagaag ctggccagag gtctgctcat    960

gctggccgag ctgtcttgca agggctctct ggccactggc gagtactcca agcagaccat   1020

tgagcttgcc cgatccgacc ccgagtttgt ggttggcttc attgcccaga accgacctaa   1080

gggcgactct gaggactggc ttattctgac cccggggtg ggtcttgacg acaagggaga   1140

cgctctcgga cagcagtacc gaactgttga ggatgtcatg tctaccggaa cggatatcat   1200

aattgtcggc cgaggtctgt acggccagaa ccgagatcct attgaggagg ccaagcgata   1260

ccagaaggct ggctgggagg cttaccagaa gattaactgt tagaggttag actatggata   1320

tgtaatttaa ctgtgtatat agagagcgtg caagtatgga gcgcttgttc agcttgtatg   1380
```

-continued

```
atggtcagac gacctgtctg atcgagtatg tatgatactg cacaacctgt gtatccgcat   1440
gatctgtcca atggggcatg ttgttgtgtt tctcgatacg gagatgctgg gtacagtgct   1500
aatacgttga actacttata cttatatgag gctcgaagaa agctgacttg tgtatgactt   1560
attctcaact acatccccag tcacaatacc accactgcac taccactaca ccaaaaccat   1620
gatcaaacca cccatggact tcctggaggc agaagaactt gttatggaaa agctcaagag   1680
agagatcata acttcgtata gcatacatta tacgaagtta tcctgcaggt aaaggaattc   1740
tggagtttct gagagaaaaa ggcaagatac gtatgtaaca aagcgacgca tggtacaata   1800
ataccggagg catgtatcat agagagttag tggttcgatg atggcactgg tgcctggtat   1860
gactttatac ggctgactac atatttgtcc tcagacatac aattacagtc aagcacttac   1920
ccttggacat ctgtaggtac cccccggcca agacgatctc agcgtgtcgt atgtcggatt   1980
ggcgtagctc cctcgctcgt caattggctc ccatctactt tcttctgctt ggctacaccc   2040
agcatgtctg ctatggctcg ttttcgtgcc ttatctatcc tcccagtatt accaactcta   2100
aatgacatga tgtgattggg tctacacttt catatcagag ataaggagta gcacagttgc   2160
ataaaaagcc caactctaat cagcttcttc ctttcttgta attagtacaa aggtgattag   2220
cgaaatctgg aagcttagtt ggccctaaaa aaatcaaaaa aagcaaaaaa cgaaaaacga   2280
aaaaccacag ttttgagaac agggaggtaa cgaaggatcg tatatatata tatatatata   2340
tatacccacg gatcccgaga ccggcctttg attcttccct acaaccaacc attctcacca   2400
ccctaattca caaccatgga gtctggaccc atgcctgctg gcattccctt ccctgagtac   2460
tatgacttct ttatggactg gaagactccc ctggccatcg ctgccaccta cactgctgcc   2520
gtcggtctct tcaaccccaa ggttggcaag gtctcccgag tggttgccaa gtcggctaac   2580
gcaaagcctg ccgagcgaac ccagtccgga gctgccatga ctgccttcgt ctttgtgcac   2640
aacctcattc tgtgtgtcta ctctggcatc accttctact acatgtttcc tgctatggtc   2700
aagaacttcc gaacccacac actgcacgaa gcctactgcg acacggatca gtccctctgg   2760
aacaacgcac ttggctactg gggttacctc ttctacctgt ccaagttcta cgaggtcatt   2820
gacaccatca tcatcatcct gaagggacga cggtcctcgc tgcttcagac ctaccaccat   2880
gctggagcca tgattaccat gtggtctggc atcaactacc aagccactcc catttggatc   2940
tttgtggtct tcaactcctt cattcacacc atcatgtact gttactatgc cttcacctct   3000
atcggattcc atcctcctgg caaaaagtac ctgacttcga tgcagattac tcagtttctg   3060
gtcggtatca ccattgccgt gtcctacctc ttcgttcctg gctgcatccg aacacccggt   3120
gctcagatgg ctgtctggat caacgtcggc tacctgtttc ccttgaccta tctgttcgtg   3180
gactttgcca agcgaaccta ctccaagcga tctgccattg ccgctcagaa aaaggctcag   3240
taagcggccg cattgatgat tggaaacaca cacatgggtt atatctaggt gagagttagt   3300
tggacagtta tatattaaat cagctatgcc aacggtaact tcattcatgt caacgaggaa   3360
ccagtgactg caagtaatat agaatttgac caccttgcca ttctcttgca ctcctttact   3420
atatctcatt tatttcttat atacaaatca cttcttcttc ccagcatcga gctcggaaac   3480
ctcatgagca ataacatcgt ggatctcgtc aatagagggc tttttggact ccttgctgtt   3540
ggccaccttg tccttgctgt ctggctcatt ctgtttcaac gccttttaat taacggagta   3600
ggtctcggtg tcggaagcga cgccagatcc gtcatcctcc tttcgctctc caaagtagat   3660
acctccgacg agctctcgga caatgatgaa gtcggtgccc tcaacgtttc ggatggggga   3720
gagatcggcg agcttgggcg acagcagctg gcagggtcgc aggttggcgt acaggttcag   3780
```

-continued

```
gtcctttcgc agcttgagga gaccctgctc gggtcgcacg tcggttcgtc cgtcgggagt   3840
ggtccatacg gtgttggcag cgcctccgac agcaccgagc ataatagagt cagcctttcg   3900
gcagatgtcg agagtagcgt cggtgatggg ctcgccctcc ttctcaatgg cagctcctcc   3960
aatgagtcgg tcctcaaaca caaactcggt gccggaggcc tcagcaacag acttgagcac   4020
cttgacggcc tcggcaatca cctcggggcc acagaagtcg ccgccgagaa gaacaatctt   4080
cttggagtca gtcttggtct tcttagtttc gggttccatt gtggatgtgt gtggttgtat   4140
gtgtgatgtg gtgtgtggag tgaaaatctg tggctggcaa acgctcttgt atatatacgc   4200
acttttgccc gtgctatgtg gaagactaaa cctccgaaga ttgtgactca ggtagtgcgg   4260
tatcggctag ggacccaaac cttgtcgatg ccgatagcat gcgacgtcgg gcccaattcg   4320
ccctatagtg agtcgtatta caattcactg gccgtcgttt tacaacgtcg tgactgggaa   4380
aaccctggcg ttacccaact taatcgcctt gcagcacatc ccccttttcgc cagctggcgt   4440
aatagcgaag aggcccgcac cgatcgccct tcccaacagt tgcgcagcct gaatggcgaa   4500
tggacgcgcc ctgtagcggc gcattaagcg cggcgggtgt ggtggttacg cgcagcgtga   4560
ccgctacact tgccagcgcc ctagcgcccg ctcctttcgc tttcttccct tcctttctcg   4620
ccacgttcgc cggctttccc cgtcaagctc taaatcgggg gctcccttta gggttccgat   4680
ttagtgcttt acggcacctc gaccccaaaa aacttgatta gggtgatggt tcacgtagtg   4740
ggccatcgcc ctgatagacg gtttttcgcc ctttgacgtt ggagtccacg ttctttaata   4800
gtggactctt gttccaaact ggaacaacac tcaaccctat ctcggtctat tcttttgatt   4860
tataagggat tttgccgatt tcggcctatt ggttaaaaaa tgagctgatt taacaaaaat   4920
ttaacgcgaa ttttaacaaa atattaacgc ttacaatttc ctgatgcggt attttctcct   4980
tacgcatctg tgcggtattt cacaccgcat caggtggcac ttttcgggga aatgtgcgcg   5040
gaacccctat ttgtttattt ttctaaatac attcaaatat gtatccgctc atgagacaat   5100
aaccctgata aatgcttcaa taatattgaa aaaggaagag tatgagtatt caacatttcc   5160
gtgtcgccct tattcccttt tttgcggcat tttgccttcc tgtttttgct cacccagaaa   5220
cgctggtgaa agtaaaagat gctgaagatc agttgggtgc acgagtgggt tacatcgaac   5280
tggatctcaa cagcggtaag atccttgaga gttttcgccc cgaagaacgt tttccaatga   5340
tgagcacttt taaagttctg ctatgtggcg cggtattatc ccgtattgac gccgggcaag   5400
agcaactcgg tcgccgcata cactattctc agaatgactt ggttgagtac tcaccagtca   5460
cagaaaagca tcttacggat ggcatgacag taagagaatt atgcagtgct gccataacca   5520
tgagtgataa cactgcggcc aacttacttc tgacaacgat cggaggaccg aaggagctaa   5580
ccgctttttt gcacaacatg ggggatcatg taactcgcct tgatcgttgg gaaccggagc   5640
tgaatgaagc cataccaaac gacgagcgtg acaccacgat gcctgtagca atggcaacaa   5700
cgttgcgcaa actattaact ggcgaactac ttactctagc ttcccggcaa caattaatag   5760
actggatgga ggcggataaa gttgcaggac cacttctgcg ctcggccctt ccggctggct   5820
ggtttattgc tgataaatct ggagccggtg agcgtgggtc tcgcggtatc attgcagcac   5880
tggggccaga tggtaagccc tcccgtatcg tagttatcta cacgacgggg agtcaggcaa   5940
ctatggatga acgaaataga cagatcgctg agataggtgc ctcactgatt aagcattggt   6000
aactgtcaga ccaagtttac tcatatatac tttagattga tttaaaactt catttttaat   6060
ttaaaaggat ctaggtgaag atcctttttg ataatctcat gaccaaaatc ccttaacgtg   6120
```

-continued agttttcgtt ccactgagcg tcagaccccg tagaaaagat caaaggatct tcttgagatc 6180 cttttttct gcgcgtaatc tgctgcttgc aaacaaaaaa accaccgcta ccagcggtgg 6240
tttgtttgcc ggatcaagag ctaccaactc tttttccgaa ggtaactggc ttcagcagag 6300
cgcagatacc aaatactgtt cttctagtgt agccgtagtt aggccaccac ttcaagaact 6360
ctgtagcacc gcctacatac ctcgctctgc taatcctgtt accagtggct gctgccagtg 6420
gcgataagtc gtgtcttacc gggttggact caagacgata gttaccggat aaggcgcagc 6480
ggtcgggctg aacggggggt tcgtgcacac agcccagctt ggagcgaacg acctacaccg 6540
aactgagata cctacagcgt gagctatgag aaagcgccac gcttcccgaa gggagaaagg 6600
cggacaggta tccggtaagc ggcagggtcg gaacaggaga gcgcacgagg gagcttccag 6660
ggggaaacgc ctggtatctt tatagtcctg tcgggtttcg ccacctctga cttgagcgtc 6720
gatttttgtg atgctcgtca ggggggcgga gcctatggaa aaacgccagc aacgcggcct 6780
ttttacggtt cctggccttt tgctggcctt ttgctcacat gttctttcct gcgttatccc 6840
ctgattctgt ggataaccgt attaccgcct ttgagtgagc tgataccgct cgccgcagcc 6900
gaacgaccga gcgcagcgag tcagtgagcg aggaagcgga agagcgccca atacgcaaac 6960
cgcctctccc cgcgcgttgg ccgattcatt aatgcagctg gcgcgcccac tgagctcgtc 7020
taacggactt gatatacaac caattaaaac aaatgaaaag aaatacagtt ctttgtatca 7080
tttgtaacaa ttaccctgta caaactaagg tattgaaatc ccacaatatt cccaaagtcc 7140 accccttcc aaattgtcat gcctacaact catataccaa gcactaacct accaaacacc 7200
actaaaaccc cacaaaatat atcttaccga atatacagta acaagctacc accacactcg 7260
ttgggtgcag tcgccagctt aaagatatct atccacatca gccacaactc ccttccttta 7320
ataaaccgac tacacccttg gctattgagg ttatgagtga atatactgta gacaagacac 7380
tttcaagaag actgtttcca aaacgtacca ctgtcctcca ctacaaacac acccaatctg 7440
cttcttctag tcaaggttgc tacaccggta aattataaat catcatttca ttagcagggc 7500
agggcccttt ttatagagtc ttatacacta gcggaccctg ccggtagacc aacccgcagg 7560
cgcgtcagtt tgctccttcc atcaatgcgt cgtagaaacg acttactcct tcttgagcag 7620
ctccttgacc ttgttggcaa caagtctccg acctcggagg tggaggaaga gcctccgata 7680
tcggcggtag tgataccagc ctcgacggac tccttgacgg cagcctcaac agcgtcaccg 7740
gcgggcttca tgttaagaga gaacttgagc atcatggcgg cagacagaat ggtggcgtac 7800
gcaactaaca tgaatgaata cgatatacat caaagactat gatacgcagt attgcacact 7860
gtacgagtaa gagcactagc cactgcactc aagtgaaacc gttgcccggg tacgagtatg 7920
agtatgtaca gtatgtttag tattgtactt ggacagtgct tgtatcgtac attctcaagt 7980
gtcaaacata aatatccgtt gctatatcct cgcaccacca cgtagctcgc tatatccctg 8040
tgttgaatcc atccatcttg gattgccaat tgtgcacaca gaaccgggca ctcacttccc 8100
catccacact tgcggccgcg cctacttaag caacgggctt gataacagcg gggggggtgc 8160
ccacgttgtt gcggttgcgg aagaacagaa cacccttacc agcaccctcg gcaccagcgc 8220
tgggctcaac ccactggcac atacgcgcac tgcggtacat ggcgcggatg aagccacgag 8280
gaccatcctg gacatcagcc cggtagtgct tgcccatgat gggcttaatg gcctcggtgg 8340
cctcgtccgc gttgtagaag ggatgctgc tgacgtagtg gtggaggaca tgagtctcga 8400
tgatgccgtg gagaaggtgg cggccgatga agcccatctc acggtcaatg gtagcagcgg 8460
caccacggac gaagttccac tcgtcgttgg tgtagtgggg aagggtaggg tcggtgtgct 8520

-continued

```
ggaggaaggt gatggcaacg agccagtggt taacccagag gtagggaaca aagtaccaga   8580
tggccatgtt gtagaaaccg aacttctgaa cgaggaagta cagagcagtg gccatcagac   8640
cgataccaat atcgctgagg acgatgagct tagcgtcact gttctcgtac agagggctgc   8700
ggggatcgaa gtggttaaca ccaccgccga ggccgttatg cttgcccttg ccgcgaccct   8760
cacgctggcg ctcgtggtag ttgtggccgg taacattggt gatgaggtag ttgggccagc   8820
cnacgannnn ctcagtaaga tgagcgagct cgtgggtcat ctttccgaga cgagtagcct   8880
gctgctcgcg ggttcgggga acgaagacca tgtcacgctc catgttgcca gtggccttgt   8940
ggtgctttcg gtgggagatt tgccagctga agtaggggac aaggagggaa gagtgaagaa   9000
cccagccagt aatgtcgttg atgatgcgag aatcggagaa agcaccgtga ccgcactcat   9060
gggcaataac ccagagacca gtaccgaaaa gaccctgaag aacggtgtac acggcccaca   9120
gaccagcgcg ggcgggggtg gaggggatat attcgggggt cacaaagttg taccagatgc   9180
tgaaagtggt agtcaggagg acaatgtcgc ggaggatata accgtatccc ttgagagcgg   9240
agcgcttgaa gcagtgctta gggatggcat tgtagatgtc cttgatggta aagtcgggaa   9300
cctcgaactg gttgccgtag gtgtcgagca tgacaccata ctcggacttg ggcttggcga   9360
tatcaacctc ggacatggac gagagcgatg tggaagaggc cgagtggcgg ggagagtctg   9420
aaggagagac ggcggcagac tcagaatccg tcacagtagt tgaggtgacg gtgcgtctaa   9480
gcgcagggtt ctgcttgggc agagccgaag tggacgccat ggttgatgtg tgtttaattc   9540
aagaatgaat atagagaaga gaagaagaaa aaagattcaa ttgagccggc gatgcagacc   9600
cttatataaa tgttgccttg gacagacgga gcaagcccgc ccaaacctac gttcggtata   9660
atatgttaag ctttttaaca caaaggtttg gcttggggta acctgatgtg gtgcaaaaga   9720
ccgggcgttg gcgagccatt gcgcgggcga atggggccgt gactcgtctc aaattcgagg   9780
gcgtgcctca attcgtgccc ccgtggcttt ttcccgccgt ttccgccccg tttgcaccac   9840
tgcagccgct tctttggttc ggacaccttg ctgcgagcta ggtgccttgt gctacttaaa   9900
aagtggcctc ccaacaccaa catgacatga gtgcgtgggc caagacacgt tggcggggtc   9960
gcagtcggct caatggcccg gaaaaaacgc tgctggagct ggttcggacg cagtccgccg  10020
cggcgtatgg atatccgcaa ggttccatag cgccattgcc ctccgtcggc gtctatcccg  10080
caacctctaa atagagcggg aatataaccc aagcttcttt tttttccttt aacacgcaca  10140
cccccaacta tcatgttgct gctgctgttt gactctactc tgtggagggg tgctcccacc  10200
caacccaacc tacaggtgga tccggcgctg tgattggctg ataagtctcc tatccggact  10260
aattctgacc aatgggacat gcgcgcagga cccaaatgcc gcaattacgt aaccccaacg  10320
aaatgcctac ccctctttgg agcccagcgg ccccaaatcc ccccaagcag cccggttcta  10380
ccggcttcca tctccaagca caagcagccc ggttctaccg gcttccatct ccaagcaccc  10440
ctttctccac accccacaaa aagacccgtg caggacatcc tactgcgtcg acatcattta  10500
aattccttca cttcaagttc attcttcatc tgcttctgtt ttactttgac aggcaaatga  10560
agacatggta cgacttgatg gaggccaaga acgccatttc accccgagac accgaagtgc  10620
ctgaaatcct ggctgccccc attgataaca tcggaaacta cggtattccg gaaagtgtat  10680
atagaacctt tccccagctt gtgtctgtgg atatggatgg tgtaatcccc tttgagtact  10740
cgtcttggct tctctccgag cagtatgagg ctctctaatc tagcgcattt aatatctcaa  10800
tgtatttata tatttatctt ctcatgcggc cgctcactga atctttttgg ctcccttgtg  10860
```

-continued

```
cttcctgacg atatacgttt gcacatagaa attcaagaac aaacacaaga ctgtgccaac  10920
ataaaagtaa ttgaagaacc agccaaacat cctcatccca tcttggcgat aacagggaat  10980
gttcctgtac ttccagacaa tgtagaaacc aacattgaat tgaatgatct gcattgatgt  11040
aatcagggat tttggcatgg ggaacttcag cttgatcaat ctggtccaat aataaccgta  11100
catgatccag tggatgaaac cattcaacag cacaaaaatc caaacagctt catttcggta  11160
attatagaac agccacatat ccatcggtgc cccccaaatga tggaagaatt gcaaccaggt  11220
cagaggcttg cccatcagtg gcaaatagaa ggagtcaata tactccagga acttgctcaa  11280
atagaacaac tgcgtggtga tcctgaagac gttgttgtca aaagccttct cgcagttgtc  11340
agacataaca ccgatggtgt acatggcata tgccattgag aggaatgatc ccaacgaata  11400
aatggacatg agaaggttgt aattggtgaa aacaaacttc atacgagact gaccttttgg  11460
accaaggggg ccaagagtga acttcaagat gacaaatgcg atggacaagt aaagcacctc  11520
acagtgactg gcatcactcc agagttgggc ataatcaact ggttgggtaa aacttcctgc  11580
ccaattgaga ctatttcatt caccacctcc atggccattg ctgtagatat gtcttgtgtg  11640
taagggggtt ggggtggttg tttgtgttct tgacttttgt gttagcaagg gaagacgggc  11700
aaaaaagtga gtgtggttgg gagggagaga cgagccttat atataatgct tgtttgtgtt  11760
tgtgcaagtg gacgccgaaa cgggcaggag ccaaactaaa caaggcagac aatgcgagct  11820
taattggatt gcctgatggg caggggttag ggctcgatca atgggggtgc gaagtgacaa  11880
aattgggaat taggttcgca agcaaggctg acaagacttt ggcccaaaca tttgtacgcg  11940
gtggacaaca ggagccaccc atcgtctgtc acgggctagc cggtcgtgcg tcctgtcagg  12000
ctccacctag gctccatgcc actccataca atcccactag tgtaccgcta ggccgctttt  12060
agctcccatc taagaccccc ccaaaacctc cactgtacag tgcactgtac tgtgtggcga  12120
tcaagggcaa gggaaaaaag gcgcaaacat gcacgcatgg aatgacgtag gtaaggcgtt  12180
actagactga aaagtggcac atttcggcgt gccaaagggt cctaggtgcg tttcgcgagc  12240
tgggcgccag gccaagccgc tccaaaacgc ctctccgact ccctccagcg gcctccatat  12300
ccccatccct ctccacagca atgttgttaa gccttgcaaa cgaaaaaata gaaaggctaa  12360
taagcttcca atattgtggt gtacgctgca taacgcaaca atgagcgcca aacaacacac  12420
acacacagca cacagcagca ttaaccacga tgaacagcat gacattacag gtgggtgtgt  12480
aatcagggcc ctgattgctg gtggtgggag cccccatcat gggcagatct gcgtacactg  12540
tttaaacagt gtacgcagat ctactataga ggaacattta aattgccccg gagaagacgg  12600
ccaggccgcc tagatgacaa attcaacaac tcacagctga ctttctgcca ttgccactag  12660
gggggggcct ttttatatgg ccaagccaag ctctccacgt cggttgggct gcacccaaca  12720
ataaatgggt agggttgcac caacaaaggg atgggatggg gggtagaaga tacgaggata  12780
acggggctca atggcacaaa taagaacgaa tactgccatt aagactcgtg atccagcgac  12840
tgacaccatt gcatcatcta agggcctcaa aactacctcg gaactgctgc gctgatctgg  12900
acaccacaga ggttccgagc actttaggtt gcaccaaatg tcccaccagg tgcaggcaga  12960
aaacgctgga acagcgtgta cagtttgtct taacaaaaag tgagggcgct gaggtcgagc  13020
agggtggtgt gacttgttat agcctttaga gctgcgaaag cgcgtatgga tttggctcat  13080
caggccagat tgagggtctg tggacacatg tcatgttagt gtacttcaat cgccccctgg  13140
atatagcccc gacaataggc cgtggcctca ttttttgcc ttccgcacat ttccattgct  13200
cgatacccac accttgcttc tcctgcactt gccaacctta atactggttt acattgacca  13260
```

-continued

```
acatcttaca agcgggggc ttgtctaggg tatatataaa cagtggctct cccaatcggt  13320

tgccagtctc ttttttcctt tctttcccca cagattcgaa atctaaacta cacatcacag  13380

aattccgagc cgtgagtatc cacgacaaga tcagtgtcga gacgacgcgt tttgtgtaat  13440

gacacaatcc gaaagtcgct agcaacacac actctctaca caaactaacc cagctctggt  13500

accatggagg tcgtgaacga aatcgtctcc attggccagg aggttcttcc caaggtcgac  13560

tatgctcagc tctggtctga tgcctcgcac tgcgaggtgc tgtacctctc catcgccttc  13620

gtcatcctga agttcaccct tggtcctctc ggacccaagg gtcagtctcg aatgaagttt  13680

gtgttcacca actacaacct gctcatgtcc atctactcgc tgggctcctt cctctctatg  13740

gcctacgcca tgtacaccat tggtgtcatg tccgacaact gcgagaaggc tttcgacaac  13800

aatgtcttcc gaatcaccac tcagctgttc tacctcagca agttcctcga gtacattgac  13860

tccttctatc tgcccctcat gggcaagcct ctgacctggt tgcagttctt tcaccatctc  13920

ggagctccta tggacatgtg gctgttctac aactaccgaa acgaagccgt ttggatcttt  13980

gtgctgctca acggcttcat tcactggatc atgtacggct actattggac ccgactgatc  14040

aagctcaagt tccctatgcc caagtccctg attacttcta tgcagatcat tcagttcaac  14100

gttggcttct acatcgtctg gaagtaccgg aacattccct gctaccgaca agatggaatg  14160

agaatgtttg gctggttttt caactacttc tacgttggta ctgtcctgtg tctgttcctc  14220

aacttctacg tgcagaccta catcgtccga aagcacaagg gagccaaaaa gattcagtga  14280

gcggccgcat gtacatacaa gattatttat agaaatgaat cgcgatcgaa caaagagtac  14340

gagtgtacga gtaggggatg atgataaaag tggaagaagt tccgcatctt tggatttatc  14400

aacgtgtagg acgatacttc ctgtaaaaat gcaatgtctt taccataggt tctgctgtag  14460

atgttattaa ctaccattaa catgtctact tgtacagttg cagaccagtt ggagtataga  14520

atggtacact taccaaaaag tgttgatggt tgtaactacg atatataaaa ctgttgacgg  14580

gatccccgct gatatgccta aggaacaatc aaagaggaag atattaattc agaatgctag  14640

tatacagtta gggat                                                   14655
```

<210> SEQ ID NO 64
<211> LENGTH: 777
<212> TYPE: DNA
<213> ORGANISM: Euglena gracilis
<220> FEATURE:
<221> NAME/KEY: misc_feature
<223> OTHER INFORMATION: synthetic delta-9 elongase (codon-optimized)
<300> PUBLICATION INFORMATION:
<302> TITLE: DELTA-9 ELONGASES AND THEIR USE IN MAKING POLYUNSATURATED
FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES: (1)..(777)

<400> SEQUENCE: 64

```
atggaggtcg tgaacgaaat cgtctccatt ggccaggagg ttcttcccaa ggtcgactat     60

gctcagctct ggtctgatgc ctcgcactgc gaggtgctgt acctctccat cgccttcgtc    120

atcctgaagt tcacccttgg tcctctcgga cccaagggtc agtctcgaat gaagtttgtg    180

ttcaccaact acaacctgct catgtccatc tactcgctgg gctccttcct ctctatggcc    240

tacgccatgt acaccattgg tgtcatgtcc gacaactgcg agaaggcttt cgacaacaat    300

gtcttccgaa tcaccactca gctgttctac ctcagcaagt tcctcgagta cattgactcc    360
```

-continued

```
ttctatctgc ccctcatggg caagcctctg acctggttgc agttctttca ccatctcgga    420

gctcctatgg acatgtggct gttctacaac taccgaaacg aagccgtttg gatctttgtg    480

ctgctcaacg gcttcattca ctggatcatg tacggctact attggacccg actgatcaag    540

ctcaagttcc ctatgcccaa gtccctgatt acttctatgc agatcattca gttcaacgtt    600

ggcttctaca tcgtctggaa gtaccggaac attccctgct accgacaaga tggaatgaga    660

atgtttggct ggtttttcaa ctacttctac gttggtactg tcctgtgtct gttcctcaac    720

ttctacgtgc agacctacat cgtccgaaag cacaagggag ccaaaaagat tcagtga       777
```

```
<210> SEQ ID NO 65
<211> LENGTH: 258
<212> TYPE: PRT
<213> ORGANISM: Euglena gracilis
<220> FEATURE:
<221> NAME/KEY: MISC_FEATURE
<222> LOCATION: (1)..(258)
<223> OTHER INFORMATION: delta-9 elongase (EgD9e)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES: (1)..(258)

<400> SEQUENCE: 65

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
```

-continued

```
            245                 250                 255

Ile Gln


<210> SEQ ID NO 66
<211> LENGTH: 34
<212> TYPE: DNA
<213> ORGANISM: Escherichia coli

<400> SEQUENCE: 66

ataacttcgt ataatgtatg ctatacgaag ttat                                34


<210> SEQ ID NO 67
<211> LENGTH: 828
<212> TYPE: DNA
<213> ORGANISM: Mortierella alpina
<220> FEATURE:
<221> NAME/KEY: CDS
<222> LOCATION: (1)..(828)
<223> OTHER INFORMATION: synthetic C16/18 elongase (codon-optimized)
<300> PUBLICATION INFORMATION:
<302> TITLE: A MORTIERELLA ALPINA C16/18 FATTY ACID ELONGASE
<310> PATENT DOCUMENT NUMBER: US 2007/0087420-A1
<311> PATENT FILING DATE: 2005-10-19
<312> PUBLICATION DATE: 2007-04-19
<313> RELEVANT RESIDUES: (1)..(828)

<400> SEQUENCE: 67

atg gag tct gga ccc atg cct gct ggc att ccc ttc cct gag tac tat       48
Met Glu Ser Gly Pro Met Pro Ala Gly Ile Pro Phe Pro Glu Tyr Tyr
1               5                   10                  15

gac ttc ttt atg gac tgg aag act ccc ctg gcc atc gct gcc acc tac       96
Asp Phe Phe Met Asp Trp Lys Thr Pro Leu Ala Ile Ala Ala Thr Tyr
            20                  25                  30

act gct gcc gtc ggt ctc ttc aac ccc aag gtt ggc aag gtc tcc cga      144
Thr Ala Ala Val Gly Leu Phe Asn Pro Lys Val Gly Lys Val Ser Arg
        35                  40                  45

gtg gtt gcc aag tcg gct aac gca aag cct gcc gag cga acc cag tcc      192
Val Val Ala Lys Ser Ala Asn Ala Lys Pro Ala Glu Arg Thr Gln Ser
    50                  55                  60

gga gct gcc atg act gcc ttc gtc ttt gtg cac aac ctc att ctg tgt      240
Gly Ala Ala Met Thr Ala Phe Val Phe Val His Asn Leu Ile Leu Cys
65                  70                  75                  80

gtc tac tct ggc atc acc ttc tac tac atg ttt cct gct atg gtc aag      288
Val Tyr Ser Gly Ile Thr Phe Tyr Tyr Met Phe Pro Ala Met Val Lys
                85                  90                  95

aac ttc cga acc cac aca ctg cac gaa gcc tac tgc gac acg gat cag      336
Asn Phe Arg Thr His Thr Leu His Glu Ala Tyr Cys Asp Thr Asp Gln
            100                 105                 110

tcc ctc tgg aac aac gca ctt ggc tac tgg ggt tac ctc ttc tac ctg      384
Ser Leu Trp Asn Asn Ala Leu Gly Tyr Trp Gly Tyr Leu Phe Tyr Leu
        115                 120                 125

tcc aag ttc tac gag gtc att gac acc atc atc atc atc ctg aag gga      432
Ser Lys Phe Tyr Glu Val Ile Asp Thr Ile Ile Ile Ile Leu Lys Gly
    130                 135                 140

cga cgg tcc tcg ctg ctt cag acc tac cac cat gct gga gcc atg att      480
Arg Arg Ser Ser Leu Leu Gln Thr Tyr His His Ala Gly Ala Met Ile
145                 150                 155                 160

acc atg tgg tct ggc atc aac tac caa gcc act ccc att tgg atc ttt      528
Thr Met Trp Ser Gly Ile Asn Tyr Gln Ala Thr Pro Ile Trp Ile Phe
                165                 170                 175

gtg gtc ttc aac tcc ttc att cac acc atc atg tac tgt tac tat gcc      576
Val Val Phe Asn Ser Phe Ile His Thr Ile Met Tyr Cys Tyr Tyr Ala
            180                 185                 190
```

-continued

```
ttc acc tct atc gga ttc cat cct cct ggc aaa aag tac ctg act tcg      624
Phe Thr Ser Ile Gly Phe His Pro Pro Gly Lys Lys Tyr Leu Thr Ser
        195                 200                 205

atg cag att act cag ttt ctg gtc ggt atc acc att gcc gtg tcc tac      672
Met Gln Ile Thr Gln Phe Leu Val Gly Ile Thr Ile Ala Val Ser Tyr
    210                 215                 220

ctc ttc gtt cct ggc tgc atc cga aca ccc ggt gct cag atg gct gtc      720
Leu Phe Val Pro Gly Cys Ile Arg Thr Pro Gly Ala Gln Met Ala Val
225                 230                 235                 240

tgg atc aac gtc ggc tac ctg ttt ccc ttg acc tat ctg ttc gtg gac      768
Trp Ile Asn Val Gly Tyr Leu Phe Pro Leu Thr Tyr Leu Phe Val Asp
                245                 250                 255

ttt gcc aag cga acc tac tcc aag cga tct gcc att gcc gct cag aaa      816
Phe Ala Lys Arg Thr Tyr Ser Lys Arg Ser Ala Ile Ala Ala Gln Lys
            260                 265                 270

aag gct cag taa                                                      828
Lys Ala Gln
        275


<210> SEQ ID NO 68
<211> LENGTH: 275
<212> TYPE: PRT
<213> ORGANISM: Mortierella alpina

<400> SEQUENCE: 68

Met Glu Ser Gly Pro Met Pro Ala Gly Ile Pro Phe Pro Glu Tyr Tyr
1               5                   10                  15

Asp Phe Phe Met Asp Trp Lys Thr Pro Leu Ala Ile Ala Ala Thr Tyr
            20                  25                  30

Thr Ala Ala Val Gly Leu Phe Asn Pro Lys Val Gly Lys Val Ser Arg
        35                  40                  45

Val Val Ala Lys Ser Ala Asn Ala Lys Pro Ala Glu Arg Thr Gln Ser
    50                  55                  60

Gly Ala Ala Met Thr Ala Phe Val Phe Val His Asn Leu Ile Leu Cys
65                  70                  75                  80

Val Tyr Ser Gly Ile Thr Phe Tyr Tyr Met Phe Pro Ala Met Val Lys
                85                  90                  95

Asn Phe Arg Thr His Thr Leu His Glu Ala Tyr Cys Asp Thr Asp Gln
            100                 105                 110

Ser Leu Trp Asn Asn Ala Leu Gly Tyr Trp Gly Tyr Leu Phe Tyr Leu
        115                 120                 125

Ser Lys Phe Tyr Glu Val Ile Asp Thr Ile Ile Ile Ile Leu Lys Gly
    130                 135                 140

Arg Arg Ser Ser Leu Leu Gln Thr Tyr His His Ala Gly Ala Met Ile
145                 150                 155                 160

Thr Met Trp Ser Gly Ile Asn Tyr Gln Ala Thr Pro Ile Trp Ile Phe
                165                 170                 175

Val Val Phe Asn Ser Phe Ile His Thr Ile Met Tyr Cys Tyr Tyr Ala
            180                 185                 190

Phe Thr Ser Ile Gly Phe His Pro Pro Gly Lys Lys Tyr Leu Thr Ser
        195                 200                 205

Met Gln Ile Thr Gln Phe Leu Val Gly Ile Thr Ile Ala Val Ser Tyr
    210                 215                 220

Leu Phe Val Pro Gly Cys Ile Arg Thr Pro Gly Ala Gln Met Ala Val
225                 230                 235                 240

Trp Ile Asn Val Gly Tyr Leu Phe Pro Leu Thr Tyr Leu Phe Val Asp
```

-continued

```
                245                 250                 255

Phe Ala Lys Arg Thr Tyr Ser Lys Arg Ser Ala Ile Ala Ala Gln Lys
            260                 265                 270

Lys Ala Gln
        275


<210> SEQ ID NO 69
<211> LENGTH: 8739
<212> TYPE: DNA
<213> ORGANISM: Artificial Sequence
<220> FEATURE:
<223> OTHER INFORMATION: Plasmid pY116

<400> SEQUENCE: 69

ggccgccacc gcggcccgag attccggcct cttcggccgc caagcgaccc gggtggacgt     60

ctagaggtac ctagcaatta acagatagtt tgccggtgat aattctctta acctcccaca    120

ctcctttgac ataacgattt atgtaacgaa actgaaattt gaccagatat tgtgtccgcg    180

gtggagctcc agcttttgtt ccctttagtg agggtttaaa cgagcttggc gtaatcatgg    240

tcatagctgt ttcctgtgtg aaattgttat ccgctcacaa ttccacacaa cgtacgagcc    300

ggaagcataa agtgtaaagc ctggggtgcc taatgagtga gctaactcac attaattgcg    360

ttgcgctcac tgcccgcttt ccagtcggga aacctgtcgt gccagctgca ttaatgaatc    420

ggccaacgcg cggggagagg cggtttgcgt attgggcgct cttccgcttc ctcgctcact    480

gactcgctgc gctcggtcgt tcggctgcgg cgagcggtat cagctcactc aaaggcggta    540

atacggttat ccacagaatc aggggataac gcaggaaaga acatgtgagc aaaaggccag    600

caaaaggcca ggaaccgtaa aaaggccgcg ttgctggcgt ttttccatag gctccgcccc    660

cctgacgagc atcacaaaaa tcgacgctca agtcagaggt ggcgaaaccc gacaggacta    720

taaagatacc aggcgtttcc ccctggaagc tccctcgtgc gctctcctgt tccgaccctg    780

ccgcttaccg gatacctgtc cgcctttctc ccttcgggaa gcgtggcgct ttctcatagc    840

tcacgctgta ggtatctcag ttcggtgtag gtcgttcgct ccaagctggg ctgtgtgcac    900

gaaccccccg ttcagcccga ccgctgcgcc ttatccggta actatcgtct tgagtccaac    960

ccggtaagac acgacttatc gccactggca gcagccactg gtaacaggat tagcagagcg   1020

aggtatgtag gcggtgctac agagttcttg aagtggtggc ctaactacgg ctacactaga   1080

aggacagtat ttggtatctg cgctctgctg aagccagtta ccttcggaaa aagagttggt   1140

agctcttgat ccggcaaaca aaccaccgct ggtagcggtg gtttttttgt ttgcaagcag   1200

cagattacgc gcagaaaaaa aggatctcaa gaagatcctt tgatcttttc tacggggtct   1260

gacgctcagt ggaacgaaaa ctcacgttaa gggattttgg tcatgagatt atcaaaaagg   1320

atcttcacct agatcctttt aaattaaaaa tgaagtttta aatcaatcta aagtatatat   1380

gagtaaactt ggtctgacag ttaccaatgc ttaatcagtg aggcacctat ctcagcgatc   1440

tgtctatttc gttcatccat agttgcctga ctccccgtcg tgtagataac tacgatacgg   1500

gagggcttac catctggccc cagtgctgca atgataccgc gagacccacg ctcaccggct   1560

ccagatttat cagcaataaa ccagccagcc ggaagggccg agcgcagaag tggtcctgca   1620

actttatccg cctccatcca gtctattaat tgttgccggg aagctagagt aagtagttcg   1680

ccagttaata gtttgcgcaa cgttgttgcc attgctacag gcatcgtggt gtcacgctcg   1740

tcgtttggta tggcttcatt cagctccggt tcccaacgat caaggcgagt tacatgatcc   1800

cccatgttgt gcaaaaaagc ggttagctcc ttcggtcctc cgatcgttgt cagaagtaag   1860
```

-continued

```
ttggccgcag tgttatcact catggttatg gcagcactgc ataattctct tactgtcatg   1920
ccatccgtaa gatgcttttc tgtgactggt gagtactcaa ccaagtcatt ctgagaatag   1980
tgtatgcggc gaccgagttg ctcttgcccg gcgtcaatac gggataatac cgcgccacat   2040
agcagaactt taaaagtgct catcattgga aaacgttctt cggggcgaaa actctcaagg   2100
atcttaccgc tgttgagatc cagttcgatg taacccactc gtgcacccaa ctgatcttca   2160
gcatctttta ctttcaccag cgtttctggg tgagcaaaaa caggaaggca aaatgccgca   2220
aaaaagggaa taagggcgac acggaaatgt tgaatactca tactcttcct ttttcaatat   2280
tattgaagca tttatcaggg ttattgtctc atgagcggat acatatttga atgtatttag   2340
aaaaataaac aaataggggt tccgcgcaca tttccccgaa aagtgccacc tgacgcgccc   2400
tgtagcggcg cattaagcgc ggcgggtgtg gtggttacgc gcagcgtgac cgctacactt   2460
gccagcgccc tagcgcccgc tcctttcgct ttcttccctt cctttctcgc cacgttcgcc   2520
ggctttcccc gtcaagctct aaatcggggg ctccctttag ggttccgatt tagtgcttta   2580
cggcacctcg accccaaaaa acttgattag ggtgatggtt cacgtagtgg gccatcgccc   2640
tgatagacgg tttttcgccc tttgacgttg gagtccacgt tctttaatag tggactcttg   2700
ttccaaactg gaacaacact caaccctatc tcggtctatt cttttgattt ataagggatt   2760
ttgccgattt cggcctattg gttaaaaaat gagctgattt aacaaaaatt taacgcgaat   2820
tttaacaaaa tattaacgct tacaatttcc attcgccatt caggctgcgc aactgttggg   2880
aagggcgatc ggtgcgggcc tcttcgctat tacgccagct ggcgaaaggg ggatgtgctg   2940
caaggcgatt aagttgggta acgccagggt tttcccagtc acgacgttgt aaaacgacgg   3000
ccagtgaatt gtaatacgac tcactatagg gcgaattggg taccgggccc cccctcgagg   3060
tcgatggtgt cgataagctt gatatcgaat tcatgtcaca caaaccgatc ttcgcctcaa   3120
ggaaacctaa ttctacatcc gagagactgc cgagatccag tctacactga ttaattttcg   3180
ggccaataat ttaaaaaaat cgtgttatat aatattatat gtattatata tatacatcat   3240
gatgatactg acagtcatgt cccattgcta aatagacaga ctccatctgc cgcctccaac   3300
tgatgttctc aatatttaag ggtcatctc gcattgttta ataataaaca gactccatct   3360
accgcctcca aatgatgttc tcaaaatata ttgtatgaac ttatttttat tacttagtat   3420
tattagacaa cttacttgct ttatgaaaaa cacttcctat ttaggaaaca atttataatg   3480
gcagttcgtt catttaacaa tttatgtaga ataaatgtta taaatgcgta tgggaaatct   3540
taaatatgga tagcataaat gatatctgca ttgcctaatt cgaaatcaac agcaacgaaa   3600
aaaatccctt gtacaacata aatagtcatc gagaaatatc aactatcaaa gaacagctat   3660
tcacacgtta ctattgagat tattattgga cgagaatcac acactcaact gtctttctct   3720
cttctagaaa tacaggtaca agtatgtact attctcattg ttcatacttc tagtcatttc   3780
atcccacata ttccttggat ttctctccaa tgaatgacat tctatcttgc aaattcaaca   3840
attataataa gatataccaa agtagcggta tagtggcaat caaaaagctt ctctggtgtg   3900
cttctcgtat ttatttttat tctaatgatc cattaaaggt atatatttat ttcttgttat   3960
ataatccttt tgtttattac atgggctgga tacataaagg tattttgatt taattttttg   4020
cttaaattca atcccccctc gttcagtgtc aactgtaatg gtaggaaatt accatacttt   4080
tgaagaagca aaaaaaatga aagaaaaaaa aaatcgtatt tccaggttag acgttccgca   4140
gaatctagaa tgcggtatgc ggtacattgt tcttcgaacg taaaagttgc gctccctgag   4200
```

-continued

```
atattgtaca tttttgcttt tacaagtaca agtacatcgt acaactatgt actactgttg   4260
atgcatccac aacagtttgt tttgtttttt tttgtttttt ttttttctaa tgattcatta   4320
ccgctatgta tacctacttg tacttgtagt aagccgggtt attggcgttc aattaatcat   4380
agacttatga atctgcacgg tgtgcgctgc gagttacttt tagcttatgc atgctacttg   4440
ggtgtaatat tgggatctgt tcggaaatca acggatgctc aaccgatttc gacagtaatt   4500
aattaatttg aatcgaatcg gagcctaaaa tgaacccgag tatatctcat aaaattctcg   4560
gtgagaggtc tgtgactgtc agtacaaggt gccttcatta tgccctcaac cttaccatac   4620
ctcactgaat gtagtgtacc tctaaaaatg aaatacagtg ccaaaagcca aggcactgag   4680
ctcgtctaac ggacttgata tacaaccaat taaaacaaat gaaaagaaat acagttcttt   4740
gtatcatttg taacaattac cctgtacaaa ctaaggtatt gaaatcccac aatattccca   4800
aagtccaccc ctttccaaat tgtcatgcct acaactcata taccaagcac taacctacca   4860
aacaccacta aaaccccaca aaatatatct taccgaatat acagtaacaa gctaccacca   4920
cactcgttgg gtgcagtcgc cagcttaaag atatctatcc acatcagcca caactccctt   4980
cctttaataa accgactaca cccttggcta ttgaggttat gagtgaatat actgtagaca   5040
agacactttc aagaagactg tttccaaaac gtaccactgt cctccactac aaacacaccc   5100
aatctgcttc ttctagtcaa ggttgctaca ccggtaaatt ataaatcatc atttcattag   5160
cagggcaggg cccttttat agagtcttat acactagcgg accctgccgg tagaccaacc   5220
cgcaggcgcg tcagtttgct ccttccatca atgcgtcgta gaaacgactt actccttctt   5280
gagcagctcc ttgaccttgt tggcaacaag tctccgacct cggaggtgga ggaagagcct   5340
ccgatatcgg cggtagtgat accagcctcg acggactcct tgacggcagc ctcaacagcg   5400
tcaccggcgg gcttcatgtt aagagagaac ttgagcatca tggcggcaga cagaatggtg   5460
gcaatggggt tgaccttctg cttgccgaga tcgggggcag atccgtgaca gggctcgtac   5520
agaccgaacg cctcgttggt gtcgggcaga gaagccagag aggcggaggg cagcagaccc   5580
agagaaccgg ggatgacgga ggcctcgtcg gagatgatat cgccaaacat gttggtggtg   5640
atgatgatac cattcatctt ggagggctgc ttgatgagga tcatggcggc cgagtcgatc   5700
agctggtggt tgagctcgag ctgggggaat tcgtccttga ggactcgagt gacagtcttt   5760
cgccaaagtc gagaggaggc cagcacgttg gccttgtcaa gagaccacac gggaagaggg   5820
gggttgtgct gaagggccag gaaggcggcc attcgggcaa ttcgctcaac ctcaggaacg   5880
gagtaggtct cggtgtcgga agcgacgcca gatccgtcat cctcctttcg ctctccaaag   5940
tagatacctc cgacgagctc tcggacaatg atgaagtcgg tgccctcaac gtttcggatg   6000
ggggagagat cggcgagctt gggcgacagc agctggcagg gtcgcaggtt ggcgtacagg   6060
ttcaggtcct ttcgcagctt gaggagaccc tgctcgggtc gcacgtcggt tcgtccgtcg   6120
ggagtggtcc atacggtgtt ggcagcgcct ccgacagcac cgagcataat agagtcagcc   6180
tttcggcaga tgtcgagagt agcgtcggtg atgggctcgc cctccttctc aatggcagct   6240
cctccaatga gtcggtcctc aaacacaaac tcggtgccgg aggcctcagc aacagacttg   6300
agcaccttga cggcctcggc aatcacctcg gggccacaga agtcgccgcc gagaagaaca   6360
atcttcttgg agtcagtctt ggtcttctta gtttcgggtt ccattgtgga tgtgtgtggt   6420
tgtatgtgtg atgtggtgtg tggagtgaaa atctgtggct ggcaaacgct cttgtatata   6480
tacgcacttt tgcccgtgct atgtggaaga ctaaacctcc gaagattgtg actcaggtag   6540
tgcggtatcg gctagggacc caaaccttgt cgatgccgat agcgctatcg aacgtacccc   6600
```

-continued agccggccgg gagtatgtcg gaggggacat acgagatcgt caagggtttg tggccaactg 6660
gtatttaaat gtagctaacg gtagcaggcg aactactggt acatacctcc cccggaatat 6720
gtacaggcat aatgcgtatc tgtgggacat gtggtcgttg cgccattatg taagcagcgt 6780
gtactcctct gactgtccat atggtttgct ccatctcacc ctcatcgttt tcattgttca 6840
caggcggcca caaaaaaact gtcttctctc cttctctctt cgccttagtc tactcggacc 6900
agttttagtt tagcttggcg ccactggata aatgagacct caggccttgt gatgaggagg 6960
tcacttatga agcatgttag gaggtgcttg tatggataga gaagcaccca aaataataag 7020
aataataata aaacaggggg cgttgtcatt tcatatcgtg ttttcaccat caatacacct 7080
ccaaacaatg cccttcatgt ggccagcccc aatattgtcc tgtagttcaa ctctatgcag 7140
ctcgtatctt attgagcaag taaaactctg tcagccgata ttgcccgacc cgcgacaagg 7200
gtcaacaagg tggtgtaagg ccttcgcaga agtcaaaact gtgccaaaca aacatctaga 7260
gtctctttgg tgtttctcgc atatatttwa tcggctgtct tacgtatttg cgcctcggta 7320
ccggactaat ttcggatcat ccccaatacg ctttttcttc gcagctgtca acagtgtcca 7380
tgatctatcc acctaaatgg gtcatatgag gcgtataatt tcgtggtgct gataataatt 7440
cccatatatt tgacacaaaa cttccccccc tagacataca tctcacaatc tcacttcttg 7500
tgcttctgtc acacatctcc tccagctgac ttcaactcac acctctgccc cagttggtct 7560
acagcggtat aaggtttctc cgcatagagg tgcaccactc ctcccgatac ttgtttgtgt 7620
gacttgtggg tcacgacata tatatctaca cacattgcgc caccctttgg ttcttccagc 7680
acaacaaaaa cacgacacgc taaccatggc caatttactg accgtacacc aaaatttgcc 7740
tgcattaccg gtcgatgcaa cgagtgatga ggttcgcaag aacctgatgg acatgttcag 7800
ggatcgccag gcgttttctg agcatacctg gaaaatgctt ctgtccgttt gccggtcgtg 7860
ggcggcatgg tgcaagttga ataaccggaa atggtttccc gcagaacctg aagatgttcg 7920
cgattatctt ctatatcttc aggcgcgcgg tctggcagta aaaactatcc agcaacattt 7980
gggccagcta aacatgcttc atcgtcggtc cgggctgcca cgaccaagtg acagcaatgc 8040
tgtttcactg gttatgcggc ggatccgaaa agaaaacgtt gatgccggtg aacgtgcaaa 8100
acaggctcta gcgttcgaac gcactgattt cgaccaggtt cgttcactca tggaaaatag 8160
cgatcgctgc caggatatac gtaatctggc atttctgggg attgcttata acaccctgtt 8220
acgtatagcc gaaattgcca ggatcagggt taaagatatc tcacgtactg acggtgggag 8280
aatgttaatc catattggca gaacgaaaac gctggttagc accgcaggtg tagagaaggc 8340
acttagcctg ggggtaacta aactggtcga gcgatggatt tccgtctctg gtgtagctga 8400
tgatccgaat aactacctgt tttgccgggt cagaaaaaat ggtgttgccg cgccatctgc 8460
caccagccag ctatcaactc gcgccctgga agggattttt gaagcaactc atcgattgat 8520
ttacggcgct aaggatgact ctggtcagag atacctggcc tggtctggac acagtgcccg 8580
tgtcggagcc gcgcgagata tggcccgcgc tggagtttca ataccggaga tcatgcaagc 8640
tggtggctgg accaatgtaa atattgtcat gaactatatc cgtaacctgg atagtgaaac 8700
aggggcaatg gtgcgcctgc tggaagatgg cgattaagc 8739

<210> SEQ ID NO 70
<211> LENGTH: 15304
<212> TYPE: DNA
<213> ORGANISM: Artificial Sequence
<220> FEATURE:

-continued

<223> OTHER INFORMATION: Plasmid pKO2UF8289
<220> FEATURE:
<221> NAME/KEY: misc_feature
<222> LOCATION: (5601)..(5601)
<223> OTHER INFORMATION: n is a, c, g, or t
<220> FEATURE:
<221> NAME/KEY: misc_feature
<222> LOCATION: (5606)..(5609)
<223> OTHER INFORMATION: n is a, c, g, or t

<400> SEQUENCE: 70
cgatcgagga agaggacaag cggctgcttc ttaagtttgt gacatcagta tccaaggcac 60
cattgcaagg attcaaggct ttgaacccgt catttgccat tcgtaacgct ggtagacagg 120
ttgatcggtt ccctacggcc tccacctgtg tcaatcttct caagctgcct gactatcagg 180
acattgatca acttcggaag aaacttttgt atgccattcg atcacatgct ggtttcgatt 240
tgtcttagag gaacgcatat acagtaatca tagagaataa acgatattca tttattaaag 300
tagatagttg aggtagaagt tgtaaagagt gataaatagc ggccgctcac tgaatctttt 360
tggctccctt gtgcttcctg acgatatacg tttgcacata gaaattcaag aacaaacaca 420
agactgtgcc aacataaaag taattgaaga accagccaaa catcctcatc ccatcttggc 480
gataacaggg aatgttcctg tacttccaga caatgtagaa accaacattg aattgaatga 540
tctgcattga tgtaatcagg gattttggca tggggaactt cagcttgatc aatctggtcc 600
aataataacc gtacatgatc cagtggatga aaccattcaa cagcacaaaa atccaaacag 660
cttcatttcg gtaattatag aacagccaca tatccatcgg tgcccccaaa tgatggaaga 720
attgcaacca ggtcagaggc ttgcccatca gtggcaaata gaaggagtca atatactcca 780
ggaacttgct caaatagaac aactgcgtgg tgatcctgaa gacgttgttg tcaaaagcct 840
tctcgcagtt gtcagacata acaccgatgg tgtacatggc atatgccatt gagaggaatg 900
atcccaacga ataaatggac atgagaaggt tgtaattggt gaaaacaaac ttcatacgag 960
actgaccttt tggaccaagg gggccaagag tgaacttcaa gatgacaaat gcgatggaca 1020
agtaaagcac ctcacagtga ctggcatcac tccagagttg ggcataatca actggttggg 1080
taaaacttcc tgcccaattg agactatttc attcaccacc tccatggtta gcgtgtcgtg 1140
tttttgttgt gctggaagaa ccaaagggtg gcgcaatgtg tgtagatata tatgtcgtga 1200
cccacaagtc acacaaacaa gtatcgggag gagtggtgca cctctatgcg gagaaacctt 1260
ataccgctgt agaccaactg ggcagaggt gtgagttgaa gtcagctgga ggagatgtgt 1320
gacagaagca caagaagtga gattgtgaga tgtatgtcta ggggggggaag ttttgtgtca 1380 aatatatggg aattattatc agcaccacga aattatacgc ctcatatgac ccatttaggt 1440
ggatagatca tggacactgt tgacagctgc gaagaaaaag cgtattgggg atgatccgaa 1500
attagtccgg taccgaggcg caaatacgta agacagccga twaaatatat gcgagaaaca 1560
ccaaagagac tctagatgtt tgtttggcac agttttgact tctgcgaagg ccttacacca 1620
ccttgttgac ccttgtcgcg ggtcgggcaa tatcggctga cagagtttta cttgctcaat 1680
aagatacgag ctgcatagag ttgaactaca ggacaatatt ggggctggcc acatgaaggg 1740
cattgtttgg aggtgtattg atggtgaaaa cacgatatga aatgacaacg ccccctgttt 1800
tattattatt cttattattt tgggtgcttc tctatccata caagcacctc ctaacatgct 1860
tcataagtga cctcctcatc acaaggcctg aggtctcatt tatccagtgg cgccaagcta 1920
aactaaaact ggtccgagta gactaaggcg aagagagaag gagagaagac agttttttttg 1980 tggccgcctg tgaacaatga aaacgatgag ggtgagatgg agcaaaccat atggtttaaa 2040

-continued

```
cagtcagagg agtacacgct gcttacataa tggcgcaacg accacatgtc ccacagatac   2100
gcatcgattc gattcaaatt aattaaaagg cgttgaaaca gaatgagcca gacagcaagg   2160
acaaggtggc caacagcaag gagtccaaaa agccctctat tgacgagatc cacgatgtta   2220
ttgctcatga ggtttccgag ctcgatgctg ggaagaagaa gtgatttgta tataagaaat   2280
aaatgagata tagtaaagga gtgcaagaga atggcaaggt ggtcaaattc tatattactt   2340
gcagtcactg gttcctcgtt gacatgaatg aagttaccgt tggcatagct gatttaatat   2400
ataactgtcc aactaactct cacctagata taacccatgt gtgtgtttcc aatcatcaat   2460
gcggccgctt actgagcctt ggcaccgggc tgcttctcgg ccattcgagc gaactgggac   2520
aggtatcgga gcaggatgac gagaccttca tggggcagag ggtttcggta ggggaggttg   2580
tgcttctggc acagctgttc cacctggtag gaaacggcag tgaggttgtg tcgaggcagg   2640
gtgggccaga gatggtgctc gatctggtag ttcaggcctc caaagaacca gtcagtaatg   2700
atgcctcgtc gaatgttcat ggtctcatgg atctgaccca cagagaagcc atgtccgtcc   2760
cagacggaat caccgatctt ctccagaggg tagtggttca tgaagaccac gatggcaatt   2820
ccgaagccac cgacgagctc ggaaacaaag aacaccagca tcgaggtcag gatggagggc   2880
ataaagaaga ggtggaacag ggtcttgaga gtccagtgca gagcgagtcc aatggcctct   2940
ttcttgtact gagatcggta gaactggttg tctcggtcct tgagggatcg aacggtcagc   3000
acagactgga aacaccagat gaatcgcagg agaatacaga tgaccaggaa atagtactgt   3060
tggaactgaa tgagctttcg ggagatggga gaagctcgag tgacatcgtc ctcggaccag   3120
gcgagcagag gcaggttatc aatgtcggga tcgtgaccct gaacgttggt agcagaatga   3180
tgggcgttgt gtctgtcctt ccaccaggtc acggagaagc cctggagtcc gttgccaaag   3240
accagaccca ggacgttatt ccagtttcgg ttcttgaagg tctggtggtg gcagatgtca   3300
tgagacagcc atcccatttg ctggtagtgc ataccgagca cgagagcacc aatgaagtac   3360
aggtggtact ggaccagcat gaagaaggca agcacgccaa gacccagggt ggtcaagatc   3420
ttgtacgagt accagagggg agaggcgtca aacatgccag tggcgatcag ctcttctcgg   3480
agctttcgga aatcctcctg agcttcgttg acggcagcct ggggaggcag ctcggaagcc   3540
tggttgatct tgggcattcg cttgagcttg tcgaaggctt cctgagagtg cataaccatg   3600
aaggcgtcag tagcatctcg tccctggtag ttctcaatga tttcagctcc accagggtgg   3660
aagttcaccc aagcggagac gtcgtacacc tttccgtcga tgacgagggg cagagcctgt   3720
cgagaagcct tcaccatggc cattgctgta gatatgtctt gtgtgtaagg gggttggggt   3780
ggttgtttgt gttcttgact tttgtgttag caagggaaga cgggcaaaaa agtgagtgtg   3840
gttgggaggg agagacgagc cttatatata atgcttgttt gtgtttgtgc aagtggacgc   3900
cgaaacgggc aggagccaaa ctaaacaagg cagacaatgc gagcttaatt ggattgcctg   3960
atgggcaggg gttagggctc gatcaatggg ggtgcgaagt gacaaaattg ggaattaggt   4020
tcgcaagcaa ggctgacaag actttggccc aaacatttgt acgcggtgga caacaggagc   4080
cacccatcgt ctgtcacggg ctagccggtc gtgcgtcctg tcaggctcca cctaggctcc   4140
atgccactcc atacaatccc actagtgtac cgctaggccg cttttagctc ccatctaaga   4200
ccccccccaaa acctccactg tacagtgcac tgtactgtgt ggcgatcaag ggcaagggaa   4260
aaaaggcgca aacatgcacg catggaatga cgtaggtaag gcgttactag actgaaaagt   4320
ggcacatttc ggcgtgccaa agggtcctag gtgcgtttcg cgagctgggc gccaggccaa   4380
```

-continued

```
gccgctccaa aacgcctctc cgactccctc cagcggcctc catatcccca tccctctcca   4440
cagcaatgtt gttaagcctt gcaaacgaaa aaatagaaag gctaataagc ttccaatatt   4500
gtggtgtacg ctgcataacg caacaatgag cgccaaacaa cacacacaca cagcacacag   4560
cagcattaac cacgatgttt aaacagtgta cgcagatccc gtcaacagtt ttatatatcg   4620
tagttacaac catcaacact ttttggtaag tgtaccattc tatactccaa ctggtctgca   4680
actgtacaag tagacatgtt aatggtagtt aataacatct acagcagaac ctatggtaaa   4740
gacattgcat ttttacagga agtatcgtcc tacacgttga taaatccaaa gatgcggaac   4800
ttcttccact tttatcatca tcccctactc gtacactcgt actctttgtt cgatcgcgat   4860
tcatttctat aaataatctt gtatgtacat gcggccgcgc ctacttaagc aacgggcttg   4920
ataacagcgg ggggggtgcc cacgttgttg cggttgcgga agaacagaac acccttacca   4980
gcaccctcgg caccagcgct gggctcaacc cactggcaca tacgcgcact gcggtacatg   5040
gcgcggatga agccacgagg accatcctgg acatcagccc ggtagtgctt gcccatgatg   5100
ggcttaatgg cctcggtggc ctcgtccgcg ttgtagaagg ggatgctgct gacgtagtgg   5160
tggaggacat gagtctcgat gatgccgtgg agaaggtggc ggccgatgaa gcccatctca   5220
cggtcaatgg tagcagcggc accacggacg aagttccact cgtcgttggt gtagtgggga   5280
agggtagggt cggtgtgctg gaggaaggtg atggcaacga gccagtggtt aacccagagg   5340
tagggaacaa agtaccagat ggccatgttg tagaaaccga acttctgaac gaggaagtac   5400
agagcagtgg ccatcagacc gataccaata tcgctgagga cgatgagctt agcgtcactg   5460
ttctcgtaca gagggctgcg gggatcgaag tggttaacac caccgccgag gccgttatgc   5520
ttgcccttgc cgcgaccctc acgctggcgc tcgtggtagt tgtggccggt aacattggtg   5580
atgaggtagt tgggccagcc nacgannnnc tcagtaagat gagcgagctc gtgggtcatc   5640
tttccgagac gagtagcctg ctgctcgcgg gttcggggaa cgaagaccat gtcacgctcc   5700
atgttgccag tggccttgtg gtgctttcgg tgggagattt gccagctgaa gtaggggaca   5760
aggagggaag agtgaagaac ccagccagta atgtcgttga tgatgcgaga atcggagaaa   5820
gcaccgtgac cgcactcatg ggcaataacc cagagaccag taccgaaaag accctgaaga   5880
acggtgtaca cggcccacag accagcgcgg gcgggggtgg aggggatata ttcgggggtc   5940
acaaagttgt accagatgct gaaagtggta gtcaggagga caatgtcgcg gaggatataa   6000
ccgtatccct tgagagcgga gcgcttgaag cagtgcttag ggatggcatt gtagatgtcc   6060
ttgatggtaa agtcgggaac ctcgaactgg ttgccgtagg tgtcgagcat gacaccatac   6120
tcggacttgg gcttggcgat atcaacctcg gacatggacg agagcgatgt ggaagaggcc   6180
gagtggcggg gagagtctga aggagagacg gcggcagact cagaatccgt cacagtagtt   6240
gaggtgacgg tgcgtctaag cgcagggttc tgcttgggca gagccgaagt ggacgccatg   6300
gttgtgaatt agggtggtga gaatggttgg ttgtagggaa gaatcaaagg ccggtctcgg   6360
gatccgtggg tatatatata tatatatata tatacgatcc ttcgttacct ccctgttctc   6420
aaaactgtgg tttttcgttt ttcgtttttt gctttttttg attttttttag ggccaactaa   6480
gcttccagat ttcgctaatc acctttgtac taattacaag aaaggaagaa gctgattaga   6540
gttgggcttt ttatgcaact gtgctactcc ttatctctga tatgaaagtg tagacccaat   6600
cacatcatgt catttagagt tggtaatact gggaggatag ataaggcacg aaaacgagcc   6660
atagcagaca tgctgggtgt agccaagcag aagaaagtag atgggagcca attgacgagc   6720
gagggagcta cgccaatccg acatacgaca cgctgagatc gtcttggccg gggggtacct   6780
```

-continued

```
acagatgtcc aagggtaagt gcttgactgt aattgtatgt ctgaggacaa atatgtagtc   6840
agccgtataa agtcatacca ggcaccagtg ccatcatcga accactaact ctctatgata   6900
catgcctccg gtattattgt accatgcgtc gctttgttac atacgtatct tgccttttc    6960
tctcagaaac tccagacttt ggctattggt cgagataagc ccggaccata gtgagtcttt   7020
cacactctac atttctccct tgctccaact atttaaattg ccccggagaa gacggccagg   7080
ccgcctagat gacaaattca acaactcaca gctgactttc tgccattgcc actagggggg   7140
ggccttttta tatggccaag ccaagctctc cacgtcggtt gggctgcacc caacaataaa   7200
tgggtagggt tgcaccaaca aagggatggg atgggggta gaagatacga ggataacggg    7260
gctcaatggc acaaataaga acgaatactg ccattaagac tcgtgatcca gcgactgaca   7320
ccattgcatc atctaagggc ctcaaaacta cctcggaact gctgcgctga tctggacacc   7380
acagaggttc cgagcacttt aggttgcacc aaatgtccca ccaggtgcag gcagaaaacg   7440
ctggaacagc gtgtacagtt tgtcttaaca aaaagtgagg gcgctgaggt cgagcagggt   7500
ggtgtgactt gttatagcct ttagagctgc gaaagcgcgt atggatttgg ctcatcaggc   7560
cagattgagg gtctgtggac acatgtcatg ttagtgtact tcaatcgccc cctggatata   7620
gccccgacaa taggccgtgg cctcattttt ttgccttccg cacatttcca ttgctcggta   7680
cccacacctt gcttctcctg cacttgccaa ccttaatact ggtttacatt gaccaacatc   7740
ttacaagcgg ggggcttgtc tagggtatat ataaacagtg gctctcccaa tcggttgcca   7800
gtctcttttt tcctttcttt ccccacagat tcgaaatcta aactacacat cacagaattc   7860
cgagccgtga gtatccacga caagatcagt gtcgagacga cgcgttttgt gtaatgacac   7920
aatccgaaag tcgctagcaa cacacactct ctacacaaac taacccagct ctggtaccat   7980
ggtgaaggct tctcgacagg ctctgcccct cgtcatcgac ggaaaggtgt acgacgtctc   8040
cgcttgggtg aacttccacc ctggtggagc tgaaatcatt gagaactacc agggacgaga   8100
tgctactgac gccttcatgg ttatgcactc tcaggaagcc ttcgacaagc tcaagcgaat   8160
gcccaagatc aaccaggctt ccgagctgcc tccccaggct gccgtcaacg aagctcagga   8220
ggatttccga aagctccgag aagagctgat cgccactggc atgtttgacg cctctcccct   8280
ctggtactcg tacaagatct tgaccaccct gggtcttggc gtgcttgcct tcttcatgct   8340
ggtccagtac cacctgtact tcattggtgc tctcgtgctc ggtatgcact accagcaaat   8400
gggatggctg tctcatgaca tctgccacca ccagaccttc aagaaccgaa actggaataa   8460
cgtcctgggt ctggtctttg gcaacggact ccagggcttc tccgtgacct ggtggaagga   8520
cagacacaac gcccatcatt ctgctaccaa cgttcagggt cacgatcccg acattgataa   8580
cctgcctctg ctcgcctggt ccgaggacga tgtcactcga gcttctccca tctcccgaaa   8640
gctcattcag ttccaacagt actatttcct ggtcatctgt attctcctgc gattcatctg   8700
gtgtttccag tctgtgctga ccgttcgatc cctcaaggac cgagacaacc agttctaccg   8760
atctcagtac aagaaagagg ccattggact cgctctgcac tggactctca agaccctgtt   8820
ccacctcttc tttatgccct ccatcctgac ctcgatgctg gtgttctttg tttccgagct   8880
cgtcggtggc ttcggaattg ccatcgtggt cttcatgaac cactaccctc tggagaagat   8940
cggtgattcc gtctgggacg gacatggctt ctctgtgggt cagatccatg agaccatgaa   9000
cattcgacga ggcatcatta ctgactggtt ctttggaggc ctgaactacc agatcgagca   9060
ccatctctgg cccaccctgc ctcgacacaa cctcactgcc gtttcctacc aggtggaaca   9120
```

-continued

```
gctgtgccag aagcacaacc tcccctaccg aaaccctctg ccccatgaag gtctcgtcat   9180
cctgctccga tacctgtccc agttcgctcg aatggccgag aagcagcccg gtgccaaggc   9240
tcagtaagcg gccgcaagtg tggatgggga agtgagtgcc cggttctgtg tgcacaattg   9300
gcaatccaag atggatggat tcaacacagg gatatagcga gctacgtggt ggtgcgagga   9360
tatagcaacg gatatttatg tttgacactt gagaatgtac gatacaagca ctgtccaagt   9420
acaatactaa acatactgta catactcata ctcgtacccg ggcaacggtt tcacttgagt   9480
gcagtggcta gtgctcttac tcgtacagtg tgcaatactg cgtatcatag tctttgatgt   9540
atatcgtatt cattcatgtt agttgcgtac gggtgaagct tccactggtc ggcgtggtag   9600
tggggcagag tggggtcggt gtgctgcagg taggtgatgg ccacgagcca gtggttgacc   9660
cacaggtagg ggatcaggta gtagagggtg acggaagcca ggccccatcg gttgatggag   9720
tatgcgatga cggacatggt gataccaata ccgacgttag agatccagat gttgaaccag   9780
tccttcttct caaacagcgg ggcgttgggg ttgaagtggt tgacagccca tttgttgagc   9840
ttggggtact tctgtccggt aacgtaagac agcagataca gaggccatcc aaacacctgc   9900
tgggtgatga ggccgtagag ggtcatgagg ggagcgtcct cagcaagctc agaccagtca   9960
tgggcgcctc ggttctccat aaactccttt cggtccttgg gcacaaacac catatcacgg  10020
gtgaggtgac cagtggactt gtggtgcatg gagtgggtca gcttccaggc gtagtaaggg  10080
accagcatgg aggagtgcag aacccatccg gtgacgttgt tgacggtgtt agagtcggag  10140
aaagcagagt ggccacactc gtgggcaaga acccacagac cggtgccaaa cagaccctgg  10200
acaatggagt acatggccca ggccacagct cggccggaag ccgagggaat aagaggcagg  10260
tacgcgtagg ccatgtaggc aaaaacggcg ataaagaagc aggcgcgcca gctgcattaa  10320
tgaatcggcc aacgcgcggg gagaggcggt ttgcgtattg ggcgctcttc cgcttcctcg  10380
ctcactgact cgctgcgctc ggtcgttcgg ctgcggcgag cggtatcagc tcactcaaag  10440
gcggtaatac ggttatccac agaatcaggg gataacgcag gaaagaacat gtgagcaaaa  10500
ggccagcaaa aggccaggaa ccgtaaaaag gccgcgttgc tggcgttttt ccataggctc  10560
cgcccccctg acgagcatca caaaaatcga cgctcaagtc agaggtggcg aaacccgaca  10620
ggactataaa gataccaggc gtttccccct ggaagctccc tcgtgcgctc tcctgttccg  10680
accctgccgc ttaccggata cctgtccgcc tttctccctt cgggaagcgt ggcgctttct  10740
catagctcac gctgtaggta tctcagttcg gtgtaggtcg ttcgctccaa gctgggctgt  10800
gtgcacgaac cccccgttca gcccgaccgc tgcgccttat ccggtaacta tcgtcttgag  10860
tccaacccgg taagacacga cttatcgcca ctggcagcag ccactggtaa caggattagc  10920
agagcgaggt atgtaggcgg tgctacagag ttcttgaagt ggtggcctaa ctacggctac  10980
actagaagaa cagtatttgg tatctgcgct ctgctgaagc cagttacctt cggaaaaaga  11040
gttggtagct cttgatccgg caaacaaacc accgctggta gcggtggttt ttttgtttgc  11100
aagcagcaga ttacgcgcag aaaaaaagga tctcaagaag atcctttgat cttttctacg  11160
gggtctgacg ctcagtggaa cgaaaactca cgttaaggga ttttggtcat gagattatca  11220
aaaaggatct tcacctagat ccttttaaat taaaaatgaa gttttaaatc aatctaaagt  11280
atatatgagt aaacttggtc tgacagttac caatgcttaa tcagtgaggc acctatctca  11340
gcgatctgtc tatttcgttc atccatagtt gcctgactcc ccgtcgtgta gataactacg  11400
atacgggagg gcttaccatc tggccccagt gctgcaatga taccgcgaga cccacgctca  11460
ccggctccag atttatcagc aataaaccag ccagccggaa gggccgagcg cagaagtggt  11520
```

-continued

```
cctgcaactt tatccgcctc catccagtct attaattgtt gccgggaagc tagagtaagt  11580
agttcgccag ttaatagttt gcgcaacgtt gttgccattg ctacaggcat cgtggtgtca  11640
cgctcgtcgt ttggtatggc ttcattcagc tccggttccc aacgatcaag gcgagttaca  11700
tgatccccca tgttgtgcaa aaaagcggtt agctccttcg gtcctccgat cgttgtcaga  11760
agtaagttgg ccgcagtgtt atcactcatg gttatggcag cactgcataa ttctcttact  11820
gtcatgccat ccgtaagatg cttttctgtg actggtgagt actcaaccaa gtcattctga  11880
gaatagtgta tgcggcgacc gagttgctct tgcccggcgt caatacggga taataccgcg  11940
ccacatagca gaactttaaa agtgctcatc attggaaaac gttcttcggg gcgaaaactc  12000
tcaaggatct taccgctgtt gagatccagt tcgatgtaac ccactcgtgc acccaactga  12060
tcttcagcat cttttacttt caccagcgtt tctgggtgag caaaaacagg aaggcaaaat  12120
gccgcaaaaa agggaataag ggcgacacgg aaatgttgaa tactcatact cttccttttt  12180
caatattatt gaagcattta tcagggttat tgtctcatga gcggatacat atttgaatgt  12240
atttagaaaa ataaacaaat aggggttccg cgcacatttc cccgaaaagt gccacctgat  12300
gcggtgtgaa ataccgcaca gatgcgtaag gagaaaatac cgcatcagga aattgtaagc  12360
gttaatattt tgttaaaatt cgcgttaaat ttttgttaaa tcagctcatt ttttaaccaa  12420
taggccgaaa tcggcaaaat cccttataaa tcaaaagaat agaccgagat agggttgagt  12480
gttgttccag tttggaacaa gagtccacta ttaaagaacg tggactccaa cgtcaaaggg  12540
cgaaaaaccg tctatcaggg cgatggccca ctacgtgaac catcacccta atcaagtttt  12600
ttggggtcga ggtgccgtaa agcactaaat cggaacccta aagggagccc ccgatttaga  12660
gcttgacggg gaaagccggc gaacgtggcg agaaaggaag ggaagaaagc gaaaggagcg  12720
ggcgctaggg cgctggcaag tgtagcggtc acgctgcgcg taaccaccac acccgccgcg  12780
cttaatgcgc cgctacaggg cgcgtccatt cgccattcag gctgcgcaac tgttgggaag  12840
ggcgatcggt gcgggcctct tcgctattac gccagctggc gaaaggggga tgtgctgcaa  12900
ggcgattaag ttgggtaacg ccagggtttt cccagtcacg acgttgtaaa acgacggcca  12960
gtgaattgta atacgactca ctatagggcg aattgggccc gacgtcgcat gcttgaatct  13020
acaagtagga gggttggagt gattaagtga aacttcttta acggctctat gccagttcta  13080
ttgatatccg aaacatcagt atgaaggtct gataagggtg acttcttccc acagattcgt  13140
atcagtacga gtacgagacc ggtacttgta acagtattga tactaaaggg aaactacaac  13200
ggttgtcagc gtaatgtgac ttcgcccatg aacgcagaca cgcagtgccg agtgcggtga  13260
tatcgcctac tcgttacgtc catggactac acaacccctc ggcttcgctt ggcttagcct  13320
cgggctcggt gctgttcagt taaaacacaa tcaaataaca tttctacttt ttagaaggca  13380
ggccgtcagg agcaactccg actccattga cgtttctaaa catctgaatg ccttccttac  13440
cttcaacaaa ctggcaggtt cgggcgacag tgtaaagaga cttgatgaag ttggtgtcgt  13500
cgtgtcggta gtgcttgccc atgaccttct tgatcttctc agtggcgatt cgggcgttgt  13560
agaagggaat tcctttacct gcaggataac ttcgtataat gtatgctata cgaagttatg  13620
atctctctct tgagcttttc cataacaagt tcttctgcct ccaggaagtc catgggtggt  13680
ttgatcatgg ttttggtgta gtggtagtgc agtggtggta ttgtgactgg ggatgtagtt  13740
gagaataagt catacacaag tcagctttct tcgagcctca tataagtata agtagttcaa  13800
cgtattagca ctgtacccag catctccgta tcgagaaaca caacaacatg ccccattgga  13860
```

-continued

```
cagatcatgc ggatacacag gttgtgcagt atcatacata ctcgatcaga caggtcgtct  13920

gaccatcata caagctgaac aagcgctcca tacttgcacg ctctctatat acacagttaa  13980

attacatatc catagtctaa cctctaacag ttaatcttct ggtaagcctc ccagccagcc  14040

ttctggtatc gcttggcctc ctcaatagga tctcggttct ggccgtacag acctcggccg  14100

acaattatga tatccgttcc ggtagacatg acatcctcaa cagttcggta ctgctgtccg  14160

agagcgtctc ccttgtcgtc aagacccacc ccgggggtca gaataagcca gtcctcagag  14220

tcgcccttag gtcggttctg ggcaatgaag ccaaccacaa actcggggtc ggatcgggca  14280

agctcaatgg tctgcttgga gtactcgcca gtggccagag agcccttgca agacagctcg  14340

gccagcatga gcagacctct ggccagcttc tcgttgggag aggggactag gaactccttg  14400

tactgggagt tctcgtagtc agagacgtcc tccttcttct gttcagagac agtttcctcg  14460

gcaccagctc gcaggccagc aatgattccg gttccgggta caccgtgggc gttggtgata  14520

tcggaccact cggcgattcg gtgacaccgg tactggtgct tgacagtgtt gccaatatct  14580

gcgaactttc tgtcctcgaa caggaagaaa ccgtgcttaa gagcaagttc cttgaggggg  14640

agcacagtgc cggcgtaggt gaagtcgtca atgatgtcga tatgggtttt gatcatgcac  14700

acataaggtc cgaccttatc ggcaagctca atgagctcct tggtggtggt aacatccaga  14760

gaagcacaca ggttggtttt cttggctgcc acgagcttga gcactcgagc ggcaaaggcg  14820

gacttgtgga cgttagctcg agcttcgtag gagggcattt tggtggtgaa gaggagactg  14880

aaataaattt agtctgcaga actttttatc ggaaccttat ctggggcagt gaagtatatg  14940

ttatggtaat agttacgagt tagttgaact tatagataga ctggactata cggctatcgg  15000

tccaaattag aaagaacgtc aatggctctc tgggcgtcgc ctttgccgac aaaaatgtga  15060

tcatgatgaa agccagcaat gacgttgcag ctgatattgt tgtcggccaa ccgcgccgaa  15120

aacgcagctg tcagacccac agcctccaac gaagaatgta tcgtcaaagt gatccaagca  15180

cactcatagt tggagtcgta ctccaaaggc ggcaatgacg agtcagacag atactcgtcg  15240

acgcgataac ttcgtataat gtatgctata cgaagttatc gtacgatagt tagtagacaa  15300

caat                                                              15304
```

<210> SEQ ID NO 71
<211> LENGTH: 1272
<212> TYPE: DNA
<213> ORGANISM: Artificial Sequence
<220> FEATURE:
<223> OTHER INFORMATION: mutant EgD8S-23
<220> FEATURE:
<221> NAME/KEY: misc_feature
<222> LOCATION: (2)..(1270)
<223> OTHER INFORMATION: mutant EgD8S-23 delta-8 desaturase CDS

<400> SEQUENCE: 71

```
catggtgaag gcttctcgac aggctctgcc cctcgtcatc gacggaaagg tgtacgacgt     60

ctccgcttgg gtgaacttcc accctggtgg agctgaaatc attgagaact accagggacg    120

agatgctact gacgccttca tggttatgca ctctcaggaa gccttcgaca agctcaagcg    180

aatgcccaag atcaaccagg cttccgagct gcctccccag gctgccgtca acgaagctca    240

ggaggatttc cgaaagctcc gagaagagct gatcgccact ggcatgtttg acgcctctcc    300

cctctggtac tcgtacaaga tcttgaccac cctgggtctt ggcgtgcttg ccttcttcat    360

gctggtccag taccacctgt acttcattgg tgctctcgtg ctcggtatgc actaccagca    420

aatgggatgg ctgtctcatg acatctgcca ccaccagacc ttcaagaacc gaaactggaa    480
```

-continued

```
taacgtcctg ggtctggtct ttggcaacgg actccagggc ttctccgtga cctggtggaa    540

ggacagacac aacgcccatc attctgctac caacgttcag ggtcacgatc ccgacattga    600

taacctgcct ctgctcgcct ggtccgagga cgatgtcact cgagcttctc ccatctcccg    660

aaagctcatt cagttccaac agtactattt cctggtcatc tgtattctcc tgcgattcat    720

ctggtgtttc cagtctgtgc tgaccgttcg atccctcaag gaccgagaca accagttcta    780

ccgatctcag tacaagaaag aggccattgg actcgctctg cactggactc tcaagaccct    840

gttccacctc ttctttatgc cctccatcct gacctcgatg ctggtgttct ttgtttccga    900

gctcgtcggt ggcttcggaa ttgccatcgt ggtcttcatg aaccactacc ctctggagaa    960

gatcggtgat tccgtctggg acggacatgg cttctctgtg ggtcagatcc atgagaccat   1020

gaacattcga cgaggcatca ttactgactg gttctttgga ggcctgaact accagatcga   1080

gcaccatctc tggcccaccc tgcctcgaca caacctcact gccgtttcct accaggtgga   1140

acagctgtgc cagaagcaca acctccccta ccgaaaccct ctgccccatg aaggtctcgt   1200

catcctgctc cgatacctgt cccagttcgc tcgaatggcc gagaagcagc ccggtgccaa   1260

ggctcagtaa gc                                                       1272


<210> SEQ ID NO 72
<211> LENGTH: 422
<212> TYPE: PRT
<213> ORGANISM: Artificial Sequence
<220> FEATURE:
<223> OTHER INFORMATION: mutant EgD8S-23, comprising M1, M2, M3, M8,
      M12, M15, M16, M18, M21, M26, M45, M46, M68 and M70 mutation sites

<400> SEQUENCE: 72

Met Val Lys Ala Ser Arg Gln Ala Leu Pro Leu Val Ile Asp Gly Lys
1               5                   10                  15

Val Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Gln Ala Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Leu Thr Thr Leu Gly
            100                 105                 110

Leu Gly Val Leu Ala Phe Phe Met Leu Val Gln Tyr His Leu Tyr Phe
        115                 120                 125

Ile Gly Ala Leu Val Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Val Leu Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205
```

-continued

```
Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Met Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ser Gln Phe Ala Arg Met Ala Glu Lys Gln
                405                 410                 415

Pro Gly Ala Lys Ala Gln
            420


<210> SEQ ID NO 73
<211> LENGTH: 777
<212> TYPE: DNA
<213> ORGANISM: Euglena gracilis
<220> FEATURE:
<221> NAME/KEY: misc_feature
<223> OTHER INFORMATION: delta-9 elongase
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES: (1)..(777)

<400> SEQUENCE: 73

atggaggtgg tgaatgaaat agtctcaatt gggcaggaag ttttacccaa agttgattat      60

gcccaactct ggagtgatgc cagtcactgt gaggtgcttt acttgtccat cgcatttgtc     120

atcttgaagt tcactcttgg cccccttggt ccaaaaggtc agtctcgtat gaagtttgtt     180

ttcaccaatt acaaccttct catgtccatt tattcgttgg gatcattcct ctcaatggca     240

tatgccatgt acaccatcgg tgttatgtct gacaactgcg agaaggcttt tgacaacaac     300

gtcttcagga tcaccacgca gttgttctat ttgagcaagt tcctggagta tattgactcc     360

ttctatttgc cactgatggg caagcctctg acctggttgc aattcttcca tcatttgggg     420

gcaccgatgg atatgtggct gttctataat taccgaaatg aagctgtttg gatttttgtg     480

ctgttgaatg gtttcatcca ctggatcatg tacggttatt attggaccag attgatcaag     540

ctgaagttcc ccatgccaaa atccctgatt acatcaatgc agatcattca attcaatgtt     600
```

-continued

```
ggtttctaca ttgtctggaa gtacaggaac attccctgtt atcgccaaga tgggatgagg    660
atgtttggct ggttcttcaa ttacttttat gttggcacag tcttgtgttt gttcttgaat    720
ttctatgtgc aaacgtatat cgtcaggaag cacaagggag ccaaaaagat tcagtga       777
```

<210> SEQ ID NO 74
<211> LENGTH: 13707
<212> TYPE: DNA
<213> ORGANISM: Artificial Sequence
<220> FEATURE:
<223> OTHER INFORMATION: Plasmid pZKSL-555R

<400> SEQUENCE: 74

```
aaacagtgta cgcagatctg cccatgatgg gggctcccac caccagcaat cagggccctg      60
attacacacc cacctgtaat gtcatgctgt tcatcgtggt taatgctgct gtgtgctgtg     120
tgtgtgtgtt gtttggcgct cattgttgcg ttatgcagcg tacaccacaa tattggaagc     180
ttattagcct ttctattttt tcgtttgcaa ggcttaacaa cattgctgtg gagagggatg     240
gggatatgga ggccgctgga gggagtcgga gaggcgtttt ggagcggctt ggcctggcgc     300
ccagctcgcg aaacgcacct aggacccttt ggcacgccga aatgtgccac ttttcagtct     360
agtaacgcct tacctacgtc attccatgcg tgcatgtttg cgcctttttt cccttgccct     420
tgatcgccac acagtacagt gcactgtaca gtggaggttt tggggggggtc ttagatggga     480
gctaaaagcg gcctagcggt acactagtgg gattgtatgg agtggcatgg agcctaggtg     540
gagcctgaca ggacgcacga ccggctagcc cgtgacagac gatgggtggc tcctgttgtc     600
caccgcgtac aaatgtttgg gccaaagtct tgtcagcctt gcttgcgaac ctaattccca     660
attttgtcac ttcgcacccc cattgatcga gccctaaccc ctgcccatca ggcaatccaa     720
ttaagctcgc attgtctgcc ttgtttagtt tggctcctgc ccgtttcggc gtccacttgc     780
acaaacacaa acaagcatta tatataaggc tcgtctctcc ctcccaacca cactcacttt     840
tttgcccgtc ttcccttgct aacacaaaag tcaagaacac aaacaaccac cccaaccccc     900
ttacacacaa gacatatcta cagcaatggc catggctctc tcccttacta ccgagcagct     960
gctcgagcga cccgacctgg ttgccatcga cggcattctc tacgatctgg aaggtcttgc    1020
caaggtccat cccggaggcg acttgatcct cgcttctggt gcctccgatg cttctcctct    1080
gttctactcc atgcaccctt acgtcaagcc cgagaactcg aagctgcttc aacagttcgt    1140
gcgaggcaag cacgaccgaa cctccaagga cattgtctac acctacgact ctccctttgc    1200
acaggacgtc aagcgaacta tgcgagaggt catgaaaggt cggaactggt atgccacacc    1260
tggattctgg ctgcgaaccg ttggcatcat tgctgtcacc gccttttgcg agtggcactg    1320
ggctactacc ggaatggtgc tgtggggtct cttgactgga ttcatgcaca tgcagatcgg    1380
cctgtccatt cagcacgatg cctctcatgg tgccatcagc aaaaagccct gggtcaacgc    1440
tctctttgcc tacggcatcg acgtcattgg atcgtccaga tggatctggc tgcagtctca    1500
catcatgcga catcacacct acaccaatca gcatggtctc gacctggatg ccgagtccgc    1560
agaaccattc cttgtgttcc acaactaccc tgctgccaac actgctcgaa agtggtttca    1620
ccgattccag gcctggtaca tgtacctcgt gcttggagcc tacggcgttt cgctggtgta    1680
caaccctctc tacatcttcc gaatgcagca caacgacacc attcccgagt ctgtcacagc    1740
catgcgagag aacggctttc tgcgacggta ccgaaccctt gcattcgtta tgcgagcttt    1800
cttcatcttt cgaaccgcct tcttgccctg gtatctcact ggaacctccc tgctcatcac    1860
```

-continued

```
cattcctctg gtgcccactg ctaccggtgc cttcctcacc ttctttttca tcttgtctca   1920

caacttcgat ggctcggagc gaatccccga caagaactgc aaggtcaaga gctccgagaa   1980

ggacgttgaa gccgatcaga tcgactggta cagagctcag gtggagacct cttccaccta   2040

cggtggaccc attgccatgt tctttactgg cggtctcaac ttccagatcg agcatcacct   2100

ctttcctcga atgtcgtctt ggcactatcc cttcgtgcag caagctgtcc gagagtgttg   2160

cgaacgacac ggagttcggt acgtcttcta ccctaccatt gtgggcaaca tcatttccac   2220

cctcaagtac atgcacaaag tcggtgtggt tcactgtgtc aaggacgctc aggattccta   2280

agcggccgca agtgtggatg gggaagtgag tgcccggttc tgtgtgcaca attggcaatc   2340

caagatggat ggattcaaca cagggatata gcgagctacg tggtggtgcg aggatatagc   2400

aacggatatt tatgtttgac acttgagaat gtacgataca agcactgtcc aagtacaata   2460

ctaaacatac tgtacatact catactcgta cccgggcaac ggtttcactt gagtgcagtg   2520

gctagtgctc ttactcgtac agtgtgcaat actgcgtatc atagtctttg atgtatatcg   2580

tattcattca tgttagttgc gtacgctgtg ttgttgtatg tggtgaagct tgacaatgga   2640

tggtgtgtcg tatcaggctg gggaacaatt gtgcttaagt atgctgcagt tgagtaagag   2700

tcatcgctcc accaaaataa agtttgccat tagggttgga gagagagatg gtggctggaa   2760

gaattaaatg acatcaagct gaggattgtg ggtgtgcaat aacacatgtt aggggtgacc   2820

tgtggctcga aatctgataa ttattttgta actttatgat tattcttaga ttttttaata   2880

ttcctctata taacacataa gtagctgtcg tctagttgtt catagcctga ctcctgcaat   2940

agattagtgc agagtgattt tgtgcaattg agagccacgg ttgagtcaag tgactttgtg   3000

tgtgaagtca tcttacgttt caagtctcac aggttactca attggttggt tgtctgccct   3060

ttacagatat ttacagtacc tgagcgtaaa gtcgttcatc cacggaatga ctgttcctgt   3120

cacgcagtca tgatcatgga tgtggctggt caggaaccat tttggatagg agacttaggg   3180

attggactat tattgaaaaa actgagccga atatgatata gttctatttg aatgcagaac   3240

ttctgatggt caattcactt atttcaggca tatcggtcat ggtggcagct gccacgatgt   3300

tatctcgttg gaaacctcgg cgcgccagct gcattaatga atcggccaac gcgcggggag   3360

aggcggtttg cgtattgggc gctcttccgc ttcctcgctc actgactcgc tgcgctcggt   3420

cgttcggctg cggcgagcgg tatcagctca ctcaaaggcg gtaatacggt tatccacaga   3480

atcaggggat aacgcaggaa agaacatgtg agcaaaaggc cagcaaaagg ccaggaaccg   3540

taaaaaggcc gcgttgctgg cgtttttcca taggctccgc ccccctgacg agcatcacaa   3600

aaatcgacgc tcaagtcaga ggtggcgaaa cccgacagga ctataaagat accaggcgtt   3660

tccccctgga agctccctcg tgcgctctcc tgttccgacc ctgccgctta ccggatacct   3720

gtccgccttt ctcccttcgg gaagcgtggc gctttctcat agctcacgct gtaggtatct   3780

cagttcggtg taggtcgttc gctccaagct gggctgtgtg cacgaacccc ccgttcagcc   3840

cgaccgctgc gccttatccg gtaactatcg tcttgagtcc aacccggtaa gacacgactt   3900

atcgccactg gcagcagcca ctggtaacag gattagcaga gcgaggtatg taggcggtgc   3960

tacagagttc ttgaagtggt ggcctaacta cggctacact agaagaacag tatttggtat   4020

ctgcgctctg ctgaagccag ttaccttcgg aaaaagagtt ggtagctctt gatccggcaa   4080

acaaaccacc gctggtagcg gtggtttttt tgtttgcaag cagcagatta cgcgcagaaa   4140

aaaaggatct caagaagatc ctttgatctt ttctacgggg tctgacgctc agtggaacga   4200

aaactcacgt taagggattt tggtcatgag attatcaaaa aggatcttca cctagatcct   4260
```

-continued

```
tttaaattaa aaatgaagtt ttaaatcaat ctaaagtata tatgagtaaa cttggtctga   4320
cagttaccaa tgcttaatca gtgaggcacc tatctcagcg atctgtctat ttcgttcatc   4380
catagttgcc tgactccccg tcgtgtagat aactacgata cgggagggct taccatctgg   4440
ccccagtgct gcaatgatac cgcgagaccc acgctcaccg gctccagatt tatcagcaat   4500
aaaccagcca gccggaaggg ccgagcgcag aagtggtcct gcaactttat ccgcctccat   4560
ccagtctatt aattgttgcc gggaagctag agtaagtagt tcgccagtta atagtttgcg   4620
caacgttgtt gccattgcta caggcatcgt ggtgtcacgc tcgtcgtttg gtatggcttc   4680
attcagctcc ggttcccaac gatcaaggcg agttacatga tcccccatgt tgtgcaaaaa   4740
agcggttagc tccttcggtc ctccgatcgt tgtcagaagt aagttggccg cagtgttatc   4800
actcatggtt atggcagcac tgcataattc tcttactgtc atgccatccg taagatgctt   4860
ttctgtgact ggtgagtact caaccaagtc attctgagaa tagtgtatgc ggcgaccgag   4920
ttgctcttgc ccggcgtcaa tacgggataa taccgcgcca catagcagaa ctttaaaagt   4980
gctcatcatt ggaaaacgtt cttcggggcg aaaactctca aggatcttac cgctgttgag   5040
atccagttcg atgtaaccca ctcgtgcacc caactgatct tcagcatctt ttactttcac   5100
cagcgtttct gggtgagcaa aaacaggaag gcaaaatgcc gcaaaaaagg gaataagggc   5160
gacacggaaa tgttgaatac tcatactctt cctttttcaa tattattgaa gcatttatca   5220
gggttattgt ctcatgagcg gatacatatt tgaatgtatt tagaaaaata aacaaatagg   5280
ggttccgcgc acatttcccc gaaaagtgcc acctgatgcg gtgtgaaata ccgcacagat   5340
gcgtaaggag aaaataccgc atcaggaaat tgtaagcgtt aatattttgt taaaattcgc   5400
gttaaatttt tgttaaatca gctcattttt taaccaatag gccgaaatcg gcaaaatccc   5460
ttataaatca aaagaataga ccgagatagg gttgagtgtt gttccagttt ggaacaagag   5520
tccactatta aagaacgtgg actccaacgt caaagggcga aaaaccgtct atcagggcga   5580
tggcccacta cgtgaaccat caccctaatc aagttttttg gggtcgaggt gccgtaaagc   5640
actaaatcgg aaccctaaag ggagcccccg atttagagct tgacggggaa agccggcgaa   5700
cgtggcgaga aaggaaggga agaaagcgaa aggagcgggc gctagggcgc tggcaagtgt   5760
agcggtcacg ctgcgcgtaa ccaccacacc cgccgcgctt aatgcgccgc tacagggcgc   5820
gtccattcgc cattcaggct gcgcaactgt tgggaagggc gatcggtgcg ggcctcttcg   5880
ctattacgcc agctggcgaa aggggggatgt gctgcaaggc gattaagttg ggtaacgcca   5940
gggttttccc agtcacgacg ttgtaaaacg acggccagtg aattgtaata cgactcacta   6000
tagggcgaat tgggcccgac gtcgcatgca ttccatagcc acacctttgc ctatggcttc   6060
acaaccgaag gcaattcgag aggtcgcgct tatggaatcg actcgtataa agctgaaggg   6120
aaagggagac gttccgagcg ctcagatgca atagtcgtcc agctaatgtg gattcaaaaa   6180
caaccccaac agtaatcttg aaaatttgaa cggatcaatc tgaacactct tgctccaggt   6240
cattcttcta acgcacatcc ccagagtcta gagggagttg tgttgtgaac atcctaataa   6300
acaatgcaat ggattcggga tatcttctgt ctcgcccccct actcgatgtc gagtaaaccg   6360
atcaccaact aacaatactc ctccgcgttc tgccattgac tctcaaacag acatcgctat   6420
caacggaaca gcatatttta gcttcttagg acaataaata ttgataatgc cggctctccc   6480
tcggtatatt aagcaatcca ttcatacact cattcatcag gttaatttta tatatataat   6540
ttgtctattc aaacaccgta aattactggt accatcatct cctcctttc aaatacacgt   6600
```

-continued

```
ctatttgcat taatgaaatt actcgccaat tcgcagaacg tgtttgtcga acagagcctt   6660
agctcgggtc cagacaggag cagtgtctcg ctgaggaagc tgcaggagag ttaattaact   6720
cacctgcagg attgagacta tgaatggatt cccgtgcccg tattactcta ctaatttgat   6780
cttggaacgc gaaaatacgt ttctaggact ccaaagaatc tcaactcttg tccttactaa   6840
atatactacc catagttgat ggtttacttg aacagagagg acatgttcac ttgacccaaa   6900
gtttctcgca tctcttggat atttgaacaa cggcgtccac tgaccgtcag ttatccagtc   6960
acaaaacccc cacattcata cattcccatg tacgtttaca aagttctcaa ttccatcgtg   7020
caaatcaaaa tcacatctat tcattcatca tatataaacc catcatgtct actaacactc   7080
acaactccat agaaaacatc gactcagaac acacgctcca tgcggccgct taggaatcct   7140
gtgcgtcctt cacgcagtgg acgacaccca ccttatgcat gtacttcagg gtggagatga   7200
tgttgccgac gatggtaggg tagaaaacat atcgcactcc atgtcgttcg caacactccc   7260
ggaccgcctg ctggacgaag gggtagtgcc aagacgacat ccggggaaag aggtggtgct   7320
cgatctggaa attgagaccg ccagtgaaga acatggcgat ggggccaccg tatgtggagg   7380
acgtctccac ctgcgcccga taccagtcaa tttggtcagc ctcaacgtcc ttctcagatc   7440
gcttaacctt gcagttcttg tcggggatcc gttcggagcc atcaaaattg tgggacaaaa   7500
tgaagaagaa cgtcaagaag gcaccagttg cggtgggcac cagaggaatg gtgatcagca   7560
atgaggtccc agtgaggtac cagggcaaga atgcggtccg gaagatgaag aaagctcgca   7620
tcacgaatgc aagtgtgcgg tagcgccgca gaaagccatt ttcccgcatg gccgtgacag   7680
actctgggat ggtgtcattg tgctgcatcc ggaaaatgta gagcgggttg tacaccagcg   7740
ataccccgta tgcccccagc acaaggtaca tgtaccaagc ctggaagcgg tggaaccact   7800
ttcgggcggt gtttgcggcg gggtagttgt ggaacaccag gaacggctct gccgactccg   7860
catccaggtc gaggccgtgc tggttggtgt aggtgtggtg ccgcatgatg tgcgactgca   7920
gccaaatcca ccgggacgat ccgatgacgt caatgccgta ggcgaagagg gcgttgaccc   7980
aaggcttctt gctgatggcc ccgtgggacg catcatgctg gatggataag ccgatctgca   8040
tgtgcatgaa tccagtcaac aggccccaca gcaccatccc cgtggtagcc cagtgccact   8100
cgcaaaaggc cgtcacggcg atgatcccaa cggtgcgcag ccagaagcca ggggttgcgt   8160
accagttcct ccctttcatc acctcgcgca ttgtccgctt aacgtcttgt gcgaagggag   8220
aatcatacgt gtagacaatg tccttcgagg tgcggtcatg cttccctcgg acgaactgtt   8280
gaagcaattt ggagttctcc ggtttgacgt atggatgcat tgaataaaag agaggggagg   8340
catcagaggc accagaagcg agaatcaaat ctcctcctgg atgaactttg gcaagccctt   8400
caaggtcgta gaggatgcca tcaatcgcaa ccaaatcagg gcgttctaac agctgttctg   8460
tggtaagact gagagccatg gagagctggg ttagtttgtg tagagagtgt gtgttgctag   8520
cgactttcgg attgtgtcat tacacaaaac gcgtcgtctc gacactgatc ttgtcgtgga   8580
tactcacggc tcggacatcg tcgccgacga tgacaccgga ctttcgctta aggacgtcag   8640
taacaggcat tgtgtgatgt gtagtttaga tttcgaatct gtggggaaag aaaggaaaaa   8700
agagactggc aaccgattgg gagagccact gtttatatat accctagaca agccccccgc   8760
ttgtaagatg ttggtcaatg taaaccagta ttaaggttgg caagtgcagg agaagcaagg   8820
tgtgggtacc gagcaatgga aatgtgcgga aggcaaaaaa atgaggccac ggcctattgt   8880
cggggctata tccagggggc gattgaagta cactaacatg acatgtgtcc acagaccctc   8940
aatctggcct gatgagccaa atccatacgc gctttcgcag ctctaaaggc tataacaagt   9000
```

-continued

```
cacaccaccc tgctcgacct cagcgccctc actttttgtt aagacaaact gtacacgctg   9060
ttccagcgtt ttctgcctgc acctggtggg acatttggtg caacctaaag tgctcggaac   9120
ctctgtggtg tccagatcag cgcagcagtt ccgaggtagt tttgaggccc ttagatgatg   9180
caatggtgtc agtcgctgga tcacgagtct taatggcagt attcgttctt atttgtgcca   9240
ttgagccccg ttatcctcgt atcttctacc ccccatccca tccctttgtt ggtgcaaccc   9300
tacccattta ttgttgggtg cagcccaacc gacgtggaga gcttggcttg gccatataaa   9360
aaggcccccc cctagtggca atggcagaaa gtcagctgtg agttgttgaa tttgtcatct   9420
aggcggcctg gccgtcttct ccggggcaat tggggctgtt ttttgggaca caaatacgcc   9480
gccaacccgg tctctcctga attccgtcgt cgcctgagtc gacatcattt atttaccagt   9540
tggccacaaa cccttgacga tctcgtatgt cccctccgac atactcccgg ccggctgggg   9600
tacgttcgat agcgctatcg gcatcgacaa ggtttgggtc cctagccgat accgcactac   9660
ctgagtcaca atcttcggag gtttagtctt ccacatagca cgggcaaaag tgcgtatata   9720
tacaagagcg tttgccagcc acagattttc actccacaca ccacatcaca catacaacca   9780
cacacatcca caatggaacc cgaaactaag aagaccaaga ctgactccaa gaagattgtt   9840
cttctcggcg gcgacttctg tggccccgag gtgattgccg aggccgtcaa ggtgctcaag   9900
tctgttgctg aggcctccgg caccgagttt gtgtttgagg accgactcat tggaggagct   9960
gccattgaga aggagggcga gcccatcacc gacgctactc tcgacatctg ccgaaaggct  10020
gactctatta tgctcggtgc tgtcggaggc gctgccaaca ccgtatggac cactcccgac  10080
ggacgaaccg acgtgcgacc cgagcagggt ctcctcaagc tgcgaaagga cctgaacctg  10140
tacgccaacc tgcgaccctg ccagctgctg tcgcccaagc tcgccgatct ctcccccatc  10200
cgaaacgttg agggcaccga cttcatcatt gtccgagagc tcgtcggagg tatctacttt  10260
ggagagcgaa aggaggatga cggatctggc gtcgcttccg acaccgagac ctactccgtt  10320
cctgaggttg agcgaattgc ccgaatggcc gccttcctgg cccttcagca caacccccct  10380
cttcccgtgt ggtctcttga caaggccaac gtgctggcct cctctcgact ttggcgaaag  10440
actgtcactc gagtcctcaa ggacgaactc cccccagctcg agctcaacca ccagctgatc  10500
gactcggccg ccatgatcct catcaagcag ccctccaaga tgaatggtat catcatcacc  10560
accaacatgt ttggcgatat catctccgac gaggcctccg tcatccccgg ttctctgggt  10620
ctgctgccct ccgcctctct ggcttctctg cccgacacca acgaggcgtt cggtctgtac  10680
gagccctgtc acggatctgc ccccgatctc ggcaagcaga aggtcaaccc cattgccacc  10740
attctgtctg ccgccatgat gctcaagttc tctcttaaca tgaagcccgc cggtgacgct  10800
gttgaggctg ccgtcaagga gtccgtcgag gctggtatca ctaccgccga tatcggaggc  10860
tcttcctcca cctccgaggt cggagacttg ttgccaacaa ggtcaaggag ctgctcaaga  10920
aggagtaagt cgtttctacg acgcattgat ggaaggagca aactgacgcg cctgcgggtt  10980
ggtctaccgg cagggtccgc tagtgtataa gactctataa aaagggccct gccctgctaa  11040
tgaaatgatg atttataatt taccggtgta gcaaccttga ctagaagaag cagattgggt  11100
gtgtttgtag tggaggacag tggtacgttt tggaaacagt cttcttgaaa gtgtcttgtc  11160
tacagtatat tcactcataa cctcaatagc caagggtgta gtcggtttat taaaggaagg  11220
gagttgtggc tgatgtggat atcgatagtt ggagcaaggg agaaatgtag agtgtgaaag  11280
actcactatg gtccgggctt atctcgacca atagccaaag tctggagttt ctgagagaaa  11340
```

-continued

```
aaggcaagat acgtatgtaa caaagcgacg catggtacaa taataccgga ggcatgtatc  11400
atagagagtt agtggttcga tgatggcact ggtgcctggt atgactttat acggctgact  11460
acatatttgt cctcagacat acaattacag tcaagcactt acccttggac atctgtaggt  11520
accccccggc caagacgatc tcagcgtgtc gtatgtcgga ttggcgtagc tccctcgctc  11580
gtcaattggc tcccatctac tttcttctgc ttggctacac ccagcatgtc tgctatggct  11640
cgttttcgtg ccttatctat cctcccagta ttaccaactc taaatgacat gatgtgattg  11700
ggtctacact ttcatatcag agataaggag tagcacagtt gcataaaaag cccaactcta  11760
atcagcttct tcctttcttg taattagtac aaaggtgatt agcgaaatct ggaagcttag  11820
ttggccctaa aaaaatcaaa aaaagcaaaa aacgaaaaac gaaaaaccac agttttgaga  11880
acagggaggt aacgaaggat cgtatatata tatatatata tatataccca cggatcccga  11940
gaccggcctt tgattcttcc ctacaaccaa ccattctcac caccctaatt cacaaccatg  12000
gctcccgacg ccgacaagct gcgacagcga aaggctcagt ccatccagga cactgccgat  12060
tctcaggcta ccgagctcaa gattggcacc ctgaagggtc tccaaggcac cgagatcgtc  12120
attgatggcg acatctacga catcaaagac ttcgatcacc ctggaggcga atccatcatg  12180
acctttggtg gcaacgacgt tactgccacc tacaagatga ttcatcccta ccactcgaag  12240
catcacctgg agaagatgaa aaaggtcggt cgagtgcccg actacacctc cgagtacaag  12300
ttcgatactc ccttcgaacg agagatcaaa caggaggtct tcaagattgt gcgaagaggt  12360
cgagagtttg gaacacctgg ctacttcttt cgagccttct gctacatcgg tctcttcttt  12420
tacctgcagt atctctgggt taccactcct accactttcg cccttgctat cttctacggt  12480
gtgtctcagg ccttcattgg cctgaacgtc cagcacgacg ccaaccacgg agctgcctcc  12540
aaaaagccct ggatcaacaa tttgctcggc ctgggtgccg actttatcgg aggctccaag  12600
tggctctgga tgaaccagca ctggacccat cacacttaca ccaaccatca cgagaaggat  12660
cccgacgccc tgggtgcaga gcctatgctg ctcttcaacg actatccctt gggtcacccc  12720
aagcgaaccc tcattcatca cttccaagcc ttctactatc tgtttgtcct tgctggctac  12780
tgggtgtctt cggtgttcaa ccctcagatc ctggacctcc agcaccgagg tgcccaggct  12840
gtcggcatga agatggagaa cgactacatt gccaagtctc gaaagtacgc tatcttcctg  12900
cgactcctgt acatctacac caacattgtg gctcccatcc agaaccaagg cttttcgctc  12960
accgtcgttg ctcacattct tactatgggt gtcgcctcca gcctgaccct cgctactctg  13020
ttcgccctct cccacaactt cgagaacgca gatcgggatc ccacctacga ggctcgaaag  13080
ggaggcgagc ctgtctgttg gttcaagtcg caggtggaaa cctcctctac ttacggtggc  13140
ttcatttccg gttgccttac aggcggactc aactttcagg tcgagcatca cctgtttcct  13200
cgaatgtcct ctgcctggta cccctacatc gctcctaccg ttcgagaggt ctgcaaaaag  13260
cacggcgtca agtacgccta ctatccctgg gtgtggcaga acctcatctc gaccgtcaag  13320
tacctgcatc agtccggaac tggctcgaac tggaagaacg gtgccaatcc ctactctggc  13380
aagctgtaag cggccgcatg tacatacaag attatttata gaaatgaatc gcgatcgaac  13440
aaagagtacg agtgtacgag taggggatga tgataaaagt ggaagaagtt ccgcatcttt  13500
ggatttatca acgtgtagga cgatacttcc tgtaaaaatg caatgtcttt accataggtt  13560
ctgctgtaga tgttattaac taccattaac atgtctactt gtacagttgc agaccagttg  13620
gagtatagaa tggtacactt accaaaaagt gttgatggtt gtaactacga tatataaaac  13680
tgttgacggg atctgcgtac actgttt                                      13707
```

-continued

<210> SEQ ID NO 75
<211> LENGTH: 1350
<212> TYPE: DNA
<213> ORGANISM: Euglena gracilis
<220> FEATURE:
<221> NAME/KEY: misc_feature
<223> OTHER INFORMATION: synthetic delta-5 desaturase (codon-optimized)
for Yarrowia lipolytica

<400> SEQUENCE: 75

```
atggctctct cccttactac cgagcagctg ctcgagcgac ccgacctggt tgccatcgac      60
ggcattctct acgatctgga aggtcttgcc aaggtccatc ccggaggcga cttgatcctc     120
gcttctggtg cctccgatgc ttctcctctg ttctactcca tgcaccctta cgtcaagccc     180
gagaactcga agctgcttca acagttcgtg cgaggcaagc acgaccgaac ctccaaggac     240
attgtctaca cctacgactc tccctttgca caggacgtca agcgaactat gcgagaggtc     300
atgaaaggtc ggaactggta tgccacacct ggattctggc tgcgaaccgt tggcatcatt     360
gctgtcaccg cctttttgcga gtggcactgg gctactaccg gaatggtgct gtggggtctc    420
ttgactggat tcatgcacat gcagatcggc ctgtccattc agcacgatgc ctctcatggt     480
gccatcagca aaaagccctg ggtcaacgct ctctttgcct acggcatcga cgtcattgga     540
tcgtccagat ggatctggct gcagtctcac atcatgcgac atcacaccta caccaatcag     600
catggtctcg acctggatgc cgagtccgca gaaccattcc ttgtgttcca caactaccct     660
gctgccaaca ctgctcgaaa gtggtttcac cgattccagg cctggtacat gtacctcgtg     720
cttggagcct acggcgtttc gctggtgtac aaccctctct acatcttccg aatgcagcac     780
aacgacacca ttcccgagtc tgtcacagcc atgcgagaga acggctttct gcgacggtac     840
cgaacccttg cattcgttat gcgagctttc ttcatctttc gaaccgcctt cttgccctgg     900
tatctcactg gaacctccct gctcatcacc attcctctgg tgcccactgc taccggtgcc     960
ttcctcacct tcttttttcat cttgtctcac aacttcgatg gctcggagcg aatccccgac    1020
aagaactgca aggtcaagag ctccgagaag gacgttgaag ccgatcagat cgactggtac    1080
agagctcagg tggagacctc ttccacctac ggtggaccca ttgccatgtt ctttactggc    1140
ggtctcaact tccagatcga gcatcacctc tttcctcgaa tgtcgtcttg gcactatccc    1200
ttcgtgcagc aagctgtccg agagtgttgc gaacgacacg gagttcggta cgtcttctac    1260
cctaccattg tgggcaacat catttccacc ctcaagtaca tgcacaaagt cggtgtggtt    1320
cactgtgtca aggacgctca ggattcctaa                                      1350
```

<210> SEQ ID NO 76
<211> LENGTH: 449
<212> TYPE: PRT
<213> ORGANISM: Euglena gracilis

<400> SEQUENCE: 76

```
Met Ala Leu Ser Leu Thr Thr Glu Gln Leu Leu Glu Arg Pro Asp Leu
1               5                   10                  15

Val Ala Ile Asp Gly Ile Leu Tyr Asp Leu Glu Gly Leu Ala Lys Val
            20                  25                  30

His Pro Gly Gly Asp Leu Ile Leu Ala Ser Gly Ala Ser Asp Ala Ser
        35                  40                  45

Pro Leu Phe Tyr Ser Met His Pro Tyr Val Lys Pro Glu Asn Ser Lys
    50                  55                  60
```

-continued

```
Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
                85                  90                  95

Met Arg Glu Val Met Lys Gly Arg Asn Trp Tyr Ala Thr Pro Gly Phe
            100                 105                 110

Trp Leu Arg Thr Val Gly Ile Ile Ala Val Thr Ala Phe Cys Glu Trp
        115                 120                 125

His Trp Ala Thr Thr Gly Met Val Leu Trp Gly Leu Leu Thr Gly Phe
    130                 135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
            180                 185                 190

Arg His His Thr Tyr Thr Asn Gln His Gly Leu Asp Leu Asp Ala Glu
        195                 200                 205

Ser Ala Glu Pro Phe Leu Val Phe His Asn Tyr Pro Ala Ala Asn Thr
    210                 215                 220

Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
            260                 265                 270

Glu Asn Gly Phe Leu Arg Arg Tyr Arg Thr Leu Ala Phe Val Met Arg
        275                 280                 285

Ala Phe Phe Ile Phe Arg Thr Ala Phe Leu Pro Trp Tyr Leu Thr Gly
    290                 295                 300

Thr Ser Leu Leu Ile Thr Ile Pro Leu Val Pro Thr Ala Thr Gly Ala
305                 310                 315                 320

Phe Leu Thr Phe Phe Phe Ile Leu Ser His Asn Phe Asp Gly Ser Glu
                325                 330                 335

Arg Ile Pro Asp Lys Asn Cys Lys Val Lys Ser Ser Glu Lys Asp Val
            340                 345                 350

Glu Ala Asp Gln Ile Asp Trp Tyr Arg Ala Gln Val Glu Thr Ser Ser
        355                 360                 365

Thr Tyr Gly Gly Pro Ile Ala Met Phe Phe Thr Gly Gly Leu Asn Phe
    370                 375                 380

Gln Ile Glu His His Leu Phe Pro Arg Met Ser Ser Trp His Tyr Pro
385                 390                 395                 400

Phe Val Gln Gln Ala Val Arg Glu Cys Cys Glu Arg His Gly Val Arg
                405                 410                 415

Tyr Val Phe Tyr Pro Thr Ile Val Gly Asn Ile Ile Ser Thr Leu Lys
            420                 425                 430

Tyr Met His Lys Val Gly Val Val His Cys Val Lys Asp Ala Gln Asp
        435                 440                 445

Ser
```

<210> SEQ ID NO 77
<211> LENGTH: 1392
<212> TYPE: DNA
<213> ORGANISM: Peridinium sp. CCMP626

-continued

<220> FEATURE:
<221> NAME/KEY: misc_feature
<223> OTHER INFORMATION: synthetic delta-5 desaturase (codon-optimized)
for Yarrowia lipolytica

<400> SEQUENCE: 77

```
atggctcccg acgccgacaa gctgcgacag cgaaaggctc agtccatcca ggacactgcc     60

gattctcagg ctaccgagct caagattggc accctgaagg gtctccaagg caccgagatc    120

gtcattgatg gcgacatcta cgacatcaaa gacttcgatc accctggagg cgaatccatc    180

atgacctttg gtggcaacga cgttactgcc acctacaaga tgattcatcc ctaccactcg    240

aagcatcacc tggagaagat gaaaaaggtc ggtcgagtgc ccgactacac ctccgagtac    300

aagttcgata ctcccttcga acgagagatc aaacaggagg tcttcaagat tgtgcgaaga    360

ggtcgagagt ttggaacacc tggctacttc tttcgagcct tctgctacat cggtctcttc    420

ttttacctgc agtatctctg ggttaccact cctaccactt tcgcccttgc tatcttctac    480

ggtgtgtctc aggccttcat tggcctgaac gtccagcacg acgccaacca cggagctgcc    540

tccaaaaagc cctggatcaa caatttgctc ggcctgggtg ccgactttat cggaggctcc    600

aagtggctct ggatgaacca gcactggacc catcacactt acaccaacca tcacgagaag    660

gatcccgacg ccctgggtgc agagcctatg ctgctcttca acgactatcc cttgggtcac    720

cccaagcgaa ccctcattca tcacttccaa gccttctact atctgtttgt ccttgctggc    780

tactgggtgt cttcggtgtt caaccctcag atcctggacc tccagcaccg aggtgcccag    840

gctgtcggca tgaagatgga gaacgactac attgccaagt ctcgaaagta cgctatcttc    900

ctgcgactcc tgtacatcta caccaacatt gtggctccca tccagaacca aggcttttcg    960

ctcaccgtcg ttgctcacat tcttactatg ggtgtcgcct ccagcctgac cctcgctact   1020

ctgttcgccc tctcccacaa cttcgagaac gcagatcggg atcccaccta cgaggctcga   1080

aagggaggcg agcctgtctg ttggttcaag tcgcaggtgg aaacctcctc tacttacggt   1140

ggcttcattt ccggttgcct tacaggcgga ctcaactttc aggtcgagca tcacctgttt   1200

cctcgaatgt cctctgcctg gtacccctac atcgctccta ccgttcgaga ggtctgcaaa   1260

aagcacggcg tcaagtacgc ctactatccc tgggtgtggc agaacctcat ctcgaccgtc   1320

aagtacctgc atcagtccgg aactggctcg aactggaaga acggtgccaa tccctactct   1380

ggcaagctgt aa                                                       1392
```

<210> SEQ ID NO 78
<211> LENGTH: 463
<212> TYPE: PRT
<213> ORGANISM: Peridinium sp. CCMP626

<400> SEQUENCE: 78

```
Met Ala Pro Asp Ala Asp Lys Leu Arg Gln Arg Lys Ala Gln Ser Ile
1               5                   10                  15

Gln Asp Thr Ala Asp Ser Gln Ala Thr Glu Leu Lys Ile Gly Thr Leu
            20                  25                  30

Lys Gly Leu Gln Gly Thr Glu Ile Val Ile Asp Gly Asp Ile Tyr Asp
        35                  40                  45

Ile Lys Asp Phe Asp His Pro Gly Gly Glu Ser Ile Met Thr Phe Gly
    50                  55                  60

Gly Asn Asp Val Thr Ala Thr Tyr Lys Met Ile His Pro Tyr His Ser
65                  70                  75                  80

Lys His His Leu Glu Lys Met Lys Lys Val Gly Arg Val Pro Asp Tyr
```

-continued

```
                85                  90                  95

Thr Ser Glu Tyr Lys Phe Asp Thr Pro Phe Glu Arg Glu Ile Lys Gln
            100                 105                 110

Glu Val Phe Lys Ile Val Arg Arg Gly Arg Glu Phe Gly Thr Pro Gly
        115                 120                 125

Tyr Phe Phe Arg Ala Phe Cys Tyr Ile Gly Leu Phe Phe Tyr Leu Gln
    130                 135                 140

Tyr Leu Trp Val Thr Thr Pro Thr Thr Phe Ala Leu Ala Ile Phe Tyr
145                 150                 155                 160

Gly Val Ser Gln Ala Phe Ile Gly Leu Asn Val Gln His Asp Ala Asn
                165                 170                 175

His Gly Ala Ala Ser Lys Lys Pro Trp Ile Asn Asn Leu Leu Gly Leu
            180                 185                 190

Gly Ala Asp Phe Ile Gly Gly Ser Lys Trp Leu Trp Met Asn Gln His
        195                 200                 205

Trp Thr His His Thr Tyr Thr Asn His His Glu Lys Asp Pro Asp Ala
    210                 215                 220

Leu Gly Ala Glu Pro Met Leu Leu Phe Asn Asp Tyr Pro Leu Gly His
225                 230                 235                 240

Pro Lys Arg Thr Leu Ile His His Phe Gln Ala Phe Tyr Tyr Leu Phe
                245                 250                 255

Val Leu Ala Gly Tyr Trp Val Ser Ser Val Phe Asn Pro Gln Ile Leu
            260                 265                 270

Asp Leu Gln His Arg Gly Ala Gln Ala Val Gly Met Lys Met Glu Asn
        275                 280                 285

Asp Tyr Ile Ala Lys Ser Arg Lys Tyr Ala Ile Phe Leu Arg Leu Leu
    290                 295                 300

Tyr Ile Tyr Thr Asn Ile Val Ala Pro Ile Gln Asn Gln Gly Phe Ser
305                 310                 315                 320

Leu Thr Val Val Ala His Ile Leu Thr Met Gly Val Ala Ser Ser Leu
                325                 330                 335

Thr Leu Ala Thr Leu Phe Ala Leu Ser His Asn Phe Glu Asn Ala Asp
            340                 345                 350

Arg Asp Pro Thr Tyr Glu Ala Arg Lys Gly Gly Glu Pro Val Cys Trp
        355                 360                 365

Phe Lys Ser Gln Val Glu Thr Ser Ser Thr Tyr Gly Gly Phe Ile Ser
    370                 375                 380

Gly Cys Leu Thr Gly Gly Leu Asn Phe Gln Val Glu His His Leu Phe
385                 390                 395                 400

Pro Arg Met Ser Ser Ala Trp Tyr Pro Tyr Ile Ala Pro Thr Val Arg
                405                 410                 415

Glu Val Cys Lys Lys His Gly Val Lys Tyr Ala Tyr Tyr Pro Trp Val
            420                 425                 430

Trp Gln Asn Leu Ile Ser Thr Val Lys Tyr Leu His Gln Ser Gly Thr
        435                 440                 445

Gly Ser Asn Trp Lys Asn Gly Ala Asn Pro Tyr Ser Gly Lys Leu
    450                 455                 460


<210> SEQ ID NO 79
<211> LENGTH: 1350
<212> TYPE: DNA
<213> ORGANISM: Euglena gracilis
<220> FEATURE:
<221> NAME/KEY: misc_feature
<222> LOCATION: (1)..(1350)
```

-continued

<223> OTHER INFORMATION: delta-5 desaturase

<400> SEQUENCE: 79
atggctctca gtcttaccac agaacagctg ttagaacgcc ctgatttggt tgcgattgat 60
ggcatcctct acgaccttga agggcttgcc aaagttcatc caggaggaga tttgattctc 120
gcttctggtg cctctgatgc ctcccctctc ttttattcaa tgcatccata cgtcaaaccg 180
gagaattcca aattgcttca acagttcgtc cgagggaagc atgaccgcac ctcgaaggac 240
attgtctaca cgtatgattc tcccttcgca caagacgtta agcggacaat gcgcgaggtg 300
atgaaaggga ggaactggta cgcaacccct ggcttctggc tgcgcaccgt tgggatcatc 360
gccgtgacgg ccttttgcga gtggcactgg gctaccacgg ggatggtgct gtggggcctg 420
ttgactggat tcatgcacat gcagatcggc ttatccatcc agcatgatgc gtcccacggg 480
gccatcagca agaagccttg ggtcaacgcc ctcttcgcct acggcattga cgtcatcgga 540
tcgtcccggt ggatttggct gcagtcgcac atcatgcggc accacaccta caccaaccag 600
cacggcctcg acctggatgc ggagtcggca gagccgttcc tggtgttcca caactacccc 660
gccgcaaaca ccgcccgaaa gtggttccac cgcttccaag cttggtacat gtaccttgtg 720
ctgggggcat acggggtatc gctggtgtac aacccgctct acattttccg gatgcagcac 780
aatgacacca tcccagagtc tgtcacggcc atgcgggaga atggctttct gcggcgctac 840
cgcacacttg cattcgtgat gcgagctttc ttcatcttcc ggaccgcatt cttgccctgg 900
tacctcactg ggacctcatt gctgatcacc attcctctgg tgcccactgc aactggtgcc 960
ttcttgacgt tcttcttcat tttgtcccac aattttgatg gctccgaacg gatccccgac 1020
aagaactgca aggttaagag ctctgagaag gacgttgagg ctgaccaaat tgactggtat 1080
cgggcgcagg tggagacgtc ctccacatac ggtggcccca tcgccatgtt cttcactggc 1140
ggtctcaatt tccagatcga gcaccacctc tttccccgga tgtcgtcttg gcactacccc 1200
ttcgtccagc aggcggtccg ggagtgttgc gaacgccatg gagtgcgata tgttttctac 1260
cctaccatcg tcggcaacat catctccacc ctgaagtaca tgcataaggt gggtgtcgtc 1320
cactgcgtga aggacgcaca ggattcctga 1350

<210> SEQ ID NO 80
<211> LENGTH: 7222
<212> TYPE: DNA
<213> ORGANISM: Artificial Sequence
<220> FEATURE:
<223> OTHER INFORMATION: Plasmid pFBAIn-MOD-1

<400> SEQUENCE: 80
catggatcca ggcctgttaa cggccattac ggcctgcagg atccgaaaaa acctcccaca 60
cctccccctg aacctgaaac ataaaatgaa tgcaattgtt gttgttaact tgtttattgc 120
agcttataat ggttacaaat aaagcaatag catcacaaat ttcacaaata aagcattttt 180
ttcactgcat tctagttgtg gtttgtccaa actcatcaat gtatcttatc atgtctgcgg 240
ccgcaagtgt ggatggggaa gtgagtgccc ggttctgtgt gcacaattgg caatccaaga 300
tggatggatt caacacaggg atatagcgag ctacgtggtg gtgcgaggat atagcaacgg 360
atatttatgt ttgacacttg agaatgtacg atacaagcac tgtccaagta caatactaaa 420
catactgtac atactcatac tcgtacccgg gcaacggttt cacttgagtg cagtggctag 480
tgctcttact cgtacagtgt gcaatactgc gtatcatagt ctttgatgta tatcgtattc 540
attcatgtta gttgcgtacg agccggaagc ataaagtgta aagcctgggg tgcctaatga 600

-continued

```
gtgagctaac tcacattaat tgcgttgcgc tcactgcccg ctttccagtc gggaaacctg    660
tcgtgccagc tgcattaatg aatcggccaa cgcgcgggga gaggcggttt gcgtattggg    720
cgctcttccg cttcctcgct cactgactcg ctgcgctcgg tcgttcggct gcggcgagcg    780
gtatcagctc actcaaaggc ggtaatacgg ttatccacag aatcagggga taacgcagga    840
aagaacatgt gagcaaaagg ccagcaaaag gccaggaacc gtaaaaaggc cgcgttgctg    900
gcgtttttcc ataggctccg cccccctgac gagcatcaca aaaatcgacg ctcaagtcag    960
aggtggcgaa acccgacagg actataaaga taccaggcgt ttccccctgg aagctccctc   1020
gtgcgctctc ctgttccgac cctgccgctt accggatacc tgtccgcctt tctcccttcg   1080
ggaagcgtgg cgctttctca tagctcacgc tgtaggtatc tcagttcggt gtaggtcgtt   1140
cgctccaagc tgggctgtgt gcacgaaccc cccgttcagc ccgaccgctg cgccttatcc   1200
ggtaactatc gtcttgagtc caacccggta agacacgact tatcgccact ggcagcagcc   1260
actggtaaca ggattagcag agcgaggtat gtaggcggtg ctacagagtt cttgaagtgg   1320
tggcctaact acggctacac tagaaggaca gtatttggta tctgcgctct gctgaagcca   1380
gttaccttcg gaaaaagagt tggtagctct tgatccggca aacaaaccac cgctggtagc   1440
ggtggttttt ttgtttgcaa gcagcagatt acgcgcagaa aaaaaggatc tcaagaagat   1500
cctttgatct tttctacggg gtctgacgct cagtggaacg aaaactcacg ttaagggatt   1560
ttggtcatga gattatcaaa aaggatcttc acctagatcc ttttaaatta aaaatgaagt   1620
tttaaatcaa tctaaagtat atatgagtaa acttggtctg acagttacca atgcttaatc   1680
agtgaggcac ctatctcagc gatctgtcta tttcgttcat ccatagttgc ctgactcccc   1740
gtcgtgtaga taactacgat acgggagggc ttaccatctg gccccagtgc tgcaatgata   1800
ccgcgagacc cacgctcacc ggctccagat ttatcagcaa taaaccagcc agccggaagg   1860
gccgagcgca gaagtggtcc tgcaacttta tccgcctcca tccagtctat taattgttgc   1920
cgggaagcta gagtaagtag ttcgccagtt aatagtttgc gcaacgttgt tgccattgct   1980
acaggcatcg tggtgtcacg ctcgtcgttt ggtatggctt cattcagctc cggttcccaa   2040
cgatcaaggc gagttacatg atcccccatg ttgtgcaaaa aagcggttag ctccttcggt   2100
cctccgatcg ttgtcagaag taagttggcc gcagtgttat cactcatggt tatggcagca   2160
ctgcataatt ctcttactgt catgccatcc gtaagatgct tttctgtgac tggtgagtac   2220
tcaaccaagt cattctgaga atagtgtatg cggcgaccga gttgctcttg cccggcgtca   2280
atacgggata ataccgcgcc acatagcaga actttaaaag tgctcatcat tggaaaacgt   2340
tcttcggggc gaaaactctc aaggatctta ccgctgttga gatccagttc gatgtaaccc   2400
actcgtgcac ccaactgatc ttcagcatct tttactttca ccagcgtttc tgggtgagca   2460
aaaacaggaa ggcaaaatgc cgcaaaaaag ggaataaggg cgacacggaa atgttgaata   2520
ctcatactct tcctttttca atattattga agcatttatc agggttattg tctcatgagc   2580
ggatacatat ttgaatgtat ttagaaaaat aaacaaatag gggttccgcg cacatttccc   2640
cgaaaagtgc cacctgacgc gccctgtagc ggcgcattaa gcgcggcggg tgtggtggtt   2700
acgcgcagcg tgaccgctac acttgccagc gccctagcgc ccgctccttt cgctttcttc   2760
ccttcctttc tcgccacgtt cgccggcttt ccccgtcaag ctctaaatcg gggggctccct   2820
ttagggttcc gatttagtgc tttacggcac ctcgacccca aaaaacttga ttagggtgat   2880
ggttcacgta gtgggccatc gccctgatag acggtttttc gccctttgac gttggagtcc   2940
```

-continued

```
acgttcttta atagtggact cttgttccaa actggaacaa cactcaaccc tatctcggtc   3000
tattcttttg atttataagg gattttgccg atttcggcct attggttaaa aaatgagctg   3060
atttaacaaa aatttaacgc gaattttaac aaaatattaa cgcttacaat ttccattcgc   3120
cattcaggct gcgcaactgt tgggaagggc gatcggtgcg ggcctcttcg ctattacgcc   3180
agctggcgaa agggggatgt gctgcaaggc gattaagttg ggtaacgcca gggttttccc   3240
agtcacgacg ttgtaaaacg acggccagtg aattgtaata cgactcacta tagggcgaat   3300
tgggtaccgg gccccccctc gaggtcgatg gtgtcgataa gcttgatatc gaattcatgt   3360
cacacaaacc gatcttcgcc tcaaggaaac ctaattctac atccgagaga ctgccgagat   3420
ccagtctaca ctgattaatt ttcgggccaa taatttaaaa aaatcgtgtt atataatatt   3480
atatgtatta tatatataca tcatgatgat actgacagtc atgtcccatt gctaaataga   3540
cagactccat ctgccgcctc caactgatgt tctcaatatt taaggggtca tctcgcattg   3600
tttaataata aacagactcc atctaccgcc tccaaatgat gttctcaaaa tatattgtat   3660
gaacttattt ttattactta gtattattag acaacttact tgctttatga aaaacacttc   3720
ctatttagga aacaatttat aatggcagtt cgttcattta acaatttatg tagaataaat   3780
gttataaatg cgtatgggaa atcttaaata tggatagcat aaatgatatc tgcattgcct   3840
aattcgaaat caacagcaac gaaaaaaatc ccttgtacaa cataaatagt catcgagaaa   3900
tatcaactat caaagaacag ctattcacac gttactattg agattattat tggacgagaa   3960
tcacacactc aactgtcttt ctctcttcta gaaatacagg tacaagtatg tactattctc   4020
attgttcata cttctagtca tttcatccca catattcctt ggatttctct ccaatgaatg   4080
acattctatc ttgcaaattc aacaattata ataagatata ccaaagtagc ggtatagtgg   4140
caatcaaaaa gcttctctgg tgtgcttctc gtatttattt ttattctaat gatccattaa   4200
aggtatatat ttatttcttg ttatataatc cttttgttta ttacatgggc tggatacata   4260
aaggtatttt gatttaattt tttgcttaaa ttcaatcccc cctcgttcag tgtcaactgt   4320
aatggtagga aattaccata cttttgaaga agcaaaaaaa atgaaagaaa aaaaaaatcg   4380
tatttccagg ttagacgttc cgcagaatct agaatgcggt atgcggtaca ttgttcttcg   4440
aacgtaaaag ttgcgctccc tgagatattg tacatttttg cttttacaag tacaagtaca   4500
tcgtacaact atgtactact gttgatgcat ccacaacagt ttgttttgtt ttttttgtt   4560
ttttttttt ctaatgattc attaccgcta tgtataccta cttgtacttg tagtaagccg   4620
ggttattggc gttcaattaa tcatagactt atgaatctgc acggtgtgcg ctgcgagtta   4680
cttttagctt atgcatgcta cttgggtgta atattgggat ctgttcggaa atcaacggat   4740
gctcaatcga tttcgacagt aattaattaa gtcatacaca agtcagcttt cttcgagcct   4800
catataagta taagtagttc aacgtattag cactgtaccc agcatctccg tatcgagaaa   4860
cacaacaaca tgccccattg gacagatcat gcggatacac aggttgtgca gtatcataca   4920
tactcgatca gacaggtcgt ctgaccatca tacaagctga acaagcgctc catacttgca   4980
cgctctctat atacacagtt aaattacata tccatagtct aacctctaac agttaatctt   5040
ctggtaagcc tcccagccag ccttctggta tcgcttggcc tcctcaatag gatctcggtt   5100
ctggccgtac agacctcggc cgacaattat gatatccgtt ccggtagaca tgacatcctc   5160
aacagttcgg tactgctgtc cgagagcgtc tcccttgtcg tcaagaccca ccccgggggt   5220
cagaataagc cagtcctcag agtcgccctt aggtcggttc tgggcaatga agccaaccac   5280
aaactcgggg tcggatcggg caagctcaat ggtctgcttg gagtactcgc cagtggccag   5340
```

-continued

```
agagcccttg caagacagct cggccagcat gagcagacct ctggccagct tctcgttggg   5400
agaggggact aggaactcct tgtactggga gttctcgtag tcagagacgt cctccttctt   5460
ctgttcagag acagtttcct cggcaccagc tcgcaggcca gcaatgattc cggttccggg   5520
tacaccgtgg gcgttggtga tatcggacca ctcggcgatt cggtgacacc ggtactggtg   5580
cttgacagtg ttgccaatat ctgcgaactt tctgtcctcg aacaggaaga aaccgtgctt   5640
aagagcaagt tccttgaggg ggagcacagt gccggcgtag gtgaagtcgt caatgatgtc   5700
gatatgggtt ttgatcatgc acacataagg tccgacctta tcggcaagct caatgagctc   5760
cttggtggtg gtaacatcca gagaagcaca caggttggtt ttcttggctg ccacgagctt   5820
gagcactcga gcggcaaagg cggacttgtg gacgttagct cgagcttcgt aggagggcat   5880
tttggtggtg aagaggagac tgaaataaat ttagtctgca gaacttttta tcggaacctt   5940
atctggggca gtgaagtata tgttatggta atagttacga gttagttgaa cttatagata   6000
gactggacta tacggctatc ggtccaaatt agaaagaacg tcaatggctc tctgggcgtc   6060
gcctttgccg acaaaaatgt gatcatgatg aaagccagca atgacgttgc agctgatatt   6120
gttgtcggcc aaccgcgccg aaaacgcagc tgtcagaccc acagcctcca acgaagaatg   6180
tatcgtcaaa gtgatccaag cacactcata gttggagtcg tactccaaag gcggcaatga   6240
cgagtcagac agatactcgt cgaaaacagt gtacgcagat ctactataga ggaacattta   6300
aattgccccg gagaagacgg ccaggccgcc tagatgacaa attcaacaac tcacagctga   6360
ctttctgcca ttgccactag gggggggcct tttatatgg ccaagccaag ctctccacgt   6420
cggttgggct gcacccaaca ataaatgggt agggttgcac caacaaaggg atgggatggg   6480
gggtagaaga tacgaggata acggggctca atggcacaaa taagaacgaa tactgccatt   6540
aagactcgtg atccagcgac tgacaccatt gcatcatcta agggcctcaa aactacctcg   6600
gaactgctgc gctgatctgg acaccacaga ggttccgagc actttaggtt gcaccaaatg   6660
tcccaccagg tgcaggcaga aaacgctgga acagcgtgta cagtttgtct taacaaaaag   6720
tgagggcgct gaggtcgagc agggtggtgt gacttgttat agcctttaga gctgcgaaag   6780
cgcgtatgga tttggctcat caggccagat tgagggtctg tggacacatg tcatgttagt   6840
gtacttcaat cgccccctgg atatagcccc gacaataggc cgtggcctca tttttttgcc   6900
ttccgcacat ttccattgct cggtacccac accttgcttc tcctgcactt gccaacctta   6960
atactggttt acattgacca acatcttaca agcggggggc ttgtctaggg tatatataaa   7020
cagtggctct cccaatcggt tgccagtctc ttttttcctt tctttcccca cagattcgaa   7080
atctaaacta cacatcacag aattccgagc cgtgagtatc cacgacaaga tcagtgtcga   7140
gacgacgcgt tttgtgtaat gacacaatcc gaaagtcgct agcaacacac actctctaca   7200
caaactaacc cagctctggt ac                                             7222
```

<210> SEQ ID NO 81
<211> LENGTH: 1086
<212> TYPE: DNA
<213> ORGANISM: Phytophthora sojae
<220> FEATURE:
<221> NAME/KEY: misc_feature
<223> OTHER INFORMATION: synthetic delta-17 desaturase (codon-optimized)

<400> SEQUENCE: 81

```
atggctacca agcagcccta ccagttccct actctgaccg agatcaagcg atctctgccc     60
tccgagtgtt tcgaggcctc cgtgcctctc tctctgtact acaccgttcg atgcctggtc    120
```

-continued

```
attgctgtgt cgctcgcctt cggacttcac catgcacgat ctctgcccgt tgtcgaaggc    180
ctctgggctc tggatgccgc tctctgcacc ggttacgtgc tgctccaggg catcgtcttc    240
tggggattct ttactgttgg tcacgacgct ggacatggtg ccttctcccg ataccacctg    300
ctcaactttg tcatcggaac cttcattcac tctctcatcc ttacaccctt cgagtcctgg    360
aagctcaccc acagacacca tcacaagaac actggcaaca tcgaccgaga cgaaatcttc    420
taccctcaac gaaaggccga cgatcatcct ctgtctcgaa acctcattct ggctttgggt    480
gcagcctggt ttgcctacct ggtcgaaggc tttcctcccc gaaaggtcaa ccacttcaac    540
cccttcgagc ctctctttgt tcgacaggtc tctgccgtgg tcatttcgct ggctgcgcac    600
tttggagtgg ctgccctgtc catctacctc agcctgcagt tcggcttcaa gactatggcc    660
atctactact atggtcccgt ctttgtgttc ggatccatgc tcgtcattac tacctttctt    720
catcacaacg acgaagagac accttggtac gcagattcgg agtggaccta cgtcaaaggc    780
aacctgtcct ctgtcgaccg atcctacggt gccctcatcg acaacctttc tcacaacatc    840
ggaacccacc agattcatca cctctttccc atcattcctc actacaagct caagcgagct    900
accgaggcct tccatcaagc ctttcccgag ctggttcgaa agtccgacga acccatcatc    960
aaggcctttt tcagagtcgg ccgactctac gcaaactacg gtgtggtcga ctcggatgcc   1020
aagctgttca ctctcaagga ggccaaggct gtttccgaag ccgctaccaa gactaaggcc   1080
acctaa                                                              1086
```

```
<210> SEQ ID NO 82
<211> LENGTH: 361
<212> TYPE: PRT
<213> ORGANISM: Phytophthora sojae
<220> FEATURE:
<221> NAME/KEY: MISC_FEATURE
<223> OTHER INFORMATION: synthetic delta-17 desaturase (codon-optimized)

<400> SEQUENCE: 82

Met Ala Thr Lys Gln Pro Tyr Gln Phe Pro Thr Leu Thr Glu Ile Lys
1               5                   10                  15

Arg Ser Leu Pro Ser Glu Cys Phe Glu Ala Ser Val Pro Leu Ser Leu
            20                  25                  30

Tyr Tyr Thr Val Arg Cys Leu Val Ile Ala Val Ser Leu Ala Phe Gly
        35                  40                  45

Leu His His Ala Arg Ser Leu Pro Val Val Glu Gly Leu Trp Ala Leu
    50                  55                  60

Asp Ala Ala Leu Cys Thr Gly Tyr Val Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Ile Gly Thr Phe Ile His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Ile Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Phe Ala Tyr Leu Val Glu Gly Phe Pro Pro Arg Lys Val
                165                 170                 175
```

-continued

```
Asn His Phe Asn Pro Phe Glu Pro Leu Phe Val Arg Gln Val Ser Ala
            180                 185                 190

Val Val Ile Ser Leu Ala Ala His Phe Gly Val Ala Ala Leu Ser Ile
        195                 200                 205

Tyr Leu Ser Leu Gln Phe Gly Phe Lys Thr Met Ala Ile Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Arg Ala Thr Glu Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Ser Asp Ala Lys Leu Phe Thr Leu Lys Glu Ala Lys Ala Val Ser
            340                 345                 350

Glu Ala Ala Thr Lys Thr Lys Ala Thr
        355                 360
```

<210> SEQ ID NO 83
<211> LENGTH: 3806
<212> TYPE: DNA
<213> ORGANISM: Artificial Sequence
<220> FEATURE:
<223> OTHER INFORMATION: Plasmid pPsD17S

<400> SEQUENCE: 83

```
atcggatccc gggcccgtcg actgcagagg cctgcatgca agcttggcgt aatcatggtc     60

atagctgttt cctgtgtgaa attgttatcc gctcacaatt ccacacaaca tacgagccgg    120

aagcataaag tgtaaagcct ggggtgccta atgagtgagc taactcacat taattgcgtt    180

gcgctcactg cccgctttcc agtcgggaaa cctgtcgtgc cagctgcatt aatgaatcgg    240

ccaacgcgcg gggagaggcg gtttgcgtat tgggcgctct tccgcttcct cgctcactga    300

ctcgctgcgc tcggtcgttc ggctgcggcg agcggtatca gctcactcaa aggcggtaat    360

acggttatcc acagaatcag gggataacgc aggaaagaac atgtgagcaa aaggccagca    420

aaaggccagg aaccgtaaaa aggccgcgtt gctggcgttt ttccataggc tccgcccccc    480

tgacgagcat cacaaaaatc gacgctcaag tcagaggtgg cgaaacccga caggactata    540

aagataccag gcgtttcccc ctggaagctc cctcgtgcgc tctcctgttc cgaccctgcc    600

gcttaccgga tacctgtccg cctttctccc ttcgggaagc gtggcgcttt ctcatagctc    660

acgctgtagg tatctcagtt cggtgtaggt cgttcgctcc aagctgggct gtgtgcacga    720

accccccgtt cagcccgacc gctgcgcctt atccggtaac tatcgtcttg agtccaaccc    780

ggtaagacac gacttatcgc cactggcagc agccactggt aacaggatta gcagagcgag    840

gtatgtaggc ggtgctacag agttcttgaa gtggtggcct aactacggct acactagaag    900

aacagtattt ggtatctgcg ctctgctgaa gccagttacc ttcggaaaaa gagttggtag    960

ctcttgatcc ggcaaacaaa ccaccgctgg tagcggtggt ttttttgttt gcaagcagca   1020
```

-continued

```
gattacgcgc agaaaaaaag gatctcaaga agatcctttg atcttttcta cggggtctga   1080
cgctcagtgg aacgaaaact cacgttaagg gattttggtc atgagattat caaaaaggat   1140
cttcacctag atccttttaa attaaaaatg aagttttaaa tcaatctaaa gtatatatga   1200
gtaaacttgg tctgacagtt accaatgctt aatcagtgag gcacctatct cagcgatctg   1260
tctatttcgt tcatccatag ttgcctgact ccccgtcgtg tagataacta cgatacggga   1320
gggcttacca tctggcccca gtgctgcaat gataccgcga gacccacgct caccggctcc   1380
agatttatca gcaataaacc agccagccgg aagggccgag cgcagaagtg gtcctgcaac   1440
tttatccgcc tccatccagt ctattaattg ttgccgggaa gctagagtaa gtagttcgcc   1500
agttaatagt ttgcgcaacg ttgttgccat tgctacaggc atcgtggtgt cacgctcgtc   1560
gtttggtatg gcttcattca gctccggttc ccaacgatca aggcgagtta catgatcccc   1620
catgttgtgc aaaaaagcgg ttagctcctt cggtcctccg atcgttgtca gaagtaagtt   1680
ggccgcagtg ttatcactca tggttatggc agcactgcat aattctctta ctgtcatgcc   1740
atccgtaaga tgcttttctg tgactggtga gtactcaacc aagtcattct gagaatagtg   1800
tatgcggcga ccgagttgct cttgcccggc gtcaatacgg gataataccg cgccacatag   1860
cagaacttta aaagtgctca tcattggaaa acgttcttcg gggcgaaaac tctcaaggat   1920
cttaccgctg ttgagatcca gttcgatgta acccactcgt gcacccaact gatcttcagc   1980
atcttttact ttcaccagcg tttctgggtg agcaaaaaca ggaaggcaaa atgccgcaaa   2040
aaagggaata agggcgacac ggaaatgttg aatactcata ctcttccttt ttcaatatta   2100
ttgaagcatt tatcagggtt attgtctcat gagcggatac atatttgaat gtatttagaa   2160
aaataaacaa ataggggttc cgcgcacatt tccccgaaaa gtgccacctg acgtctaaga   2220
aaccattatt atcatgacat taacctataa aaataggcgt atcacgaggc cctttcgtct   2280
cgcgcgtttc ggtgatgacg gtgaaaacct ctgacacatg cagctcccgg agacggtcac   2340
agcttgtctg taagcggatg ccgggagcag acaagcccgt cagggcgcgt cagcgggtgt   2400
tggcgggtgt cggggctggc ttaactatgc ggcatcagag cagattgtac tgagagtgca   2460
ccatatgcgg tgtgaaatac cgcacagatg cgtaaggaga aaataccgca tcaggcgcca   2520
ttcgccattc aggctgcgca actgttggga agggcgatcg gtgcgggcct cttcgctatt   2580
acgccagctg gcgaaagggg gatgtgctgc aaggcgatta agttgggtaa cgccagggtt   2640
ttcccagtca cgacgttgta aaacgacggc cagtgaattc gagctcggta cctcgcgaat   2700
gcatctagat ccatggctac caagcagccc taccagttcc ctactctgac cgagatcaag   2760
cgatctctgc cctccgagtg tttcgaggcc tccgtgcctc tctctctgta ctacaccgtt   2820
cgatgcctgg tcattgctgt gtcgctcgcc ttcggacttc accatgcacg atctctgccc   2880
gttgtcgaag gcctctgggc tctggatgcc gctctctgca ccggttacgt gctgctccag   2940
ggcatcgtct tctggggatt ctttactgtt ggtcacgacg ctggacatgg tgccttctcc   3000
cgataccacc tgctcaactt tgtcatcgga accttcattc actctctcat ccttacaccc   3060
ttcgagtcct ggaagctcac ccacagacac catcacaaga acactggcaa catcgaccga   3120
gacgaaatct tctaccctca acgaaaggcc gacgatcatc ctctgtctcg aaacctcatt   3180
ctggctttgg gtgcagcctg gtttgcctac ctggtcgaag gctttcctcc ccgaaaggtc   3240
aaccacttca accccttcga gcctctcttt gttcgacagg tctctgccgt ggtcatttcg   3300
ctggctgcgc actttggagt ggctgccctg tccatctacc tcagcctgca gttcggcttc   3360
```

-continued

```
aagactatgg ccatctacta ctatggtccc gtctttgtgt tcggatccat gctcgtcatt   3420

actacctttc ttcatcacaa cgacgaagag acaccttggt acgcagattc ggagtggacc   3480

tacgtcaaag gcaacctgtc ctctgtcgac cgatcctacg gtgccctcat cgacaacctt   3540

tctcacaaca tcggaaccca ccagattcat cacctctttc ccatcattcc tcactacaag   3600

ctcaagcgag ctaccgaggc cttccatcaa gcctttcccg agctggttcg aaagtccgac   3660

gaacccatca tcaaggcctt tttcagagtc ggccgactct acgcaaacta cggtgtggtc   3720

gactcggatg ccaagctgtt cactctcaag gaggccaagg ctgtttccga agccgctacc   3780

aagactaagg ccacctaagc ggccgc                                         3806
```

<210> SEQ ID NO 84
<211> LENGTH: 1086
<212> TYPE: DNA
<213> ORGANISM: Phytophthora ramorum
<220> FEATURE:
<221> NAME/KEY: misc_feature
<223> OTHER INFORMATION: synthetic delta-17 desaturase (codon-optimized)

<400> SEQUENCE: 84

```
atggctacca agcagcccta ccagttccct actctgaccg agatcaagcg atctcttccc     60

tccgagtgct ttgaagcctc ggtccctctg tccttgtact acaccgtgcg aatcgtcgct    120

attgccgttg ctctggcctt cggactcaac tacgctcgag cccttcccgt ggtcgagtct    180

ctgtgggcac tcgacgctgc cctttgttgc ggttacgttc tgctccaagg cattgtcttc    240

tggggattct ttaccgtggg tcacgatgct ggacatggtg ccttctctcg ataccacctg    300

ctcaactttg tcgttggcac ctttatccac tccctcattc ttactccctt cgagtcgtgg    360

aagctcacac atcgacacca tcacaagaac accggaaaca tcgaccgaga cgaaatcttc    420

taccctcagc gaaaggccga cgatcatcct ctgtctcgaa acctcgtcct ggctctcggt    480

gccgcttggt ttgcctacct tgtcgagggc tttcctcccc gaaaggtcaa ccacttcaac    540

cccttcgaac ctctgtttgt gcgacaggtg gctgccgttg tcatttccct ctctgctcac    600

ttcgccgtcc tggcactgtc cgtgtatctg agctttcagt tcggtctcaa gacaatggct    660

ctgtactact atggacccgt cttcgtgttc ggctccatgc tcgtcattac tacctttctg    720

catcacaatg acgaggaaac tccttggtac ggagattccg actggaccta cgtcaagggc    780

aacttgtctt ccgtggaccg atcttacggt gccttcatcg acaacctctc gcacaacatt    840

ggcacacacc agatccacca tctgtttccc atcattcctc actacaagct caaccgagcc    900

accgctgcct tccaccaggc ctttcccgaa cttgtccgaa agagcgacga gcccattctc    960

aaggctttct ggagagttgg tcgactttac gccaactacg gagtcgtgga tcccgacgca   1020

aagctgttta ctctcaagga ggccaaagct gcctccgagg ctgccaccaa gaccaaggct   1080

acttaa                                                              1086
```

<210> SEQ ID NO 85
<211> LENGTH: 3806
<212> TYPE: DNA
<213> ORGANISM: Artificial Sequencec
<220> FEATURE:
<223> OTHER INFORMATION: Plasmid pPrD17S

<400> SEQUENCE: 85

```
ggccgcatcg gatcccgggc ccgtcgactg cagaggcctg catgcaagct tggcgtaatc     60

atggtcatag ctgtttcctg tgtgaaattg ttatccgctc acaattccac acaacatacg    120
```

-continued

```
agccggaagc ataaagtgta aagcctgggg tgcctaatga gtgagctaac tcacattaat    180
tgcgttgcgc tcactgcccg ctttccagtc gggaaacctg tcgtgccagc tgcattaatg    240
aatcggccaa cgcgcgggga gaggcggttt gcgtattggg cgctcttccg cttcctcgct    300
cactgactcg ctgcgctcgg tcgttcggct gcggcgagcg gtatcagctc actcaaaggc    360
ggtaatacgg ttatccacag aatcagggga taacgcagga aagaacatgt gagcaaaagg    420
ccagcaaaag gccaggaacc gtaaaaaggc cgcgttgctg gcgtttttcc ataggctccg    480
cccccctgac gagcatcaca aaaatcgacg ctcaagtcag aggtggcgaa acccgacagg    540
actataaaga taccaggcgt ttccccctgg aagctccctc gtgcgctctc ctgttccgac    600
cctgccgctt accggatacc tgtccgcctt tctcccttcg ggaagcgtgg cgctttctca    660
tagctcacgc tgtaggtatc tcagttcggt gtaggtcgtt cgctccaagc tgggctgtgt    720
gcacgaaccc cccgttcagc ccgaccgctg cgccttatcc ggtaactatc gtcttgagtc    780
caacccggta agacacgact tatcgccact ggcagcagcc actggtaaca ggattagcag    840
agcgaggtat gtaggcggtg ctacagagtt cttgaagtgg tggcctaact acggctacac    900
tagaagaaca gtatttggta tctgcgctct gctgaagcca gttaccttcg gaaaaagagt    960
tggtagctct tgatccggca aacaaaccac cgctggtagc ggtggttttt ttgtttgcaa   1020
gcagcagatt acgcgcagaa aaaaaggatc tcaagaagat cctttgatct tttctacggg   1080
gtctgacgct cagtggaacg aaaactcacg ttaagggatt ttggtcatga gattatcaaa   1140
aaggatcttc acctagatcc ttttaaatta aaaatgaagt tttaaatcaa tctaaagtat   1200
atatgagtaa acttggtctg acagttacca atgcttaatc agtgaggcac ctatctcagc   1260
gatctgtcta tttcgttcat ccatagttgc ctgactcccc gtcgtgtaga taactacgat   1320
acgggagggc ttaccatctg gccccagtgc tgcaatgata ccgcgagacc cacgctcacc   1380
ggctccagat ttatcagcaa taaaccagcc agccggaagg gccgagcgca gaagtggtcc   1440
tgcaacttta tccgcctcca tccagtctat taattgttgc cgggaagcta gagtaagtag   1500
ttcgccagtt aatagtttgc gcaacgttgt tgccattgct acaggcatcg tggtgtcacg   1560
ctcgtcgttt ggtatggctt cattcagctc cggttcccaa cgatcaaggc gagttacatg   1620
atcccccatg ttgtgcaaaa aagcggttag ctccttcggt cctccgatcg ttgtcagaag   1680
taagttggcc gcagtgttat cactcatggt tatggcagca ctgcataatt ctcttactgt   1740
catgccatcc gtaagatgct tttctgtgac tggtgagtac tcaaccaagt cattctgaga   1800
atagtgtatg cggcgaccga gttgctcttg cccggcgtca atacgggata ataccgcgcc   1860
acatagcaga actttaaaag tgctcatcat tggaaaacgt tcttcggggc gaaaactctc   1920
aaggatctta ccgctgttga gatccagttc gatgtaaccc actcgtgcac ccaactgatc   1980
ttcagcatct tttactttca ccagcgtttc tgggtgagca aaaacaggaa ggcaaaatgc   2040
cgcaaaaaag ggaataaggg cgacacggaa atgttgaata ctcatactct tcctttttca   2100
atattattga agcatttatc agggttattg tctcatgagc ggatacatat ttgaatgtat   2160
ttagaaaaat aaacaaatag gggttccgcg cacatttccc cgaaaagtgc cacctgacgt   2220
ctaagaaacc attattatca tgacattaac ctataaaaat aggcgtatca cgaggccctt   2280
tcgtctcgcg cgtttcggtg atgacggtga aaacctctga cacatgcagc tcccggagac   2340
ggtcacagct tgtctgtaag cggatgccgg gagcagacaa gcccgtcagg gcgcgtcagc   2400
gggtgttggc gggtgtcggg gctggcttaa ctatgcggca tcagagcaga ttgtactgag   2460
agtgcaccat atgcggtgtg aaataccgca cagatgcgta aggagaaaat accgcatcag   2520
```

-continued gcgccattcg ccattcaggc tgcgcaactg ttgggaaggg cgatcggtgc gggcctcttc 2580
gctattacgc cagctggcga aagggggatg tgctgcaagg cgattaagtt gggtaacgcc 2640
agggttttcc cagtcacgac gttgtaaaac gacggccagt gaattcgagc tcggtacctc 2700
gcgaatgcat ctagatccat ggctaccaag cagccctacc agttccctac tctgaccgag 2760
atcaagcgat ctcttccctc cgagtgcttt gaagcctcgg tccctctgtc cttgtactac 2820
accgtgcgaa tcgtcgctat tgccgttgct ctggccttcg gactcaacta cgctcgagcc 2880
cttcccgtgg tcgagtctct gtgggcactc gacgctgccc tttgttgcgg ttacgttctg 2940
ctccaaggca ttgtcttctg ggggattcttt accgtgggtc acgatgctgg acatggtgcc 3000
ttctctcgat accacctgct caactttgtc gttggcacct ttatccactc cctcattctt 3060
actcccttcg agtcgtggaa gctcacacat cgacaccatc acaagaacac cggaaacatc 3120
gaccgagacg aaatcttcta ccctcagcga aaggccgacg atcatcctct gtctcgaaac 3180
ctcgtcctgg ctctcggtgc cgcttggttt gcctaccttg tcgagggctt tcctccccga 3240
aaggtcaacc acttcaaccc cttcgaacct ctgtttgtgc gacaggtggc tgccgttgtc 3300
atttccctct ctgctcactt cgccgtcctg gcactgtccg tgtatctgag ctttcagttc 3360
ggtctcaaga caatggctct gtactactat ggacccgtct tcgtgttcgg ctccatgctc 3420
gtcattacta cctttctgca tcacaatgac gaggaaactc cttggtacgg agattccgac 3480
tggacctacg tcaagggcaa cttgtcttcc gtggaccgat cttacggtgc cttcatcgac 3540
aacctctcgc acaacattgg cacacaccag atccaccatc tgtttcccat cattcctcac 3600
tacaagctca accgagccac cgctgccttc caccaggcct ttcccgaact tgtccgaaag 3660
agcgacgagc ccattctcaa ggctttctgg agagttggtc gactttacgc caactacgga 3720
gtcgtggatc ccgacgcaaa gctgtttact ctcaaggagg ccaaagctgc ctccgaggct 3780
gccaccaaga ccaaggctac ttaagc 3806

<210> SEQ ID NO 86
<211> LENGTH: 1209
<212> TYPE: DNA
<213> ORGANISM: Fusarium monoliforme
<300> PUBLICATION INFORMATION:
<302> TITLE: DELTA-15 DESATURASES SUITABLE FOR ALTERING LEVELS OF
POLYUNSATURATED FATTY ACIDS IN OLEAGINOUS PLANTS AND YEAST
<310> PATENT DOCUMENT NUMBER: WO 2005/047480
<311> PATENT FILING DATE: 2004-11-10
<312> PUBLICATION DATE: 2005-05-26
<313> RELEVANT RESIDUES: (1)..(1209)

<400> SEQUENCE: 86
atggcgactc gacagcgaac tgccaccact gttgtggtcg aggaccttcc caaggtcact 60
cttgaggcca agtctgaacc tgtgttcccc gatatcaaga ccatcaagga tgccattccc 120
gcgcactgct tccagccctc gctcgtcacc tcattctact acgtcttccg cgattttgct 180
atggtctctg ccctcgtctg ggctgctctc acctacatcc ccagcatccc cgaccagacc 240
ctccgcgtcg cagcttggat ggtctacggc ttcgtccagg gtctgttctg caccggtgtc 300
tggattctcg gccatgagtg cggccacggt gctttctctc tccacggaaa ggtcaacaat 360
gtgaccggct ggttcctcca ctcgttcctc ctcgtcccct acttcagctg gaagtactct 420
caccaccgcc accaccgctt caccggccac atggatctcg acatggcttt cgtccccaag 480
actgagccca agccctccaa gtcgctcatg attgctggca ttgacgtcgc cgagcttgtt 540
gaggacaccc ccgctgctca gatggtcaag ctcatcttcc accagctttt cggatggcag 600

-continued

```
gcgtacctct tcttcaacgc tagctctggc aagggcagca agcagtggga gcccaagact    660

ggcctctcca agtggttccg agtcagtcac ttcgagccta ccagcgctgt cttccgcccc    720

aacgaggcca tcttcatcct catctccgat atcggtcttg ctctaatggg aactgctctg    780

tactttgctt ccaagcaagt tggtgtttcg accattctct tcctctacct tgttccctac    840

ctgtgggttc accactggct cgttgccatt acctacctcc accaccacca caccgagctc    900

cctcactaca ccgctgaggg ctggacctac gtcaagggag ctctcgccac tgtcgaccgt    960

gagtttggct tcatcggaaa gcacctcttc cacggtatca ttgagaagca cgttgttcac   1020

catctcttcc ctaagatccc cttctacaag gctgacgagg ccaccgaggc catcaagccc   1080

gtcattggcg accactactg ccacgacgac cgaagcttcc tgggccagct gtggaccatc   1140

ttcggcacgc tcaagtacgt cgagcacgac cctgcccgac ccggtgccat gcgatggaac   1200

aaggactag                                                           1209
```

```
<210> SEQ ID NO 87
<211> LENGTH: 402
<212> TYPE: PRT
<213> ORGANISM: Fusarium monoliforme
<300> PUBLICATION INFORMATION:
<302> TITLE: DELTA-15 DESATURASES SUITABLE FOR ALTERING LEVELS OF
      POLYUNSATURATED FATTY ACIDS IN OLEAGINOUS PLANTS AND YEAST
<310> PATENT DOCUMENT NUMBER: WO 2005/047480
<311> PATENT FILING DATE: 2004-11-10
<312> PUBLICATION DATE: 2005-05-26
<313> RELEVANT RESIDUES: (1)..(402)

<400> SEQUENCE: 87

Met Ala Thr Arg Gln Arg Thr Ala Thr Thr Val Val Val Glu Asp Leu
1               5                   10                  15

Pro Lys Val Thr Leu Glu Ala Lys Ser Glu Pro Val Phe Pro Asp Ile
            20                  25                  30

Lys Thr Ile Lys Asp Ala Ile Pro Ala His Cys Phe Gln Pro Ser Leu
        35                  40                  45

Val Thr Ser Phe Tyr Tyr Val Phe Arg Asp Phe Ala Met Val Ser Ala
    50                  55                  60

Leu Val Trp Ala Ala Leu Thr Tyr Ile Pro Ser Ile Pro Asp Gln Thr
65                  70                  75                  80

Leu Arg Val Ala Ala Trp Met Val Tyr Gly Phe Val Gln Gly Leu Phe
                85                  90                  95

Cys Thr Gly Val Trp Ile Leu Gly His Glu Cys Gly His Gly Ala Phe
            100                 105                 110

Ser Leu His Gly Lys Val Asn Asn Val Thr Gly Trp Phe Leu His Ser
        115                 120                 125

Phe Leu Leu Val Pro Tyr Phe Ser Trp Lys Tyr Ser His His Arg His
    130                 135                 140

His Arg Phe Thr Gly His Met Asp Leu Asp Met Ala Phe Val Pro Lys
145                 150                 155                 160

Thr Glu Pro Lys Pro Ser Lys Ser Leu Met Ile Ala Gly Ile Asp Val
                165                 170                 175

Ala Glu Leu Val Glu Asp Thr Pro Ala Ala Gln Met Val Lys Leu Ile
            180                 185                 190

Phe His Gln Leu Phe Gly Trp Gln Ala Tyr Leu Phe Phe Asn Ala Ser
        195                 200                 205

Ser Gly Lys Gly Ser Lys Gln Trp Glu Pro Lys Thr Gly Leu Ser Lys
    210                 215                 220
```

-continued

```
Trp Phe Arg Val Ser His Phe Glu Pro Thr Ser Ala Val Phe Arg Pro
225                 230                 235                 240

Asn Glu Ala Ile Phe Ile Leu Ile Ser Asp Ile Gly Leu Ala Leu Met
                245                 250                 255

Gly Thr Ala Leu Tyr Phe Ala Ser Lys Gln Val Gly Val Ser Thr Ile
            260                 265                 270

Leu Phe Leu Tyr Leu Val Pro Tyr Leu Trp Val His His Trp Leu Val
        275                 280                 285

Ala Ile Thr Tyr Leu His His His His Thr Glu Leu Pro His Tyr Thr
    290                 295                 300

Ala Glu Gly Trp Thr Tyr Val Lys Gly Ala Leu Ala Thr Val Asp Arg
305                 310                 315                 320

Glu Phe Gly Phe Ile Gly Lys His Leu Phe His Gly Ile Ile Glu Lys
                325                 330                 335

His Val Val His His Leu Phe Pro Lys Ile Pro Phe Tyr Lys Ala Asp
            340                 345                 350

Glu Ala Thr Glu Ala Ile Lys Pro Val Ile Gly Asp His Tyr Cys His
        355                 360                 365

Asp Asp Arg Ser Phe Leu Gly Gln Leu Trp Thr Ile Phe Gly Thr Leu
    370                 375                 380

Lys Tyr Val Glu His Asp Pro Ala Arg Pro Gly Ala Met Arg Trp Asn
385                 390                 395                 400

Lys Asp


<210> SEQ ID NO 88
<211> LENGTH: 7668
<212> TYPE: DNA
<213> ORGANISM: Artificial Sequence
<220> FEATURE:
<223> OTHER INFORMATION: Plasmid pY6.GPD.Leu2

<400> SEQUENCE: 88

gtacgagccg gaagcataaa gtgtaaagcc tggggtgcct aatgagtgag ctaactcaca     60

ttaattgcgt tgcgctcact gcccgctttc cagtcgggaa acctgtcgtg ccagctgcat    120

taatgaatcg gccaacgcgc ggggagaggc ggtttgcgta ttgggcgctc ttccgcttcc    180

tcgctcactg actcgctgcg ctcggtcgtt cggctgcggc gagcggtatc agctcactca    240

aaggcggtaa tacggttatc cacagaatca ggggataacg caggaaagaa catgtgagca    300

aaaggccagc aaaaggccag gaaccgtaaa aaggccgcgt tgctggcgtt tttccatagg    360

ctccgccccc ctgacgagca tcacaaaaat cgacgctcaa gtcagaggtg gcgaaacccg    420

acaggactat aaagatacca ggcgtttccc cctggaagct ccctcgtgcg ctctcctgtt    480

ccgaccctgc cgcttaccgg atacctgtcc gcctttctcc cttcgggaag cgtggcgctt    540

tctcatagct cacgctgtag gtatctcagt tcggtgtagg tcgttcgctc caagctgggc    600

tgtgtgcacg aaccccccgt tcagcccgac cgctgcgcct tatccggtaa ctatcgtctt    660

gagtccaacc cggtaagaca cgacttatcg ccactggcag cagccactgg taacaggatt    720

agcagagcga ggtatgtagg cggtgctaca gagttcttga agtggtggcc taactacggc    780

tacactagaa ggacagtatt tggtatctgc gctctgctga agccagttac cttcggaaaa    840

agagttggta gctcttgatc cggcaaacaa accaccgctg gtagcggtgg tttttttgtt    900

tgcaagcagc agattacgcg cagaaaaaaa ggatctcaag aagatccttt gatcttttct    960

acggggtctg acgctcagtg gaacgaaaac tcacgttaag ggattttggt catgagatta   1020
```

-continued

```
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
```

-continued

```
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttgc ttaaattcaa tccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca accgatttcg   4200
acagtaatta attaatttga atcgaatcgg agcctaaaat gaacccgagt atatctcata   4260
aaattctcgg tgagaggtct gtgactgtca gtacaaggtg ccttcattat gccctcaacc   4320
ttaccatacc tcactgaatg tagtgtacct ctaaaaatga aatacagtgc caaaagccaa   4380
ggcactgagc tcgtctaacg gacttgatat acaaccaatt aaaacaaatg aaaagaaata   4440
cagttctttg tatcatttgt aacaattacc ctgtacaaac taaggtattg aaatcccaca   4500
atattcccaa agtccacccc tttccaaatt gtcatgccta caactcatat accaagcact   4560
aacctaccaa acaccactaa aaccccacaa aatatatctt accgaatata cagtaacaag   4620
ctaccaccac actcgttggg tgcagtcgcc agcttaaaga tatctatcca catcagccac   4680
aactcccttc ctttaataaa ccgactacac ccttggctat tgaggttatg agtgaatata   4740
ctgtagacaa gacactttca agaagactgt ttccaaaacg taccactgtc ctccactaca   4800
aacacaccca atctgcttct tctagtcaag gttgctacac cggtaaatta taaatcatca   4860
tttcattagc agggcagggc cctttttata gagtcttata cactagcgga ccctgccggt   4920
agaccaaccc gcaggcgcgt cagtttgctc cttccatcaa tgcgtcgtag aaacgactta   4980
ctccttcttg agcagctcct tgaccttgtt ggcaacaagt ctccgacctc ggaggtggag   5040
gaagagcctc cgatatcggc ggtagtgata ccagcctcga cggactcctt gacggcagcc   5100
tcaacagcgt caccggcggg cttcatgtta agagagaact tgagcatcat ggcggcagac   5160
agaatggtgg caatggggtt gaccttctgc ttgccgagat cgggggcaga tccgtgacag   5220
ggctcgtaca gaccgaacgc ctcgttggtg tcgggcagag aagccagaga ggcggagggc   5280
agcagaccca gagaaccggg gatgacggag gcctcgtcgg agatgatatc gccaaacatg   5340
ttggtggtga tgatgatacc attcatcttg gagggctgct tgatgaggat catggcggcc   5400
gagtcgatca gctggtggtt gagctcgagc tgggggaatt cgtccttgag gactcgagtg   5460
acagtctttc gccaaagtcg agaggaggcc agcacgttgg ccttgtcaag agaccacacg   5520
ggaagagggg ggttgtgctg aagggccagg aaggcggcca ttcgggcaat tcgctcaacc   5580
tcaggaacgg agtaggtctc ggtgtcggaa gcgacgccag atccgtcatc ctcctttcgc   5640
tctccaaagt agatacctcc gacgagctct cggacaatga tgaagtcggt gccctcaacg   5700
tttcggatgg gggagagatc ggcgagcttg ggcgacagca gctggcaggg tcgcaggttg   5760
```

-continued

```
gcgtacaggt tcaggtcctt tcgcagcttg aggagaccct gctcgggtcg cacgtcggtt   5820

cgtccgtcgg gagtggtcca tacggtgttg gcagcgcctc cgacagcacc gagcataata   5880

gagtcagcct ttcggcagat gtcgagagta gcgtcggtga tgggctcgcc ctccttctca   5940

atggcagctc ctccaatgag tcggtcctca aacacaaact cggtgccgga ggcctcagca   6000

acagacttga gcaccttgac ggcctcggca atcacctcgg ggccacagaa gtcgccgccg   6060

agaagaacaa tcttcttgga gtcagtcttg gtcttcttag tttcgggttc cattgtggat   6120

gtgtgtggtt gtatgtgtga tgtggtgtgt ggagtgaaaa tctgtggctg gcaaacgctc   6180

ttgtatatat acgcactttt gcccgtgcta tgtggaagac taaacctccg aagattgtga   6240

ctcaggtagt gcggtatcgg ctagggaccc aaaccttgtc gatgccgata gcgctatcga   6300

acgtacccca gccggccggg agtatgtcgg aggggacata cgagatcgtc aagggtttgt   6360

ggccaactgg taaataaatg atgtcgacgc agtaggatgt cctgcacggg tctttttgtg   6420

gggtgtggag aaaggggtgc ttggagatgg aagccggtag aaccgggctg cttgtgcttg   6480

gagatggaag ccggtagaac cgggctgctt ggggggattt ggggccgctg ggctccaaag   6540

aggggtaggc atttcgttgg ggttacgtaa ttgcggcatt tgggtcctgc gcgcatgtcc   6600

cattggtcag aattagtccg gataggagac ttatcagcca atcacagcgc cggatccacc   6660

tgtaggttgg gttgggtggg agcacccctc cacagagtag agtcaaacag cagcagcaac   6720

atgatagttg gggtgtgcg tgttaaagga aaaaaaagaa gcttgggtta tattcccgct   6780

ctatttagag gttgcgggat agacgccgac ggagggcaat ggcgctatgg aaccttgcgg   6840

atatccatac gccgcggcgg actgcgtccg aaccagctcc agcagcgttt tttccgggcc   6900

attgagccga ctgcgacccc gccaacgtgt cttggcccac gcactcatgt catgttggtg   6960

ttgggaggcc actttttaag tagcacaagg cacctagctc gcagcaaggt gtccgaacca   7020

aagaagcggc tgcagtggtg caaacggggc ggaaacggcg ggaaaaagcc acgggggcac   7080

gaattgaggc acgccctcga atttgagacg agtcacggcc ccattcgccc gcgcaatggc   7140

tcgccaacgc ccggtctttt gcaccacatc aggttacccc aagccaaacc tttgtgttaa   7200

aaagcttaac atattatacc gaacgtaggt ttgggcgggc ttgctccgtc tgtccaaggc   7260

aacatttata taagggtctg catcgccggc tcaattgaat ctttttcttt cttctcttct   7320

ctatattcat tcttgaatta aacacacatc aaccatggat ccactagttc tagagcggcc   7380

gccaccgcgg cccgagattc cggcctcttc ggccgccaag cgacccgggt ggacgtctag   7440

aggtacctag caattaacag atagtttgcc ggtgataatt ctcttaacct cccacactcc   7500

tttgacataa cgatttatgt aacgaaactg aaatttgacc agatattgtg tccgcggtgg   7560

agctccagct tttgttccct ttagtgaggg ttaatttcga gcttggcgta atcatggtca   7620

tagctgtttc ctgtgtgaaa ttgttatccg ctcacaattc cacacaac               7668
```

```
<210> SEQ ID NO 89
<211> LENGTH: 9048
<212> TYPE: DNA
<213> ORGANISM: Artificial Sequence
<220> FEATURE:
<223> OTHER INFORMATION: Plasmid pY130

<400> SEQUENCE: 89
```

```
gtacgagccg gaagcataaa gtgtaaagcc tggggtgcct aatgagtgag ctaactcaca     60

ttaattgcgt tgcgctcact gcccgctttc cagtcgggaa acctgtcgtg ccagctgcat    120
```

-continued

```
taatgaatcg gccaacgcgc ggggagaggc ggtttgcgta ttgggcgctc ttccgcttcc    180
tcgctcactg actcgctgcg ctcggtcgtt cggctgcggc gagcggtatc agctcactca    240
aaggcggtaa tacggttatc cacagaatca ggggataacg caggaaagaa catgtgagca    300
aaaggccagc aaaaggccag gaaccgtaaa aaggccgcgt tgctggcgtt tttccatagg    360
ctccgccccc ctgacgagca tcacaaaaat cgacgctcaa gtcagaggtg gcgaaacccg    420
acaggactat aaagatacca ggcgtttccc cctggaagct ccctcgtgcg ctctcctgtt    480
ccgaccctgc cgcttaccgg atacctgtcc gcctttctcc cttcgggaag cgtggcgctt    540
tctcatagct cacgctgtag gtatctcagt tcggtgtagg tcgttcgctc caagctgggc    600
tgtgtgcacg aaccccccgt tcagcccgac cgctgcgcct tatccggtaa ctatcgtctt    660
gagtccaacc cggtaagaca cgacttatcg ccactggcag cagccactgg taacaggatt    720
agcagagcga ggtatgtagg cggtgctaca gagttcttga agtggtggcc taactacggc    780
tacactagaa ggacagtatt tggtatctgc gctctgctga agccagttac cttcggaaaa    840
agagttggta gctcttgatc cggcaaacaa accaccgctg gtagcggtgg tttttttgtt    900
tgcaagcagc agattacgcg cagaaaaaaa ggatctcaag aagatccttt gatcttttct    960
acggggtctg acgctcagtg gaacgaaaac tcacgttaag ggattttggt catgagatta   1020
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
```

-continued

```
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttgc ttaaattcaa tcccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca accgatttcg   4200
acagtaataa tttgaatcga atcggagcct aaaatgaacc cgagtatatc tcataaaatt   4260
ctcggtgaga ggtctgtgac tgtcagtaca aggtgccttc attatgccct caaccttacc   4320
atacctcact gaatgtagtg tacctctaaa aatgaaatac agtgccaaaa gccaaggcac   4380
tgagctcgtc taacggactt gatatacaac caattaaaac aaatgaaaag aaatacagtt   4440
ctttgtatca tttgtaacaa ttaccctgta caaactaagg tattgaaatc ccacaatatt   4500
cccaaagtcc accccttcc aaattgtcat gcctacaact catataccaa gcactaacct   4560
accaaacacc actaaaaccc cacaaaatat atcttaccga atatacagta acaagctacc   4620
accacactcg ttgggtgcag tcgccagctt aaagatatct atccacatca gccacaactc   4680
ccttccttta ataaaccgac tacacccttg gctattgagg ttatgagtga atatactgta   4740
gacaagacac tttcaagaag actgtttcca aaacgtacca ctgtcctcca ctacaaacac   4800
acccaatctg cttcttctag tcaaggttgc tacaccggta aattataaat catcatttca   4860
```

-continued

```
ttagcagggc agggcccttt ttatagagtc ttatacacta gcggaccctg ccggtagacc   4920
aacccgcagg cgcgtcagtt tgctccttcc atcaatgcgt cgtagaaacg acttactcct   4980
tcttgagcag ctccttgacc ttgttggcaa caagtctccg acctcggagg tggaggaaga   5040
gcctccgata tcggcggtag tgataccagc ctcgacggac tccttgacgg cagcctcaac   5100
agcgtcaccg gcgggcttca tgttaagaga gaacttgagc atcatggcgg cagacagaat   5160
ggtggcaatg gggttgacct tctgcttgcc gagatcgggg gcagatccgt gacagggctc   5220
gtacagaccg aacgcctcgt tggtgtcggg cagagaagcc agagaggcgg agggcagcag   5280
acccagagaa ccggggatga cggaggcctc gtcggagatg atatcgccaa acatgttggt   5340
ggtgatgatg ataccattca tcttggaggg ctgcttgatg aggatcatgg cggccgagtc   5400
gatcagctgg tggttgagct cgagctgggg gaattcgtcc ttgaggactc gagtgacagt   5460
ctttcgccaa agtcgagagg aggccagcac gttggccttg tcaagagacc acacgggaag   5520
agggggg ttg tgctgaaggg ccaggaaggc ggccattcgg gcaattcgct caacctcagg   5580
aacggagtag gtctcggtgt cggaagcgac gccagatccg tcatcctcct ttcgctctcc   5640
aaagtagata cctccgacga gctctcggac aatgatgaag tcggtgccct caacgtttcg   5700
gatgggggag agatcggcga gcttgggcga cagcagctgg cagggtcgca ggttggcgta   5760
caggttcagg tcctttcgca gcttgaggag accctgctcg ggtcgcacgt cggttcgtcc   5820
gtcgggagtg gtccatacgg tgttggcagc gcctccgaca gcaccgagca taatagagtc   5880
agcctttcgg cagatgtcga gagtagcgtc ggtgatgggc tcgccctcct tctcaatggc   5940
agctcctcca atgagtcggt cctcaaacac aaactcggtg ccggaggcct cagcaacaga   6000
cttgagcacc ttgacggcct cggcaatcac ctcggggcca cagaagtcgc cgccgagaag   6060
aacaatcttc ttggagtcag tcttggtctt cttagtttcg ggttccattg tggatgtgtg   6120
tggttgtatg tgtgatgtgg tgtgtggagt gaaaatctgt ggctggcaaa cgctcttgta   6180
tatatacgca cttttgcccg tgctatgtgg aagactaaac ctccgaagat tgtgactcag   6240
gtagtgcggt atcggctagg gacccaaacc ttgtcgatgc cgatagcgct atcgaacgta   6300
ccccagccgg ccgggagtat gtcggagggg acatacgaga tcgtcaaggg tttgtggcca   6360
actggtattt aaatgatgtc gacgcagtag gatgtcctgc acgggtcttt ttgtggggtg   6420
tggagaaagg ggtgcttgga gatggaagcc ggtagaaccg ggctgcttgt gcttggagat   6480
ggaagccggt agaaccgggc tgcttggggg gatttggggc cgctgggctc caaagagggg   6540
taggcatttc gttggggtta cgtaattgcg gcatttgggt cctgcgcgca tgtcccattg   6600
gtcagaatta gtccggatag gagacttatc agccaatcac agcgccggat ccacctgtag   6660
gttgggttgg gtgggagcac ccctccacag agtagagtca aacagcagca gcaacatgat   6720
agttgggggt gtgcgtgtta aaggaaaaaa aagaagcttg ggttatattc ccgctctatt   6780
tagaggttgc gggatagacg ccgacggagg gcaatggcgc tatggaacct tgcggatatc   6840
catacgccgc ggcggactgc gtccgaacca gctccagcag cgttttttcc gggccattga   6900
gccgactgcg accccgccaa cgtgtcttgg cccacgcact catgtcatgt tggtgttggg   6960
aggccacttt ttaagtagca caaggcacct agctcgcagc aaggtgtccg aaccaaagaa   7020
gcggctgcag tggtgcaaac ggggcggaaa cggcgggaaa aagccacggg ggcacgaatt   7080
gaggcacgcc ctcgaatttg agacgagtca cggccccatt cgcccgcgca atggctcgcc   7140
aacgcccggt cttttgcacc acatcaggtt accccaagcc aaacctttgt gttaaaaagc   7200
ttaacatatt ataccgaacg taggtttggg cgggcttgct ccgtctgtcc aaggcaacat   7260
```

-continued

```
ttatataagg gtctgcatcg ccggctcaat tgaatctttt ttcttcttct cttctctata   7320

ttcattcttg aattaaacac acatcaacca tggcgactcg acagcgaact gccaccactg   7380

ttgtggtcga ggaccttccc aaggtcactc ttgaggccaa gtctgaacct gtgttccccg   7440

atatcaagac catcaaggat gccattcccg cgcactgctt ccagccctcg ctcgtcacct   7500

cattctacta cgtcttccgc gattttgcta tggtctctgc cctcgtctgg gctgctctca   7560

cctacatccc cagcatcccc gaccagaccc tccgcgtcgc agcttggatg gtctacggct   7620

tcgtccaggg tctgttctgc accggtgtct ggattctcgg ccatgagtgc ggccacggtg   7680

ctttctctct ccacggaaag gtcaacaatg tgaccggctg gttcctccac tcgttcctcc   7740

tcgtccccta cttcagctgg aagtactctc accaccgcca ccaccgcttc accggccaca   7800

tggatctcga catggctttc gtccccaaga ctgagcccaa gccctccaag tcgctcatga   7860

ttgctggcat tgacgtcgcc gagcttgttg aggacacccc cgctgctcag atggtcaagc   7920

tcatcttcca ccagcttttc ggatggcagg cgtacctctt cttcaacgct agctctggca   7980

agggcagcaa gcagtgggag cccaagactg gcctctccaa gtggttccga gtcagtcact   8040

tcgagcctac cagcgctgtc ttccgcccca acgaggccat cttcatcctc atctccgata   8100

tcggtcttgc tctaatggga actgctctgt actttgcttc caagcaagtt ggtgtttcga   8160

ccattctctt cctctacctt gttccctacc tgtgggttca ccactggctc gttgccatta   8220

cctacctcca ccaccaccac accgagctcc ctcactacac cgctgagggc tggacctacg   8280

tcaagggagc tctcgccact gtcgaccgtg agtttggctt catcggaaag cacctcttcc   8340

acggtatcat tgagaagcac gttgttcacc atctcttccc taagatcccc ttctacaagg   8400

ctgacgaggc caccgaggcc atcaagcccg tcattggcga ccactactgc cacgacgacc   8460

gaagcttcct gggccagctg tggaccatct tcggcacgct caagtacgtc gagcacgacc   8520

ctgcccgacc cggtgccatg cgatggaaca aggactaggc ggccgcatga gaagataaat   8580

atataaatac attgagatat taaatgcgct agattagaga gcctcatact gctcggagag   8640

aagccaagac gagtactcaa aggggattac accatccata tccacagaca caagctgggg   8700

aaaggttcta tatacacttt ccggaatacc gtagtttccg atgttatcaa tgggggcagc   8760

caggatttca ggcacttcgg tgtctcgggg tgaaatggcg ttcttggcct ccatcaagtc   8820

gtaccatgtc ttcatttgcc tgtcaaagta aaacagaagc agatgaagaa tgaacttgaa   8880

gtgaaggaat ttaaatgtaa cgaaactgaa atttgaccag atattgtgtc cgcggtggag   8940

ctccagcttt tgttcccttt agtgagggtt aatttcgagc ttggcgtaat catggtcata   9000

gctgtttcct gtgtgaaatt gttatccgct cacaagcttc cacacaac               9048
```

<210> SEQ ID NO 90
<211> LENGTH: 8925
<212> TYPE: DNA
<213> ORGANISM: Artificial Sequence
<220> FEATURE:
<223> OTHER INFORMATION: Plasmid p138

<400> SEQUENCE: 90

```
gtacgagccg gaagcataaa gtgtaaagcc tggggtgcct aatgagtgag ctaactcaca     60

ttaattgcgt tgcgctcact gcccgctttc cagtcgggaa acctgtcgtg ccagctgcat    120

taatgaatcg gccaacgcgc ggggagaggc ggtttgcgta ttgggcgctc ttccgcttcc    180

tcgctcactg actcgctgcg ctcggtcgtt cggctgcggc gagcggtatc agctcactca    240
```

-continued

```
aaggcggtaa tacggttatc cacagaatca ggggataacg caggaaagaa catgtgagca    300
aaaggccagc aaaaggccag gaaccgtaaa aaggccgcgt tgctggcgtt tttccatagg    360
ctccgccccc ctgacgagca tcacaaaaat cgacgctcaa gtcagaggtg gcgaaacccg    420
acaggactat aaagatacca ggcgtttccc cctggaagct ccctcgtgcg ctctcctgtt    480
ccgaccctgc cgcttaccgg atacctgtcc gcctttctcc cttcgggaag cgtggcgctt    540
tctcatagct cacgctgtag gtatctcagt tcggtgtagg tcgttcgctc caagctgggc    600
tgtgtgcacg aaccccccgt tcagcccgac cgctgcgcct tatccggtaa ctatcgtctt    660
gagtccaacc cggtaagaca cgacttatcg ccactggcag cagccactgg taacaggatt    720
agcagagcga ggtatgtagg cggtgctaca gagttcttga agtggtggcc taactacggc    780
tacactagaa ggacagtatt tggtatctgc gctctgctga agccagttac cttcggaaaa    840
agagttggta gctcttgatc cggcaaacaa accaccgctg gtagcggtgg tttttttgtt    900
tgcaagcagc agattacgcg cagaaaaaaa ggatctcaag aagatccttt gatcttttct    960
acggggtctg acgctcagtg gaacgaaaac tcacgttaag ggattttggt catgagatta   1020
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
```

-continued

```
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttgc ttaaattcaa tccccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgtttttt ttgtttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca accgatttcg   4200
acagtaataa tttgaatcga atcggagcct aaaatgaacc cgagtatatc tcataaaatt   4260
ctcggtgaga ggtctgtgac tgtcagtaca aggtgccttc attatgccct caaccttacc   4320
atacctcact gaatgtagtg tacctctaaa aatgaaatac agtgccaaaa gccaaggcac   4380
tgagctcgtc taacggactt gatatacaac caattaaaac aaatgaaaag aaatacagtt   4440
ctttgtatca tttgtaacaa ttaccctgta caaactaagg tattgaaatc ccacaatatt   4500
cccaaagtcc acccctttcc aaattgtcat gcctacaact catataccaa gcactaacct   4560
accaaacacc actaaaaccc cacaaaatat atcttaccga atatacagta acaagctacc   4620
accacactcg ttgggtgcag tcgccagctt aaagatatct atccacatca gccacaactc   4680
ccttccttta ataaaccgac tacacccttg gctattgagg ttatgagtga atatactgta   4740
gacaagacac tttcaagaag actgtttcca aaacgtacca ctgtcctcca ctacaaacac   4800
acccaatctg cttcttctag tcaaggttgc tacaccggta aattataaat catcatttca   4860
ttagcagggc agggcccttt ttatagagtc ttatacacta gcggaccctg ccggtagacc   4920
aacccgcagg cgcgtcagtt tgctccttcc atcaatgcgt cgtagaaacg acttactcct   4980
```

-continued

```
tcttgagcag ctccttgacc ttgttggcaa caagtctccg acctcggagg tggaggaaga   5040
gcctccgata tcggcggtag tgataccagc ctcgacggac tccttgacgg cagcctcaac   5100
agcgtcaccg gcgggcttca tgttaagaga gaacttgagc atcatggcgg cagacagaat   5160
ggtggcaatg gggttgacct tctgcttgcc gagatcgggg gcagatccgt gacagggctc   5220
gtacagaccg aacgcctcgt tggtgtcggg cagagaagcc agagaggcgg agggcagcag   5280
acccagagaa ccggggatga cggaggcctc gtcggagatg atatcgccaa acatgttggt   5340
ggtgatgatg ataccattca tcttggaggg ctgcttgatg aggatcatgg cggccgagtc   5400
gatcagctgg tggttgagct cgagctgggg gaattcgtcc ttgaggactc gagtgacagt   5460
ctttcgccaa agtcgagagg aggccagcac gttggccttg tcaagagacc acacgggaag   5520
agggggggttg tgctgaaggg ccaggaaggc ggccattcgg gcaattcgct caacctcagg   5580
aacggagtag gtctcggtgt cggaagcgac gccagatccg tcatcctcct ttcgctctcc   5640
aaagtagata cctccgacga gctctcggac aatgatgaag tcggtgccct caacgtttcg   5700
gatgggggag agatcggcga gcttgggcga cagcagctgg cagggtcgca ggttggcgta   5760
caggttcagg tcctttcgca gcttgaggag accctgctcg ggtcgcacgt cggttcgtcc   5820
gtcgggagtg gtccatacgg tgttggcagc gcctccgaca gcaccgagca taatagagtc   5880
agcctttcgg cagatgtcga gagtagcgtc ggtgatgggc tcgccctcct tctcaatggc   5940
agctcctcca atgagtcggt cctcaaacac aaactcggtg ccggaggcct cagcaacaga   6000
cttgagcacc ttgacggcct cggcaatcac ctcggggcca cagaagtcgc cgccgagaag   6060
aacaatcttc ttggagtcag tcttggtctt cttagtttcg ggttccattg tggatgtgtg   6120
tggttgtatg tgtgatgtgg tgtgtggagt gaaaatctgt ggctggcaaa cgctcttgta   6180
tatatacgca cttttgcccg tgctatgtgg aagactaaac ctccgaagat tgtgactcag   6240
gtagtgcggt atcggctagg gacccaaacc ttgtcgatgc cgatagcgct atcgaacgta   6300
ccccagccgg ccgggagtat gtcggagggg acatacgaga tcgtcaaggg tttgtggcca   6360
actggtattt aaatgatgtc gacgcagtag gatgtcctgc acgggtcttt ttgtggggtg   6420
tggagaaagg ggtgcttgga gatggaagcc ggtagaaccg ggctgcttgt gcttggagat   6480
ggaagccggt agaaccgggc tgcttggggg gatttggggc cgctgggctc caaagagggg   6540
taggcatttc gttggggtta cgtaattgcg gcatttgggt cctgcgcgca tgtcccattg   6600
gtcagaatta gtccggatag gagacttatc agccaatcac agcgccggat ccacctgtag   6660
gttgggttgg gtgggagcac ccctccacag agtagagtca aacagcagca gcaacatgat   6720
agttgggggt gtgcgtgtta aaggaaaaaa aagaagcttg ggttatattc ccgctctatt   6780
tagaggttgc gggatagacg ccgacggagg gcaatggcgc tatggaacct tgcggatatc   6840
catacgccgc ggcggactgc gtccgaacca gctccagcag cgttttttcc gggccattga   6900
gccgactgcg accccgccaa cgtgtcttgg cccacgcact catgtcatgt tggtgttggg   6960
aggccacttt ttaagtagca caaggcacct agctcgcagc aaggtgtccg aaccaaagaa   7020
gcggctgcag tggtgcaaac ggggcggaaa cggcgggaaa aagccacggg ggcacgaatt   7080
gaggcacgcc ctcgaatttg agacgagtca cggccccatt cgcccgcgca atggctcgcc   7140
aacgcccggt cttttgcacc acatcaggtt accccaagcc aaacctttgt gttaaaaagc   7200
ttaacatatt ataccgaacg taggtttggg cgggcttgct ccgtctgtcc aaggcaacat   7260
ttatataagg gtctgcatcg ccggctcaat tgaatctttt ttcttcttct cttctctata   7320
ttcattcttg aattaaacac acatcaacca tggctaccaa gcagccctac cagttcccta   7380
```

-continued

```
ctctgaccga gatcaagcga tctcttccct ccgagtgctt tgaagcctcg gtccctctgt   7440

ccttgtacta caccgtgcga atcgtcgcta ttgccgttgc tctggccttc ggactcaact   7500

acgctcgagc ccttcccgtg gtcgagtctc tgtgggcact cgacgctgcc ctttgttgcg   7560

gttacgttct gctccaaggc attgtcttct ggggattctt taccgtgggt cacgatgctg   7620

gacatggtgc cttctctcga taccacctgc tcaactttgt cgttggcacc tttatccact   7680

ccctcattct tactcccttc gagtcgtgga agctcacaca tcgacaccat cacaagaaca   7740

ccggaaacat cgaccgagac gaaatcttct accctcagcg aaaggccgac gatcatcctc   7800

tgtctcgaaa cctcgtcctg gctctcggtg ccgcttggtt tgcctacctt gtcgagggct   7860

ttcctccccg aaaggtcaac cacttcaacc ccttcgaacc tctgtttgtg cgacaggtgg   7920

ctgccgttgt catttccctc tctgctcact tcgccgtcct ggcactgtcc gtgtatctga   7980

gctttcagtt cggtctcaag acaatggctc tgtactacta tggacccgtc ttcgtgttcg   8040

gctccatgct cgtcattact acctttctgc atcacaatga cgaggaaact ccttggtacg   8100

gagattccga ctggacctac gtcaagggca acttgtcttc cgtggaccga tcttacggtg   8160

ccttcatcga caacctctcg cacaacattg gcacacacca gatccaccat ctgtttccca   8220

tcattcctca ctacaagctc aaccgagcca ccgctgcctt ccaccaggcc tttcccgaac   8280

ttgtccgaaa gagcgacgag cccattctca aggctttctg gagagttggt cgactttacg   8340

ccaactacgg agtcgtggat cccgacgcaa agctgtttac tctcaaggag gccaaagctg   8400

cctccgaggc tgccaccaag accaaggcta cttaagcggc cgcatgagaa gataaatata   8460

taaatacatt gagatattaa atgcgctaga ttagagagcc tcatactgct cggagagaag   8520

ccaagacgag tactcaaagg ggattacacc atccatatcc acagacacaa gctggggaaa   8580

ggttctatat acactttccg gaataccgta gtttccgatg ttatcaatgg gggcagccag   8640

gatttcaggc acttcggtgt ctcggggtga aatggcgttc ttggcctcca tcaagtcgta   8700

ccatgtcttc atttgcctgt caaagtaaaa cagaagcaga tgaagaatga acttgaagtg   8760

aaggaattta aatgtaacga aactgaaatt tgaccagata ttgtgtccgc ggtggagctc   8820

cagcttttgt tccctttagt gagggttaat ttcgagcttg gcgtaatcat ggtcatagct   8880

gtttcctgtg tgaaattgtt atccgctcac aagcttccac acaac                    8925
```

<210> SEQ ID NO 91
<211> LENGTH: 8925
<212> TYPE: DNA
<213> ORGANISM: Artificial Sequence
<220> FEATURE:
<223> OTHER INFORMATION: Plasmid p139

<400> SEQUENCE: 91

```
gtacgagccg gaagcataaa gtgtaaagcc tggggtgcct aatgagtgag ctaactcaca     60

ttaattgcgt tgcgctcact gcccgctttc cagtcgggaa acctgtcgtg ccagctgcat    120

taatgaatcg gccaacgcgc ggggagaggc ggtttgcgta ttgggcgctc ttccgcttcc    180

tcgctcactg actcgctgcg ctcggtcgtt cggctgcggc gagcggtatc agctcactca    240

aaggcggtaa tacggttatc cacagaatca ggggataacg caggaaagaa catgtgagca    300

aaaggccagc aaaaggccag gaaccgtaaa aaggccgcgt tgctggcgtt tttccatagg    360

ctccgccccc ctgacgagca tcacaaaaat cgacgctcaa gtcagaggtg gcgaaacccg    420

acaggactat aaagatacca ggcgtttccc cctggaagct ccctcgtgcg ctctcctgtt    480
```

-continued

```
ccgaccctgc cgcttaccgg atacctgtcc gcctttctcc cttcgggaag cgtggcgctt    540
tctcatagct cacgctgtag gtatctcagt tcggtgtagg tcgttcgctc caagctgggc    600
tgtgtgcacg aaccccccgt tcagcccgac cgctgcgcct tatccggtaa ctatcgtctt    660
gagtccaacc cggtaagaca cgacttatcg ccactggcag cagccactgg taacaggatt    720
agcagagcga ggtatgtagg cggtgctaca gagttcttga agtggtggcc taactacggc    780
tacactagaa ggacagtatt tggtatctgc gctctgctga agccagttac cttcggaaaa    840
agagttggta gctcttgatc cggcaaacaa accaccgctg gtagcggtgg tttttttgtt    900
tgcaagcagc agattacgcg cagaaaaaaa ggatctcaag aagatccttt gatcttttct    960
acggggtctg acgctcagtg gaacgaaaac tcacgttaag ggattttggt catgagatta   1020
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
```

-continued

```
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttgc ttaaattcaa tccccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca accgatttcg   4200
acagtaataa tttgaatcga atcggagcct aaaatgaacc cgagtatatc tcataaaatt   4260
ctcggtgaga ggtctgtgac tgtcagtaca aggtgccttc attatgccct caaccttacc   4320
atacctcact gaatgtagtg tacctctaaa aatgaaatac agtgccaaaa gccaaggcac   4380
tgagctcgtc taacggactt gatatacaac caattaaaac aaatgaaaag aaatacagtt   4440
ctttgtatca tttgtaacaa ttaccctgta caaactaagg tattgaaatc ccacaatatt   4500
cccaaagtcc accccttcc aaattgtcat gcctacaact catataccaa gcactaacct   4560
accaaacacc actaaaaccc cacaaaatat atcttaccga atatacagta acaagctacc   4620
accacactcg ttgggtgcag tcgccagctt aaagatatct atccacatca gccacaactc   4680
ccttccttta ataaaccgac tacacccttg gctattgagg ttatgagtga atatactgta   4740
gacaagacac tttcaagaag actgtttcca aaacgtacca ctgtcctcca ctacaaacac   4800
acccaatctg cttcttctag tcaaggttgc tacaccggta aattataaat catcatttca   4860
ttagcagggc agggcccttt ttatagagtc ttatacacta gcggaccctg ccggtagacc   4920
aacccgcagg cgcgtcagtt tgctccttcc atcaatgcgt cgtagaaacg acttactcct   4980
tcttgagcag ctccttgacc ttgttggcaa caagtctccg acctcggagg tggaggaaga   5040
gcctccgata tcggcggtag tgataccagc ctcgacggac tccttgacgg cagcctcaac   5100
agcgtcaccg gcgggcttca tgttaagaga gaacttgagc atcatggcgg cagacagaat   5160
ggtggcaatg ggttgacct tctgcttgcc gagatcgggg gcagatccgt gacagggctc   5220
```

-continued

```
gtacagaccg aacgcctcgt tggtgtcggg cagagaagcc agagaggcgg agggcagcag   5280
acccagagaa ccggggatga cggaggcctc gtcggagatg atatcgccaa acatgttggt   5340
ggtgatgatg ataccattca tcttggaggg ctgcttgatg aggatcatgg cggccgagtc   5400
gatcagctgg tggttgagct cgagctgggg gaattcgtcc ttgaggactc gagtgacagt   5460
ctttcgccaa agtcgagagg aggccagcac gttggccttg tcaagagacc acacgggaag   5520
agggggggttg tgctgaaggg ccaggaaggc ggccattcgg gcaattcgct caacctcagg   5580
aacggagtag gtctcggtgt cggaagcgac gccagatccg tcatcctcct ttcgctctcc   5640
aaagtagata cctccgacga gctctcggac aatgatgaag tcggtgccct caacgtttcg   5700
gatgggggag agatcggcga gcttgggcga cagcagctgg cagggtcgca ggttggcgta   5760
caggttcagg tcctttcgca gcttgaggag accctgctcg ggtcgcacgt cggttcgtcc   5820
gtcgggagtg gtccatacgg tgttggcagc gcctccgaca gcaccgagca taatagagtc   5880
agcctttcgg cagatgtcga gagtagcgtc ggtgatgggc tcgccctcct tctcaatggc   5940
agctcctcca atgagtcggt cctcaaacac aaactcggtg ccggaggcct cagcaacaga   6000
cttgagcacc ttgacggcct cggcaatcac ctcggggcca cagaagtcgc cgccgagaag   6060
aacaatcttc ttggagtcag tcttggtctt cttagtttcg ggttccattg tggatgtgtg   6120
tggttgtatg tgtgatgtgg tgtgtggagt gaaaatctgt ggctggcaaa cgctcttgta   6180
tatatacgca cttttgcccg tgctatgtgg aagactaaac ctccgaagat tgtgactcag   6240
gtagtgcggt atcggctagg gacccaaacc ttgtcgatgc cgatagcgct atcgaacgta   6300
ccccagccgg ccgggagtat gtcggagggg acatacgaga tcgtcaaggg tttgtggcca   6360
actggtattt aaatgatgtc gacgcagtag gatgtcctgc acgggtcttt ttgtggggtg   6420
tggagaaagg ggtgcttgga gatggaagcc ggtagaaccg ggctgcttgt gcttggagat   6480
ggaagccggt agaaccgggc tgcttggggg gatttggggc cgctgggctc caaagagggg   6540
taggcatttc gttggggtta cgtaattgcg gcatttgggt cctgcgcgca tgtcccattg   6600
gtcagaatta gtccggatag gagacttatc agccaatcac agcgccggat ccacctgtag   6660
gttgggttgg gtgggagcac ccctccacag agtagagtca aacagcagca gcaacatgat   6720
agttgggggt gtgcgtgtta aaggaaaaaa aagaagcttg ggttatattc ccgctctatt   6780
tagaggttgc gggatagacg ccgacggagg gcaatggcgc tatggaacct tgcggatatc   6840
catacgccgc ggcggactgc gtccgaacca gctccagcag cgtttttttcc gggccattga   6900
gccgactgcg accccgccaa cgtgtcttgg cccacgcact catgtcatgt tggtgttggg   6960
aggccacttt ttaagtagca caaggcacct agctcgcagc aaggtgtccg aaccaaagaa   7020
gcggctgcag tggtgcaaac ggggcggaaa cggcgggaaa aagccacggg ggcacgaatt   7080
gaggcacgcc ctcgaatttg agacgagtca cggccccatt cgcccgcgca atggctcgcc   7140
aacgcccggt cttttgcacc acatcaggtt accccaagcc aaacctttgt gttaaaaagc   7200
ttaacatatt ataccgaacg taggtttggg cgggcttgct ccgtctgtcc aaggcaacat   7260
ttatataagg gtctgcatcg ccggctcaat tgaatctttt ttcttcttct cttctctata   7320
ttcattcttg aattaaacac acatcaacca tggctaccaa gcagccctac cagttcccta   7380
ctctgaccga gatcaagcga tctctgccct ccgagtgttt cgaggcctcc gtgcctctct   7440
ctctgtacta caccgttcga tgcctggtca ttgctgtgtc gctcgccttc ggacttcacc   7500
atgcacgatc tctgcccgtt gtcgaaggcc tctgggctct ggatgccgct ctctgcaccg   7560
gttacgtgct gctccagggc atcgtcttct ggggattctt tactgttggt cacgacgctg   7620
```

-continued

```
gacatggtgc cttctcccga taccacctgc tcaactttgt catcggaacc ttcattcact   7680

ctctcatcct tacacccttc gagtcctgga agctcaccca cagacaccat cacaagaaca   7740

ctggcaacat cgaccgagac gaaatcttct accctcaacg aaaggccgac gatcatcctc   7800

tgtctcgaaa cctcattctg gctttgggtg cagcctggtt tgcctacctg gtcgaaggct   7860

ttcctccccg aaaggtcaac cacttcaacc ccttcgagcc tctctttgtt cgacaggtct   7920

ctgccgtggt catttcgctg gctgcgcact ttggagtggc tgccctgtcc atctacctca   7980

gcctgcagtt cggcttcaag actatggcca tctactacta tggtcccgtc tttgtgttcg   8040

gatccatgct cgtcattact acctttcttc atcacaacga cgaagagaca ccttggtacg   8100

cagattcgga gtggacctac gtcaaaggca acctgtcctc tgtcgaccga tcctacggtg   8160

ccctcatcga caacctttct cacaacatcg gaacccacca gattcatcac ctctttccca   8220

tcattcctca ctacaagctc aagcgagcta ccgaggcctt ccatcaagcc tttcccgagc   8280

tggttcgaaa gtccgacgaa cccatcatca aggccttttt cagagtcggc cgactctacg   8340

caaactacgg tgtggtcgac tcggatgcca agctgttcac tctcaaggag gccaaggctg   8400

tttccgaagc cgctaccaag actaaggcca cctaagcggc cgcatgagaa gataaatata   8460

taaatacatt gagatattaa atgcgctaga ttagagagcc tcatactgct cggagagaag   8520

ccaagacgag tactcaaagg ggattacacc atccatatcc acagacacaa gctggggaaa   8580

ggttctatat acactttccg gaataccgta gtttccgatg ttatcaatgg gggcagccag   8640

gatttcaggc acttcggtgt ctcggggtga aatggcgttc ttggcctcca tcaagtcgta   8700

ccatgtcttc atttgcctgt caaagtaaaa cagaagcaga tgaagaatga acttgaagtg   8760

aaggaattta aatgtaacga aactgaaatt tgaccagata ttgtgtccgc ggtggagctc   8820

cagcttttgt tccctttagt gagggttaat ttcgagcttg gcgtaatcat ggtcatagct   8880

gtttcctgtg tgaaattgtt atccgctcac aagcttccac acaac                   8925
```

<210> SEQ ID NO 92
<211> LENGTH: 8919
<212> TYPE: DNA
<213> ORGANISM: Artificial Sequence
<220> FEATURE:
<223> OTHER INFORMATION: Plasmid pY140

<400> SEQUENCE: 92

```
gtacgagccg gaagcataaa gtgtaaagcc tggggtgcct aatgagtgag ctaactcaca     60

ttaattgcgt tgcgctcact gcccgctttc cagtcgggaa acctgtcgtg ccagctgcat    120

taatgaatcg gccaacgcgc ggggagaggc ggtttgcgta ttgggcgctc ttccgcttcc    180

tcgctcactg actcgctgcg ctcggtcgtt cggctgcggc gagcggtatc agctcactca    240

aaggcggtaa tacggttatc cacagaatca ggggataacg caggaaagaa catgtgagca    300

aaaggccagc aaaaggccag gaaccgtaaa aaggccgcgt tgctggcgtt tttccatagg    360

ctccgccccc ctgacgagca tcacaaaaat cgacgctcaa gtcagaggtg gcgaaacccg    420

acaggactat aaagatacca ggcgtttccc cctggaagct ccctcgtgcg ctctcctgtt    480

ccgaccctgc cgcttaccgg atacctgtcc gcctttctcc cttcgggaag cgtggcgctt    540

tctcatagct cacgctgtag gtatctcagt tcggtgtagg tcgttcgctc caagctgggc    600

tgtgtgcacg aaccccccgt tcagcccgac cgctgcgcct tatccggtaa ctatcgtctt    660

gagtccaacc cggtaagaca cgacttatcg ccactggcag cagccactgg taacaggatt    720
```

-continued agcagagcga ggtatgtagg cggtgctaca gagttcttga agtggtggcc taactacggc 780
tacactagaa ggacagtatt tggtatctgc gctctgctga agccagttac cttcggaaaa 840
agagttggta gctcttgatc cggcaaacaa accaccgctg gtagcggtgg tttttttgtt 900
tgcaagcagc agattacgcg cagaaaaaaa ggatctcaag aagatccttt gatcttttct 960
acggggtctg acgctcagtg gaacgaaaac tcacgttaag ggattttggt catgagatta 1020
tcaaaaagga tcttcaccta gatcctttta aattaaaaat gaagttttaa atcaatctaa 1080
agtatatatg agtaaacttg gtctgacagt taccaatgct taatcagtga ggcacctatc 1140
tcagcgatct gtctatttcg ttcatccata gttgcctgac tccccgtcgt gtagataact 1200
acgatacggg agggcttacc atctggcccc agtgctgcaa tgataccgcg agacccacgc 1260
tcaccggctc cagatttatc agcaataaac cagccagccg gaagggccga gcgcagaagt 1320
ggtcctgcaa ctttatccgc ctccatccag tctattaatt gttgccggga agctagagta 1380
agtagttcgc cagttaatag tttgcgcaac gttgttgcca ttgctacagg catcgtggtg 1440
tcacgctcgt cgtttggtat ggcttcattc agctccggtt cccaacgatc aaggcgagtt 1500
acatgatccc ccatgttgtg caaaaaagcg gttagctcct tcggtcctcc gatcgttgtc 1560
agaagtaagt tggccgcagt gttatcactc atggttatgg cagcactgca taattctctt 1620
actgtcatgc catccgtaag atgcttttct gtgactggtg agtactcaac caagtcattc 1680
tgagaatagt gtatgcggcg accgagttgc tcttgcccgg cgtcaatacg ggataatacc 1740
gcgccacata gcagaacttt aaaagtgctc atcattggaa aacgttcttc ggggcgaaaa 1800
ctctcaagga tcttaccgct gttgagatcc agttcgatgt aacccactcg tgcacccaac 1860
tgatcttcag catcttttac tttcaccagc gtttctgggt gagcaaaaac aggaaggcaa 1920
aatgccgcaa aaaagggaat aagggcgaca cggaaatgtt gaatactcat actcttcctt 1980
tttcaatatt attgaagcat ttatcagggt tattgtctca tgagcggata catatttgaa 2040
tgtatttaga aaaataaaca aataggggtt ccgcgcacat ttccccgaaa agtgccacct 2100
gacgcgccct gtagcggcgc attaagcgcg gcgggtgtgg tggttacgcg cagcgtgacc 2160
gctacacttg ccagcgccct agcgcccgct cctttcgctt tcttcccttc ctttctcgcc 2220
acgttcgccg gctttccccg tcaagctcta aatcgggggc tccctttagg gttccgattt 2280
agtgctttac ggcacctcga ccccaaaaaa cttgattagg gtgatggttc acgtagtggg 2340
ccatcgccct gatagacggt ttttcgccct ttgacgttgg agtccacgtt ctttaatagt 2400
ggactcttgt tccaaactgg aacaacactc aaccctatct cggtctattc ttttgattta 2460
taagggattt tgccgatttc ggcctattgg ttaaaaaatg agctgattta acaaaaattt 2520
aacgcgaatt ttaacaaaat attaacgctt acaatttcca ttcgccattc aggctgcgca 2580
actgttggga agggcgatcg gtgcgggcct cttcgctatt acgccagctg gcgaaagggg 2640
gatgtgctgc aaggcgatta agttgggtaa cgccagggtt ttcccagtca cgacgttgta 2700
aaacgacggc cagtgaattg taatacgact cactataggg cgaattgggt accgggcccc 2760
ccctcgaggt cgatggtgtc gataagcttg atatcgaatt catgtcacac aaaccgatct 2820
tcgcctcaag gaaacctaat tctacatccg agagactgcc gagatccagt ctacactgat 2880
taattttcgg gccaataatt taaaaaaatc gtgttatata atattatatg tattatatat 2940
atacatcatg atgatactga cagtcatgtc ccattgctaa atagacagac tccatctgcc 3000
gcctccaact gatgttctca atatttaagg ggtcatctcg cattgtttaa taataaacag 3060
actccatcta ccgcctccaa atgatgttct caaaatatat tgtatgaact tatttttatt 3120

-continued

```
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttgc ttaaattcaa tccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca accgatttcg   4200
acagtaataa tttgaatcga atcggagcct aaaatgaacc cgagtatatc tcataaaatt   4260
ctcggtgaga ggtctgtgac tgtcagtaca aggtgccttc attatgccct caaccttacc   4320
atacctcact gaatgtagtg tacctctaaa aatgaaatac agtgccaaaa gccaaggcac   4380
tgagctcgtc taacggactt gatatacaac caattaaaac aaatgaaaag aaatacagtt   4440
ctttgtatca tttgtaacaa ttaccctgta caaactaagg tattgaaatc ccacaatatt   4500
cccaaagtcc accccttcc aaattgtcat gcctacaact catataccaa gcactaacct   4560
accaaacacc actaaaaccc cacaaaatat atcttaccga atatacagta acaagctacc   4620
accacactcg ttgggtgcag tcgccagctt aaagatatct atccacatca gccacaactc   4680
ccttccttta ataaaccgac tacacccttg gctattgagg ttatgagtga atatactgta   4740
gacaagacac tttcaagaag actgtttcca aaacgtacca ctgtcctcca ctacaaacac   4800
acccaatctg cttcttctag tcaaggttgc tacaccggta aattataaat catcatttca   4860
ttagcagggc agggcccttt ttatagagtc ttatacacta gcggaccctg ccggtagacc   4920
aacccgcagg cgcgtcagtt tgctccttcc atcaatgcgt cgtagaaacg acttactcct   4980
tcttgagcag ctccttgacc ttgttggcaa caagtctccg acctcggagg tggaggaaga   5040
gcctccgata tcggcggtag tgataccagc ctcgacggac tccttgacgg cagcctcaac   5100
agcgtcaccg gcgggcttca tgttaagaga gaacttgagc atcatggcgg cagacagaat   5160
ggtggcaatg gggttgacct tctgcttgcc gagatcgggg gcagatccgt gacagggctc   5220
gtacagaccg aacgcctcgt tggtgtcggg cagagaagcc agagaggcgg agggcagcag   5280
acccagagaa ccggggatga cggaggcctc gtcggagatg atatcgccaa acatgttggt   5340
ggtgatgatg ataccattca tcttggaggg ctgcttgatg aggatcatgg cggccgagtc   5400
gatcagctgg tggttgagct cgagctgggg gaattcgtcc ttgaggactc gagtgacagt   5460
```

-continued

```
ctttcgccaa agtcgagagg aggccagcac gttggccttg tcaagagacc acacgggaag   5520
aggggggttg tgctgaaggg ccaggaaggc ggccattcgg gcaattcgct caacctcagg   5580
aacggagtag gtctcggtgt cggaagcgac gccagatccg tcatcctcct ttcgctctcc   5640
aaagtagata cctccgacga gctctcggac aatgatgaag tcggtgccct caacgtttcg   5700
gatgggggag agatcggcga gcttgggcga cagcagctgg cagggtcgca ggttggcgta   5760
caggttcagg tcctttcgca gcttgaggag accctgctcg ggtcgcacgt cggttcgtcc   5820
gtcgggagtg gtccatacgg tgttggcagc gcctccgaca gcaccgagca taatagagtc   5880
agcctttcgg cagatgtcga gagtagcgtc ggtgatgggc tcgccctcct tctcaatggc   5940
agctcctcca atgagtcggt cctcaaacac aaactcggtg ccggaggcct cagcaacaga   6000
cttgagcacc ttgacggcct cggcaatcac ctcggggcca cagaagtcgc cgccgagaag   6060
aacaatcttc ttggagtcag tcttggtctt cttagtttcg ggttccattg tggatgtgtg   6120
tggttgtatg tgtgatgtgg tgtgtggagt gaaaatctgt ggctggcaaa cgctcttgta   6180
tatatacgca cttttgcccg tgctatgtgg aagactaaac ctccgaagat tgtgactcag   6240
gtagtgcggt atcggctagg gacccaaacc ttgtcgatgc cgatagcgct atcgaacgta   6300
ccccagccgg ccgggagtat gtcggagggg acatacgaga tcgtcaaggg tttgtggcca   6360
actggtattt aaatgatgtc gacgcagtag gatgtcctgc acgggtcttt ttgtggggtg   6420
tggagaaagg ggtgcttgga gatggaagcc ggtagaaccg ggctgcttgt gcttggagat   6480
ggaagccggt agaaccgggc tgcttggggg gatttggggc cgctgggctc caaagagggg   6540
taggcatttc gttggggtta cgtaattgcg gcatttgggt cctgcgcgca tgtcccattg   6600
gtcagaatta gtccggatag gagacttatc agccaatcac agcgccggat ccacctgtag   6660
gttgggttgg gtgggagcac ccctccacag agtagagtca aacagcagca gcaacatgat   6720
agttgggggt gtgcgtgtta aaggaaaaaa aagaagcttg ggttatattc ccgctctatt   6780
tagaggttgc gggatagacg ccgacggagg gcaatggcgc tatggaacct tgcggatatc   6840
catacgccgc ggcggactgc gtccgaacca gctccagcag cgttttttcc gggccattga   6900
gccgactgcg accccgccaa cgtgtcttgg cccacgcact catgtcatgt tggtgttggg   6960
aggccacttt ttaagtagca caaggcacct agctcgcagc aaggtgtccg aaccaaagaa   7020
gcggctgcag tggtgcaaac ggggcggaaa cggcgggaaa aagccacggg ggcacgaatt   7080
gaggcacgcc ctcgaatttg agacgagtca cggccccatt cgcccgcgca atggctcgcc   7140
aacgcccggt cttttgcacc acatcaggtt accccaagcc aaacctttgt gttaaaaagc   7200
ttaacatatt ataccgaacg taggtttggg cgggcttgct ccgtctgtcc aaggcaacat   7260
ttatataagg gtctgcatcg ccggctcaat tgaatctttt ttcttcttct cttctctata   7320
ttcattcttg aattaaacac acatcaacca tggcttcctc taccgttgcc gctccctacg   7380
agttccctac tctcaccgag atcaagcgat ccctgcctgc ccactgcttc gaagcctctg   7440
ttccctggtc cctctactat accgtgcgag ctctgggcat tgccggttcc cttgctctcg   7500
gactgtacta tgctcgagcc cttgctatcg tgcaggagtt tgcactgctc gatgccgtcc   7560
tttgcactgg ctacattctg ctccagggta tcgtgttctg gggattcttt accatcggtc   7620
acgactgtgg acatggtgcc ttctcgcgat cccacctgct caacttctct gttggcacac   7680
tcattcactc catcattctg actccctacg agtcgtggaa gatcagccat cgacaccatc   7740
acaagaacac cggcaacatc gacaaggatg agatcttcta ccctcagcga gaagccgact   7800
ctcatcccct gtcccgacac atggtcatct cccttggttc ggcttggttt gcctacctcg   7860
```

-continued ttgctggatt tcctccccga aaggtcaacc acttcaatcc ctgggagcct ctctacctgc 7920
gaagaatgtc tgccgtcatc atttccctcg gctctctcgt ggcctttgct ggtctgtacg 7980
cctaccttac ctacgtctac ggcctcaaga ccatggctct gtattacttc gcacctctct 8040
ttggattcgc caccatgctg gttgtcacta ccttcctcca tcacaacgac gaggaaactc 8100
cctggtacgc cgattcggag tggacctatg tcaagggcaa cttgtcctct gtggaccgaa 8160
gctacggagc cctcatcgac aacctgtccc acaacattgg tacacatcag atccaccatc 8220
tgtttcccat cattcctcac tacaagctca acgaggccac tgctgccttc gctcaggcct 8280
ttcccgaact ggtgcgaaag tcggcttctc ccatcattcc caccttcatc cgaattggtc 8340
ttatgtacgc caagtacggc gtggtcgaca aggatgccaa gatgtttacc ctcaaggagg 8400
ccaaggctgc caagaccaaa gccaactaag cggccgcatg agaagataaa tatataaata 8460
cattgagata ttaaatgcgc tagattagag agcctcatac tgctcggaga gaagccaaga 8520
cgagtactca aaggggatta caccatccat atccacagac acaagctggg gaaaggttct 8580
atatacactt tccggaatac cgtagtttcc gatgttatca atgggggcag ccaggatttc 8640
aggcacttcg gtgtctcggg gtgaaatggc gttcttggcc tccatcaagt cgtaccatgt 8700
cttcatttgc ctgtcaaagt aaaacagaag cagatgaaga atgaacttga agtgaaggaa 8760
tttaaatgta acgaaactga aatttgacca gatattgtgt ccgcggtgga gctccagctt 8820
ttgttccctt tagtgagggt taatttcgag cttggcgtaa tcatggtcat agctgtttcc 8880
tgtgtgaaat tgttatccgc tcacaagctt ccacacaac 8919

<210> SEQ ID NO 93
<211> LENGTH: 6267
<212> TYPE: DNA
<213> ORGANISM: Artificial Sequence
<220> FEATURE:
<223> OTHER INFORMATION: Plasmid pY137

<400> SEQUENCE: 93
taactttggc cggcctttac ctgcaggata acttcgtata atgtatgcta tacgaagtta 60
tgaattctgt aatattggga tctgttcgga aatcaacgga tgctcaaccg atttcgacag 120
taataatttg aatcgaatcg gagcctaaaa tgaacccgag tatatctcat aaaattctcg 180
gtgagaggtc tgtgactgtc agtacaaggt gccttcatta tgccctcaac cttaccatac 240
ctcactgaat gtagtgtacc tctaaaaatg aaatacagtg ccaaaagcca aggcactgag 300
ctcgtctaac ggacttgata tacaaccaat taaaacaaat gaaaagaaat acagttcttt 360
gtatcatttg taacaattac cctgtacaaa ctaaggtatt gaaatcccac aatattccca 420
aagtccaccc ctttccaaat tgtcatgcct acaactcata taccaagcac taacctacca 480
aacaccacta aaaccccaca aaatatatct taccgaatat acagtaacaa gctaccacca 540
cactcgttgg gtgcagtcgc cagcttaaag atatctatcc acatcagcca caactccctt 600
cctttaataa accgactaca cccttggcta ttgaggttat gagtgaatat actgtagaca 660
agacactttc aagaagactg tttccaaaac gtaccactgt cctccactac aaacacaccc 720
aatctgcttc ttctagtcaa ggttgctaca ccggtaaatt ataaatcatc atttcattag 780
cagggcaggg cccttttat agagtcttat acactagcgg accctgccgg tagaccaacc 840
cgcaggcgcg tcagtttgct ccttccatca atgcgtcgta gaaacgactt actccttctt 900
gagcagctcc ttgaccttgt tggcaacaag tctccgacct cggaggtgga ggaagagcct 960

-continued

```
ccgatatcgg cggtagtgat accagcctcg acggactcct tgacggcagc ctcaacagcg   1020
tcaccggcgg gcttcatgtt aagagagaac ttgagcatca tggcggcaga cagaatggtg   1080
gcaatggggt tgaccttctg cttgccgaga tcgggggcag atccgtgaca gggctcgtac   1140
agaccgaacg cctcgttggt gtcgggcaga gaagccagag aggcggaggg cagcagaccc   1200
agagaaccgg ggatgacgga ggcctcgtcg gagatgatat cgccaaacat gttggtggtg   1260
atgatgatac cattcatctt ggagggctgc ttgatgagga tcatggcggc cgagtcgatc   1320
agctggtggt tgagctcgag ctgggggaat tcgtccttga ggactcgagt gacagtcttt   1380
cgccaaagtc gagaggaggc cagcacgttg gccttgtcaa gagaccacac gggaagaggg   1440
gggttgtgct gaagggccag gaaggcggcc attcgggcaa ttcgctcaac ctcaggaacg   1500
gagtaggtct cggtgtcgga agcgacgcca gatccgtcat cctcctttcg ctctccaaag   1560
tagatacctc cgacgagctc tcggacaatg atgaagtcgg tgccctcaac gtttcggatg   1620
ggggagagat cggcgagctt gggcgacagc agctggcagg gtcgcaggtt ggcgtacagg   1680
ttcaggtcct ttcgcagctt gaggagaccc tgctcgggtc gcacgtcggt tcgtccgtcg   1740
ggagtggtcc atacggtgtt ggcagcgcct ccgacagcac cgagcataat agagtcagcc   1800
tttcggcaga tgtcgagagt agcgtcggtg atgggctcgc cctccttctc aatggcagct   1860
cctccaatga gtcggtcctc aaacacaaac tcggtgccgg aggcctcagc aacagacttg   1920
agcaccttga cggcctcggc aatcacctcg gggccacaga agtcgccgcc gagaagaaca   1980
atcttcttgg agtcagtctt ggtcttctta gtttcgggtt ccattgtgga tgtgtgtggt   2040
tgtatgtgtg atgtggtgtg tggagtgaaa atctgtggct ggcaaacgct cttgtatata   2100
tacgcacttt tgcccgtgct atgtggaaga ctaaacctcc gaagattgtg actcaggtag   2160
tgcggtatcg gctagggacc caaaccttgt cgatgccgat agcgctatcg aacgtacccc   2220
agccggccgg gagtatgtcg gaggggacat acgagatcgt caagggtttg tggccaactg   2280
gtatttaaat gatgtcgact catcgatata acttcgtata atgtatgcta tacgaagtta   2340
tcctaggtat agatctgtta ccggacagaa gtaccccaag ctcaacaaat gggctgtcaa   2400
ccacttcaac cccaacgccc cgctgtttga gaagaaggac tggttcaaca tctggatctc   2460
taacgtcggt attggtatca ccatgtccgt catcgcatac tccatcaacc gatggggcct   2520
ggcttccgtc accctctact acctgatccc ctacctgtgg gtcaaccact ggctcgtggc   2580
catcacctac ctgcagcaca ccgaccccac tctgccccac taccacgccg accagtggaa   2640
cttcacccga ggagccgccg ccaccatcga ccgagagttt ggcttcatcg gctccttctg   2700
cttccatgac atcatcgaga cccacgttct gcaccactac gtgtctcgaa ttcccttcta   2760
caacgcccga atcgccactg agaagatcaa gaaggtcatg ggcaagcact accgacacga   2820
cgacaccaac ttcatcaagt ctctttacac tgtcgcccga acctgccagt ttgttgaagg   2880
taaggaaggc attcagatgt ttagaaacgt caatggagtc ggagttgctc ctgacggcct   2940
gccttctaaa ggcgcgccag ctgcattaat gaatcggcca acgcgcgggg agaggcggtt   3000
tgcgtattgg gcgctcttcc gcttcctcgc tcactgactc gctgcgctcg gtcgttcggc   3060
tgcggcgagc ggtatcagct cactcaaagg cggtaatacg gttatccaca gaatcagggg   3120
ataacgcagg aaagaacatg tgagcaaaag gccagcaaaa ggccaggaac cgtaaaaagg   3180
ccgcgttgct ggcgtttttc cataggctcc gcccccctga cgagcatcac aaaaatcgac   3240
gctcaagtca gaggtggcga aacccgacag gactataaag ataccaggcg tttccccctg   3300
gaagctccct cgtgcgctct cctgttccga ccctgccgct taccggatac ctgtccgcct   3360
```

-continued

```
ttctcccttc gggaagcgtg gcgctttctc atagctcacg ctgtaggtat ctcagttcgg   3420

tgtaggtcgt tcgctccaag ctgggctgtg tgcacgaacc ccccgttcag cccgaccgct   3480

gcgccttatc cggtaactat cgtcttgagt ccaacccggt aagacacgac ttatcgccac   3540

tggcagcagc cactggtaac aggattagca gagcgaggta tgtaggcggt gctacagagt   3600

tcttgaagtg gtggcctaac tacggctaca ctagaagaac agtatttggt atctgcgctc   3660

tgctgaagcc agttaccttc ggaaaaagag ttggtagctc ttgatccggc aaacaaacca   3720

ccgctggtag cggtggtttt tttgtttgca agcagcagat tacgcgcaga aaaaaaggat   3780

ctcaagaaga tcctttgatc ttttctacgg ggtctgacgc tcagtggaac gaaaactcac   3840

gttaagggat tttggtcatg agattatcaa aaaggatctt cacctagatc cttttaaatt   3900

aaaaatgaag ttttaaatca atctaaagta tatatgagta aacttggtct gacagttacc   3960

aatgcttaat cagtgaggca cctatctcag cgatctgtct atttcgttca tccatagttg   4020

cctgactccc cgtcgtgtag ataactacga tacgggaggg cttaccatct ggccccagtg   4080

ctgcaatgat accgcgagac ccacgctcac cggctccaga tttatcagca ataaaccagc   4140

cagccggaag ggccgagcgc agaagtggtc ctgcaacttt atccgcctcc atccagtcta   4200

ttaattgttg ccgggaagct agagtaagta gttcgccagt taatagtttg cgcaacgttg   4260

ttgccattgc tacaggcatc gtggtgtcac gctcgtcgtt tggtatggct tcattcagct   4320

ccggttccca acgatcaagg cgagttacat gatcccccat gttgtgcaaa aaagcggtta   4380

gctccttcgg tcctccgatc gttgtcagaa gtaagttggc cgcagtgtta tcactcatgg   4440

ttatggcagc actgcataat tctcttactg tcatgccatc cgtaagatgc ttttctgtga   4500

ctggtgagta ctcaaccaag tcattctgag aatagtgtat gcggcgaccg agttgctctt   4560

gcccggcgtc aatacgggat aataccgcgc cacatagcag aactttaaaa gtgctcatca   4620

ttggaaaacg ttcttcgggg cgaaaactct caaggatctt accgctgttg agatccagtt   4680

cgatgtaacc cactcgtgca cccaactgat cttcagcatc ttttactttc accagcgttt   4740

ctgggtgagc aaaaacagga aggcaaaatg ccgcaaaaaa gggaataagg gcgacacgga   4800

aatgttgaat actcatactc ttcctttttc aatattattg aagcatttat cagggttatt   4860

gtctcatgag cggatacata tttgaatgta tttagaaaaa taaacaaata ggggttccgc   4920

gcacatttcc ccgaaaagtg ccacctgatg cggtgtgaaa taccgcacag atgcgtaagg   4980

agaaaatacc gcatcaggaa attgtaagcg ttaatatttt gttaaaattc gcgttaaatt   5040

tttgttaaat cagctcattt tttaaccaat aggccgaaat cggcaaaatc ccttataaat   5100

caaaagaata gaccgagata gggttgagtg ttgttccagt ttggaacaag agtccactat   5160

taaagaacgt ggactccaac gtcaaagggc gaaaaaccgt ctatcagggc gatggcccac   5220

tacgtgaacc atcaccctaa tcaagttttt tggggtcgag gtgccgtaaa gcactaaatc   5280

ggaaccctaa agggagcccc cgatttagag cttgacgggg aaagccggcg aacgtggcga   5340

gaaaggaagg gaagaaagcg aaaggagcgg gcgctagggc gctggcaagt gtagcggtca   5400

cgctgcgcgt aaccaccaca cccgccgcgc ttaatgcgcc gctacagggc gcgtccattc   5460

gccattcagg ctgcgcaact gttgggaagg gcgatcggtg cgggcctctt cgctattacg   5520

ccagctggcg aaagggggat gtgctgcaag gcgattaagt tgggtaacgc cagggttttc   5580

ccagtcacga cgttgtaaaa cgacggccag tgaattgtaa tacgactcac tatagggcga   5640

attgggcccg acgtcgcatg catggattcg accacgcaga ccaacaccgg caccggcaag   5700
```

-continued

```
gtggccgtgc agccccccac ggccttcatt aagcccattg agaaggtgtc cgagcccgtc   5760

tacgacacct ttggcaacga gttcactcct ccagactact ctatcaagga tattctggat   5820

gccattcccc aggagtgcta caagcggtcc tacgttaagt cctactcgta cgtggcccga   5880

gactgcttct ttatcgccgt ttttgcctac atggcctacg cgtacctgcc tcttattccc   5940

tcggcttccg gccgagctgt ggcctgggcc atgtactcca ttgtccaggg tctgtttggc   6000

accggtctgt gggttcttgc ccacgagtgt ggccactctg ctttctccga ctctaacacc   6060

gtcaacaacg tcaccggatg ggttctgcac tcctccatgc tggtccctta ctacgcctgg   6120

aagctgaccc actccatgca ccacaagtcc actggtcacc tcacccgtga tatggtgttt   6180

gtgcccaagg accgaaagga gtttatggag aaccgaggcg cccatgactg gtctgagctt   6240

gctgaggacg ctcccctcat gattaat                                     6267
```

```
<210> SEQ ID NO 94
<211> LENGTH: 9570
<212> TYPE: DNA
<213> ORGANISM: Artificial Sequence
<220> FEATURE:
<223> OTHER INFORMATION: Plasmid pY117

<400> SEQUENCE: 94

ggccgccacc gcggcccgag attccggcct cttcggccgc caagcgaccc gggtggacgt     60

ctagaggtac ctagcaatta acagatagtt tgccggtgat aattctctta acctcccaca    120

ctcctttgac ataacgattt atgtaacgaa actgaaattt gaccagatat tgtgtccgcg    180

gtggagctcc agcttttgtt ccctttagtg agggtttaaa cgagcttggc gtaatcatgg    240

tcatagctgt ttcctgtgtg aaattgttat ccgctcacaa ttccacacaa cgtacgagcc    300

ggaagcataa agtgtaaagc ctggggtgcc taatgagtga gctaactcac attaattgcg    360

ttgcgctcac tgcccgcttt ccagtcggga aacctgtcgt gccagctgca ttaatgaatc    420

ggccaacgcg cggggagagg cggtttgcgt attgggcgct cttccgcttc ctcgctcact    480

gactcgctgc gctcggtcgt tcggctgcgg cgagcggtat cagctcactc aaaggcggta    540

atacggttat ccacagaatc aggggataac gcaggaaaga acatgtgagc aaaaggccag    600

caaaaggcca ggaaccgtaa aaaggccgcg ttgctggcgt ttttccatag gctccgcccc    660

cctgacgagc atcacaaaaa tcgacgctca agtcagaggt ggcgaaaccc gacaggacta    720

taaagatacc aggcgtttcc ccctggaagc tccctcgtgc gctctcctgt tccgaccctg    780

ccgcttaccg gatacctgtc cgcctttctc ccttcgggaa gcgtggcgct ttctcatagc    840

tcacgctgta ggtatctcag ttcggtgtag gtcgttcgct ccaagctggg ctgtgtgcac    900

gaaccccccg ttcagcccga ccgctgcgcc ttatccggta actatcgtct tgagtccaac    960

ccggtaagac acgacttatc gccactggca gcagccactg gtaacaggat tagcagagcg   1020

aggtatgtag gcggtgctac agagttcttg aagtggtggc ctaactacgg ctacactaga   1080

aggacagtat ttggtatctg cgctctgctg aagccagtta ccttcggaaa aagagttggt   1140

agctcttgat ccggcaaaca aaccaccgct ggtagcggtg gtttttttgt ttgcaagcag   1200

cagattacgc gcagaaaaaa aggatctcaa gaagatcctt tgatcttttc tacggggtct   1260

gacgctcagt ggaacgaaaa ctcacgttaa gggattttgg tcatgagatt atcaaaaagg   1320

atcttcacct agatcctttt aaattaaaaa tgaagtttta aatcaatcta aagtatatat   1380

gagtaaactt ggtctgacag ttaccaatgc ttaatcagtg aggcacctat ctcagcgatc   1440

tgtctatttc gttcatccat agttgcctga ctccccgtcg tgtagataac tacgatacgg   1500
```

-continued

```
gagggcttac catctggccc cagtgctgca atgataccgc gagacccacg ctcaccggct   1560
ccagatttat cagcaataaa ccagccagcc ggaagggccg agcgcagaag tggtcctgca   1620
actttatccg cctccatcca gtctattaat tgttgccggg aagctagagt aagtagttcg   1680
ccagttaata gtttgcgcaa cgttgttgcc attgctacag gcatcgtggt gtcacgctcg   1740
tcgtttggta tggcttcatt cagctccggt tcccaacgat caaggcgagt tacatgatcc   1800
cccatgttgt gcaaaaaagc ggttagctcc ttcggtcctc cgatcgttgt cagaagtaag   1860
ttggccgcag tgttatcact catggttatg gcagcactgc ataattctct tactgtcatg   1920
ccatccgtaa gatgcttttc tgtgactggt gagtactcaa ccaagtcatt ctgagaatag   1980
tgtatgcggc gaccgagttg ctcttgcccg gcgtcaatac gggataatac cgcgccacat   2040
agcagaactt taaaagtgct catcattgga aaacgttctt cggggcgaaa actctcaagg   2100
atcttaccgc tgttgagatc cagttcgatg taacccactc gtgcacccaa ctgatcttca   2160
gcatctttta ctttcaccag cgtttctggg tgagcaaaaa caggaaggca aaatgccgca   2220
aaaaagggaa taagggcgac acggaaatgt tgaatactca tactcttcct ttttcaatat   2280
tattgaagca tttatcaggg ttattgtctc atgagcggat acatatttga atgtatttag   2340
aaaaataaac aaataggggt tccgcgcaca tttccccgaa aagtgccacc tgacgcgccc   2400
tgtagcggcg cattaagcgc ggcgggtgtg gtggttacgc gcagcgtgac cgctacactt   2460
gccagcgccc tagcgcccgc tcctttcgct ttcttccctt cctttctcgc cacgttcgcc   2520
ggctttcccc gtcaagctct aaatcggggg ctccctttag ggttccgatt tagtgcttta   2580
cggcacctcg accccaaaaa acttgattag ggtgatggtt cacgtagtgg gccatcgccc   2640
tgatagacgg tttttcgccc tttgacgttg gagtccacgt tctttaatag tggactcttg   2700
ttccaaactg gaacaacact caaccctatc tcggtctatt cttttgattt ataagggatt   2760
ttgccgattt cggcctattg gttaaaaaat gagctgattt aacaaaaatt taacgcgaat   2820
tttaacaaaa tattaacgct tacaatttcc attcgccatt caggctgcgc aactgttggg   2880
aagggcgatc ggtgcgggcc tcttcgctat tacgccagct ggcgaaaggg ggatgtgctg   2940
caaggcgatt aagttgggta acgccagggt tttcccagtc acgacgttgt aaaacgacgg   3000
ccagtgaatt gtaatacgac tcactatagg gcgaattggg taccgggccc cccctcgagg   3060
tcgatggtgt cgataagctt gatatcgaat tcatgtcaca caaaccgatc ttcgcctcaa   3120
ggaaacctaa ttctacatcc gagagactgc cgagatccag tctacactga ttaattttcg   3180
ggccaataat ttaaaaaaat cgtgttatat aatattatat gtattatata tatacatcat   3240
gatgatactg acagtcatgt cccattgcta aatagacaga ctccatctgc cgcctccaac   3300
tgatgttctc aatatttaag gggtcatctc gcattgttta ataataaaca gactccatct   3360
accgcctcca aatgatgttc tcaaaatata ttgtatgaac ttatttttat tacttagtat   3420
tattagacaa cttacttgct ttatgaaaaa cacttcctat ttaggaaaca atttataatg   3480
gcagttcgtt catttaacaa tttatgtaga ataaatgtta taaatgcgta tgggaaatct   3540
taaatatgga tagcataaat gatatctgca ttgcctaatt cgaaatcaac agcaacgaaa   3600
aaaatccctt gtacaacata aatagtcatc gagaaatatc aactatcaaa gaacagctat   3660
tcacacgtta ctattgagat tattattgga cgagaatcac acactcaact gtctttctct   3720
cttctagaaa tacaggtaca agtatgtact attctcattg ttcatacttc tagtcatttc   3780
atcccacata ttccttggat ttctctccaa tgaatgacat tctatcttgc aaattcaaca   3840
```

-continued

```
attataataa gatataccaa agtagcggta tagtggcaat caaaaagctt ctctggtgtg   3900
cttctcgtat ttatttttat tctaatgatc cattaaaggt atatatttat ttcttgttat   3960
ataatccttt tgtttattac atgggctgga tacataaagg tattttgatt taatttttg    4020
cttaaattca atccccccctc gttcagtgtc aactgtaatg gtaggaaatt accatacttt   4080
tgaagaagca aaaaaaatga aagaaaaaaa aaatcgtatt tccaggttag acgttccgca   4140
gaatctagaa tgcggtatgc ggtacattgt tcttcgaacg taaaagttgc gctccctgag   4200
atattgtaca tttttgcttt tacaagtaca agtacatcgt acaactatgt actactgttg   4260
atgcatccac aacagtttgt tttgtttttt tttgtttttt ttttttctaa tgattcatta   4320
ccgctatgta tacctacttg tacttgtagt aagccgggtt attggcgttc aattaatcat   4380
agacttatga atctgcacgg tgtgcgctgc gagttacttt tagcttatgc atgctacttg   4440
ggtgtaatat tgggatctgt tcggaaatca acggatgctc aaccgatttc gacagtaatt   4500
aattaattcc ctagtcccag tgtacacccg ccgatatcgc ttaccctgca gccggattaa   4560
ggttggcaat ttttcacgtc cttgtctccg caattactca ccgggtggtt tataagattg   4620
caagcgtctt gatttgtctc tgtatactaa catgcaatcg cgactcgccc gacgggccac   4680
taacctggcc agaatctcca gatccaagta ttctcttggt ctgcgatatg tttccaacac   4740
aaaagcccct gctgcccagc cggcaactgc tgagtgagta ttccttgcca taaacgaccc   4800
agaaccactg tatagtgttt ggaagcacta gtcagaagac cagcgaaaac aggtggaaaa   4860
aactgagacg aaaagcaacg accagaaatg taatgtgtgg aaaagcgaca cacacagagc   4920
agataaagag gtgacaaata acgacaaatg aaatatcagt atcttcccac aatcactacc   4980
tctcagctgt ctgaaggtgc ggctgatata tccatcccac gtctaacgta tggagtgtga   5040
tagaatatga cgacacaagc atgagaactc gctctctatc caaccaccga aacactgtca   5100
ctacagccgt tcttgttgct ccattcgctt ttgtgattcc atgccttctc tggtgactga   5160
caacattcct tccttttctc cagccctgtt gttatctgct catgacctac ggccactctc   5220
tatcgcatac taacatagac gatcccagcc cgctccccac ttccagggca ccgttggcaa   5280
gcctcctatc ctcaagaagg ctgaggctgc caacgctgac atggacgagt ccttcatcgg   5340
aatgtctgga ggagagatct tccacgagat gatgctgcga cacaacgtcg acactgtctt   5400
cggttacccc ggtggagcca ttctccccgt ctttgacgcc attcacaact ctgagtactt   5460
caactttgtg ctccctcgac acgagcaggg tgccggccac atggccgagg gctacgctcg   5520
agcctctggt aagcccggtg tcgttctcgt cacctctggc cccggtgcca ccaacgtcat   5580
cacccccatg caggacgctc tttccgatgg taccccccatg gttgtcttca ccggtcaggt   5640
cctgacctcc gttatcggca ctgacgcctt ccaggaggcc gatgttgtcg gcatctcccg   5700
atcttgcacc aagtggaacg tcatggtcaa gaacgttgct gagctccccc gacgaatcaa   5760
cgaggccttt gagattgcta cttccggccg acccggtccc gttctcgtcg atctgcccaa   5820
ggatgttact gctgccatcc tgcgagagcc catccccacc aagtccacca ttccctcgca   5880
ttctctgacc aacctcacct ctgccgccgc caccgagttc cagaagcagg ctatccagcg   5940
agccgccaac ctcatcaacc agtccaagaa gcccgtcctt tacgtcggac agggtatcct   6000
tggctccgag gagggtccta agctgcttaa ggagctggct gagaaggccg agattcccgt   6060
caccactact ctgcagggtc ttggtgcctt tgacgagcga gaccccaagt ctctgcacat   6120
gctcggtatg cacggttccg gctacgccaa catggccatg cagaacgctg actgtatcat   6180
tgctctcggc gcccgatttg atgaccgagt taccggctcc atccccaagt ttgcccccga   6240
```

-continued

```
ggctcgagcc gctgcccttg agggtcgagg tggtattgtt cactttgaga tccaggccaa   6300
gaacatcaac aaggttgttc aggccaccga agccgttgag ggagacgtta ccgagtctgt   6360
ccgacagctc atccccctca tcaacaaggt ctctgccgct gagcgagctc cctggactga   6420
gactatccag tcctggaagc agcagttccc cttcctcttc gaggctgaag gtgaggatgg   6480
tgttatcaag ccccagtccg tcattgctct gctctctgac ctgacagaga acaacaagga   6540
caagaccatc atcaccaccg gtgttggtca gcatcagatg tggactgccc agcatttccg   6600
atggcgacac cctcgaacca tgatcacttc tggtggtctt ggaactatgg gttacggcct   6660
gcccgccgct atcggcgcca aggttgcccg acctgactgc gacgtcattg acatcgatgg   6720
tgacgcttct ttcaacatga ctctgaccga gctgtccacc gccgttcagt tcaacattgg   6780
cgtcaaggct attgtcctca acaacgagga acagggtatg gtcacccagc tgcagtctct   6840
cttctacgag aaccgatact gccacactca tcagaagaac cccgacttca tgaagctggc   6900
cgagtccatg ggcatgaagg gtatccgaat cactcacatt gaccagctgg aggccggtct   6960
caaggagatg ctcgcataca agggccctgt gctcgttgag gttgttgtcg acaagaagat   7020
ccccgttctt cccatggttc ccgctggtaa ggctttgcat gagttccttg tctacgacgc   7080
tgacgccgag gctgcttctc gacccgatcg actgaagaat gcccccgccc ctcacgtcca   7140
ccagaccacc tttgagaact aagtggaaag gaacacaagc aatccgaacc aaaaataatt   7200
ggggtcccgt gcccacagag tctagtgcag acctaaaatg accacagtaa attatagctg   7260
ttattaaaca tgagattttg accaacaaga gcgtaggaat gttattagct actacttgta   7320
catacacagc atttgtttta aataatgttg cctccagggg cagtgagatc aggacccaga   7380
tccgtggcca gctctctgac ttcagaccgc ttgtacttaa gcagctcgca acactgttgt   7440
cgaggattga acttgccata ttcgattttg tggtcatgaa tccagcacac ctcatttaaa   7500
tgtagctaac ggtagcaggc gaactactgg tacatacctc ccccggaata tgtacaggca   7560
taatgcgtat ctgtgggaca tgtggtcgtt gcgccattat gtaagcagcg tgtactcctc   7620
tgactgtcca tatggtttgc tccatctcac cctcatcgtt ttcattgttc acaggcggcc   7680
acaaaaaaac tgtcttctct ccttctctct tcgccttagt ctactcggac cagttttagt   7740
ttagcttggc gccactggat aaatgagacc tcaggccttg tgatgaggag gtcacttatg   7800
aagcatgtta ggaggtgctt gtatggatag agaagcaccc aaaataataa gaataataat   7860
aaaacagggg gcgttgtcat ttcatatcgt gttttcacca tcaatacacc tccaaacaat   7920
gcccttcatg tggccagccc caatattgtc ctgtagttca actctatgca gctcgtatct   7980
tattgagcaa gtaaaactct gtcagccgat attgcccgac ccgcgacaag ggtcaacaag   8040
gtggtgtaag gccttcgcag aagtcaaaac tgtgccaaac aaacatctag agtctctttg   8100
gtgtttctcg catatatttw atcggctgtc ttacgtattt gcgcctcggt accggactaa   8160
tttcggatca tccccaatac gctttttctt cgcagctgtc aacagtgtcc atgatctatc   8220
cacctaaatg ggtcatatga ggcgtataat ttcgtggtgc tgataataat tcccatatat   8280
ttgacacaaa acttcccccc ctagacatac atctcacaat ctcacttctt gtgcttctgt   8340
cacacatctc ctccagctga cttcaactca cacctctgcc ccagttggtc tacagcggta   8400
taaggtttct ccgcatagag gtgcaccact cctcccgata cttgtttgtg tgacttgtgg   8460
gtcacgacat atatatctac acacattgcg ccaccctttg gttcttccag cacaacaaaa   8520
acacgacacg ctaaccatgg ccaatttact gaccgtacac caaaatttgc ctgcattacc   8580
```

-continued

```
ggtcgatgca acgagtgatg aggttcgcaa gaacctgatg gacatgttca gggatcgcca   8640

ggcgttttct gagcatacct ggaaaatgct tctgtccgtt tgccggtcgt gggcggcatg   8700

gtgcaagttg aataaccgga aatggtttcc cgcagaacct gaagatgttc gcgattatct   8760

tctatatctt caggcgcgcg gtctggcagt aaaaactatc cagcaacatt tgggccagct   8820

aaacatgctt catcgtcggt ccgggctgcc acgaccaagt gacagcaatg ctgtttcact   8880

ggttatgcgg cggatccgaa aagaaaacgt tgatgccggt gaacgtgcaa aacaggctct   8940

agcgttcgaa cgcactgatt tcgaccaggt tcgttcactc atggaaaata gcgatcgctg   9000

ccaggatata cgtaatctgg catttctggg gattgcttat aacaccctgt tacgtatagc   9060

cgaaattgcc aggatcaggg ttaaagatat ctcacgtact gacggtggga gaatgttaat   9120

ccatattggc agaacgaaaa cgctggttag caccgcaggt gtagagaagg cacttagcct   9180

gggggtaact aaactggtcg agcgatggat ttccgtctct ggtgtagctg atgatccgaa   9240

taactacctg ttttgccggg tcagaaaaaa tggtgttgcc gcgccatctg ccaccagcca   9300

gctatcaact cgcgccctgg aagggatttt tgaagcaact catcgattga tttacggcgc   9360

taaggatgac tctggtcaga gatacctggc ctggtctgga cacagtgccc gtgtcggagc   9420

cgcgcgagat atggcccgcg ctggagtttc aataccggag atcatgcaag ctggtggctg   9480

gaccaatgta aatattgtca tgaactatat ccgtaacctg gatagtgaaa caggggcaat   9540

ggtgcgcctg ctggaagatg gcgattaagc                                    9570
```

<210> SEQ ID NO 95
<211> LENGTH: 358
<212> TYPE: PRT
<213> ORGANISM: Saprolegnia diclina (GenBank Accession No. AAR20444)

<400> SEQUENCE: 95

```
Met Thr Glu Asp Lys Thr Lys Val Glu Phe Pro Thr Leu Thr Glu Leu
1               5                   10                  15

Lys His Ser Ile Pro Asn Ala Cys Phe Glu Ser Asn Leu Gly Leu Ser
            20                  25                  30

Leu Tyr Tyr Thr Ala Arg Ala Ile Phe Asn Ala Ser Ala Ser Ala Ala
        35                  40                  45

Leu Leu Tyr Ala Ala Arg Ser Thr Pro Phe Ile Ala Asp Asn Val Leu
    50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His His
        115                 120                 125

His Lys Asn Thr Gly Asn Ile Asp Lys Asp Glu Ile Phe Tyr Pro His
    130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser
            180                 185                 190

Ala Val Ile Val Ser Leu Gly Val Trp Ala Ala Phe Phe Ala Ala Tyr
```

-continued

```
        195                 200                 205

Ala Tyr Leu Thr Tyr Ser Leu Gly Phe Ala Val Met Gly Leu Tyr Tyr
    210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
            260                 265                 270

Phe Val Asp Asn Leu Ser His His Ile Gly Thr His Gln Val His His
        275                 280                 285

Leu Phe Pro Ile Ile Pro His Tyr Lys Leu Asn Glu Ala Thr Lys His
    290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
            340                 345                 350

Ala Lys Ala Lys Ser Asp
        355


<210> SEQ ID NO 96
<211> LENGTH: 9
<212> TYPE: PRT
<213> ORGANISM: Artificial Sequence
<220> FEATURE:
<223> OTHER INFORMATION: Delta-17 Desaturase Motif #1
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 96

Phe Thr Xaa Gly His Asp Xaa Gly His
1               5


<210> SEQ ID NO 97
<211> LENGTH: 9
<212> TYPE: PRT
<213> ORGANISM: Artificial Sequence
<220> FEATURE:
<223> OTHER INFORMATION: Delta-17 Desaturase Motif #2

<400> SEQUENCE: 97

His Arg His His His Lys Asn Thr Gly
1               5


<210> SEQ ID NO 98
<211> LENGTH: 11
<212> TYPE: PRT
<213> ORGANISM: Artificial Sequence
<220> FEATURE:
<223> OTHER INFORMATION: Delta-17 Desaturase Motif #3
<220> FEATURE:
<221> NAME/KEY: misc_feature
<222> LOCATION: (6)..(6)
<223> OTHER INFORMATION: Xaa can be any naturally occurring amino acid

<400> SEQUENCE: 98
```

-continued

Ile Gly Thr His Gln Xaa His His Leu Phe Pro
1 5 10

<210> SEQ ID NO 99
<211> LENGTH: 5
<212> TYPE: PRT
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(4)
<223> OTHER INFORMATION: Xaa can be any naturally occurring amino acid

<400> SEQUENCE: 99

His Xaa Xaa Xaa His
1 5

<210> SEQ ID NO 100
<211> LENGTH: 5
<212> TYPE: PRT
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 100

His Xaa Xaa His His
1 5

<210> SEQ ID NO 101
<211> LENGTH: 5
<212> TYPE: PRT
<213> ORGANISM: Artificial Sequence
<220> FEATURE:
<223> OTHER INFORMATION: His-rich motif
<220> FEATURE:
<221> NAME/KEY: MISC_FEATURE
<222> LOCATION: (1)..(1)
<223> OTHER INFORMATION: Xaa = His [H] or Gln [Q]
<220> FEATURE:
<221> NAME/KEY: misc_feature
<222> LOCATION: (2)..(3)
<223> OTHER INFORMATION: Xaa can be any naturally occurring amino acid

<400> SEQUENCE: 101

Xaa Xaa Xaa His His
1 5

<210> SEQ ID NO 102
<211> LENGTH: 8067
<212> TYPE: DNA
<213> ORGANISM: Artificial Sequence
<220> FEATURE:
<223> OTHER INFORMATION: Plasmid pFBAINPaD17S

<400> SEQUENCE: 102
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300

-continued

```
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
```

-continued

```
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg ttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
```

-continued

```
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgaaaaca gtgtacgcag atctactata gaggaacatt   6060
taaattgccc cggagaagac ggccaggccg cctagatgac aaattcaaca actcacagct   6120
gactttctgc cattgccact aggggggggc ctttttatat ggccaagcca agctctccac   6180
gtcggttggg ctgcacccaa caataaatgg gtagggttgc accaacaaag ggatgggatg   6240
gggggtagaa gatacgagga taacggggct caatggcaca aataagaacg aatactgcca   6300
ttaagactcg tgatccagcg actgacacca ttgcatcatc taagggcctc aaaactacct   6360
cggaactgct gcgctgatct ggacaccaca gaggttccga gcactttagg ttgcaccaaa   6420
tgtcccacca ggtgcaggca gaaaacgctg gaacagcgtg tacagtttgt cttaacaaaa   6480
agtgagggcg ctgaggtcga gcagggtggt gtgacttgtt atagccttta gagctgcgaa   6540
agcgcgtatg gatttggctc atcaggccag attgagggtc tgtggacaca tgtcatgtta   6600
gtgtacttca atcgcccccct ggatatagcc ccgacaatag gccgtggcct catttttttg   6660
ccttccgcac atttccattg ctcggtaccc acaccttgct tctcctgcac ttgccaacct   6720
taatactggt ttacattgac caacatctta caagcggggg gcttgtctag ggtatatata   6780
aacagtggct ctcccaatcg gttgccagtc tcttttttcc tttctttccc cacagattcg   6840
aaatctaaac tacacatcac agaattccga gccgtgagta tccacgacaa gatcagtgtc   6900
gagacgacgc gttttgtgta atgacacaat ccgaaagtcg ctagcaacac acactctcta   6960
cacaaactaa cccagctctg gtaccatggc ttcctctacc gttgccgctc cctacgagtt   7020
ccctactctc accgagatca agcgatccct gcctgcccac tgcttcgaag cctctgttcc   7080
ctggtccctc tactataccg tgcgagctct gggcattgcc ggttcccttg ctctcggact   7140
gtactatgct cgagcccttg ctatcgtgca ggagtttgca ctgctcgatg ccgtcctttg   7200
cactggctac attctgctcc agggtatcgt gttctgggga ttctttacca tcggtcacga   7260
ctgtggacat ggtgccttct cgcgatccca cctgctcaac ttctctgttg gcacactcat   7320
tcactccatc attctgactc cctacgagtc gtggaagatc agccatcgac accatcacaa   7380
gaacaccggc aacatcgaca aggatgagat cttctaccct cagcgagaag ccgactctca   7440
```

-continued

```
tcccctgtcc cgacacatgg tcatctccct tggttcggct tggtttgcct acctcgttgc   7500
tggatttcct ccccgaaagg tcaaccactt caatccctgg gagcctctct acctgcgaag   7560
aatgtctgcc gtcatcattt ccctcggctc tctcgtggcc tttgctggtc tgtacgccta   7620
ccttacctac gtctacggcc tcaagaccat ggctctgtat tacttcgcac ctctctttgg   7680
attcgccacc atgctggttg tcactacctt cctccatcac aacgacgagg aaactccctg   7740
gtacgccgat tcggagtgga cctatgtcaa gggcaacttg tcctctgtgg accgaagcta   7800
cggagccctc atcgacaacc tgtcccacaa cattggtaca catcagatcc accatctgtt   7860
tcccatcatt cctcactaca agctcaacga ggccactgct gccttcgctc aggcctttcc   7920
cgaactggtg cgaaagtcgg cttctcccat cattcccacc ttcatccgaa ttggtcttat   7980
gtacgccaag tacggcgtgg tcgacaagga tgccaagatg tttaccctca aggaggccaa   8040
ggctgccaag accaaagcca actaagc                                       8067
```